US009688727B2

(12) United States Patent
Lieber et al.

(10) Patent No.: US 9,688,727 B2
(45) Date of Patent: *Jun. 27, 2017

(54) DESMOGLEIN 2 (DSG2) BINDING PROTEINS AND USES THEREFOR

(71) Applicant: UNIVERSITY OF WASHINGTON THROUGH ITS CENTER FOR COMMERCIALIZATION, Seattle, WA (US)

(72) Inventors: Andre Lieber, Seattle, WA (US); Hongjie Wang, Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/429,803

(22) PCT Filed: Sep. 24, 2014

(86) PCT No.: PCT/US2014/057139
§ 371 (c)(1),
(2) Date: Mar. 20, 2015

(87) PCT Pub. No.: WO2015/048081
PCT Pub. Date: Apr. 2, 2015

(65) Prior Publication Data
US 2016/0257721 A1 Sep. 8, 2016

Related U.S. Application Data

(63) Continuation-in-part of application No. PCT/US2013/061431, filed on Sep. 24, 2013.

(60) Provisional application No. 61/954,822, filed on Mar. 18, 2014.

(51) Int. Cl.
C07K 14/005 (2006.01)
C12N 15/86 (2006.01)
C12N 15/10 (2006.01)
A61K 47/42 (2017.01)
C07K 7/06 (2006.01)
A61K 38/00 (2006.01)
C12N 5/077 (2010.01)
C12N 7/00 (2006.01)

(52) U.S. Cl.
CPC ............ *C07K 14/005* (2013.01); *A61K 47/42* (2013.01); *C07K 7/06* (2013.01); *C12N 5/0652* (2013.01); *C12N 7/00* (2013.01); *C12N 15/10* (2013.01); *C12N 15/86* (2013.01); *A61K 38/00* (2013.01); *C07K 2319/74* (2013.01); *C12N 2501/998* (2013.01); *C12N 2506/00* (2013.01); *C12N 2710/10321* (2013.01); *C12N 2710/10322* (2013.01); *C12N 2710/10333* (2013.01)

(58) Field of Classification Search
None
See application file for complete search history.

(56) References Cited

U.S. PATENT DOCUMENTS

| 5,527,773 A | 6/1996 | Steinert et al. |
| 6,169,071 B1 | 1/2001 | Blaschuk et al. |
| 6,245,888 B1 | 6/2001 | Staddon |
| 6,407,058 B1 | 6/2002 | Staddon et al. |
| 2002/0016876 A1 | 2/2002 | Farmwald et al. |
| 2002/0127198 A1 | 9/2002 | Rothbard et al. |
| 2004/0229811 A1 | 11/2004 | Blaschuk et al. |
| 2006/0006792 A1 | 1/2006 | Strip et al. |
| 2006/0025166 A1 | 2/2006 | Dang et al. |
| 2006/0067927 A1 | 3/2006 | Chandrasekaran et al. |
| 2006/0251663 A1 | 11/2006 | Mariscal-Gonzalez et al. |
| 2008/0125364 A1 | 5/2008 | Nusrat et al. |

FOREIGN PATENT DOCUMENTS

WO 91/04745 A1 4/1991

OTHER PUBLICATIONS

PDB: 4LIY_A. Chain A, Structure of the Adenovirus 3 Knob Domain K217e and F224s Mutant. Dated May 28, 2014.*
Wang et al. Multimerization of adenovirus serotype 3 fiber knob domains is required for efficient binding of virus to desmoglein 2 and subsequent opening of epithelial junctions. J Virol. Jul. 2011;85(13):6390-402. Epub Apr. 27, 2011.*
GenBank: AAP31205.1. fiber [Human adenovirus B3]. Dated Jun. 19, 2003. https://www.ncbi.nlm.nih.gov/protein/32127278?report=genbank&log$=protalign&blast_rank=7&RID=XK79G68Z01R.*
Beatty et al. Adenovirus Strategies for Tissue-Specific Targeting. Adv Cancer Res. 2012 ; 115: 39-67.*
Wang et al. Structural and functional studies on the interaction of adenovirus fiber knobs and desmoglein 2. J. Virol. 87(21), 11346-11362 (2013).*
Adams, et al., "PHENIX: a comprehensive Python-based system for macromolecular structure solution," Acta Cryst, vol. D66, pp. 213-221, 2010.
Belousova, et al., "Modification of Adenovirus Capsid with a Designed Protein Ligand Yields a Gene Vector Targeted to a Major Molecular Marker of Cancer," Journal of Virology, vol. 82, No. 2, pp. 630-637, 2008.
Bewley, et al, "Structural Analysis of the Mechanism of Adenovirus Binding to Its Human Cellular Receptor, CAR," Science, vol. 286, pp. 1579-1583, 1999.
Beyer, "Epithelial junction opener JO-1 improves monoclonal antibody therapy of cancer," Cancer Res, vol. 71, No. 22, pp. 7080-7090, 2011.
Beyer, et al., "Co-administration of epithelial junction opener JO-1 improves the efficacy and safety of chemotherapeutic drugs," Clin Cancer Res, vol. 18, No. 12, pp. 3340-3351, 2012.

(Continued)

*Primary Examiner* — Nick Zou
(74) *Attorney, Agent, or Firm* — McDonnell Boehnen Hulbert & Berghoff LLP

(57) ABSTRACT

The present invention provides recombinant adenoviral compositions and methods for their use in treating disorders associated with epithelial tissues.

28 Claims, 26 Drawing Sheets

(56) References Cited

OTHER PUBLICATIONS

Cadwell, et al., "Randomization of Genes by PCR Mutagenesis," pcr Methods and Applications, vol. 2, pp. 28-33, 1992.
Cadwell, et al., "Mutagenic PCR," PCR Methods and Applications, vol. 3, pp. S136-S140, 1994.
Campos, et al, "Avidin-Based Targeting and Purification of a Protein IX-Modified, Metabolically Biotinylated Adenoviral Vector," Mol Ther, vol. 9, No. 6, pp. 942-954, 2004.
Carr, et al., "Deaths Associated with Human Adenovirus-14p1 Infections, Europe, 2009-2010," Emerging Infectious Diseases, vol. 17, No. 8, 2011.
Cupelli, et al., "Viral attachment strategies: the many faces of adenoviruses," Current Opinion inj Virology, vol. 1, pp. 84-91, 2011.
Cupelli, et al., "Structure of Adenovirus Type 21 Knob in Complex with CD46 Reveals Key Differences in Receptor Contacts among Species B Adenoviruses," Journal of Virology, vol. 84, No. 7, 2010.
Durmort, et al., "Structure of the Fiber Head of Ad3, a Non-CAR-Binding Serotype of Adenovirus," Virology, No. 295, pp. 302-312, 2001.
Emsley, et al., "Features and development of Coot," Acta Crystallography, D66, pp. 486-501, 2010.
Esposito, et al., "Outbreak of Pneumonia Associated with Emergent Human Adenovirus Serotype 14—Southeast Alaska, 2008," JID, pp. 214-222, 2010.
Girouard, et al., "AdenovirusSerotype 14 Infection, New Brunswick, Canada, 2011," Emerging Infectious Diseases, vol. 19, No. 1, 2013.
Hasegawa, et al., "Affinity Thresholds for Membrane Fusion Triggering by Viral Glycoproteins," Journal of Virology, vol. 81, No. 23, pp. 13149-13157, 2007.
Hemminki, et al., "Ad3-hTERT-E1A, a Fully Serotype 3 Oncolytic Adenovirus, in Patients With Chemotherapy Refractory Cancer," Molecular Therapy, vol. 20, No. 9, pp. 1821-1830, 2012.
Incardona, et al., "EDNA: a framework for plugin-based applications applied to X-ray experiment online data analysis," Journal of Synchrotron Radiation, No. 16, pp. 872-879, 2009.
Kabsch, "Integration, scaling, space-group assignment and post-refinement," Acta Cryst, D66, pp. 133-144, 2010.
Kabsch, "XDS," Acta Cryst, D66, pp. 125-132, 2010.
Kajon, et al., "Molecular Epidemiology and Brief History of Emerging Adenovirus 14—Associated Respiratory Disease in the United States," JID, vol. 202, pp. 93-103 , 2010.
Lewis, et al.,"A Community-Based Outbreak of Severe Respiratory Illness Caused by Human Adenovirus Serotype 14," JID, vol. 199, pp. 1428-1434, 2009.
Louie, et al., "Severe Pneumonia Due to Adenovirus Serotype 14: A New Respiratory Threat?" CID, vol. 46, pp. 421-425, 2008.
McCoy, et al., "Phaser crystallographic software," J Appl Cryst, vol. 40, pp. 658-674, 2007.
Metzgar, et al., "Abrupt Emergence of Diverse Species B Adenoviruses at US Military Recruit Training Centers," JID, vol. 196, pp. 1465-1473, 2007.
MMWR, "Acute Respiratory Disease Associated with Adenovirus Serotype 14—Four States, 2006-2007," Center for Disease Control, pp. 1-6, 2007.
Pache, et al, "Conservation of fiber structure and CD46 usage by subgroup B2 adenoviruses," Virology, vol. 375, pp. 573-579, 2008.

Persson, et al., "Adenovirus type 11 binding alters the conformation of its receptor CD46," Nature Structural & Molecular Biology, vol. 14, No. 2, 2007.
Shayakhmetov, et al., "Efficient Gene Transfer into Human CD341 Cells by a Retargeted Adenovirus Vector," Journal of Virology, vol. 74, No. 6, pp. 2567-2583, 2000.
Strauss, et al., "The epithelial phenotype confers resistance of ovarian cancer cells to oncolytic adenoviruses," Cancer Res, vol. 69, No. 12, pp. 5115-5125, 2009.
Strauss, et al., "Anatomical and physical barriers to tumor targeting with oncolytic adenoviruses in vivo," Current Opinion in Molecular Therapeutics, vol. 11, No. 5, pp. 513-522, 2009.
Strauss, et al., "Analysis of Epithelial and Mesenchymal Markers in Ovarian Cancer Reveals Phenotypic Heterogeneity and Plasticity," PLoS One, vol. 6, No. 1, 2011.
Tang, et al., "Genome and Bioinformatic Analysis of a HAdV-B14p1 Virus Isolated from a Baby with Pneumonia in Beijing, China," PLoS One, vol. 8, No. 3, 2013.
Trei, et al., "Spread of Adenovirus to Geographically Dispersed Military Installations, May-Oct. 2007," Emerging Infectious Diseases, vol. 16, No. 5, 2010.
Schlegel, et al., "Desmoglein 2-mediated adhesion is required for intestinal epithelial barrier integrity," Am J Physiol Gatrointest Liver Physiol, 298: G774-G783, 2010.
Trinh, et al., "Avidity Binding of Human Adenovirus Serotypes 3 and 7 to the Membrane Cofactor CD46 Triggers Infection," Journal of Virology, vol. 86, No. 3, pp. 1623-1637, 2012.
Tuve, et al., "Combination of Tumor Site-Located CTL-Associated Antigen-4 Blockade and Systemic Regulatory T-Cell Depletion Induces Tumor-Destructive Immune Responses," Cancer Res, vol. 67, No. 12, pp. 5929-5939 ,2007.
Tvuve, et al., "A New Group B Adenovirus Receptor is Expressed at High Levels on Human Stem and Tumor Cells," Journal of Virology, vol. 80, No. 24, pp. 12109-12120, 2006.
Ueno, et al., "Targeting EGFR in Triple Negative Breast Cancer," Journal of Cancer, vol. 2, pp. 324-328, 2011.
Walters, et al., "Adenovirus Fiber Disrupts CAR-Mediated Intercellular Adhesion Allowing Virus Escape," Cell, vol. 110, pp. 789-799, 200.
Wang, et al., "Identification of CD46 Binding Sites within the Adenovirus Serotype 35 Fiber Knob," Journal of Virology, vol. 81, No. 23, pp. 12785-12792, 2007.
Wang, et al., "Multimerization of Adenovirus Serotype 3 Fiber Knob Domains Is Required for Efficient Binding of Virus to Desmoglein 2 and Subsequent Opening of Epithelial Junctions," Journal of Virology, vol. 85, No. 13, pp. 6390-6402, 2011.
Wang, et al., "A New Human DSG2-Transgenic Mouse Model for Studying the Tropism and Pathology of Human Adenoviruses," Journal of Virology, vol. 86, No. 11, pp. 6286-6302, 2012.
Wang, et al., "Desmoglein 2 is a receptor for adenovirus serotypes 3, 7, 11, and 14," Nat Med, vol. 17, No. 1, pp. 96-104, 2011.
Wang, et al., "Receptor usage of a newly emergent adenovirus type 14," Virology, vol. 387, No. 2, pp. 436-441, 2009.
Zeng, et al., "A ligand-pseudoreceptor system based on de novo designed peptides for the generation of adenoviral vectors with altered tropism," The Journal of Gene Medicine, vol. 10, pp. 355-367, 2008.
Cale, et al., "D0EZ30_9ADEN", EMBL-EBI, Nov. 2009.
Sirena, et al., "Q2Y0F8_ADE03", EMBL-EBI, Dec. 2005.

* cited by examiner

| Mutant | Ka (1/Ms) | Kd (1/s) | $K_D$ (nM) |
|---|---|---|---|
| Y250F (noDD) | 2.32E+05 | 2.64E-03 | 24.9 |
| K217E, F224S (noDD) | 5.88E+04 | 3.17E-03 | 53.9 |
| N293S (noDD) | 1.19E+03 | 8.70E-05 | 73.2 |
| V239Q (noDD) | 1.07E+05 | 2.66E-03 | 11.4 |
| F224L (noDD) | 3.42E+04 | 2.69E-03 | 78.7 |
| E248G, K258E (noDD) | 2.98E+04 | 1.47E-03 | 49.4 |
| L277R, N293D (noDD) | 1.35E+02 | 4.30E-03 | 31800 |
| Wt (noDD) | 5.27E+02 | 5.72E-03 | 10100 |

FIGURE 7b

SEQUENCE LISTING

```
<160> NUMBER OF SEQ ID NOS: 48

<210> SEQ ID NO 1
<211> LENGTH: 195
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: X is V or P
<220> FEATURE:
<221> NAME/KEY: MISC_FEATURE
<222> LOCATION: (7)..(7)
<223> OTHER INFORMATION: X is N or K
<220> FEATURE:
<221> NAME/KEY: MISC_FEATURE
<222> LOCATION: (9)..(9)
<223> OTHER INFORMATION: X is T or absent
<220> FEATURE:
<221> NAME/KEY: MISC_FEATURE
<222> LOCATION: (10)..(10)
<223> OTHER INFORMATION: X is E or R
<220> FEATURE:
<221> NAME/KEY: MISC_FEATURE
<222> LOCATION: (14)..(14)
<223> OTHER INFORMATION: X is Q or I
<220> FEATURE:
<221> NAME/KEY: MISC_FEATURE
<222> LOCATION: (15)..(15)
<223> OTHER INFORMATION: X is M or I
<220> FEATURE:
<221> NAME/KEY: MISC_FEATURE
<222> LOCATION: (16)..(16)
<223> OTHER INFORMATION: X is M or E
<220> FEATURE:
<221> NAME/KEY: MISC_FEATURE
<222> LOCATION: (17)..(17)
<223> OTHER INFORMATION: X is Y, A, N or D
<220> FEATURE:
<221> NAME/KEY: MISC_FEATURE
<222> LOCATION: (18)..(18)
<223> OTHER INFORMATION: X is S or G
<220> FEATURE:
<221> NAME/KEY: MISC_FEATURE
<222> LOCATION: (19)..(19)
<223> OTHER INFORMATION: X is S or K
<220> FEATURE:
<221> NAME/KEY: MISC_FEATURE
<222> LOCATION: (20)..(20)
<223> OTHER INFORMATION: X is E or Q
```

```
<220> FEATURE:
<221> NAME/KEY: MISC_FEATURE
<222> LOCATION: (21)..(21)
<223> OTHER INFORMATION: X is S or N
<220> FEATURE:
<221> NAME/KEY: MISC_FEATURE
<222> LOCATION: (22)..(22)
<223> OTHER INFORMATION: X is P or N
<220> FEATURE:
<221> NAME/KEY: MISC_FEATURE
<222> LOCATION: (24)..(24)
<223> OTHER INFORMATION: X is C or S
<220> FEATURE:
<221> NAME/KEY: MISC_FEATURE
<222> LOCATION: (27)..(27)
<223> OTHER INFORMATION: X is T or I
<220> FEATURE:
<221> NAME/KEY: MISC_FEATURE
<222> LOCATION: (29)..(29)
<223> OTHER INFORMATION: X is I or T
<220> FEATURE:
<221> NAME/KEY: MISC_FEATURE
<222> LOCATION: (33)..(33)
<223> OTHER INFORMATION: X is N or T
<220> FEATURE:
<221> NAME/KEY: MISC_FEATURE
<222> LOCATION: (35)..(35)
<223> OTHER INFORMATION: X is A or G
<220> FEATURE:
<221> NAME/KEY: MISC_FEATURE
<222> LOCATION: (36)..(36)
<223> OTHER INFORMATION: X is L or I
<220> FEATURE:
<221> NAME/KEY: MISC_FEATURE
<222> LOCATION: (38)..(38)
<223> OTHER INFORMATION: X is T or N
<220> FEATURE:
<221> NAME/KEY: MISC_FEATURE
<222> LOCATION: (39)..(39)
<223> OTHER INFORMATION: X is A or G
<220> FEATURE:
<221> NAME/KEY: MISC_FEATURE
<222> LOCATION: (40)..(40)
<223> OTHER INFORMATION: X is F or Y
<220> FEATURE:
<221> NAME/KEY: MISC_FEATURE
<222> LOCATION: (42)..(42)
<223> OTHER INFORMATION: X is Y or T
<220> FEATURE:
<221> NAME/KEY: MISC_FEATURE
<222> LOCATION: (43)..(43)
<223> OTHER INFORMATION: X is V or L
<220> FEATURE:
<221> NAME/KEY: MISC_FEATURE
<222> LOCATION: (44)..(44)
<223> OTHER INFORMATION: X is I or M
<220> FEATURE:
<221> NAME/KEY: MISC_FEATURE
<222> LOCATION: (46)..(46)
<223> OTHER INFORMATION: X is V or A
<220> FEATURE:
<221> NAME/KEY: MISC_FEATURE
<222> LOCATION: (48)..(48)
<223> OTHER INFORMATION: X is N or D
<220> FEATURE:
<221> NAME/KEY: MISC_FEATURE
<222> LOCATION: (49)..(49)
<223> OTHER INFORMATION: X is N, Y or D
<220> FEATURE:
<221> NAME/KEY: MISC_FEATURE
<222> LOCATION: (50)..(50)
<223> OTHER INFORMATION: X is F or V
<220> FEATURE:
<221> NAME/KEY: MISC_FEATURE
<222> LOCATION: (52)..(52)
<223> OTHER INFORMATION: X is M or T
<220> FEATURE:
<221> NAME/KEY: MISC_FEATURE
<222> LOCATION: (54)..(54)
```

-continued

```
<223> OTHER INFORMATION: X is F or T
<220> FEATURE:
<221> NAME/KEY: MISC_FEATURE
<222> LOCATION: (55)..(55)
<223> OTHER INFORMATION: X is K or T
<220> FEATURE:
<221> NAME/KEY: MISC_FEATURE
<222> LOCATION: (56)..(56)
<223> OTHER INFORMATION: X is Y, H or N
<220> FEATURE:
<221> NAME/KEY: MISC_FEATURE
<222> LOCATION: (57)..(57)
<223> OTHER INFORMATION: X is R or K
<220> FEATURE:
<221> NAME/KEY: MISC_FEATURE
<222> LOCATION: (59)..(59)
<223> OTHER INFORMATION: X is I or V
<220> FEATURE:
<221> NAME/KEY: MISC_FEATURE
<222> LOCATION: (60)..(60)
<223> OTHER INFORMATION: X is N or S
<220> FEATURE:
<221> NAME/KEY: MISC_FEATURE
<222> LOCATION: (61)..(61)
<223> OTHER INFORMATION: X is F or I
<220> FEATURE:
<221> NAME/KEY: MISC_FEATURE
<222> LOCATION: (62)..(62)
<223> OTHER INFORMATION: X is T or N
<220> FEATURE:
<221> NAME/KEY: MISC_FEATURE
<222> LOCATION: (63)..(63)
<223> OTHER INFORMATION: X is A or V
<220> FEATURE:
<221> NAME/KEY: MISC_FEATURE
<222> LOCATION: (66)..(66)
<223> OTHER INFORMATION: X is F or Y
<220> FEATURE:
<221> NAME/KEY: MISC_FEATURE
<222> LOCATION: (69)..(69)
<223> OTHER INFORMATION: X is S or A
<220> FEATURE:
<221> NAME/KEY: MISC_FEATURE
<222> LOCATION: (70)..(70)
<223> OTHER INFORMATION: X is T or A
<220> FEATURE:
<221> NAME/KEY: MISC_FEATURE
<222> LOCATION: (72)..(72)
<223> OTHER INFORMATION: X is N or H
<220> FEATURE:
<221> NAME/KEY: MISC_FEATURE
<222> LOCATION: (73)..(73)
<223> OTHER INFORMATION: X is L or I
<220> FEATURE:
<221> NAME/KEY: MISC_FEATURE
<222> LOCATION: (75)..(75)
<223> OTHER INFORMATION: X is T or P
<220> FEATURE:
<221> NAME/KEY: MISC_FEATURE
<222> LOCATION: (76)..(76)
<223> OTHER INFORMATION: X is S, R or D
<220> FEATURE:
<221> NAME/KEY: MISC_FEATURE
<222> LOCATION: (77)..(77)
<223> OTHER INFORMATION: X is S or L
<220> FEATURE:
<221> NAME/KEY: MISC_FEATURE
<222> LOCATION: (83)..(83)
<223> OTHER INFORMATION: X is P or D
<220> FEATURE:
<221> NAME/KEY: MISC_FEATURE
<222> LOCATION: (85)..(85)
<223> OTHER INFORMATION: X is N or E
<220> FEATURE:
<221> NAME/KEY: MISC_FEATURE
<222> LOCATION: (86)..(86)
<223> OTHER INFORMATION: X is H, L or P
<220> FEATURE:
<221> NAME/KEY: MISC_FEATURE
```

```
<222> LOCATION: (87)..(87)
<223> OTHER INFORMATION: X is K or E
<220> FEATURE:
<221> NAME/KEY: MISC_FEATURE
<222> LOCATION: (88)..(88)
<223> OTHER INFORMATION: X is S or Y
<220> FEATURE:
<221> NAME/KEY: MISC_FEATURE
<222> LOCATION: (89)..(89)
<223> OTHER INFORMATION: X is G or K
<220> FEATURE:
<221> NAME/KEY: MISC_FEATURE
<222> LOCATION: (91)..(91)
<223> OTHER INFORMATION: X is N or T
<220> FEATURE:
<221> NAME/KEY: MISC_FEATURE
<222> LOCATION: (92)..(92)
<223> OTHER INFORMATION: X is M or absent
<220> FEATURE:
<221> NAME/KEY: MISC_FEATURE
<222> LOCATION: (93)..(93)
<223> OTHER INFORMATION: X is A or absent
<220> FEATURE:
<221> NAME/KEY: MISC_FEATURE
<222> LOCATION: (94)..(94)
<223> OTHER INFORMATION: X is T or absent
<220> FEATURE:
<221> NAME/KEY: MISC_FEATURE
<222> LOCATION: (95)..(95)
<223> OTHER INFORMATION: X is G or absent
<220> FEATURE:
<221> NAME/KEY: MISC_FEATURE
<222> LOCATION: (97)..(97)
<223> OTHER INFORMATION: X is I, L or D
<220> FEATURE:
<221> NAME/KEY: MISC_FEATURE
<222> LOCATION: (98)..(98)
<223> OTHER INFORMATION: X is T, F, S, or L
<220> FEATURE:
<221> NAME/KEY: MISC_FEATURE
<222> LOCATION: (99)..(99)
<223> OTHER INFORMATION: X is N or S
<220> FEATURE:
<221> NAME/KEY: MISC_FEATURE
<222> LOCATION: (101)..(101)
<223> OTHER INFORMATION: X is K or R
<220> FEATURE:
<221> NAME/KEY: MISC_FEATURE
<222> LOCATION: (102)..(102)
<223> OTHER INFORMATION: X is S or G
<220> FEATURE:
<221> NAME/KEY: MISC_FEATURE
<222> LOCATION: (113)..(113)
<223> OTHER INFORMATION: X is V, D or absent
<220> FEATURE:
<221> NAME/KEY: MISC_FEATURE
<222> LOCATION: (114)..(114)
<223> OTHER INFORMATION: X is L or absent
<220> FEATURE:
<221> NAME/KEY: MISC_FEATURE
<222> LOCATION: (115)..(115)
<223> OTHER INFORMATION: X is N or P
<220> FEATURE:
<221> NAME/KEY: MISC_FEATURE
<222> LOCATION: (116)..(116)
<223> OTHER INFORMATION: X is N, D or V
<220> FEATURE:
<221> NAME/KEY: MISC_FEATURE
<222> LOCATION: (117)..(117)
<223> OTHER INFORMATION: X is N or A
<220> FEATURE:
<221> NAME/KEY: MISC_FEATURE
<222> LOCATION: (118)..(118)
<223> OTHER INFORMATION: X is S or G
<220> FEATURE:
<221> NAME/KEY: MISC_FEATURE
<222> LOCATION: (119)..(119)
<223> OTHER INFORMATION: X is R or T
<220> FEATURE:
```

```
<221> NAME/KEY: MISC_FEATURE
<222> LOCATION: (120)..(120)
<223> OTHER INFORMATION: X is E or H
<220> FEATURE:
<221> NAME/KEY: MISC_FEATURE
<222> LOCATION: (121)..(121)
<223> OTHER INFORMATION: X is N, K or absent
<220> FEATURE:
<221> NAME/KEY: MISC_FEATURE
<222> LOCATION: (122)..(122)
<223> OTHER INFORMATION: X is E, G or absent
<220> FEATURE:
<221> NAME/KEY: MISC_FEATURE
<222> LOCATION: (124)..(124)
<223> OTHER INFORMATION: X is Y or F
<220> FEATURE:
<221> NAME/KEY: MISC_FEATURE
<222> LOCATION: (126)..(126)
<223> OTHER INFORMATION: X is Y or F
<220> FEATURE:
<221> NAME/KEY: MISC_FEATURE
<222> LOCATION: (128)..(128)
<223> OTHER INFORMATION: X is T or Q
<220> FEATURE:
<221> NAME/KEY: MISC_FEATURE
<222> LOCATION: (130)..(130)
<223> OTHER INFORMATION: X is H or Y
<220> FEATURE:
<221> NAME/KEY: MISC_FEATURE
<222> LOCATION: (132)..(132)
<223> OTHER INFORMATION: X is T, K or E
<220> FEATURE:
<221> NAME/KEY: MISC_FEATURE
<222> LOCATION: (136)..(136)
<223> OTHER INFORMATION: X is H, G or R
<220> FEATURE:
<221> NAME/KEY: MISC_FEATURE
<222> LOCATION: (137)..(137)
<223> OTHER INFORMATION: X is T or A
<220> FEATURE:
<221> NAME/KEY: MISC_FEATURE
<222> LOCATION: (138)..(138)
<223> OTHER INFORMATION: X is L or A
<220> FEATURE:
<221> NAME/KEY: MISC_FEATURE
<222> LOCATION: (141)..(141)
<223> OTHER INFORMATION: X is L or I
<220> FEATURE:
<221> NAME/KEY: MISC_FEATURE
<222> LOCATION: (142)..(142)
<223> OTHER INFORMATION: X is D or E
<220> FEATURE:
<221> NAME/KEY: MISC_FEATURE
<222> LOCATION: (143)..(143)
<223> OTHER INFORMATION: X is I or V
<220> FEATURE:
<221> NAME/KEY: MISC_FEATURE
<222> LOCATION: (144)..(144)
<223> OTHER INFORMATION: X is S or T
<220> FEATURE:
<221> NAME/KEY: MISC_FEATURE
<222> LOCATION: (149)..(149)
<223> OTHER INFORMATION: X is Q, R or K
<220> FEATURE:
<221> NAME/KEY: MISC_FEATURE
<222> LOCATION: (151)..(151)
<223> OTHER INFORMATION: X is A or L
<220> FEATURE:
<221> NAME/KEY: MISC_FEATURE
<222> LOCATION: (152)..(152)
<223> OTHER INFORMATION: X is I, P or L
<220> FEATURE:
<221> NAME/KEY: MISC_FEATURE
<222> LOCATION: (153)..(153)
<223> OTHER INFORMATION: X is R, N or D
<220> FEATURE:
<221> NAME/KEY: MISC_FEATURE
<222> LOCATION: (154)..(154)
<223> OTHER INFORMATION: X is A, N, S or D
```

```
<220> FEATURE:
<221> NAME/KEY: MISC_FEATURE
<222> LOCATION: (155)..(155)
<223> OTHER INFORMATION: X is E, R or D
<220> FEATURE:
<221> NAME/KEY: MISC_FEATURE
<222> LOCATION: (159)..(159)
<223> OTHER INFORMATION: X is C or V
<220> FEATURE:
<221> NAME/KEY: MISC_FEATURE
<222> LOCATION: (160)..(160)
<223> OTHER INFORMATION: X is I or M
<220> FEATURE:
<221> NAME/KEY: MISC_FEATURE
<222> LOCATION: (161)..(161)
<223> OTHER INFORMATION: X is R or T
<220> FEATURE:
<221> NAME/KEY: MISC_FEATURE
<222> LOCATION: (162)..(162)
<223> OTHER INFORMATION: X is I, V or F
<220> FEATURE:
<221> NAME/KEY: MISC_FEATURE
<222> LOCATION: (163)..(163)
<223> OTHER INFORMATION: X is T or L
<220> FEATURE:
<221> NAME/KEY: MISC_FEATURE
<222> LOCATION: (166)..(166)
<223> OTHER INFORMATION: X is W or L
<220> FEATURE:
<221> NAME/KEY: MISC_FEATURE
<222> LOCATION: (167)..(167)
<223> OTHER INFORMATION: X is N or S
<220> FEATURE:
<221> NAME/KEY: MISC_FEATURE
<222> LOCATION: (168)..(168)
<223> OTHER INFORMATION: X is T or A
<220> FEATURE:
<221> NAME/KEY: MISC_FEATURE
<222> LOCATION: (170)..(170)
<223> OTHER INFORMATION: X is D, L, or V
<220> FEATURE:
<221> NAME/KEY: MISC_FEATURE
<222> LOCATION: (174)..(174)
<223> OTHER INFORMATION: X is G, V or absent
<220> FEATURE:
<221> NAME/KEY: MISC_FEATURE
<222> LOCATION: (175)..(175)
<223> OTHER INFORMATION: X is Q or absent
<220> FEATURE:
<221> NAME/KEY: MISC_FEATURE
<222> LOCATION: (177)..(177)
<223> OTHER INFORMATION: X is S or T
<220> FEATURE:
<221> NAME/KEY: MISC_FEATURE
<222> LOCATION: (178)..(178)
<223> OTHER INFORMATION: X is A or Q
<220> FEATURE:
<221> NAME/KEY: MISC_FEATURE
<222> LOCATION: (179)..(179)
<223> OTHER INFORMATION: X is A or T
<220> FEATURE:
<221> NAME/KEY: MISC_FEATURE
<222> LOCATION: (182)..(182)
<223> OTHER INFORMATION: X is V or I
<220> FEATURE:
<221> NAME/KEY: MISC_FEATURE
<222> LOCATION: (189)..(189)
<223> OTHER INFORMATION: X is Y or S

<400> SEQUENCE: 1

Thr Leu Trp Thr Gly Xaa Xaa Pro Xaa Xaa Ala Asn Cys Xaa Xaa Xaa
1               5                   10                  15

Xaa Xaa Xaa Xaa Xaa Xaa Asp Xaa Lys Leu Xaa Leu Xaa Leu Val Lys
            20                  25                  30

Xaa Gly Xaa Xaa Val Xaa Xaa Xaa Val Xaa Xaa Xaa Gly Xaa Ser Xaa
        35                  40                  45
```

```
Xaa Xaa Asn Xaa Leu Xaa Xaa Xaa Asn Xaa Xaa Xaa Xaa Glu
    50              55                  60

Leu Xaa Phe Asp Xaa Xaa Gly Xaa Xaa Leu Xaa Xaa Ser Ser Leu
65              70              75                  80

Lys Thr Xaa Leu Xaa Xaa Xaa Xaa Gln Xaa Xaa Xaa Xaa Ala
                85                  90              95

Xaa Xaa Xaa Ala Xaa Xaa Phe Met Pro Ser Thr Thr Ala Tyr Pro Phe
            100             105             110

Xaa Xaa Xaa Xaa Xaa Xaa Xaa Xaa Xaa Asn Xaa Ile Xaa Gly Xaa
        115             120             125

Cys Xaa Tyr Xaa Ala Ser Asp Xaa Xaa Xaa Phe Pro Xaa Xaa Xaa Xaa
    130             135                 140

Val Met Leu Asn Xaa Arg Xaa Xaa Xaa Xaa Thr Ser Tyr Xaa Xaa
145             150             155                 160

Xaa Xaa Xaa Trp Ser Xaa Xaa Xaa Gly Xaa Ala Pro Glu Xaa Xaa Thr
            165             170             175

Xaa Xaa Xaa Thr Leu Xaa Thr Ser Pro Phe Thr Phe Xaa Tyr Ile Arg
            180             185             190

Glu Asp Asp
        195

<210> SEQ ID NO 2
<211> LENGTH: 188
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: X is V or P
<220> FEATURE:
<221> NAME/KEY: MISC_FEATURE
<222> LOCATION: (7)..(7)
<223> OTHER INFORMATION: X is N or K
<220> FEATURE:
<221> NAME/KEY: MISC_FEATURE
<222> LOCATION: (9)..(9)
<223> OTHER INFORMATION: X is E or R
<220> FEATURE:
<221> NAME/KEY: MISC_FEATURE
<222> LOCATION: (13)..(13)
<223> OTHER INFORMATION: X is Q or I
<220> FEATURE:
<221> NAME/KEY: MISC_FEATURE
<222> LOCATION: (14)..(14)
<223> OTHER INFORMATION: X is M or I
<220> FEATURE:
<221> NAME/KEY: MISC_FEATURE
<222> LOCATION: (15)..(15)
<223> OTHER INFORMATION: X is M or E
<220> FEATURE:
<221> NAME/KEY: MISC_FEATURE
<222> LOCATION: (16)..(16)
<223> OTHER INFORMATION: X is Y, A, N or D
<220> FEATURE:
<221> NAME/KEY: MISC_FEATURE
<222> LOCATION: (17)..(17)
<223> OTHER INFORMATION: X is S or G
<220> FEATURE:
<221> NAME/KEY: MISC_FEATURE
<222> LOCATION: (18)..(18)
<223> OTHER INFORMATION: X is S or K
<220> FEATURE:
<221> NAME/KEY: MISC_FEATURE
<222> LOCATION: (19)..(19)
<223> OTHER INFORMATION: X is E or Q
<220> FEATURE:
<221> NAME/KEY: MISC_FEATURE
<222> LOCATION: (20)..(20)
```

-continued

```
<223> OTHER INFORMATION: X is S or N
<220> FEATURE:
<221> NAME/KEY: MISC_FEATURE
<222> LOCATION: (21)..(21)
<223> OTHER INFORMATION: X is P or N
<220> FEATURE:
<221> NAME/KEY: MISC_FEATURE
<222> LOCATION: (23)..(23)
<223> OTHER INFORMATION: X is C or S
<220> FEATURE:
<221> NAME/KEY: MISC_FEATURE
<222> LOCATION: (26)..(26)
<223> OTHER INFORMATION: X is I or T
<220> FEATURE:
<221> NAME/KEY: MISC_FEATURE
<222> LOCATION: (28)..(28)
<223> OTHER INFORMATION: X is I or T
<220> FEATURE:
<221> NAME/KEY: MISC_FEATURE
<222> LOCATION: (32)..(32)
<223> OTHER INFORMATION: X is N or T
<220> FEATURE:
<221> NAME/KEY: MISC_FEATURE
<222> LOCATION: (34)..(34)
<223> OTHER INFORMATION: X is A or G
<220> FEATURE:
<221> NAME/KEY: MISC_FEATURE
<222> LOCATION: (35)..(35)
<223> OTHER INFORMATION: X is L or I
<220> FEATURE:
<221> NAME/KEY: MISC_FEATURE
<222> LOCATION: (37)..(37)
<223> OTHER INFORMATION: X is T or N
<220> FEATURE:
<221> NAME/KEY: MISC_FEATURE
<222> LOCATION: (38)..(38)
<223> OTHER INFORMATION: X is A or G
<220> FEATURE:
<221> NAME/KEY: MISC_FEATURE
<222> LOCATION: (39)..(39)
<223> OTHER INFORMATION: X is F or Y
<220> FEATURE:
<221> NAME/KEY: MISC_FEATURE
<222> LOCATION: (41)..(41)
<223> OTHER INFORMATION: X is T or Y
<220> FEATURE:
<221> NAME/KEY: MISC_FEATURE
<222> LOCATION: (42)..(42)
<223> OTHER INFORMATION: X is V or L
<220> FEATURE:
<221> NAME/KEY: MISC_FEATURE
<222> LOCATION: (43)..(43)
<223> OTHER INFORMATION: X is I or M
<220> FEATURE:
<221> NAME/KEY: MISC_FEATURE
<222> LOCATION: (45)..(45)
<223> OTHER INFORMATION: X is V or A
<220> FEATURE:
<221> NAME/KEY: MISC_FEATURE
<222> LOCATION: (47)..(47)
<223> OTHER INFORMATION: X is N or D
<220> FEATURE:
<221> NAME/KEY: MISC_FEATURE
<222> LOCATION: (48)..(48)
<223> OTHER INFORMATION: X is N, Y or D
<220> FEATURE:
<221> NAME/KEY: MISC_FEATURE
<222> LOCATION: (49)..(49)
<223> OTHER INFORMATION: X is F or V
<220> FEATURE:
<221> NAME/KEY: MISC_FEATURE
<222> LOCATION: (51)..(51)
<223> OTHER INFORMATION: X is M or T
<220> FEATURE:
<221> NAME/KEY: MISC_FEATURE
<222> LOCATION: (53)..(53)
<223> OTHER INFORMATION: X is F or T
<220> FEATURE:
<221> NAME/KEY: MISC_FEATURE
```

-continued

```
<222> LOCATION: (54)..(54)
<223> OTHER INFORMATION: X is K or T
<220> FEATURE:
<221> NAME/KEY: MISC_FEATURE
<222> LOCATION: (55)..(55)
<223> OTHER INFORMATION: X is Y, H or N
<220> FEATURE:
<221> NAME/KEY: MISC_FEATURE
<222> LOCATION: (56)..(56)
<223> OTHER INFORMATION: X is R or K
<220> FEATURE:
<221> NAME/KEY: MISC_FEATURE
<222> LOCATION: (58)..(58)
<223> OTHER INFORMATION: X is I or V
<220> FEATURE:
<221> NAME/KEY: MISC_FEATURE
<222> LOCATION: (59)..(59)
<223> OTHER INFORMATION: X is N or S
<220> FEATURE:
<221> NAME/KEY: MISC_FEATURE
<222> LOCATION: (60)..(60)
<223> OTHER INFORMATION: X is F or I
<220> FEATURE:
<221> NAME/KEY: MISC_FEATURE
<222> LOCATION: (61)..(61)
<223> OTHER INFORMATION: X is T or N
<220> FEATURE:
<221> NAME/KEY: MISC_FEATURE
<222> LOCATION: (62)..(62)
<223> OTHER INFORMATION: X is A or V
<220> FEATURE:
<221> NAME/KEY: MISC_FEATURE
<222> LOCATION: (65)..(65)
<223> OTHER INFORMATION: X is F or Y
<220> FEATURE:
<221> NAME/KEY: MISC_FEATURE
<222> LOCATION: (68)..(68)
<223> OTHER INFORMATION: X is S or A
<220> FEATURE:
<221> NAME/KEY: MISC_FEATURE
<222> LOCATION: (69)..(69)
<223> OTHER INFORMATION: X is T or A
<220> FEATURE:
<221> NAME/KEY: MISC_FEATURE
<222> LOCATION: (71)..(71)
<223> OTHER INFORMATION: X is N or H
<220> FEATURE:
<221> NAME/KEY: MISC_FEATURE
<222> LOCATION: (72)..(72)
<223> OTHER INFORMATION: X is L or I
<220> FEATURE:
<221> NAME/KEY: MISC_FEATURE
<222> LOCATION: (74)..(74)
<223> OTHER INFORMATION: X is T or P
<220> FEATURE:
<221> NAME/KEY: MISC_FEATURE
<222> LOCATION: (75)..(75)
<223> OTHER INFORMATION: X is S, R or D
<220> FEATURE:
<221> NAME/KEY: MISC_FEATURE
<222> LOCATION: (76)..(76)
<223> OTHER INFORMATION: X is L or S
<220> FEATURE:
<221> NAME/KEY: MISC_FEATURE
<222> LOCATION: (82)..(82)
<223> OTHER INFORMATION: X is P or D
<220> FEATURE:
<221> NAME/KEY: MISC_FEATURE
<222> LOCATION: (84)..(84)
<223> OTHER INFORMATION: X is N or E
<220> FEATURE:
<221> NAME/KEY: MISC_FEATURE
<222> LOCATION: (85)..(85)
<223> OTHER INFORMATION: X is H, L or P
<220> FEATURE:
<221> NAME/KEY: MISC_FEATURE
<222> LOCATION: (86)..(86)
<223> OTHER INFORMATION: X is K or E
<220> FEATURE:
```

```
<221> NAME/KEY: MISC_FEATURE
<222> LOCATION: (87)..(87)
<223> OTHER INFORMATION: X is S or Y
<220> FEATURE:
<221> NAME/KEY: MISC_FEATURE
<222> LOCATION: (88)..(88)
<223> OTHER INFORMATION: X is G or K
<220> FEATURE:
<221> NAME/KEY: MISC_FEATURE
<222> LOCATION: (90)..(90)
<223> OTHER INFORMATION: X is N or T
<220> FEATURE:
<221> NAME/KEY: MISC_FEATURE
<222> LOCATION: (92)..(92)
<223> OTHER INFORMATION: X is I, L or D
<220> FEATURE:
<221> NAME/KEY: MISC_FEATURE
<222> LOCATION: (93)..(93)
<223> OTHER INFORMATION: X is T, F, S, or L
<220> FEATURE:
<221> NAME/KEY: MISC_FEATURE
<222> LOCATION: (94)..(94)
<223> OTHER INFORMATION: X is N or S
<220> FEATURE:
<221> NAME/KEY: MISC_FEATURE
<222> LOCATION: (96)..(96)
<223> OTHER INFORMATION: X is K or R
<220> FEATURE:
<221> NAME/KEY: MISC_FEATURE
<222> LOCATION: (97)..(97)
<223> OTHER INFORMATION: X is S or G
<220> FEATURE:
<221> NAME/KEY: MISC_FEATURE
<222> LOCATION: (108)..(108)
<223> OTHER INFORMATION: X is V, D or absent
<220> FEATURE:
<221> NAME/KEY: MISC_FEATURE
<222> LOCATION: (109)..(109)
<223> OTHER INFORMATION: X is L or absent
<220> FEATURE:
<221> NAME/KEY: MISC_FEATURE
<222> LOCATION: (110)..(110)
<223> OTHER INFORMATION: X is N or P
<220> FEATURE:
<221> NAME/KEY: MISC_FEATURE
<222> LOCATION: (111)..(111)
<223> OTHER INFORMATION: X is N, D or V
<220> FEATURE:
<221> NAME/KEY: MISC_FEATURE
<222> LOCATION: (112)..(112)
<223> OTHER INFORMATION: X is N or A
<220> FEATURE:
<221> NAME/KEY: MISC_FEATURE
<222> LOCATION: (113)..(113)
<223> OTHER INFORMATION: X is S or G
<220> FEATURE:
<221> NAME/KEY: MISC_FEATURE
<222> LOCATION: (114)..(114)
<223> OTHER INFORMATION: X is R or T
<220> FEATURE:
<221> NAME/KEY: MISC_FEATURE
<222> LOCATION: (115)..(115)
<223> OTHER INFORMATION: X is E or H
<220> FEATURE:
<221> NAME/KEY: MISC_FEATURE
<222> LOCATION: (116)..(116)
<223> OTHER INFORMATION: X is N, K or absent
<220> FEATURE:
<221> NAME/KEY: MISC_FEATURE
<222> LOCATION: (117)..(117)
<223> OTHER INFORMATION: X is E, G or absent
<220> FEATURE:
<221> NAME/KEY: MISC_FEATURE
<222> LOCATION: (119)..(119)
<223> OTHER INFORMATION: X is Y or F
<220> FEATURE:
<221> NAME/KEY: MISC_FEATURE
<222> LOCATION: (121)..(121)
<223> OTHER INFORMATION: X is Y or F
```

-continued

```
<220> FEATURE:
<221> NAME/KEY: MISC_FEATURE
<222> LOCATION: (123)..(123)
<223> OTHER INFORMATION: X is T or Q
<220> FEATURE:
<221> NAME/KEY: MISC_FEATURE
<222> LOCATION: (125)..(125)
<223> OTHER INFORMATION: X is H or Y
<220> FEATURE:
<221> NAME/KEY: MISC_FEATURE
<222> LOCATION: (127)..(127)
<223> OTHER INFORMATION: X is T, K or E
<220> FEATURE:
<221> NAME/KEY: MISC_FEATURE
<222> LOCATION: (131)..(131)
<223> OTHER INFORMATION: X is H, G or R
<220> FEATURE:
<221> NAME/KEY: MISC_FEATURE
<222> LOCATION: (132)..(132)
<223> OTHER INFORMATION: X is T or A
<220> FEATURE:
<221> NAME/KEY: MISC_FEATURE
<222> LOCATION: (133)..(133)
<223> OTHER INFORMATION: X is L or A
<220> FEATURE:
<221> NAME/KEY: MISC_FEATURE
<222> LOCATION: (136)..(136)
<223> OTHER INFORMATION: X is L or I
<220> FEATURE:
<221> NAME/KEY: MISC_FEATURE
<222> LOCATION: (137)..(137)
<223> OTHER INFORMATION: X is D or E
<220> FEATURE:
<221> NAME/KEY: MISC_FEATURE
<222> LOCATION: (138)..(138)
<223> OTHER INFORMATION: X is I or V
<220> FEATURE:
<221> NAME/KEY: MISC_FEATURE
<222> LOCATION: (139)..(139)
<223> OTHER INFORMATION: X is S or T
<220> FEATURE:
<221> NAME/KEY: MISC_FEATURE
<222> LOCATION: (144)..(144)
<223> OTHER INFORMATION: X is Q, R or K
<220> FEATURE:
<221> NAME/KEY: MISC_FEATURE
<222> LOCATION: (146)..(146)
<223> OTHER INFORMATION: X is A or L
<220> FEATURE:
<221> NAME/KEY: MISC_FEATURE
<222> LOCATION: (147)..(147)
<223> OTHER INFORMATION: X is I, P or L
<220> FEATURE:
<221> NAME/KEY: MISC_FEATURE
<222> LOCATION: (148)..(148)
<223> OTHER INFORMATION: X is R, N or D
<220> FEATURE:
<221> NAME/KEY: MISC_FEATURE
<222> LOCATION: (149)..(149)
<223> OTHER INFORMATION: X is A, S, N or D
<220> FEATURE:
<221> NAME/KEY: MISC_FEATURE
<222> LOCATION: (150)..(150)
<223> OTHER INFORMATION: X is D, E, or R
<220> FEATURE:
<221> NAME/KEY: MISC_FEATURE
<222> LOCATION: (154)..(154)
<223> OTHER INFORMATION: X is C or V
<220> FEATURE:
<221> NAME/KEY: MISC_FEATURE
<222> LOCATION: (155)..(155)
<223> OTHER INFORMATION: X is I or M
<220> FEATURE:
<221> NAME/KEY: MISC_FEATURE
<222> LOCATION: (156)..(156)
<223> OTHER INFORMATION: X is R or T
<220> FEATURE:
<221> NAME/KEY: MISC_FEATURE
<222> LOCATION: (157)..(157)
```

<223> OTHER INFORMATION: X is I, V or F
<220> FEATURE:
<221> NAME/KEY: MISC_FEATURE
<222> LOCATION: (158)..(158)
<223> OTHER INFORMATION: X is T or L
<220> FEATURE:
<221> NAME/KEY: MISC_FEATURE
<222> LOCATION: (161)..(161)
<223> OTHER INFORMATION: X is W or L
<220> FEATURE:
<221> NAME/KEY: MISC_FEATURE
<222> LOCATION: (162)..(162)
<223> OTHER INFORMATION: X is N or S
<220> FEATURE:
<221> NAME/KEY: MISC_FEATURE
<222> LOCATION: (163)..(163)
<223> OTHER INFORMATION: X is T or A
<220> FEATURE:
<221> NAME/KEY: MISC_FEATURE
<222> LOCATION: (165)..(165)
<223> OTHER INFORMATION: X is D, L or V
<220> FEATURE:
<221> NAME/KEY: MISC_FEATURE
<222> LOCATION: (170)..(170)
<223> OTHER INFORMATION: X is S or T
<220> FEATURE:
<221> NAME/KEY: MISC_FEATURE
<222> LOCATION: (171)..(171)
<223> OTHER INFORMATION: X is A or Q
<220> FEATURE:
<221> NAME/KEY: MISC_FEATURE
<222> LOCATION: (172)..(172)
<223> OTHER INFORMATION: X is A or T
<220> FEATURE:
<221> NAME/KEY: MISC_FEATURE
<222> LOCATION: (175)..(175)
<223> OTHER INFORMATION: X is V or I
<220> FEATURE:
<221> NAME/KEY: MISC_FEATURE
<222> LOCATION: (182)..(182)
<223> OTHER INFORMATION: X is Y or S

<400> SEQUENCE: 2

```
Thr Leu Trp Thr Gly Xaa Xaa Pro Xaa Ala Asn Cys Xaa Xaa Xaa Xaa
1               5                   10                  15

Xaa Xaa Xaa Xaa Xaa Asp Xaa Lys Leu Xaa Leu Xaa Leu Val Lys Xaa
            20                  25                  30

Gly Xaa Xaa Val Xaa Xaa Xaa Val Xaa Xaa Xaa Gly Xaa Ser Xaa Xaa
        35                  40                  45

Xaa Asn Xaa Leu Xaa Xaa Xaa Xaa Asn Xaa Xaa Xaa Xaa Xaa Glu Leu
    50                  55                  60

Xaa Phe Asp Xaa Xaa Gly Xaa Xaa Leu Xaa Xaa Xaa Xaa Ser Ser Leu Lys
65                  70                  75                  80

Thr Xaa Leu Xaa Xaa Xaa Xaa Xaa Gln Xaa Ala Xaa Xaa Xaa Ala Xaa
            85                  90                  95

Xaa Phe Met Pro Ser Thr Thr Ala Tyr Pro Phe Xaa Xaa Xaa Xaa
                100                 105                 110

Xaa Xaa Xaa Xaa Xaa Asn Xaa Ile Xaa Gly Xaa Cys Xaa Tyr Xaa Ala
            115                 120                 125

Ser Asp Xaa Xaa Xaa Phe Pro Xaa Xaa Xaa Val Met Leu Asn Xaa
            130                 135                 140

Arg Xaa Xaa Xaa Xaa Xaa Thr Ser Tyr Xaa Xaa Xaa Xaa Xaa Trp Ser
145                 150                 155                 160

Xaa Xaa Xaa Gly Xaa Ala Pro Glu Thr Xaa Xaa Xaa Thr Leu Xaa Thr
            165                 170                 175

Ser Pro Phe Thr Phe Xaa Tyr Ile Arg Glu Asp Asp
                180                 185
```

```
<210> SEQ ID NO 3
<211> LENGTH: 188
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: X is V or P
<220> FEATURE:
<221> NAME/KEY: MISC_FEATURE
<222> LOCATION: (7)..(7)
<223> OTHER INFORMATION: X is N or K
<220> FEATURE:
<221> NAME/KEY: MISC_FEATURE
<222> LOCATION: (9)..(9)
<223> OTHER INFORMATION: X is E or R
<220> FEATURE:
<221> NAME/KEY: MISC_FEATURE
<222> LOCATION: (13)..(13)
<223> OTHER INFORMATION: X is Q or I
<220> FEATURE:
<221> NAME/KEY: MISC_FEATURE
<222> LOCATION: (14)..(14)
<223> OTHER INFORMATION: X is M or I
<220> FEATURE:
<221> NAME/KEY: MISC_FEATURE
<222> LOCATION: (15)..(15)
<223> OTHER INFORMATION: X is M or E
<220> FEATURE:
<221> NAME/KEY: MISC_FEATURE
<222> LOCATION: (16)..(16)
<223> OTHER INFORMATION: X is Y, A, N or D
<220> FEATURE:
<221> NAME/KEY: MISC_FEATURE
<222> LOCATION: (17)..(17)
<223> OTHER INFORMATION: X is S or G
<220> FEATURE:
<221> NAME/KEY: MISC_FEATURE
<222> LOCATION: (18)..(18)
<223> OTHER INFORMATION: X is S or K
<220> FEATURE:
<221> NAME/KEY: MISC_FEATURE
<222> LOCATION: (19)..(19)
<223> OTHER INFORMATION: X is E or Q
<220> FEATURE:
<221> NAME/KEY: MISC_FEATURE
<222> LOCATION: (20)..(20)
<223> OTHER INFORMATION: X is S or N
<220> FEATURE:
<221> NAME/KEY: MISC_FEATURE
<222> LOCATION: (21)..(21)
<223> OTHER INFORMATION: X is P or N
<220> FEATURE:
<221> NAME/KEY: MISC_FEATURE
<222> LOCATION: (23)..(23)
<223> OTHER INFORMATION: X is C or S
<220> FEATURE:
<221> NAME/KEY: MISC_FEATURE
<222> LOCATION: (26)..(26)
<223> OTHER INFORMATION: X is I or T
<220> FEATURE:
<221> NAME/KEY: MISC_FEATURE
<222> LOCATION: (28)..(28)
<223> OTHER INFORMATION: X is I or T
<220> FEATURE:
<221> NAME/KEY: MISC_FEATURE
<222> LOCATION: (32)..(32)
<223> OTHER INFORMATION: X is N or T
<220> FEATURE:
<221> NAME/KEY: MISC_FEATURE
<222> LOCATION: (34)..(34)
<223> OTHER INFORMATION: X is A or G
<220> FEATURE:
<221> NAME/KEY: MISC_FEATURE
<222> LOCATION: (35)..(35)
<223> OTHER INFORMATION: X is L or I
<220> FEATURE:
```

```
<221> NAME/KEY: MISC_FEATURE
<222> LOCATION: (37)..(37)
<223> OTHER INFORMATION: X is T or N
<220> FEATURE:
<221> NAME/KEY: MISC_FEATURE
<222> LOCATION: (38)..(38)
<223> OTHER INFORMATION: X is A or G
<220> FEATURE:
<221> NAME/KEY: MISC_FEATURE
<222> LOCATION: (39)..(39)
<223> OTHER INFORMATION: X is F or Y
<220> FEATURE:
<221> NAME/KEY: MISC_FEATURE
<222> LOCATION: (41)..(41)
<223> OTHER INFORMATION: X is T or Y
<220> FEATURE:
<221> NAME/KEY: MISC_FEATURE
<222> LOCATION: (42)..(42)
<223> OTHER INFORMATION: X is V or L
<220> FEATURE:
<221> NAME/KEY: MISC_FEATURE
<222> LOCATION: (43)..(43)
<223> OTHER INFORMATION: X is I or M
<220> FEATURE:
<221> NAME/KEY: MISC_FEATURE
<222> LOCATION: (45)..(45)
<223> OTHER INFORMATION: X is V or A
<220> FEATURE:
<221> NAME/KEY: MISC_FEATURE
<222> LOCATION: (47)..(47)
<223> OTHER INFORMATION: X is N or D
<220> FEATURE:
<221> NAME/KEY: MISC_FEATURE
<222> LOCATION: (48)..(48)
<223> OTHER INFORMATION: X is N, Y or D
<220> FEATURE:
<221> NAME/KEY: MISC_FEATURE
<222> LOCATION: (49)..(49)
<223> OTHER INFORMATION: X is F or V
<220> FEATURE:
<221> NAME/KEY: MISC_FEATURE
<222> LOCATION: (51)..(51)
<223> OTHER INFORMATION: X is M or T
<220> FEATURE:
<221> NAME/KEY: MISC_FEATURE
<222> LOCATION: (53)..(53)
<223> OTHER INFORMATION: X is F or T
<220> FEATURE:
<221> NAME/KEY: MISC_FEATURE
<222> LOCATION: (54)..(54)
<223> OTHER INFORMATION: X is K or T
<220> FEATURE:
<221> NAME/KEY: MISC_FEATURE
<222> LOCATION: (55)..(55)
<223> OTHER INFORMATION: X is Y, H or N
<220> FEATURE:
<221> NAME/KEY: MISC_FEATURE
<222> LOCATION: (56)..(56)
<223> OTHER INFORMATION: X is R or K
<220> FEATURE:
<221> NAME/KEY: MISC_FEATURE
<222> LOCATION: (58)..(58)
<223> OTHER INFORMATION: X is I or V
<220> FEATURE:
<221> NAME/KEY: MISC_FEATURE
<222> LOCATION: (59)..(59)
<223> OTHER INFORMATION: X is N or S
<220> FEATURE:
<221> NAME/KEY: MISC_FEATURE
<222> LOCATION: (60)..(60)
<223> OTHER INFORMATION: X is F or I
<220> FEATURE:
<221> NAME/KEY: MISC_FEATURE
<222> LOCATION: (61)..(61)
<223> OTHER INFORMATION: X is T or N
<220> FEATURE:
<221> NAME/KEY: MISC_FEATURE
<222> LOCATION: (62)..(62)
<223> OTHER INFORMATION: X is A or V
```

```
<220> FEATURE:
<221> NAME/KEY: MISC_FEATURE
<222> LOCATION: (65)..(65)
<223> OTHER INFORMATION: X is F or Y
<220> FEATURE:
<221> NAME/KEY: MISC_FEATURE
<222> LOCATION: (68)..(68)
<223> OTHER INFORMATION: X is A or S
<220> FEATURE:
<221> NAME/KEY: MISC_FEATURE
<222> LOCATION: (69)..(69)
<223> OTHER INFORMATION: X is A or T
<220> FEATURE:
<221> NAME/KEY: MISC_FEATURE
<222> LOCATION: (71)..(71)
<223> OTHER INFORMATION: X is N or H
<220> FEATURE:
<221> NAME/KEY: MISC_FEATURE
<222> LOCATION: (72)..(72)
<223> OTHER INFORMATION: X is L or I
<220> FEATURE:
<221> NAME/KEY: MISC_FEATURE
<222> LOCATION: (74)..(74)
<223> OTHER INFORMATION: X is T or P
<220> FEATURE:
<221> NAME/KEY: MISC_FEATURE
<222> LOCATION: (75)..(75)
<223> OTHER INFORMATION: X is S, R or D
<220> FEATURE:
<221> NAME/KEY: MISC_FEATURE
<222> LOCATION: (76)..(76)
<223> OTHER INFORMATION: X is L or S
<220> FEATURE:
<221> NAME/KEY: MISC_FEATURE
<222> LOCATION: (82)..(82)
<223> OTHER INFORMATION: X is P or D
<220> FEATURE:
<221> NAME/KEY: MISC_FEATURE
<222> LOCATION: (84)..(84)
<223> OTHER INFORMATION: X is N or E
<220> FEATURE:
<221> NAME/KEY: MISC_FEATURE
<222> LOCATION: (85)..(85)
<223> OTHER INFORMATION: X is H, L or P
<220> FEATURE:
<221> NAME/KEY: MISC_FEATURE
<222> LOCATION: (86)..(86)
<223> OTHER INFORMATION: X is K or E
<220> FEATURE:
<221> NAME/KEY: MISC_FEATURE
<222> LOCATION: (87)..(87)
<223> OTHER INFORMATION: X is S or Y
<220> FEATURE:
<221> NAME/KEY: MISC_FEATURE
<222> LOCATION: (88)..(88)
<223> OTHER INFORMATION: X is G or K
<220> FEATURE:
<221> NAME/KEY: MISC_FEATURE
<222> LOCATION: (90)..(90)
<223> OTHER INFORMATION: X is N or T
<220> FEATURE:
<221> NAME/KEY: MISC_FEATURE
<222> LOCATION: (92)..(92)
<223> OTHER INFORMATION: X is I, L or D
<220> FEATURE:
<221> NAME/KEY: MISC_FEATURE
<222> LOCATION: (93)..(93)
<223> OTHER INFORMATION: X is T, F, S, or L
<220> FEATURE:
<221> NAME/KEY: MISC_FEATURE
<222> LOCATION: (94)..(94)
<223> OTHER INFORMATION: X is N or S
<220> FEATURE:
<221> NAME/KEY: MISC_FEATURE
<222> LOCATION: (96)..(96)
<223> OTHER INFORMATION: X is K or R
<220> FEATURE:
<221> NAME/KEY: MISC_FEATURE
<222> LOCATION: (97)..(97)
```

```
<223> OTHER INFORMATION: X is S or G
<220> FEATURE:
<221> NAME/KEY: MISC_FEATURE
<222> LOCATION: (108)..(108)
<223> OTHER INFORMATION: X is V, D or absent
<220> FEATURE:
<221> NAME/KEY: MISC_FEATURE
<222> LOCATION: (110)..(110)
<223> OTHER INFORMATION: X is N or P
<220> FEATURE:
<221> NAME/KEY: MISC_FEATURE
<222> LOCATION: (111)..(111)
<223> OTHER INFORMATION: X is N, D or V
<220> FEATURE:
<221> NAME/KEY: MISC_FEATURE
<222> LOCATION: (112)..(112)
<223> OTHER INFORMATION: X is N or A
<220> FEATURE:
<221> NAME/KEY: MISC_FEATURE
<222> LOCATION: (113)..(113)
<223> OTHER INFORMATION: X is S or G
<220> FEATURE:
<221> NAME/KEY: MISC_FEATURE
<222> LOCATION: (114)..(114)
<223> OTHER INFORMATION: X is R or T
<220> FEATURE:
<221> NAME/KEY: MISC_FEATURE
<222> LOCATION: (115)..(115)
<223> OTHER INFORMATION: X is E or H
<220> FEATURE:
<221> NAME/KEY: MISC_FEATURE
<222> LOCATION: (116)..(116)
<223> OTHER INFORMATION: X is N, K or absent
<220> FEATURE:
<221> NAME/KEY: MISC_FEATURE
<222> LOCATION: (117)..(117)
<223> OTHER INFORMATION: X is E, G or absent
<220> FEATURE:
<221> NAME/KEY: MISC_FEATURE
<222> LOCATION: (119)..(119)
<223> OTHER INFORMATION: X is Y or F
<220> FEATURE:
<221> NAME/KEY: MISC_FEATURE
<222> LOCATION: (121)..(121)
<223> OTHER INFORMATION: X is Y or F
<220> FEATURE:
<221> NAME/KEY: MISC_FEATURE
<222> LOCATION: (123)..(123)
<223> OTHER INFORMATION: X is T or Q
<220> FEATURE:
<221> NAME/KEY: MISC_FEATURE
<222> LOCATION: (125)..(125)
<223> OTHER INFORMATION: X is Y or H
<220> FEATURE:
<221> NAME/KEY: MISC_FEATURE
<222> LOCATION: (127)..(127)
<223> OTHER INFORMATION: X is T, K or E
<220> FEATURE:
<221> NAME/KEY: MISC_FEATURE
<222> LOCATION: (131)..(131)
<223> OTHER INFORMATION: X is H, G or R
<220> FEATURE:
<221> NAME/KEY: MISC_FEATURE
<222> LOCATION: (132)..(132)
<223> OTHER INFORMATION: X is T or A
<220> FEATURE:
<221> NAME/KEY: MISC_FEATURE
<222> LOCATION: (133)..(133)
<223> OTHER INFORMATION: X is L or A
<220> FEATURE:
<221> NAME/KEY: MISC_FEATURE
<222> LOCATION: (136)..(136)
<223> OTHER INFORMATION: X is L or I
<220> FEATURE:
<221> NAME/KEY: MISC_FEATURE
<222> LOCATION: (137)..(137)
<223> OTHER INFORMATION: X is D or E
<220> FEATURE:
<221> NAME/KEY: MISC_FEATURE
```

```
<222> LOCATION: (138)..(138)
<223> OTHER INFORMATION: X is I or V
<220> FEATURE:
<221> NAME/KEY: MISC_FEATURE
<222> LOCATION: (139)..(139)
<223> OTHER INFORMATION: X is S or T
<220> FEATURE:
<221> NAME/KEY: MISC_FEATURE
<222> LOCATION: (144)..(144)
<223> OTHER INFORMATION: X is Q, R, or K
<220> FEATURE:
<221> NAME/KEY: MISC_FEATURE
<222> LOCATION: (146)..(146)
<223> OTHER INFORMATION: X is A or L
<220> FEATURE:
<221> NAME/KEY: MISC_FEATURE
<222> LOCATION: (147)..(147)
<223> OTHER INFORMATION: X is I, P or L
<220> FEATURE:
<221> NAME/KEY: MISC_FEATURE
<222> LOCATION: (148)..(148)
<223> OTHER INFORMATION: X is R, N or D
<220> FEATURE:
<221> NAME/KEY: MISC_FEATURE
<222> LOCATION: (149)..(149)
<223> OTHER INFORMATION: X is A, S, N or D
<220> FEATURE:
<221> NAME/KEY: MISC_FEATURE
<222> LOCATION: (150)..(150)
<223> OTHER INFORMATION: X is E, R or D
<220> FEATURE:
<221> NAME/KEY: MISC_FEATURE
<222> LOCATION: (154)..(154)
<223> OTHER INFORMATION: X is C or V
<220> FEATURE:
<221> NAME/KEY: MISC_FEATURE
<222> LOCATION: (155)..(155)
<223> OTHER INFORMATION: X is I or M
<220> FEATURE:
<221> NAME/KEY: MISC_FEATURE
<222> LOCATION: (156)..(156)
<223> OTHER INFORMATION: X is R or T
<220> FEATURE:
<221> NAME/KEY: MISC_FEATURE
<222> LOCATION: (157)..(157)
<223> OTHER INFORMATION: X is I, V or F
<220> FEATURE:
<221> NAME/KEY: MISC_FEATURE
<222> LOCATION: (158)..(158)
<223> OTHER INFORMATION: X is T or L
<220> FEATURE:
<221> NAME/KEY: MISC_FEATURE
<222> LOCATION: (161)..(161)
<223> OTHER INFORMATION: X is W or L
<220> FEATURE:
<221> NAME/KEY: MISC_FEATURE
<222> LOCATION: (162)..(162)
<223> OTHER INFORMATION: X is N or S
<220> FEATURE:
<221> NAME/KEY: MISC_FEATURE
<222> LOCATION: (163)..(163)
<223> OTHER INFORMATION: X is T or A
<220> FEATURE:
<221> NAME/KEY: MISC_FEATURE
<222> LOCATION: (165)..(165)
<223> OTHER INFORMATION: X is D, L or V
<220> FEATURE:
<221> NAME/KEY: MISC_FEATURE
<222> LOCATION: (170)..(170)
<223> OTHER INFORMATION: X is S or T
<220> FEATURE:
<221> NAME/KEY: MISC_FEATURE
<222> LOCATION: (171)..(171)
<223> OTHER INFORMATION: X is A or Q
<220> FEATURE:
<221> NAME/KEY: MISC_FEATURE
<222> LOCATION: (172)..(172)
<223> OTHER INFORMATION: X is A or T
<220> FEATURE:
```

<221> NAME/KEY: MISC_FEATURE
<222> LOCATION: (175)..(175)
<223> OTHER INFORMATION: X is V or I
<220> FEATURE:
<221> NAME/KEY: MISC_FEATURE
<222> LOCATION: (182)..(182)
<223> OTHER INFORMATION: X is Y or S

<400> SEQUENCE: 3

```
Thr Leu Trp Thr Gly Xaa Xaa Pro Xaa Ala Asn Cys Xaa Xaa Xaa Xaa
1               5                   10                  15

Xaa Xaa Xaa Xaa Xaa Asp Xaa Lys Leu Xaa Leu Xaa Leu Val Lys Xaa
            20                  25                  30

Gly Xaa Xaa Val Xaa Xaa Xaa Val Xaa Xaa Xaa Gly Xaa Ser Xaa Xaa
            35                  40                  45

Xaa Asn Xaa Leu Xaa Xaa Xaa Xaa Asn Xaa Xaa Xaa Xaa Xaa Glu Leu
            50                  55                  60

Xaa Phe Asp Xaa Xaa Gly Xaa Xaa Leu Xaa Xaa Xaa Ser Ser Leu Lys
65                  70                  75                  80

Thr Xaa Leu Xaa Xaa Xaa Xaa Gln Xaa Ala Xaa Xaa Xaa Ala Xaa
            85                  90                  95

Xaa Phe Met Pro Ser Thr Thr Ala Tyr Pro Phe Xaa Leu Xaa Xaa Xaa
            100                 105                 110

Xaa Xaa Xaa Xaa Xaa Asn Xaa Ile Xaa Gly Xaa Cys Xaa Tyr Xaa Ala
            115                 120                 125

Ser Asp Xaa Xaa Xaa Phe Pro Xaa Xaa Xaa Xaa Val Met Leu Asn Xaa
            130                 135                 140

Arg Xaa Xaa Xaa Xaa Thr Ser Tyr Xaa Xaa Xaa Xaa Xaa Xaa Trp Ser
145                 150                 155                 160

Xaa Xaa Xaa Gly Xaa Ala Pro Glu Thr Xaa Xaa Xaa Thr Leu Xaa Thr
                165                 170                 175

Ser Pro Phe Thr Phe Xaa Tyr Ile Arg Glu Asp Asp
            180                 185
```

<210> SEQ ID NO 4
<211> LENGTH: 188
<212> TYPE: PRT
<213> ORGANISM: Homo sapiens
<220> FEATURE:
<221> NAME/KEY: MISC_FEATURE
<222> LOCATION: (35)..(35)
<223> OTHER INFORMATION: X is I or L
<220> FEATURE:
<221> NAME/KEY: MISC_FEATURE
<222> LOCATION: (85)..(85)
<223> OTHER INFORMATION: X is H, L or P
<220> FEATURE:
<221> NAME/KEY: MISC_FEATURE
<222> LOCATION: (86)..(86)
<223> OTHER INFORMATION: X is K or E
<220> FEATURE:
<221> NAME/KEY: MISC_FEATURE
<222> LOCATION: (93)..(93)
<223> OTHER INFORMATION: X is T, F, S, or L
<220> FEATURE:
<221> NAME/KEY: MISC_FEATURE
<222> LOCATION: (108)..(108)
<223> OTHER INFORMATION: X is V, D or absent
<220> FEATURE:
<221> NAME/KEY: MISC_FEATURE
<222> LOCATION: (117)..(117)
<223> OTHER INFORMATION: X is E, G or absent
<220> FEATURE:
<221> NAME/KEY: MISC_FEATURE
<222> LOCATION: (119)..(119)
<223> OTHER INFORMATION: X is Y or F

```
<220> FEATURE:
<221> NAME/KEY: MISC_FEATURE
<222> LOCATION: (127)..(127)
<223> OTHER INFORMATION: X is T, K or E
<220> FEATURE:
<221> NAME/KEY: MISC_FEATURE
<222> LOCATION: (162)..(162)
<223> OTHER INFORMATION: X is N or S

<400> SEQUENCE: 4
```

Thr Leu Trp Thr Gly Pro Lys Pro Glu Ala Asn Cys Ile Ile Glu Tyr
1               5                   10                  15

Gly Lys Gln Asn Pro Asp Ser Lys Leu Thr Leu Ile Leu Val Lys Asn
            20                  25                  30

Gly Gly Xaa Val Asn Gly Tyr Val Thr Leu Met Gly Ala Ser Asp Tyr
        35                  40                  45

Val Asn Thr Leu Phe Lys Asn Lys Asn Val Ser Ile Asn Val Glu Leu
    50                  55                  60

Tyr Phe Asp Ala Thr Gly His Ile Leu Pro Asp Ser Ser Leu Lys
65                  70                  75                  80

Thr Asp Leu Glu Xaa Xaa Tyr Lys Gln Thr Ala Asp Xaa Ser Ala Arg
                85                  90                  95

Gly Phe Met Pro Ser Thr Thr Ala Tyr Pro Phe Xaa Leu Pro Asn Ala
                100                 105                 110

Gly Thr His Asn Xaa Asn Xaa Ile Phe Gly Gln Cys Tyr Tyr Xaa Ala
                115                 120                 125

Ser Asp Gly Ala Leu Phe Pro Leu Glu Val Thr Val Met Leu Asn Lys
            130                 135                 140

Arg Leu Pro Asp Ser Arg Thr Ser Tyr Val Met Thr Phe Leu Trp Ser
145                 150                 155                 160

Leu Xaa Ala Gly Leu Ala Pro Glu Thr Thr Gln Ala Thr Leu Ile Thr
                165                 170                 175

Ser Pro Phe Thr Phe Ser Tyr Ile Arg Glu Asp Asp
                180                 185

```
<210> SEQ ID NO 5
<211> LENGTH: 188
<212> TYPE: PRT
<213> ORGANISM: Homo sapiens

<400> SEQUENCE: 5
```

Thr Leu Trp Thr Gly Pro Lys Pro Glu Ala Asn Cys Ile Ile Glu Tyr
1               5                   10                  15

Gly Lys Gln Asn Pro Asp Ser Lys Leu Thr Leu Ile Leu Val Lys Asn
            20                  25                  30

Gly Gly Ile Val Asn Gly Tyr Val Thr Leu Met Gly Ala Ser Asp Tyr
        35                  40                  45

Val Asn Thr Leu Phe Lys Asn Lys Asn Val Ser Ile Asn Val Glu Leu
    50                  55                  60

Tyr Phe Asp Ala Thr Gly His Ile Leu Pro Asp Ser Ser Leu Lys
65                  70                  75                  80

Thr Asp Leu Glu Leu Lys Tyr Lys Gln Thr Ala Asp Phe Ser Ala Arg
                85                  90                  95

Gly Phe Met Pro Ser Thr Thr Ala Tyr Pro Phe Val Leu Pro Asn Ala
                100                 105                 110

Gly Thr His Asn Glu Asn Phe Ile Phe Gly Gln Cys Tyr Tyr Lys Ala
                115                 120                 125

```
Ser Asp Gly Ala Leu Phe Pro Leu Glu Val Thr Val Met Leu Asn Lys
        130                 135                 140

Arg Leu Pro Asp Ser Arg Thr Ser Tyr Val Met Thr Phe Leu Trp Ser
145                 150                 155                 160

Leu Asn Ala Gly Leu Ala Pro Glu Thr Thr Gln Ala Thr Leu Ile Thr
                165                 170                 175

Ser Pro Phe Thr Phe Ser Tyr Ile Arg Glu Asp Asp
            180                 185

<210> SEQ ID NO 6
<211> LENGTH: 188
<212> TYPE: PRT
<213> ORGANISM: Homo sapiens

<400> SEQUENCE: 6

Thr Leu Trp Thr Gly Pro Lys Pro Glu Ala Asn Cys Ile Ile Glu Tyr
1               5                   10                  15

Gly Lys Gln Asn Pro Asp Ser Lys Leu Thr Leu Ile Leu Val Lys Asn
            20                  25                  30

Gly Gly Ile Val Asn Gly Tyr Val Thr Leu Met Gly Ala Ser Asp Tyr
        35                  40                  45

Val Asn Thr Leu Phe Lys Asn Lys Val Ser Ile Asn Val Glu Leu
 50                  55                  60

Tyr Phe Asp Ala Thr Gly His Ile Leu Pro Asp Ser Ser Ser Leu Lys
 65                  70                  75                  80

Thr Asp Leu Glu Leu Glu Tyr Lys Gln Thr Ala Asp Ser Ser Ala Arg
                85                  90                  95

Gly Phe Met Pro Ser Thr Thr Ala Tyr Pro Phe Val Leu Pro Asn Ala
            100                 105                 110

Gly Thr His Asn Glu Asn Tyr Ile Phe Gly Gln Cys Tyr Tyr Lys Ala
        115                 120                 125

Ser Asp Gly Ala Leu Phe Pro Leu Glu Val Thr Val Met Leu Asn Lys
130                 135                 140

Arg Leu Pro Asp Ser Arg Thr Ser Tyr Val Met Thr Phe Leu Trp Ser
145                 150                 155                 160

Leu Asn Ala Gly Leu Ala Pro Glu Thr Thr Gln Ala Thr Leu Ile Thr
                165                 170                 175

Ser Pro Phe Thr Phe Ser Tyr Ile Arg Glu Asp Asp
            180                 185

<210> SEQ ID NO 7
<211> LENGTH: 188
<212> TYPE: PRT
<213> ORGANISM: Homo sapiens

<400> SEQUENCE: 7

Thr Leu Trp Thr Gly Pro Lys Pro Glu Ala Asn Cys Ile Ile Glu Tyr
1               5                   10                  15

Gly Lys Gln Asn Pro Asp Ser Lys Leu Thr Leu Ile Leu Val Lys Asn
            20                  25                  30

Gly Gly Ile Val Asn Gly Tyr Val Thr Leu Met Gly Ala Ser Asp Tyr
        35                  40                  45

Val Asn Thr Leu Phe Lys Asn Lys Val Ser Ile Asn Val Glu Leu
 50                  55                  60

Tyr Phe Asp Ala Thr Gly His Ile Leu Pro Asp Ser Ser Ser Leu Lys
 65                  70                  75                  80
```

```
Thr Asp Leu Glu Leu Lys Tyr Lys Gln Thr Ala Asp Phe Ser Ala Arg
             85                  90                  95

Gly Phe Met Pro Ser Thr Thr Ala Tyr Pro Phe Val Leu Pro Asn Ala
            100                 105                 110

Gly Thr His Asn Glu Asn Tyr Ile Phe Gly Gln Cys Tyr Tyr Lys Ala
            115                 120                 125

Ser Asp Gly Ala Leu Phe Pro Leu Glu Val Thr Val Met Leu Asn Lys
            130                 135                 140

Arg Leu Pro Asp Ser Arg Thr Ser Tyr Val Met Thr Phe Leu Trp Ser
145                 150                 155                 160

Leu Ser Ala Gly Leu Ala Pro Glu Thr Thr Gln Ala Thr Leu Ile Thr
                165                 170                 175

Ser Pro Phe Thr Phe Ser Tyr Ile Arg Glu Asp Asp
            180                 185

<210> SEQ ID NO 8
<211> LENGTH: 188
<212> TYPE: PRT
<213> ORGANISM: Homo sapiens

<400> SEQUENCE: 8

Thr Leu Trp Thr Gly Pro Lys Pro Glu Ala Asn Cys Ile Ile Glu Tyr
1               5                   10                  15

Gly Lys Gln Asn Pro Asp Ser Lys Leu Thr Leu Ile Leu Val Lys Asn
            20                  25                  30

Gly Gly Ile Val Asn Gly Tyr Val Thr Leu Met Gly Ala Ser Asp Tyr
            35                  40                  45

Val Asn Thr Leu Phe Lys Asn Lys Asn Val Ser Ile Asn Val Glu Leu
        50                  55                  60

Tyr Phe Asp Ala Thr Gly His Ile Leu Pro Asp Ser Ser Ser Leu Lys
65                  70                  75                  80

Thr Asp Leu Glu Leu Lys Tyr Lys Gln Thr Ala Asp Phe Ser Ala Arg
             85                  90                  95

Gly Phe Met Pro Ser Thr Thr Ala Tyr Pro Phe Asp Leu Pro Asn Ala
            100                 105                 110

Gly Thr His Asn Glu Asn Tyr Ile Phe Gly Gln Cys Tyr Tyr Lys Ala
            115                 120                 125

Ser Asp Gly Ala Leu Phe Pro Leu Glu Val Thr Val Met Leu Asn Lys
            130                 135                 140

Arg Leu Pro Asp Ser Arg Thr Ser Tyr Val Met Thr Phe Leu Trp Ser
145                 150                 155                 160

Leu Asn Ala Gly Leu Ala Pro Glu Thr Thr Gln Ala Thr Leu Ile Thr
                165                 170                 175

Ser Pro Phe Thr Phe Ser Tyr Ile Arg Glu Asp Asp
            180                 185

<210> SEQ ID NO 9
<211> LENGTH: 188
<212> TYPE: PRT
<213> ORGANISM: Homo sapiens

<400> SEQUENCE: 9

Thr Leu Trp Thr Gly Pro Lys Pro Glu Ala Asn Cys Ile Ile Glu Tyr
1               5                   10                  15

Gly Lys Gln Asn Pro Asp Ser Lys Leu Thr Leu Ile Leu Val Lys Asn
            20                  25                  30
```

Gly Gly Leu Val Asn Gly Tyr Val Thr Leu Met Gly Ala Ser Asp Tyr
            35                  40                  45

Val Asn Thr Leu Phe Lys Asn Lys Asn Val Ser Ile Asn Val Glu Leu
 50                  55                  60

Tyr Phe Asp Ala Thr Gly His Ile Leu Pro Asp Ser Ser Ser Leu Lys
 65                  70                  75                  80

Thr Asp Leu Glu Pro Lys Tyr Lys Gln Thr Ala Asp Phe Ser Ala Arg
                 85                  90                  95

Gly Phe Met Pro Ser Thr Thr Ala Tyr Pro Phe Val Leu Pro Asn Ala
            100                 105                 110

Gly Thr His Asn Glu Asn Tyr Ile Phe Gly Gln Cys Tyr Tyr Glu Ala
            115                 120                 125

Ser Asp Gly Ala Leu Phe Pro Leu Glu Val Thr Val Met Leu Asn Lys
    130                 135                 140

Arg Leu Pro Asp Ser Arg Thr Ser Tyr Val Met Thr Phe Leu Trp Ser
145                 150                 155                 160

Leu Asn Ala Gly Leu Ala Pro Glu Thr Thr Gln Ala Thr Leu Ile Thr
                165                 170                 175

Ser Pro Phe Thr Phe Ser Tyr Ile Arg Glu Asp Asp
            180                 185

<210> SEQ ID NO 10
<211> LENGTH: 188
<212> TYPE: PRT
<213> ORGANISM: Homo sapiens

<400> SEQUENCE: 10

Thr Leu Trp Thr Gly Pro Lys Pro Glu Ala Asn Cys Ile Ile Glu Tyr
 1               5                  10                  15

Gly Lys Gln Asn Pro Asp Ser Lys Leu Thr Leu Ile Leu Val Lys Asn
                 20                  25                  30

Gly Gly Ile Val Asn Gly Tyr Val Thr Leu Met Gly Ala Ser Asp Tyr
            35                  40                  45

Val Asn Thr Leu Phe Lys Asn Lys Asn Val Ser Ile Asn Val Glu Leu
 50                  55                  60

Tyr Phe Asp Ala Thr Gly His Ile Leu Pro Asp Ser Ser Ser Leu Lys
 65                  70                  75                  80

Thr Asp Leu Glu Leu Lys Tyr Lys Gln Thr Ala Asp Leu Ser Ala Arg
                 85                  90                  95

Gly Phe Met Pro Ser Thr Thr Ala Tyr Pro Phe Val Leu Pro Asn Ala
            100                 105                 110

Gly Thr His Asn Glu Asn Tyr Ile Phe Gly Gln Cys Tyr Tyr Lys Ala
            115                 120                 125

Ser Asp Gly Ala Leu Phe Pro Leu Glu Val Thr Val Met Leu Asn Lys
    130                 135                 140

Arg Leu Pro Asp Ser Arg Thr Ser Tyr Val Met Thr Phe Leu Trp Ser
145                 150                 155                 160

Leu Asn Ala Gly Leu Ala Pro Glu Thr Thr Gln Ala Thr Leu Ile Thr
                165                 170                 175

Ser Pro Phe Thr Phe Ser Tyr Ile Arg Glu Asp Asp
            180                 185

<210> SEQ ID NO 11
<211> LENGTH: 188
<212> TYPE: PRT
<213> ORGANISM: Homo sapiens

<400> SEQUENCE: 11

Thr Leu Trp Thr Gly Pro Lys Pro Glu Ala Asn Cys Ile Ile Glu Tyr
1               5                   10                  15

Gly Lys Gln Asn Pro Asp Ser Lys Leu Thr Leu Ile Leu Val Lys Asn
            20                  25                  30

Gly Gly Ile Val Asn Gly Tyr Val Thr Leu Met Gly Ala Ser Asp Tyr
        35                  40                  45

Val Asn Thr Leu Phe Lys Asn Lys Val Ser Ile Asn Val Glu Leu
50                  55                  60

Tyr Phe Asp Ala Thr Gly His Ile Leu Pro Asp Ser Ser Ser Leu Lys
65                  70                  75                  80

Thr Asp Leu Glu Leu Lys Tyr Lys Gln Thr Ala Asp Phe Ser Ala Arg
                85                  90                  95

Gly Phe Met Pro Ser Thr Thr Ala Tyr Pro Phe Val Leu Pro Asn Ala
                100                 105                 110

Gly Thr His Asn Gly Asn Tyr Ile Phe Gly Gln Cys Tyr Tyr Glu Ala
            115                 120                 125

Ser Asp Gly Ala Leu Phe Pro Leu Glu Val Thr Val Met Leu Asn Lys
130                 135                 140

Arg Leu Pro Asp Ser Arg Thr Ser Tyr Val Met Thr Phe Leu Trp Ser
145                 150                 155                 160

Leu Asn Ala Gly Leu Ala Pro Glu Thr Thr Gln Ala Thr Leu Ile Thr
                165                 170                 175

Ser Pro Phe Thr Phe Ser Tyr Ile Arg Glu Asp Asp
            180                 185

<210> SEQ ID NO 12
<211> LENGTH: 91
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: X is T or S
<220> FEATURE:
<221> NAME/KEY: MISC_FEATURE
<222> LOCATION: (8)..(8)
<223> OTHER INFORMATION: X is L or V
<220> FEATURE:
<221> NAME/KEY: MISC_FEATURE
<222> LOCATION: (9)..(9)
<223> OTHER INFORMATION: X is T or N
<220> FEATURE:
<221> NAME/KEY: MISC_FEATURE
<222> LOCATION: (14)..(14)
<223> OTHER INFORMATION: X is T or A
<220> FEATURE:
<221> NAME/KEY: MISC_FEATURE
<222> LOCATION: (15)..(15)
<223> OTHER INFORMATION: X is G or S
<220> FEATURE:
<221> NAME/KEY: MISC_FEATURE
<222> LOCATION: (24)..(24)
<223> OTHER INFORMATION: X is G or S
<220> FEATURE:
<221> NAME/KEY: MISC_FEATURE
<222> LOCATION: (30)..(30)
<223> OTHER INFORMATION: X is D or T
<220> FEATURE:
<221> NAME/KEY: MISC_FEATURE
<222> LOCATION: (32)..(32)
<223> OTHER INFORMATION: X is D or N
<220> FEATURE:
<221> NAME/KEY: MISC_FEATURE
<222> LOCATION: (34)..(34)

```
<223> OTHER INFORMATION: X is T, F or S
<220> FEATURE:
<221> NAME/KEY: MISC_FEATURE
<222> LOCATION: (36)..(36)
<223> OTHER INFORMATION: X is Q, K or E
<220> FEATURE:
<221> NAME/KEY: MISC_FEATURE
<222> LOCATION: (40)..(40)
<223> OTHER INFORMATION: X is G, K or S
<220> FEATURE:
<221> NAME/KEY: MISC_FEATURE
<222> LOCATION: (41)..(41)
<223> OTHER INFORMATION: X is A or V
<220> FEATURE:
<221> NAME/KEY: MISC_FEATURE
<222> LOCATION: (42)..(42)
<223> OTHER INFORMATION: X is T or N
<220> FEATURE:
<221> NAME/KEY: MISC_FEATURE
<222> LOCATION: (46)..(46)
<223> OTHER INFORMATION: X is T or V
<220> FEATURE:
<221> NAME/KEY: MISC_FEATURE
<222> LOCATION: (48)..(48)
<223> OTHER INFORMATION: X is T or S
<220> FEATURE:
<221> NAME/KEY: MISC_FEATURE
<222> LOCATION: (49)..(49)
<223> OTHER INFORMATION: X is G or N
<220> FEATURE:
<221> NAME/KEY: MISC_FEATURE
<222> LOCATION: (53)..(53)
<223> OTHER INFORMATION: X is G or N
<220> FEATURE:
<221> NAME/KEY: MISC_FEATURE
<222> LOCATION: (55)..(55)
<223> OTHER INFORMATION: X is S or P
<220> FEATURE:
<221> NAME/KEY: MISC_FEATURE
<222> LOCATION: (56)..(56)
<223> OTHER INFORMATION: X is L or I
<220> FEATURE:
<221> NAME/KEY: MISC_FEATURE
<222> LOCATION: (58)..(58)
<223> OTHER INFORMATION: X is A, P or N
<220> FEATURE:
<221> NAME/KEY: MISC_FEATURE
<222> LOCATION: (61)..(61)
<223> OTHER INFORMATION: X is G or Q
<220> FEATURE:
<221> NAME/KEY: MISC_FEATURE
<222> LOCATION: (62)..(62)
<223> OTHER INFORMATION: X is T or I
<220> FEATURE:
<221> NAME/KEY: MISC_FEATURE
<222> LOCATION: (63)..(63)
<223> OTHER INFORMATION: X is D or E
<220> FEATURE:
<221> NAME/KEY: MISC_FEATURE
<222> LOCATION: (64)..(64)
<223> OTHER INFORMATION: X is Q or E
<220> FEATURE:
<221> NAME/KEY: MISC_FEATURE
<222> LOCATION: (69)..(69)
<223> OTHER INFORMATION: X is T, S or A
<220> FEATURE:
<221> NAME/KEY: MISC_FEATURE
<222> LOCATION: (73)..(73)
<223> OTHER INFORMATION: X is E, Q or N
<220> FEATURE:
<221> NAME/KEY: MISC_FEATURE
<222> LOCATION: (78)..(78)
<223> OTHER INFORMATION: X is N or D
<220> FEATURE:
<221> NAME/KEY: MISC_FEATURE
<222> LOCATION: (80)..(80)
<223> OTHER INFORMATION: X is N or S
<220> FEATURE:
<221> NAME/KEY: MISC_FEATURE
```

-continued

```
<222> LOCATION: (82)..(82)
<223> OTHER INFORMATION: X is I or S
<220> FEATURE:
<221> NAME/KEY: MISC_FEATURE
<222> LOCATION: (83)..(83)
<223> OTHER INFORMATION: X is I or C
<220> FEATURE:
<221> NAME/KEY: MISC_FEATURE
<222> LOCATION: (84)..(84)
<223> OTHER INFORMATION: X is I or A
<220> FEATURE:
<221> NAME/KEY: MISC_FEATURE
<222> LOCATION: (85)..(85)
<223> OTHER INFORMATION: X is D, N or L
<220> FEATURE:
<221> NAME/KEY: MISC_FEATURE
<222> LOCATION: (86)..(86)
<223> OTHER INFORMATION: X is D or K
<220> FEATURE:
<221> NAME/KEY: MISC_FEATURE
<222> LOCATION: (88)..(88)
<223> OTHER INFORMATION: X is I or absent

<400> SEQUENCE: 12

Gly Val Leu Xaa Leu Lys Cys Xaa Xaa Pro Leu Thr Thr Xaa Xaa Gly
1               5                   10                  15

Ser Leu Gln Leu Lys Val Gly Xaa Gly Leu Thr Val Asp Xaa Thr Xaa
            20                  25                  30

Gly Xaa Leu Xaa Glu Asn Ile Xaa Xaa Xaa Thr Pro Leu Xaa Lys Xaa
        35                  40                  45

Xaa His Ser Ile Xaa Leu Xaa Xaa Gly Xaa Gly Leu Xaa Xaa Xaa Xaa
    50                  55                  60

Asn Lys Leu Cys Xaa Lys Leu Gly Xaa Gly Leu Thr Phe Xaa Ser Xaa
65                  70                  75                  80

Asn Xaa Xaa Xaa Xaa Xaa Asn Xaa Asn Thr Leu
                85                  90

<210> SEQ ID NO 13

<400> SEQUENCE: 13

000

<210> SEQ ID NO 14
<211> LENGTH: 91
<212> TYPE: PRT
<213> ORGANISM: Homo sapiens

<400> SEQUENCE: 14

Asn Gly Val Leu Ser Leu Lys Cys Val Asn Pro Leu Thr Thr Ala Ser
1               5                   10                  15

Gly Ser Leu Gln Leu Lys Val Gly Ser Gly Leu Thr Val Asp Thr Thr
            20                  25                  30

Asp Gly Ser Leu Glu Glu Asn Ile Lys Val Asn Thr Pro Leu Thr Lys
        35                  40                  45

Ser Asn His Ser Ile Asn Leu Pro Ile Gly Asn Gly Leu Gln Ile Glu
    50                  55                  60

Gln Asn Lys Leu Cys Ser Lys Leu Gly Asn Gly Leu Thr Phe Asp Ser
65                  70                  75                  80

Ser Asn Ser Ile Ala Leu Lys Asn Asn Thr Leu
                85                  90

<210> SEQ ID NO 15
<211> LENGTH: 92
```

-continued

<212> TYPE: PRT
<213> ORGANISM: Homo sapiens

<400> SEQUENCE: 15

Asp Gly Val Leu Thr Leu Lys Cys Leu Thr Pro Leu Thr Thr Thr Gly
1               5                   10                  15

Gly Ser Leu Gln Leu Lys Val Gly Gly Leu Thr Ile Asp Asp Thr
            20                  25                  30

Asp Gly Phe Leu Lys Glu Asn Ile Ser Ala Thr Thr Pro Leu Val Lys
        35                  40                  45

Thr Gly His Ser Ile Gly Leu Ser Leu Gly Pro Gly Leu Gly Thr Asn
    50                  55                  60

Glu Asn Lys Leu Cys Ala Lys Leu Gly Glu Gly Leu Thr Phe Asn Ser
65                  70                  75                  80

Asn Asn Ile Cys Ile Asn Asp Asn Ile Asn Thr Leu
                85                  90

<210> SEQ ID NO 16
<211> LENGTH: 92
<212> TYPE: PRT
<213> ORGANISM: Homo sapiens

<400> SEQUENCE: 16

Asn Gly Val Leu Thr Leu Lys Cys Leu Thr Pro Leu Thr Thr Thr Gly
1               5                   10                  15

Gly Ser Leu Gln Leu Lys Val Gly Gly Leu Thr Val Asp Asp Thr
            20                  25                  30

Asn Gly Phe Leu Lys Glu Asn Ile Ser Ala Thr Thr Pro Leu Val Lys
        35                  40                  45

Thr Gly His Ser Ile Gly Leu Pro Leu Gly Ala Gly Leu Gly Thr Asn
    50                  55                  60

Glu Asn Lys Leu Cys Ile Lys Leu Gly Gln Gly Leu Thr Phe Asn Ser
65                  70                  75                  80

Asn Asn Ile Cys Ile Asp Asp Asn Ile Asn Thr Leu
                85                  90

<210> SEQ ID NO 17
<211> LENGTH: 91
<212> TYPE: PRT
<213> ORGANISM: Homo sapiens

<400> SEQUENCE: 17

Gly Val Leu Thr Leu Lys Cys Leu Thr Pro Leu Thr Thr Thr Gly Gly
1               5                   10                  15

Ser Leu Gln Leu Lys Val Gly Gly Leu Thr Val Asp Asp Thr Asp
            20                  25                  30

Gly Thr Leu Gln Glu Asn Ile Gly Ala Thr Thr Pro Leu Val Lys Thr
        35                  40                  45

Gly His Ser Ile Gly Leu Ser Leu Gly Ala Gly Leu Gly Thr Asp Glu
    50                  55                  60

Asn Lys Leu Cys Thr Lys Leu Gly Glu Gly Leu Thr Phe Asn Ser Asn
65                  70                  75                  80

Asn Ile Cys Ile Asp Asp Asn Ile Asn Thr Leu
                85                  90

<210> SEQ ID NO 18
<211> LENGTH: 92
<212> TYPE: PRT

<213> ORGANISM: Homo sapiens

<400> SEQUENCE: 18

Asp Gly Val Leu Thr Leu Lys Cys Leu Thr Pro Leu Thr Thr Thr Gly
1               5                   10                  15

Gly Ser Leu Gln Leu Lys Val Gly Gly Gly Leu Thr Val Asp Asp Thr
            20                  25                  30

Asp Gly Thr Leu Gln Glu Asn Ile Gly Ala Thr Thr Pro Leu Val Lys
        35                  40                  45

Thr Gly His Ser Ile Gly Leu Ser Leu Gly Ala Gly Leu Gly Thr Asp
    50                  55                  60

Glu Asn Lys Leu Cys Thr Lys Leu Gly Glu Gly Leu Thr Phe Asn Ser
65                  70                  75                  80

Asn Asn Ile Cys Ile Asp Asp Ile Asn Thr Leu
                85                  90

<210> SEQ ID NO 19
<211> LENGTH: 16
<212> TYPE: PRT
<213> ORGANISM: Homo sapiens

<400> SEQUENCE: 19

Asp Phe Leu Val Ile Tyr Ile Glu Glu Ala His Ala Ser Asp Gly Trp
1               5                   10                  15

<210> SEQ ID NO 20
<211> LENGTH: 12
<212> TYPE: PRT
<213> ORGANISM: Homo sapiens

<400> SEQUENCE: 20

Ala Asp Phe Leu Tyr Ile Glu Ala His Asp Gly Trp
1               5                   10

<210> SEQ ID NO 21
<211> LENGTH: 20
<212> TYPE: PRT
<213> ORGANISM: Homo sapiens

<400> SEQUENCE: 21

Gln Gly Pro Lys Glu Pro Phe Arg Asp Tyr Val Asp Arg Phe Tyr Lys
1               5                   10                  15

Thr Leu Arg Ala
            20

<210> SEQ ID NO 22
<211> LENGTH: 25
<212> TYPE: PRT
<213> ORGANISM: Homo sapiens

<400> SEQUENCE: 22

His Met Lys Gln Leu Asp Val Glu Glu Leu Ser Asn Tyr His Leu Asn
1               5                   10                  15

Val Ala Arg Leu Lys Val Gly Glu Arg
            20                  25

<210> SEQ ID NO 23
<211> LENGTH: 33
<212> TYPE: PRT
<213> ORGANISM: Homo sapiens

<400> SEQUENCE: 23

```
Gly Val Thr Gln Leu Met Arg Glu Met Leu Gln Leu Ile Lys Phe Gln
1               5                   10                  15

Phe Ser Leu Asn Tyr Gln Glu Ser Leu Ser Tyr Gln Arg Leu Val
            20                  25                  30

Thr

<210> SEQ ID NO 24
<211> LENGTH: 7
<212> TYPE: PRT
<213> ORGANISM: Homo sapiens

<400> SEQUENCE: 24

Glu Val Ser Ala Leu Glu Lys
1               5

<210> SEQ ID NO 25
<211> LENGTH: 7
<212> TYPE: PRT
<213> ORGANISM: Homo sapiens

<400> SEQUENCE: 25

Lys Val Ser Ala Leu Lys Glu
1               5

<210> SEQ ID NO 26
<211> LENGTH: 4
<212> TYPE: PRT
<213> ORGANISM: Artificial Sequence
<220> FEATURE:
<223> OTHER INFORMATION: Synthetic

<400> SEQUENCE: 26

Gly Gly Gly Ser
1

<210> SEQ ID NO 27
<211> LENGTH: 246
<212> TYPE: PRT
<213> ORGANISM: Homo sapiens

<400> SEQUENCE: 27

Met Lys Val Ser Ala Leu Lys Glu Lys Val Ser Ala Leu Lys Glu Lys
1               5                   10                  15

Val Ser Ala Leu Lys Glu Lys Val Ser Ala Leu Lys Glu Lys Val Ser
            20                  25                  30

Ala Leu Lys Glu Gly Ser Gly Gly Ser Gly Gly Ser Gly Gly Ser Gly
        35                  40                  45

Gly Ser Asn Ser Ile Ala Leu Lys Asn Thr Leu Trp Thr Gly Pro
    50                  55                  60

Lys Pro Glu Ala Asn Cys Ile Ile Glu Tyr Gly Lys Gln Asn Pro Asp
65                  70                  75                  80

Ser Lys Leu Thr Leu Ile Leu Val Lys Asn Gly Gly Ile Val Asn Gly
                85                  90                  95

Tyr Val Thr Leu Met Gly Ala Ser Asp Tyr Val Asn Thr Leu Phe Lys
                100                 105                 110

Asn Lys Asn Val Ser Ile Asn Val Glu Leu Tyr Phe Asp Ala Thr Gly
            115                 120                 125

His Ile Leu Pro Asp Ser Ser Ser Leu Lys Thr Asp Leu Glu Leu Lys
        130                 135                 140
```

```
Tyr Lys Gln Thr Ala Asp Phe Ser Ala Arg Gly Phe Met Pro Ser Thr
145                 150                 155                 160

Thr Ala Tyr Pro Phe Val Leu Pro Asn Ala Gly Thr His Asn Glu Asn
                165                 170                 175

Tyr Ile Phe Gly Gln Cys Tyr Tyr Lys Ala Ser Asp Gly Ala Leu Phe
            180                 185                 190

Pro Leu Glu Val Thr Val Met Leu Asn Lys Arg Leu Pro Asp Ser Arg
        195                 200                 205

Thr Ser Tyr Val Met Thr Phe Leu Trp Ser Leu Asn Ala Gly Leu Ala
    210                 215                 220

Pro Glu Thr Thr Gln Ala Thr Leu Ile Thr Ser Pro Phe Thr Phe Ser
225                 230                 235                 240

Tyr Ile Arg Glu Asp Asp
                245

<210> SEQ ID NO 28
<211> LENGTH: 248
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Optionally absent

<400> SEQUENCE: 28

Met Gly Ser Lys Val Ser Ala Leu Lys Glu Lys Val Ser Ala Leu Lys
1               5                   10                  15

Glu Lys Val Ser Ala Leu Lys Glu Lys Val Ser Ala Leu Lys Glu Lys
            20                  25                  30

Val Ser Ala Leu Lys Glu Gly Ser Gly Gly Gly Ser Gly Gly Gly Ser
        35                  40                  45

Gly Gly Gly Ser Asn Ser Ile Ala Leu Lys Asn Asn Thr Leu Trp Thr
    50                  55                  60

Gly Pro Lys Pro Glu Ala Asn Cys Ile Ile Glu Tyr Lys Gln Asn
65                  70                  75                  80

Pro Asp Ser Lys Leu Thr Leu Ile Leu Val Lys Asn Gly Gly Ile Val
                85                  90                  95

Asn Gly Tyr Val Thr Leu Met Gly Ala Ser Asp Tyr Val Asn Thr Leu
            100                 105                 110

Phe Lys Asn Lys Asn Val Ser Ile Asn Val Glu Leu Tyr Phe Asp Ala
        115                 120                 125

Thr Gly His Ile Leu Pro Asp Ser Ser Ser Leu Lys Thr Asp Leu Glu
    130                 135                 140

Leu Lys Tyr Lys Gln Thr Ala Asp Phe Ser Ala Arg Gly Phe Met Pro
145                 150                 155                 160

Ser Thr Thr Ala Tyr Pro Phe Val Leu Pro Asn Ala Gly Thr His Asn
                165                 170                 175

Glu Asn Phe Ile Phe Gly Gln Cys Tyr Tyr Lys Ala Ser Asp Gly Ala
            180                 185                 190

Leu Phe Pro Leu Glu Val Thr Val Met Leu Asn Lys Arg Leu Pro Asp
        195                 200                 205

Ser Arg Thr Ser Tyr Val Met Thr Phe Leu Trp Ser Leu Asn Ala Gly
    210                 215                 220

Leu Ala Pro Glu Thr Thr Gln Ala Thr Leu Ile Thr Ser Pro Phe Thr
225                 230                 235                 240

Phe Ser Tyr Ile Arg Glu Asp Asp
```

-continued

```
<210> SEQ ID NO 29
<211> LENGTH: 248
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Optionally absent

<400> SEQUENCE: 29

Met Gly Ser Lys Val Ser Ala Leu Lys Glu Lys Val Ser Ala Leu Lys
1               5                   10                  15

Glu Lys Val Ser Ala Leu Lys Glu Lys Val Ser Ala Leu Lys Glu Lys
            20                  25                  30

Val Ser Ala Leu Lys Glu Gly Ser Gly Gly Ser Gly Gly Gly Ser
        35                  40                  45

Gly Gly Gly Ser Asn Ser Ile Ala Leu Lys Asn Asn Thr Leu Trp Thr
    50                  55                  60

Gly Pro Lys Pro Glu Ala Asn Cys Ile Ile Glu Tyr Gly Lys Gln Asn
65                  70                  75                  80

Pro Asp Ser Lys Leu Thr Leu Ile Leu Val Lys Asn Gly Gly Ile Val
                85                  90                  95

Asn Gly Tyr Val Thr Leu Met Gly Ala Ser Asp Tyr Val Asn Thr Leu
            100                 105                 110

Phe Lys Asn Lys Asn Val Ser Ile Asn Val Glu Leu Tyr Phe Asp Ala
        115                 120                 125

Thr Gly His Ile Leu Pro Asp Ser Ser Ser Leu Lys Thr Asp Leu Glu
    130                 135                 140

Leu Glu Tyr Lys Gln Thr Ala Asp Ser Ser Ala Arg Gly Phe Met Pro
145                 150                 155                 160

Ser Thr Thr Ala Tyr Pro Phe Val Leu Pro Asn Ala Gly Thr His Asn
                165                 170                 175

Glu Asn Tyr Ile Phe Gly Gln Cys Tyr Tyr Lys Ala Ser Asp Gly Ala
            180                 185                 190

Leu Phe Pro Leu Glu Val Thr Val Met Leu Asn Lys Arg Leu Pro Asp
        195                 200                 205

Ser Arg Thr Ser Tyr Val Met Thr Phe Leu Trp Ser Leu Asn Ala Gly
    210                 215                 220

Leu Ala Pro Glu Thr Thr Gln Ala Thr Leu Ile Thr Ser Pro Phe Thr
225                 230                 235                 240

Phe Ser Tyr Ile Arg Glu Asp Asp
                245

<210> SEQ ID NO 30
<211> LENGTH: 248
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Optionally absent

<400> SEQUENCE: 30

Met Gly Ser Lys Val Ser Ala Leu Lys Glu Lys Val Ser Ala Leu Lys
1               5                   10                  15

Glu Lys Val Ser Ala Leu Lys Glu Lys Val Ser Ala Leu Lys Glu Lys
            20                  25                  30
```

```
Val Ser Ala Leu Lys Glu Gly Ser Gly Gly Ser Gly Gly Ser
        35                  40                  45

Gly Gly Gly Ser Asn Ser Ile Ala Leu Lys Asn Asn Thr Leu Trp Thr
 50                  55                  60

Gly Pro Lys Pro Glu Ala Asn Cys Ile Ile Glu Tyr Gly Lys Gln Asn
 65                  70                  75                  80

Pro Asp Ser Lys Leu Thr Leu Ile Leu Val Lys Asn Gly Gly Ile Val
                85                  90                  95

Asn Gly Tyr Val Thr Leu Met Gly Ala Ser Asp Tyr Val Asn Thr Leu
                100                 105                 110

Phe Lys Asn Lys Asn Val Ser Ile Asn Val Glu Leu Tyr Phe Asp Ala
                115                 120                 125

Thr Gly His Ile Leu Pro Asp Ser Ser Ser Leu Lys Thr Asp Leu Glu
                130                 135                 140

Leu Lys Tyr Lys Gln Thr Ala Asp Phe Ser Ala Arg Gly Phe Met Pro
145                 150                 155                 160

Ser Thr Thr Ala Tyr Pro Phe Val Leu Pro Asn Ala Gly Thr His Asn
                165                 170                 175

Glu Asn Tyr Ile Phe Gly Gln Cys Tyr Tyr Lys Ala Ser Asp Gly Ala
                180                 185                 190

Leu Phe Pro Leu Glu Val Thr Val Met Leu Asn Lys Arg Leu Pro Asp
                195                 200                 205

Ser Arg Thr Ser Tyr Val Met Thr Phe Leu Trp Ser Leu Ser Ala Gly
                210                 215                 220

Leu Ala Pro Glu Thr Thr Gln Ala Thr Leu Ile Thr Ser Pro Phe Thr
225                 230                 235                 240

Phe Ser Tyr Ile Arg Glu Asp Asp
                245

<210> SEQ ID NO 31
<211> LENGTH: 248
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Optionally absent

<400> SEQUENCE: 31

Met Gly Ser Lys Val Ser Ala Leu Lys Glu Lys Val Ser Ala Leu Lys
1               5                   10                  15

Glu Lys Val Ser Ala Leu Lys Glu Lys Val Ser Ala Leu Lys Glu Lys
                20                  25                  30

Val Ser Ala Leu Lys Glu Gly Ser Gly Gly Ser Gly Gly Ser
        35                  40                  45

Gly Gly Gly Ser Asn Ser Ile Ala Leu Lys Asn Asn Thr Leu Trp Thr
 50                  55                  60

Gly Pro Lys Pro Glu Ala Asn Cys Ile Ile Glu Tyr Gly Lys Gln Asn
 65                  70                  75                  80

Pro Asp Ser Lys Leu Thr Leu Ile Leu Val Lys Asn Gly Gly Ile Val
                85                  90                  95

Asn Gly Tyr Val Thr Leu Met Gly Ala Ser Asp Tyr Val Asn Thr Leu
                100                 105                 110

Phe Lys Asn Lys Asn Val Ser Ile Asn Val Glu Leu Tyr Phe Asp Ala
                115                 120                 125
```

```
Thr Gly His Ile Leu Pro Asp Ser Ser Leu Lys Thr Asp Leu Glu
    130                 135                 140

Leu Lys Tyr Lys Gln Thr Ala Asp Phe Ser Ala Arg Gly Phe Met Pro
145                 150                 155                 160

Ser Thr Thr Ala Tyr Pro Phe Asp Leu Pro Asn Ala Gly Thr His Asn
                165                 170                 175

Glu Asn Tyr Ile Phe Gly Gln Cys Tyr Tyr Lys Ala Ser Asp Gly Ala
                180                 185                 190

Leu Phe Pro Leu Glu Val Thr Val Met Leu Asn Lys Arg Leu Pro Asp
            195                 200                 205

Ser Arg Thr Ser Tyr Val Met Thr Phe Leu Trp Ser Leu Asn Ala Gly
    210                 215                 220

Leu Ala Pro Glu Thr Thr Gln Ala Thr Leu Ile Thr Ser Pro Phe Thr
225                 230                 235                 240

Phe Ser Tyr Ile Arg Glu Asp Asp
                245

<210> SEQ ID NO 32
<211> LENGTH: 248
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Optionally absent

<400> SEQUENCE: 32

Met Gly Ser Lys Val Ser Ala Leu Lys Glu Lys Val Ser Ala Leu Lys
1               5                   10                  15

Glu Lys Val Ser Ala Leu Lys Glu Lys Val Ser Ala Leu Lys Glu Lys
                20                  25                  30

Val Ser Ala Leu Lys Glu Gly Ser Gly Gly Ser Gly Gly Gly Gly Ser
            35                  40                  45

Gly Gly Gly Ser Asn Ser Ile Ala Leu Lys Asn Asn Thr Leu Trp Thr
    50                  55                  60

Gly Pro Lys Pro Glu Ala Asn Cys Ile Ile Glu Tyr Gly Lys Gln Asn
65                  70                  75                  80

Pro Asp Ser Lys Leu Thr Leu Ile Leu Val Lys Asn Gly Gly Leu Val
                85                  90                  95

Asn Gly Tyr Val Thr Leu Met Gly Ala Ser Asp Tyr Val Asn Thr Leu
                100                 105                 110

Phe Lys Asn Lys Asn Val Ser Ile Asn Val Glu Leu Tyr Phe Asp Ala
            115                 120                 125

Thr Gly His Ile Leu Pro Asp Ser Ser Leu Lys Thr Asp Leu Glu
    130                 135                 140

Pro Lys Tyr Lys Gln Thr Ala Asp Phe Ser Ala Arg Gly Phe Met Pro
145                 150                 155                 160

Ser Thr Thr Ala Tyr Pro Phe Val Leu Pro Asn Ala Gly Thr His Asn
                165                 170                 175

Glu Asn Tyr Ile Phe Gly Gln Cys Tyr Tyr Glu Ala Ser Asp Gly Ala
                180                 185                 190

Leu Phe Pro Leu Glu Val Thr Val Met Leu Asn Lys Arg Leu Pro Asp
            195                 200                 205

Ser Arg Thr Ser Tyr Val Met Thr Phe Leu Trp Ser Leu Asn Ala Gly
    210                 215                 220

Leu Ala Pro Glu Thr Thr Gln Ala Thr Leu Ile Thr Ser Pro Phe Thr
```

-continued 225                 230                 235                 240
Phe Ser Tyr Ile Arg Glu Asp Asp
                245

<210> SEQ ID NO 33
<211> LENGTH: 248
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Optionally absent

<400> SEQUENCE: 33

Met Gly Ser Lys Val Ser Ala Leu Lys Glu Lys Val Ser Ala Leu Lys
1               5                   10                  15

Glu Lys Val Ser Ala Leu Lys Glu Lys Val Ser Ala Leu Lys Glu Lys
            20                  25                  30

Val Ser Ala Leu Lys Glu Gly Ser Gly Gly Ser Gly Gly Gly Ser
        35                  40                  45

Gly Gly Gly Ser Asn Ser Ile Ala Leu Lys Asn Asn Thr Leu Trp Thr
    50                  55                  60

Gly Pro Lys Pro Glu Ala Asn Cys Ile Ile Glu Tyr Gly Lys Gln Asn
65                  70                  75                  80

Pro Asp Ser Lys Leu Thr Leu Ile Leu Val Lys Asn Gly Gly Ile Val
                85                  90                  95

Asn Gly Tyr Val Thr Leu Met Gly Ala Ser Asp Tyr Val Asn Thr Leu
            100                 105                 110

Phe Lys Asn Lys Asn Val Ser Ile Asn Val Glu Leu Tyr Phe Asp Ala
        115                 120                 125

Thr Gly His Ile Leu Pro Asp Ser Ser Leu Lys Thr Asp Leu Glu
    130                 135                 140

Leu Lys Tyr Lys Gln Thr Ala Asp Leu Ser Ala Arg Gly Phe Met Pro
145                 150                 155                 160

Ser Thr Thr Ala Tyr Pro Phe Val Leu Pro Asn Ala Gly Thr His Asn
                165                 170                 175

Glu Asn Tyr Ile Phe Gly Gln Cys Tyr Tyr Lys Ala Ser Asp Gly Ala
            180                 185                 190

Leu Phe Pro Leu Glu Val Thr Val Met Leu Asn Lys Arg Leu Pro Asp
        195                 200                 205

Ser Arg Thr Ser Tyr Val Met Thr Phe Leu Trp Ser Leu Asn Ala Gly
    210                 215                 220

Leu Ala Pro Glu Thr Thr Gln Ala Thr Leu Ile Thr Ser Pro Phe Thr
225                 230                 235                 240

Phe Ser Tyr Ile Arg Glu Asp Asp
                245

<210> SEQ ID NO 34
<211> LENGTH: 248
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Optionally absent

<400> SEQUENCE: 34

Met Gly Ser Lys Val Ser Ala Leu Lys Glu Lys Val Ser Ala Leu Lys
1               5                   10                  15

Glu Lys Val Ser Ala Leu Lys Glu Lys Val Ser Ala Leu Lys Glu Lys
            20                  25                  30

Val Ser Ala Leu Lys Glu Gly Ser Gly Gly Ser Gly Gly Gly Ser
            35                  40                  45

Gly Gly Gly Ser Asn Ser Ile Ala Leu Lys Asn Thr Leu Trp Thr
 50                  55                  60

Gly Pro Lys Pro Glu Ala Asn Cys Ile Ile Glu Tyr Gly Lys Gln Asn
 65                  70                  75                  80

Pro Asp Ser Lys Leu Thr Leu Ile Leu Val Lys Asn Gly Ile Val
                85                  90                  95

Asn Gly Tyr Val Thr Leu Met Gly Ala Ser Asp Tyr Val Asn Thr Leu
                100                 105                 110

Phe Lys Asn Lys Asn Val Ser Ile Asn Val Glu Leu Tyr Phe Asp Ala
            115                 120                 125

Thr Gly His Ile Leu Pro Asp Ser Ser Ser Leu Lys Thr Asp Leu Glu
            130                 135                 140

Leu Lys Tyr Lys Gln Thr Ala Asp Phe Ser Ala Arg Gly Phe Met Pro
145                 150                 155                 160

Ser Thr Thr Ala Tyr Pro Phe Val Leu Pro Asn Ala Gly Thr His Asn
                165                 170                 175

Gly Asn Tyr Ile Phe Gly Gln Cys Tyr Tyr Glu Ala Ser Asp Gly Ala
                180                 185                 190

Leu Phe Pro Leu Glu Val Thr Val Met Leu Asn Lys Arg Leu Pro Asp
            195                 200                 205

Ser Arg Thr Ser Tyr Val Met Thr Phe Leu Trp Ser Leu Asn Ala Gly
            210                 215                 220

Leu Ala Pro Glu Thr Thr Gln Ala Thr Leu Ile Thr Ser Pro Phe Thr
225                 230                 235                 240

Phe Ser Tyr Ile Arg Glu Asp Asp
                245

<210> SEQ ID NO 35
<211> LENGTH: 68
<212> TYPE: DNA
<213> ORGANISM: Artificial Sequence
<220> FEATURE:
<223> OTHER INFORMATION: Synthetic

<400> SEQUENCE: 35
atcacggatc cggtggcggt tctggcggtg gctccggtgg cggttctaac aaactttgca    60
gtaaactc                                                            68

<210> SEQ ID NO 36
<211> LENGTH: 39
<212> TYPE: DNA
<213> ORGANISM: Artificial Sequence
<220> FEATURE:
<223> OTHER INFORMATION: Synthetic

<400> SEQUENCE: 36
ctcagctaat taagcttagt catcttctct aatatagga                           39

<210> SEQ ID NO 37
<211> LENGTH: 41
<212> TYPE: DNA
<213> ORGANISM: Artificial Sequence
<220> FEATURE:
<223> OTHER INFORMATION: Synthetic

```
<400> SEQUENCE: 37
ccaattctat tgcacttaag aataacactt tatggacagg t                          41

<210> SEQ ID NO 38
<211> LENGTH: 34
<212> TYPE: DNA
<213> ORGANISM: Artificial Sequence
<220> FEATURE:
<223> OTHER INFORMATION: Synthetic

<400> SEQUENCE: 38
gtccaagctc agctaattaa gcttagtcat cttc                                  34

<210> SEQ ID NO 39
<211> LENGTH: 77
<212> TYPE: DNA
<213> ORGANISM: Artificial Sequence
<220> FEATURE:
<223> OTHER INFORMATION: Synthetic

<400> SEQUENCE: 39
catcacggat ccggtggcgg ttctggcggt ggctccggtg gcggttctaa taaactttgt       60
accaaattgg gagaagg                                                     77

<210> SEQ ID NO 40
<211> LENGTH: 40
<212> TYPE: DNA
<213> ORGANISM: Artificial Sequence
<220> FEATURE:
<223> OTHER INFORMATION: Synthetic

<400> SEQUENCE: 40
gctaattaag cttagtcgtc ttctctgatg tagtaaaagg                            40

<210> SEQ ID NO 41
<211> LENGTH: 26
<212> TYPE: DNA
<213> ORGANISM: Artificial Sequence
<220> FEATURE:
<223> OTHER INFORMATION: Synthetic

<400> SEQUENCE: 41
aacaccctgt ggacaggagt taaccc                                           26

<210> SEQ ID NO 42
<211> LENGTH: 24
<212> TYPE: DNA
<213> ORGANISM: Artificial Sequence
<220> FEATURE:
<223> OTHER INFORMATION: Synthetic

<400> SEQUENCE: 42
ctcagctaat taagcttagt cgtc                                             24

<210> SEQ ID NO 43
<211> LENGTH: 10
<212> TYPE: PRT
<213> ORGANISM: Homo sapiens

<400> SEQUENCE: 43

Asn Ser Ile Ala Leu Lys Asn Asn Thr Leu
1               5                   10
```

```
<210> SEQ ID NO 44
<211> LENGTH: 14
<212> TYPE: PRT
<213> ORGANISM: Homo sapiens

<400> SEQUENCE: 44

Asn Ser Asn Asn Ile Cys Ile Asn Asp Asn Ile Asn Thr Leu
1               5                   10

<210> SEQ ID NO 45
<211> LENGTH: 15
<212> TYPE: PRT
<213> ORGANISM: Homo sapiens

<400> SEQUENCE: 45

Gly Ala Ile Thr Val Gly Asn Lys Asn Asp Lys Leu Thr Leu
1               5                   10              15

<210> SEQ ID NO 46
<211> LENGTH: 14
<212> TYPE: PRT
<213> ORGANISM: Homo sapiens

<400> SEQUENCE: 46

Asn Ser Asn Asn Ile Cys Ile Asp Asp Asn Ile Asn Thr Leu
1               5                   10

<210> SEQ ID NO 47
<211> LENGTH: 14
<212> TYPE: PRT
<213> ORGANISM: Homo sapiens

<400> SEQUENCE: 47

Asn Ser Asn Asn Ile Cys Ile Asp Asp Asn Ile Asn Thr Leu
1               5                   10

<210> SEQ ID NO 48
<211> LENGTH: 12
<212> TYPE: PRT
<213> ORGANISM: Homo sapiens

<400> SEQUENCE: 48

Gly Asp Ile Cys Ile Lys Asp Ser Ile Asn Thr Leu
1               5                   10
```

DESMOGLEIN 2 (DSG2) BINDING PROTEINS AND USES THEREFOR

CROSS REFERENCE

This application is a U.S. National Phase of International Application No. PCT/US2014/057139, filed Sep. 24, 2014, which claims priority to International Application No. PCT/US2013/061431 filed Sep. 24, 2013, and to U.S. Provisional Application Ser. No. 61/954,822 filed Mar. 18, 2014, each of which is incorporated by reference in its entirety.

STATEMENT OF GOVERNMENT RIGHTS

This invention was made with U.S. Government support under R01 CA080192 and R01 HLA078836 awarded by the National Institutes of Health. The U.S. Government has certain rights in this invention.

BACKGROUND

Human adenoviruses (Ads) have been classified into six species (A to F), currently containing 51 serotypes. Most Ad serotypes utilize the coxsackie-adenovirus receptor (CAR) as a primary attachment receptor (Bergelson et al., 1997). This is, however, not the case for species B Ad serotypes. Recently, we have suggested a new grouping of species B Ads based on their receptor usage (Tuve et al., 2006). Group 1 (Ad16, 21, 35, 50) nearly exclusively utilize CD46 as a receptor; Group 2 (Ad3, Ad7, 14) share a common, unidentified receptor/s, which is not CD46 and which was tentatively named receptor X; Group 3 (Ad11) preferentially interacts with CD46, but also utilizes receptor X if CD46 is blocked.

Species B Ads are common human pathogens. Since 2005, a simultaneous emergence of diverse species B serotypes at the majority of US military training facilities was observed. This included serotypes Ad3, Ad7, and Ad14 (Metzgar et al., 2007). In 2007 a new, highly pathogenic strain and possibly more virulent strain of Ad14, Ad14a, has been discovered at several sites in the US and in Asia (Louie et al., 2008; Tate et al., 2009). We recently demonstrated that Ad14a belongs to species B group 2 Ads with regards to their receptor usage (Wang et al., 2009). Collectively, all receptor X utilizing serotypes (Ad3, Ad7, Ad14, Ad14a, and Ad11) are referred to herein as AdB-2/3.

AdB-2/3 have great relevance as gene transfer vectors, particularly with regard to tumors of epithelial origin, representing most solid tumors (Yamamoto and Curiel, 2010). Epithelial cells maintain several intercellular junctions and an apical-basal polarity. Key features of epithelial cells are conserved in epithelial cancers in situ and in cancer cell lines (Turley et al., 2008). Both CAR and CD46 are often trapped in tight and adherence junctions of epithelial cancer cells and are not accessible to Ads that use these attachment receptors (Coyne and Bergelson, 2005; Strauss et al., 2009). In contrast, AdB-2/3 efficiently infect epithelial cancer cells, which is accomplished in part through induction of processes that are reminiscent of Epithelial-to-Mesenchymal Transition (EMT) (Strauss et al., 2009). Another distinctive feature of AdB-2/3 is their ability to produce subviral dodecahedral particles during their replication, consisting of Ad fiber and penton base (Norrby et al., 1967). Penton-Dodecahedra (PtDd) cannot assemble from full-length penton base protein, but require spontaneous N-terminal truncation by proteolysis between residues 37 and 38 (Fuschiotti et al., 2006). This cleaved site is conserved in Ad3, Ad7, Ad11, and Ad14 but is not present in Ad2 and Ad5. In the case of Ad3 the PtDd are formed at a massive excess of $5.5 \times 10^6$ PtDd per infectious virus (Fender et al., 2005), and it has been suggested that PtDd enhance Ad3 infectivity by disturbing intercellular junctions, thus favoring virus spreading (Walters et al., 2002).

SUMMARY OF THE INVENTION

In one aspect, the present invention provides isolated polypeptides comprising the amino acid sequence of any one of SEQ ID NOS: 1-11. In another aspect, the present invention provides recombinant AdB-2/3 fiber polypeptides, comprising:

(a) one or more AdB-2/3 fiber polypeptide shaft domains, shaft domain motifs, or functional equivalents thereof;

(b) an AdB-2/3 fiber polypeptide knob domain operatively linked to and located C-terminal to the one or more AdB-2/3 fiber polypeptide shaft domains or shaft domain motifs, wherein the AdB-2/3 fiber polypeptide knob domain comprises the polypeptide of any SEQ ID NOS:1-11 and (c) one or more non-AdB-2/3-derived dimerization domains operatively linked to and located N-terminal to the one or more AdB-2/3 fiber polypeptide shaft domains or shaft domain motifs.

In one embodiment, the AdB-2/3 fiber polypeptide does not include an AdB-2/3 fiber polypeptide tail domain. In another embodiment, each shaft domain or shaft domain motifs selected from the group consisting of an Ad3 fiber polypeptide shaft domain or shaft domain motif, an Ad7 fiber polypeptide shaft domain or shaft domain motif, an Ad11 fiber polypeptide shaft domain or shaft domain motif, an Ad 14 fiber polypeptide shaft domain or shaft domain motif, an Ad14a fiber polypeptide shaft domain, or shaft domain motif combinations thereof, and functional equivalents thereof. In a further embodiment, each shaft domain or shaft domain motif comprises the amino acid sequence of any one of SEQ ID NOS:12-18, SEQ ID NO:43-48, or combinations thereof. In another embodiment, the dimerization domain comprises an amino acid sequence selected from the group consisting of SEQ ID NO:24 and SEQ ID NO: 25. In a still further embodiment, the recombinant AdB-2/3 fiber polypeptide comprises or consists of the amino acid sequence of any one of SEQ ID NO:28-34. In another embodiment, the AdB-2/3 fiber polypeptide is multimerized, such as dimerized. In a further embodiment, the AdB-2/3 fiber polypeptide further comprises one or more compounds conjugated to the recombinant AdB-2/3 fiber polypeptide, such as therapeutics, diagnostics, and imaging agents.

In a further aspect, the present invention provides isolated nucleic acids encoding the isolated peptide or the recombinant AdB-2/3 fiber polypeptides of the invention, recombinant expression vectors comprising the isolated nucleic acids, and host cells comprising the recombinant expression vectors.

In another aspect, the present invention provides pharmaceutical compositions, comprising (a) the AdB-2/3 fiber multimer of any embodiment or combination of embodiments of the invention; and a pharmaceutically acceptable carrier.

In a still further aspect, the present invention provides methods for enhancing therapeutic treatment, or diagnosis of a disorder associated with epithelial tissue, and/or imaging epithelial tissues, comprising administering to a subject in need thereof:

(a) an amount of one or more therapeutics sufficient to treat the disorder, diagnostic sufficient to diagnose the disorder, and/or imaging agent sufficient to image the epithelial tissue; and (b) an amount of an AdB-2/3 fiber multimer or pharmaceutical composition of any embodiment or combination of embodiments of the invention, sufficient to enhance efficacy of the one or more therapeutics, diagnostics, and/or imaging agents.

Exemplary such disorders associated with epithelial tissue include solid tumors, irritable bowel syndrome, inflammatory bowel disorder, Crohn's disease, ulcerative colitis, constipation, gastroesophageal reflux disease, Barrett's esophagus, chronic obstructive pulmonary disease, asthma, bronchitis, pulmonary emphysema, cystic fibrosis, interstitial lung disease, pneumonia, primary pulmonary hypertension, pulmonary embolism, pulmonary sarcoidosis, tuberculosis, pancreatitis, pancreatic duct disorders, bile duct obstruction, cholecystitis, choledocholithiasis, brain disorders, psoriasis, dermatitis, glomerulonephritis, hepatitis, diabetes, thyroid disorders, cellulitis, infection, pyelonephritis, and gallstones.

In another aspect, the present invention provides methods for treating a disorder associated with epithelial tissue, comprising administering to a subject in need thereof an amount of an AdB-2/3 fiber multimer or pharmaceutical composition of any embodiment or combination of embodiments of the invention, sufficient to treat the disorder. In exemplary embodiments, such a disorder may be a viral infection or a solid tumor.

In a further aspect, the present invention provides methods for improving delivery of a compound to an epithelial tissue, comprising contacting the epithelial tissue with one or more compounds to be delivered to the epithelial tissue; and an amount of an AdB-2/3 fiber multimer or pharmaceutical composition of any embodiment or combination of embodiments of the invention, sufficient to enhance delivery of the one or more compounds to the epithelial tissue. In exemplary embodiments, the one or more compounds may be diagnostic or imaging agents.

In a still further aspect, the present invention provides methods for improving delivery of a substance to a tissue expressing desmoglein 2 (DSG2), comprising contacting the tissue expressing DSG2 with (a) one or more compound to be delivered to the tissue; and (b) an amount of an AdB-2/3 fiber multimer or pharmaceutical composition of any embodiment or combination of embodiments of the invention, sufficient to enhance delivery of the one or more compounds to the tissue.

In another aspect, the present invention provides methods for inducing an epithelial to mesenchymal transition (EMT) in a tissue, comprising contacting the epithelial tissue with an amount of an AdB-2/3 fiber multimer or pharmaceutical composition of any embodiment or combination of embodiments of the invention, sufficient to induce EMT.

In a further aspect, the present invention provides methods for identifying candidate compounds for one or more of treating a disorder associated with epithelial tissue, improving delivery of a substance to an epithelial tissue, for improving delivery of a substance tissue expressing DSG2, inducing an EMT in a tissue, and/or treating an AdB-2/3 infection comprising (a) contacting an AdB-2/3 fiber multimer of any embodiment or combination of embodiments of the invention, to DSG2 under conditions to promote multimer binding to DSG2, wherein the contacting is carried out in the presence of one or more test compounds; and (b) identifying positive test compounds that compete with the AdB-2/3 fiber multimer for binding to DSG2 compared to control;

wherein the positive test compounds are candidate compounds for one or more of treating a disorder associated with epithelial tissue, improving delivery of a substance to an epithelial tissue, for improving delivery of a substance tissue expressing DSG2, inducing an EMT in a tissue, and/or treating an AdB-2/3 infection.

DESCRIPTION OF THE FIGURES

FIG. 5. Correlation of reduced DSG2 binding with the ability to open epithelial junctions. A) Transepithelial electrical resistance (TEER) measured on polarized colon cancer T84 cells. Cells were cultured in transwell chambers until the TEER was constant, i.e. tight junctions had formed. A total of 5 µg of dimeric Ad3 fiber knobs in PBS was then added for 1 hour to the apical chamber. TEER was measured at the indicated time points. N=6. For time points 1.5 and 4 hours the difference between JO-1 vs D261N and N186D was significant (p<0.01). The arrows indicate the addition and removal of Ad3 fiber knobs. B) Enhancement of irinotecan therapy. A total of $4 \times 10^6$ A549 cells were injected subcutaneously into CB17-SCID/beige mice. Once the tumor reached a volume of ~100 mm$^3$ (day 15 after implantation), the mice were injected intravenously with 2 mg/kg JO-1, E299V, N186D, or PBS, followed by an intravenous injection of irinotecan (37.5 mg/kg) one hour later. The treatment was repeated on day 25. N=5. The differences between the groups "irinotecan" vs "E299V+irinotecan" or "irinotecan" vs "N186+irinotecan" were not significant. The difference between "irinotecan" vs "JO-1+irinotecan" was significant (p<0.01) from day 20 on.

-continued

Figure 1A:
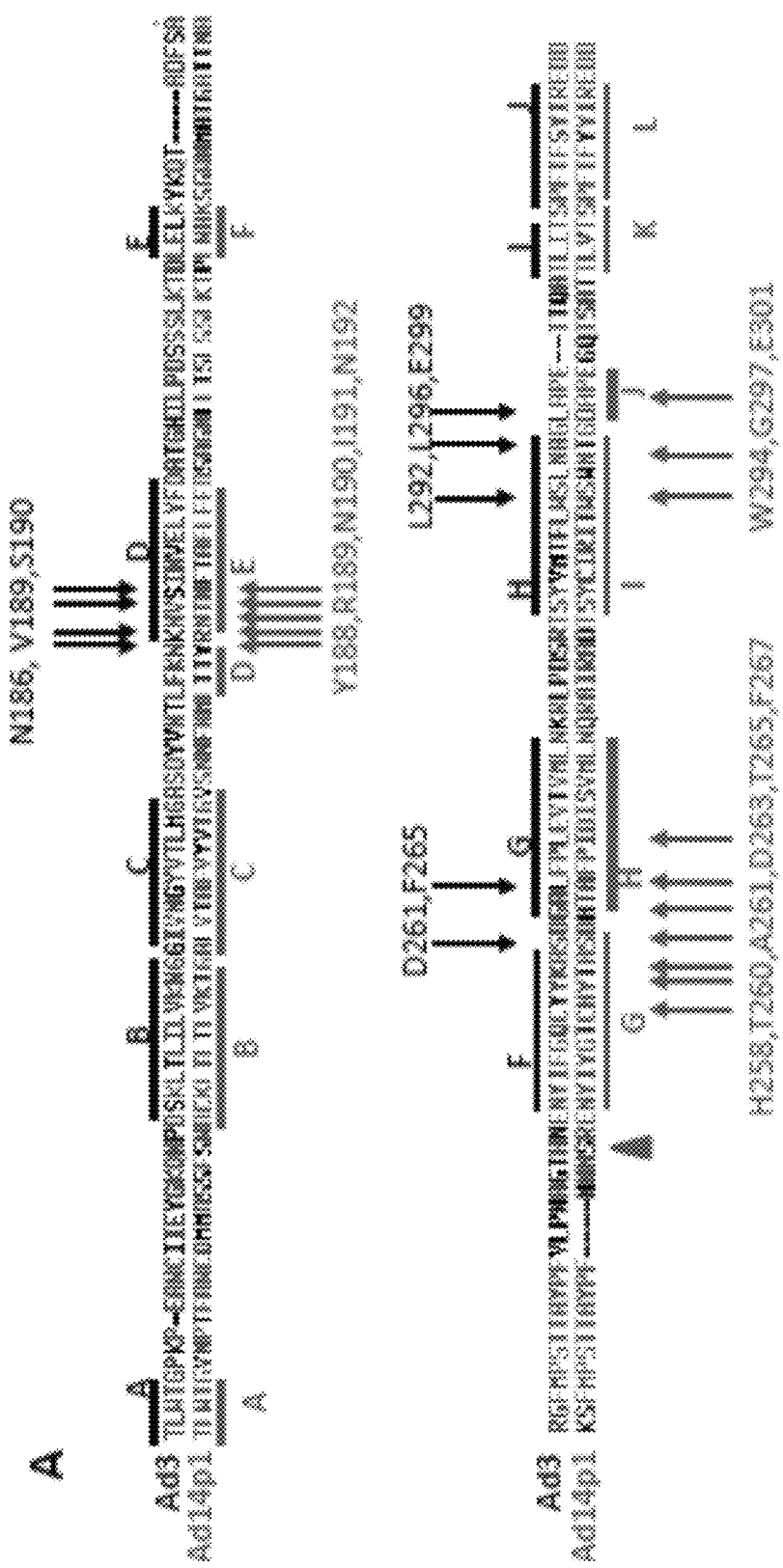
FIG. 1. Residues found to be critically involved in binding to DSG2. A) Shown are the amino acid sequences of the Ad3 (SEQ ID NO: 43) and Ad14p1 (SEQ ID NO: 44) fiber knob. Beta sheets present in the Ad3 knob (PDB accession number 1H7Z_A) and Ad14 knob (PDB: 3FOY_A) are indicated by lines. Black arrows indicate residues within the Ad3 fiber knob which, when mutated individually, ablate or reduce binding to DSG2. Compared to the parental strain Ad14 (deWit), Ad14p1 had a deletion of two amino acid residues within the FG loop of the fiber protein knob (24) indicated by a triangle. B) Schematic structure of dimeric Ad3 fiber knob mutants. The fiber knob domain and one shaft motif was fused through a flexible linker to a homodimerizing K-coil domain (SEQ ID NO: 25) (41). The proteins are self-multimerizing and can be purified by His-Ni-NTA affinity chromatography. C-F) Analysis of binding of di-or trimeric Ad3 fiber knob mutants to soluble DSG2. C and D) Coomassie staining. 10 µg of purified Ad3 fiber knob (unboiled) were loaded per lane. Trimeric forms of the fiber knobs are indicated by an arrow. The gel contained SDS and the loading buffer containing DTT, which caused the disassembly of multimers of trimeric fiber knobs as previously reported (41). E and F): Western blot using soluble recombinant DSG2 as a probe, followed by anti-DSG2-mAb and anti-mouse IgG-HRP. For comparison, JO-1 (0.5 µg/lane) is shown. The Western blots were scanned and signals were quantified.
Figures 1B, 1C, 1D, 1E, 1F:
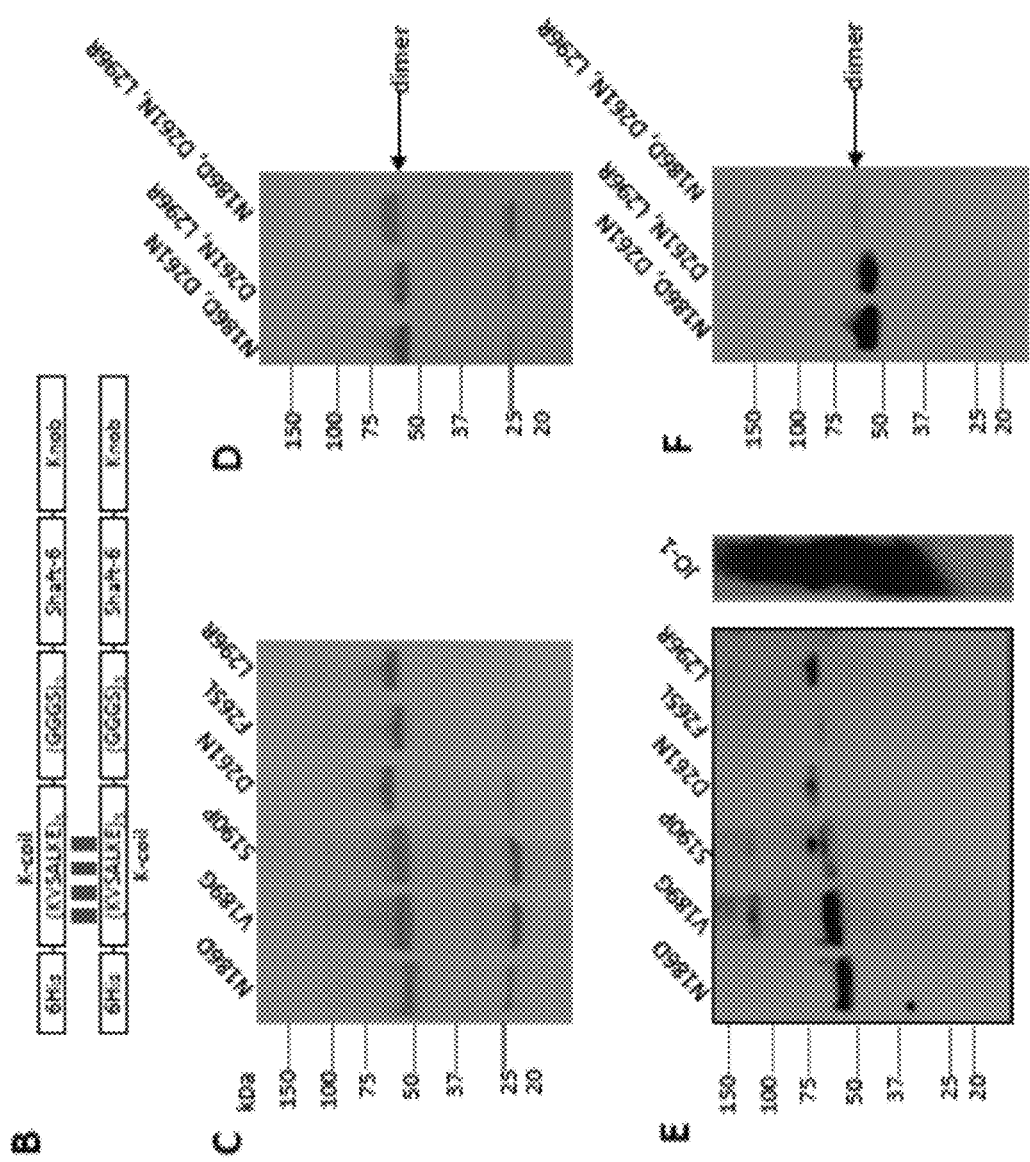
Figure 2:
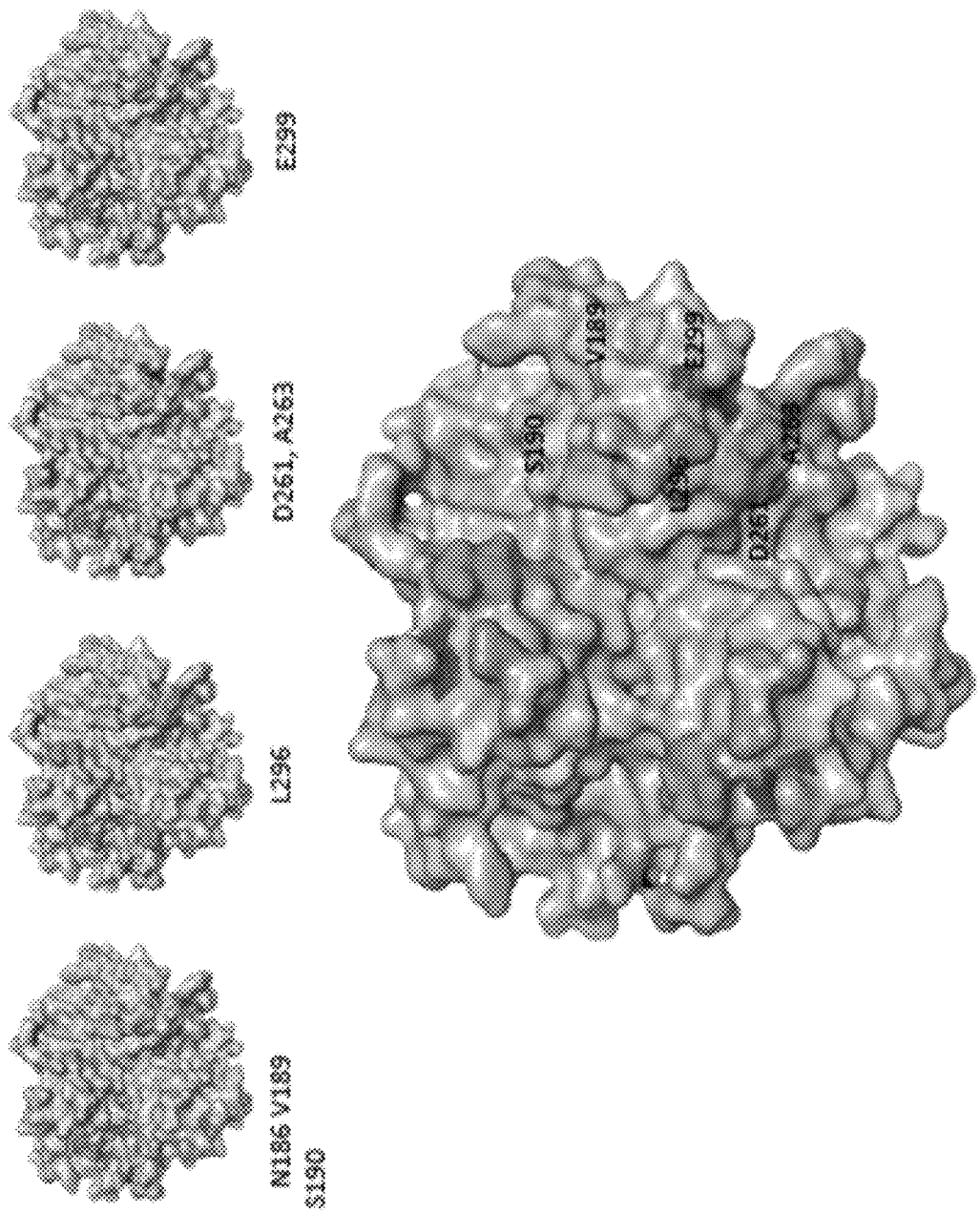
FIG. 2. 3D model of the Ad3 fiber knob. The structure is based on PDB accession number 1H7Z_A. Upper panel: Four critical areas involved in DSG2 binding. The critical residues are shown on the isosurface of the trimeric fiber knob. View from the top (apical side) facing the receptor. Lower panel: All critical residues combined. Right side: An enlargement of the groove after a slight side rotation.
Figure 3A:
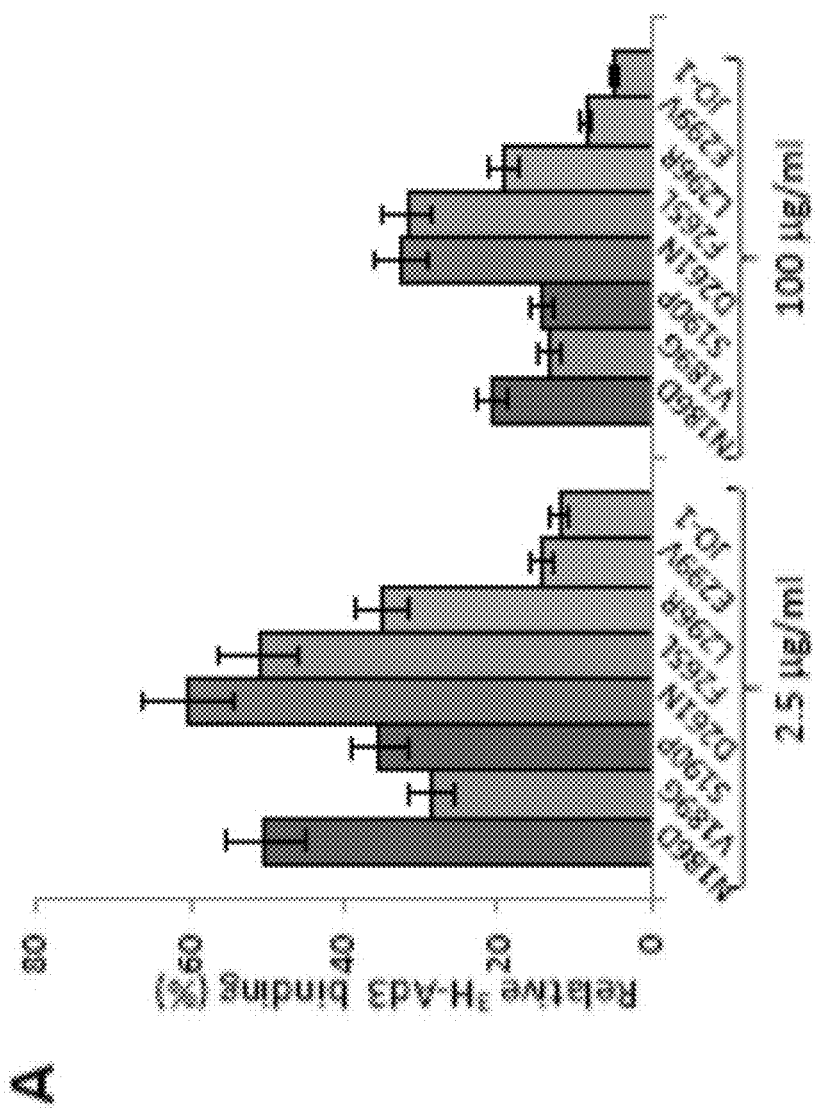
FIG. 3. Competition of Ad3 virus by dimerized Ad3 knob mutants. A) Relative attachment of $^3$H-labeled Ad3 virus in the presence of dimeric fiber knob mutants. $1.8 \times 10^5$ HeLa cells were incubated with Ad3 knob mutants at a concentration of 2.5 and 100 µg/ml on ice for 1 hour. Then 400 pfu/cell of $^3$H-Ad3 virus was added on ice for another hour. Unbound virus particles were washed away. Attachment of virus particles incubated with PBS was taken as 100%. N=3. B) Competition of Ad3-GFP virus infection on HeLa cells. $1.5 \times 10^5$ HeLa cells were seeded into 24 well plates. Cells were incubated with the Ad3 knob mutants at increasing concentrations for one hour at room temperature. 100 pfu/cell of Ad3-GFP virus were then added and GFP expression was analyzed 18 hours later by flow cytometry. Left panel: percentage of GFP positive cells. Right panel: mean fluorescence intensity. N=3. The standard deviation was less than 10%. C) Relative attachment of $^3$H-labeled Ad3 virus in the presence of dimeric fiber knob mutants with multiple mutations. The study was performed as described in B) The standard deviation was less than 10%. D) Competition of Ad3-GFP virus infection on HeLa cells. The study was performed as described in C) The standard deviation was less than 10%.
Figure 3B:
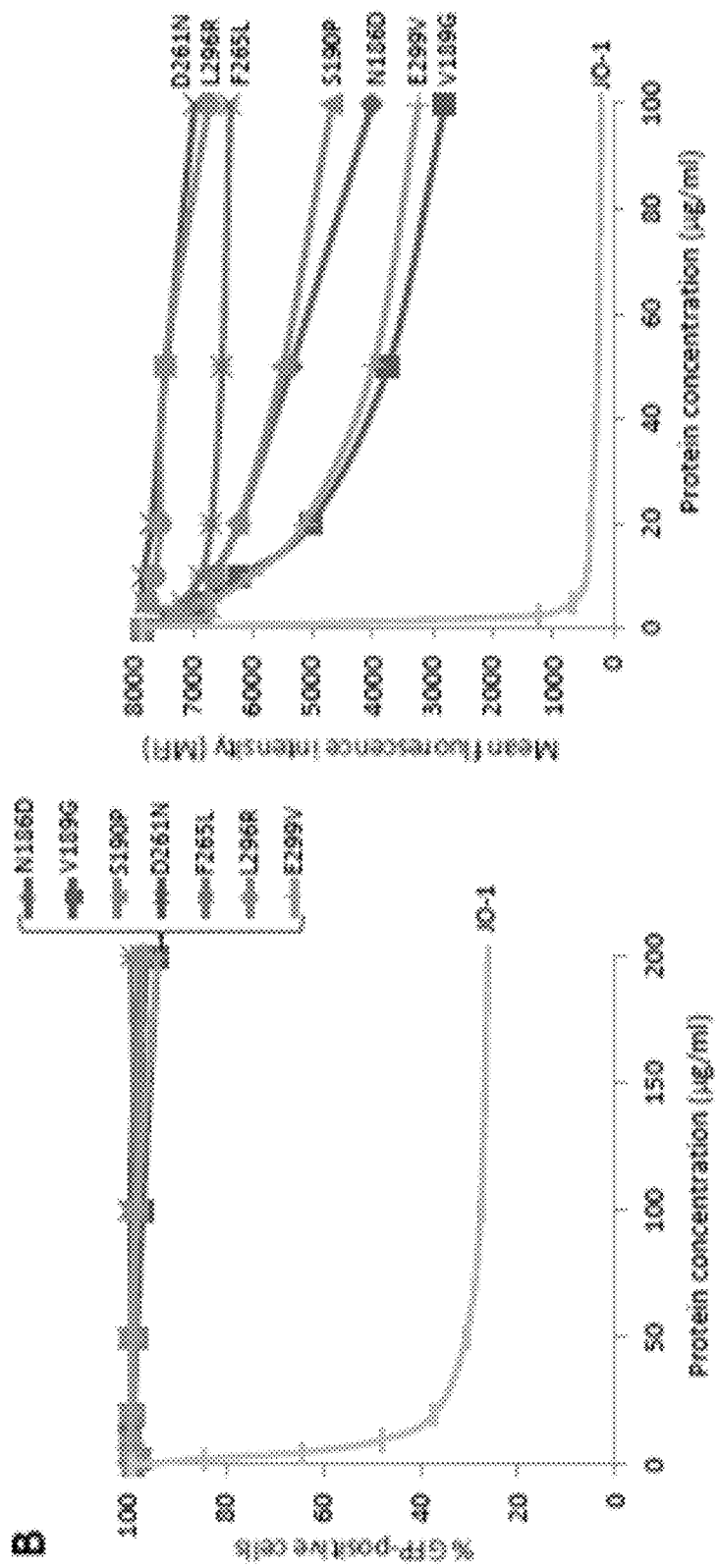
Figures 3C, 3D:
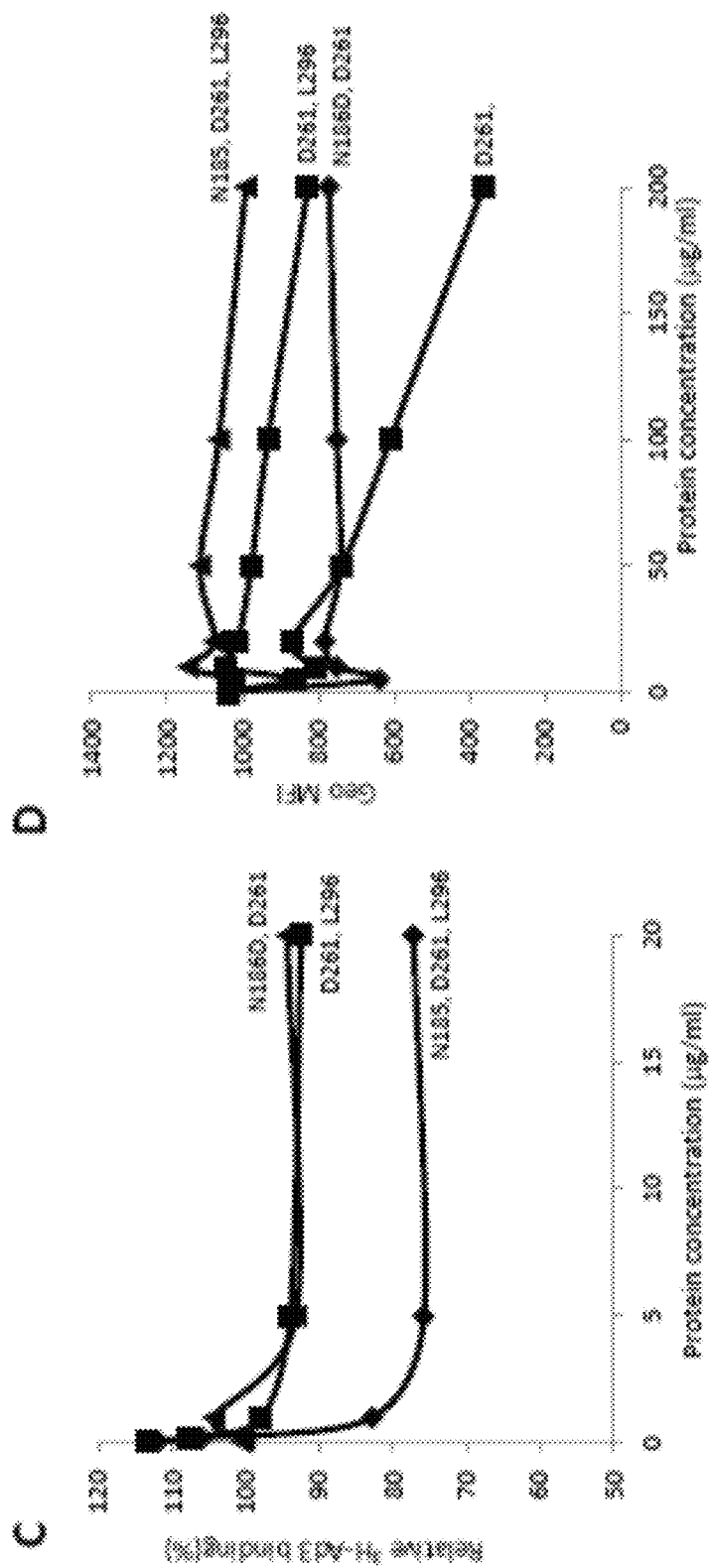
Figure 4:
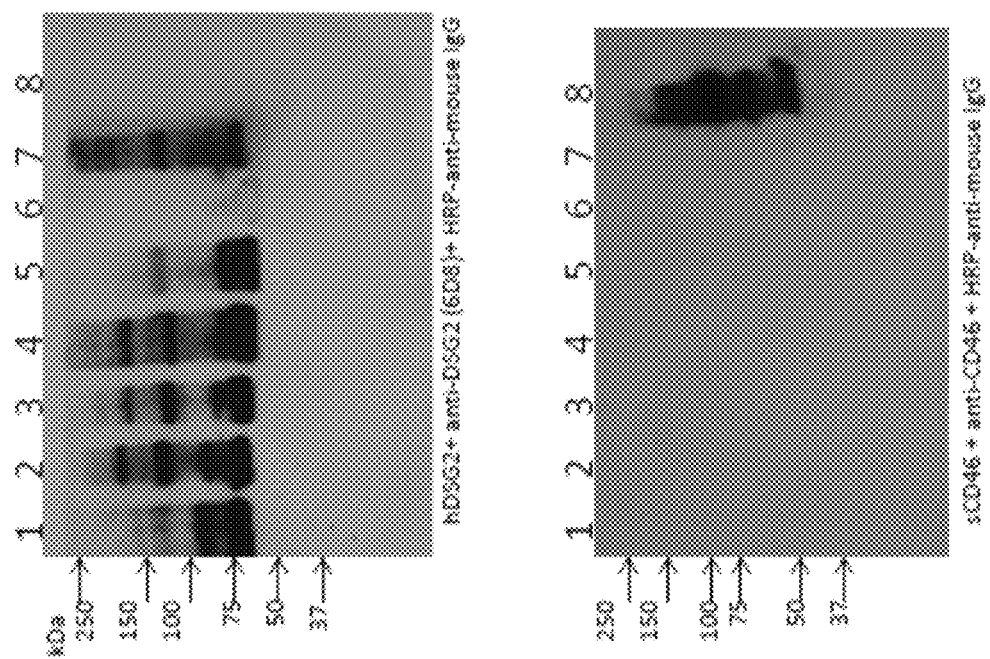
FIG. 4. Analysis of Ad3 fiber knob binding to soluble CD46. Ad3 fiber knobs containing different numbers shaft motifs and the wild-type Ad3 fiber knob (lane 1: Ad3-S6/Kn, lane 2: Ad3-S5/Kn, lane 3: Ad3-S4/Kn, lane 4: Ad3-S3/Kn, lane 5: Ad3-S2/Kn, lane 6: Ad3-S/Kn), JO-1 (lane 7) and the CD46-binding Ad35 fiber knob (lane 8) were blotted and hybridized with soluble DSG2 (upper panel) or soluble CD46 (lower panel). Binding was detected by anti-DSG2 mAb or anti-CD46 mAb.

```
FMPSTTAYPFX5(--/L)(N/P)(N/D/V)(N/A)(S/G)(R/T)(E/H)

(N/K/--)X6NX7I(Y/F)G(T/Q)C(H/Y)YX8ASD(H/G/R)(T/A)

(A/L)FP(I/L)(D/E)(I/V)(S/T)VMLN(Q/R/K)R(A/L)(I/L/P)

(R/N/D)(A/D/N/S)(D/E/R)TSY(C/V)(I/M)(R/T)(I/V/F)

(T/L)WS(W/L)X9(T/A)G(D/L/V)APET(S/T)(A/Q)(T/A)TL (V/I)TSPFTF(Y/S)YIREDD
```

In another embodiment, the isolated polypeptides of the first aspect of the invention comprises or consists of the amino acid sequence

```
                                           (SEQ ID NO: 3)
TLWTG(V/P)(N/K)P(E/R)ANC(Q/I)(M/I)(M/E)(Y/A/N/D)

(S/G)(SK)(E/Q)(S/N)(N/P)D(C/S)KL(I/T)L(I/T)LVK (T/N)G(A/G)(L/I)V(T/N)(A/G)(F/Y)V(Y/T)(V/L)(I/M)

G(V/A)S(N/D)(N/D/Y)(F/V)N(M/T)L(T/F)(T/K)(Y/H/N)

(R/K)N(I/V)(N/S)(F/I)(T/N)(A/V)EL(F/Y)FD(S/A)

(A/T)G(N/H)(L/I)L(T/P)(S/R/D)(L/S)SSLKT(P/D)L(N/E)

X2X3(S/Y)(G/K)Q(N/T)A(I/L/D)

X4(N/S)A(K/R)(S/G)FMPSTTAYPFX5L(N/P)(N/D/V)(N/A)

(S/G)(R/T)(E/H)(N/K/)X6NX7I(Y/F)G(T/Q)C(H/Y)YX8

ASD(H/G/R)(T/A)(A/L)FP(I/L)(D/E)(I/V)(S/T)VMLN (Q/R/K)R(A/L)(I/L/P)(R/N/D)(A/D/N/S)(D/E/R)TSY(C/V)

(I/M)(R/T)(I/V/F)(T/L)WS(W/L)X9(T/A)G(D/L/V)

APET(S/T)(A/Q)(T/A)M(V/I)TSPFTF(Y/S)YIREDD.
```

In a further embodiment, the isolated polypeptides of the first aspect of the invention comprises or consists of the amino acid sequence

```
                                           (SEQ ID NO: 4)
TLWTGPKPEA NCIIEYGKQN PDSKLTLILV KNGG(I/L)VNGYV TLMGASDYVN

TLFKNKNVSI NVELYFDATG HILPDSSSLK TDLEX2X3YKQT ADX4SARGFMP

STTAYPFX5LP NAGTHNX6NX7I FGQCYY X8 ASD GALFPLEVTV MLNKRLPDSR

TSYVMTFLWS LX9AGLAPETT QATLITSPFT FSYIREDD.
```

In all of these embodiments, at least one of the following is true:
X2 is P;
X3 is E;
X4 is S, or L;
X5 is D;
X6 is G);
X7 is F;
X8 is E; or
X9 is S.

In various embodiments, at least 2, 3, 4, 5, 6, 7, or all 8 of these statements is true. In one exemplary embodiment, at least X7 is F. In another embodiment, at least X3 is E and X4 is S. In another embodiment, at least X9 is S. In a further embodiment, at least X5 is D. In another embodiment, at least X4 is L. In another embodiment, at least X2 is P and X8 is E. IN another embodiment, at least X6 is G and X8 is E.

In various further embodiments, the isolated polypeptide comprises or consists of one of the following peptides:

(a)
```
                                           (SEQ ID NO: 5)
TLWTGPKEANCIIEYGKQNPDSKLTLILVKNGGIVNGYVTLMGASDYVNT

LFKNKNVSINVELYFDATGHILPDSSSLKTDLELKYKQTADFSARGFMPS

TTAYPFVLPNAGTHNENFIFGQCYYKASDGALFPLEVTVMLNKRLPDSRT

SYVMTFLWSLNAGLAPETTQATLITSPFTFSYIREDD;
```

(b)
```
                                           (SEQ ID NO: 6)
TLWTGPKPEANCIEEYGKQNPDSKLTLILVKNGGIVNGYVTLMGASDYVN

TLFKNKNVSINVELYFDATGHILPDSSSLKTDLELEYKQTADSSARGFMP

STTAYPFVLPNAGTHNENYIFGQCYYKASDGALFPLEVTVMLNKRLPDSR

TSYVMTFLWSLNAGLAPETTQATLITSPFTFSYIREDD;
```

(c)
```
                                           (SEQ ID NO: 7)
TLWTGPKPEANCIEEYGKQNPDSKLTLILVKNGGIVNGYVTLMGASDYVN

TLFKNKNVSINVELYFDATGHILPDSSSLKTDLELKYKQTADFSARGFMP

STTAYPFVLPNAGTHNENYIFGQCYYKASDGALFPLEVTVMLNDRLPDSR

TSYVMTFLWSLSAGLAPETTQATLITSPFTFSYIREDD;
```

(d)
```
                                           (SEQ ID NO: 8)
TLWTGPKPEANCIIEYGKQNPDSKLTLILVKNGGIVNGYVTLMGASDYVN

TLFKNKNVSINVELYFDATGHILPDSSSLKTDLELKYKQTADFSARGFMP

STTAYPFDLPNAGTHNENYIFGQCYYKASDGALFPLEVTVMLNKRLPDSR

TSYVMTFLWSLNAGLAPETTQATLITSPFTFSYIREDD;
```

-continued (e)
```
                                           (SEQ ID NO: 9)
TLWTGPKPEANCIIEYGKQNPDSKLTLILVKNGGLVNGYVTLMGASDYVN

TLFKNKNVSINVELYFDATGHILPDSSSLKTDLEPKYKQTADFSARGFMP

STTAYPFVLPNAGTHNENYIFGQCYYEASDGALFPLEVTVMLNKRLPDSR

TSYYMTFLWSLNAGLAPETTQATLITSPFTFSYIREDD;
```

(f)
```
                                           (SEQ ID NO: 10)
TLWTGPKPEANCIIEYGKQNPDSKLTLILVKNGGIVNGYVTLMGASDYV

NTLFKNKNVSINVELYFDATGHILPDSSSLKTDLELKYKQTADLSARGF
```

-continued

MPSTTAYPFVLPNAGTHNENYIFGQCYYKASDGALFPLEVTVMLNKRLP

DSRTSYVMTFLWSLNAGLAPETTQATLITSPFTFSYIREDD;
and (SEQ ID NO: 11)
TLWTGPKEANCIIEYGKQNPDSKLTLILVKNGGIVNGYVTLMGASDYV

NTLFKNKNVSINVELYFDATGHILPDSSSLKTDLELKYKQTADFSARGF

MPSTTAYPFVLPNAGTHNGNYIFGQCYYEASDGALFPLVTVMLNKRLPD

SRTSYVMTFLWSLNAGLAPETTQATLITSPFTFSYIREDD.

In a second aspect, the present invention provides recombinant AdB-2/3 fiber polypeptide, comprising:

(a) one or more AdB-2/3 fiber polypeptide shaft domains, shaft domain motifs or functional equivalents thereof;

(b) an AdB-2/3 fiber polypeptide knob domain, operatively linked to and located C-terminal to the one or more AdB-2/3 fiber polypeptide shaft domains or shaft domain motifs, wherein the AdB-2/3 fiber polypeptide knob domain comprises the polypeptide of any embodiment or combination of embodiments of the first aspect of the invention; and (c) one or more non-AdB-2/3-derived dimerization domains operatively linked to and located N-terminal to the one or more AdB-2/3 fiber polypeptide shaft domains or shaft domain motifs.

As used herein, "AdB-2/3" is any adenovirus serotype that uses DSG2 as an epithelial cell receptor for viral binding. To date, Ad3, Ad7, Ad11, Ad14, and Ad14a serotypes have been identified. As other Ad serotypes are identified, those of skill in the art can readily identify those that belong to the AbD-2/3 family based on DSG2 binding assays as disclosed herein. For example, surface plasmon resonance (SPR) studies using sensors containing immobilized recombinant DSG2 can be used to determine if new Ad serotypes bind to DSG2, combined with DSG2 competition studies. Further exemplary studies, such as loss and gain of function analyses, are described in detail in WO 2011/156761.

The adenovirus virion is an icosahedron characterized by a fiber located at the base of each of the 12 vertices of the capsid. The fiber on the virion is a homotrimeric structure consisting of 3 individual fiber polypeptides. Each adenovirus fiber polypeptide is an asymmetrical structure consisting of an N-terminal tail, which interacts with the penton base protein of the capsid and contains the signals necessary for transport of the protein to the cell nucleus; a shaft, which contains a number of 15-residue repeating units; and a C-terminal knob domain that contains the determinants for receptor binding (J. S. Hong and J. A. Engler, *Journal of Virology* 70:7071-7078 (1996)). All adenoviruses attach to their receptors through the knob structure on the end of the fiber. Thus, as used herein, the term AdB-2/3"fiber polypeptide" refers to a full length fiber polypeptide that comprises an N-terminal tail domain, a shaft domain or shaft domain motif, and a C-terminal knob domain. The fiber polypeptides spontaneously assemble into homotrimers, referred to as "fibers," which are located on the outside of the adenovirus virion at the base of each of the twelve vertices of the capsid.

In a preferred embodiment, the recombinant polypeptides do not include a tail domain from an Ad fiber polypeptide. As is disclosed in detail below, the inventors identified critical residues, mutation of which result in fiber polypeptides with significantly enhanced affinity for DSG2, and with significantly enhanced therapeutic potency. The polypeptides of this aspect of the invention can thus be used, for example, to form AdB-2/3 fiber multimers for use in the various methods of the invention discussed above. In this aspect, the recombinant polypeptides can include shaft domains or shaft domain motifs from any AdB-2/3 virus, or any mutants (substitutions, additions, deletions, chimeras, etc.) to such shaft domains or shaft domain motifs that retain or improve binding affinity to DSG2, and are capable of forming multimers (such as dimers) via the dimerization domain (functional equivalents). For example, surface plasmon resonance (SPR) studies using sensors containing immobilized recombinant DSG2 can be used to determine if recombinant polypeptides being assessed bind to DSG2, combined with DSG2 competition studies.

As used throughout the present application, the term "polypeptide" is used in its broadest sense to refer to a sequence of subunit amino acids. The polypeptides of the invention may comprise L-amino acids, D-amino acids (which are resistant to L-amino acid-specific proteases in vivo), or a combination of D- and L-amino acids. The polypeptides described herein may be chemically synthesized or recombinantly expressed. The polypeptides may be linked to other compounds to promote an increased half-life in vivo, such as by PEGylation, HESylation, PASylation, glycosylation, or may be produced as an Fc-fusion or in deimmunized variants. Such linkage can be covalent or non-covalent as is understood by those of skill in the art.

As used herein, the term "operatively linked" refers to an arrangement of elements wherein the domains are configured so that they function as a unit for their intended purpose. The term does not require that the domains are immediately adjacent on the polypeptide, as spacer/linker sequences may be present between the domains, the lengths of which can be quite variable. In one non-limiting embodiment, the spacer length between any two domains of the recombinant AdB-2/3 fiber polypeptides can be between about 0 amino acids and about 20 amino acids. In various other non-limiting embodiments, the spacer length can be 0-20, 0-19, 0-18, 0-17, 0-16, 0-15, 0-14, 0-13, 0-12, 0-11, 0-10, 0-9, 0-8, 0-7, 0-6, 0-5, 0-4, 0-3, 0-2, 0-1, 1-20, 1-19, 1-18, 1-17, 1-16, 1-15, 1-14, 1-13, 1-12, 1-11, 1-10, 1-9, 1-8, 1-7, 1-6, 1-5, 1-4, 1-3, 1-2, 2-20, 2-19, 2-18, 2-17, 2-16, 2-15, 2-14, 2-13, 2-12, 2-11, 2-10, 2-9, 2-8, 2-7, 2-6, 2-5, 2-4, 2-3, 3-20, 3-19, 3-18, 3-17, 3-16, 3-15, 3-14, 3-13, 3-12, 3-11, 3-10, 3-9, 3-8, 3-7, 3-6, 3-5, 3-4, 4-20, 4-19, 4-18, 4-17, 4-16, 4-15, 4-14, 4-13, 4-12, 4-11, 4-10, 4-9, 4-8, 4-7, 4-6, 4-5, 5-20, 5-19, 5-18, 5-17, 5-16, 5-15, 5-14, 5-13, 5-12, 5-11, 5-10, 5-9, 5-8, 5-7, 5-6, 6-20, 6-19, 6-18, 6-17, 6-16, 6-15, 6-14, 6-13, 6-12, 6-11, 6-10, 6-9, 6-8, 6-7, 7-20, 7-19, 7-18, 7-17, 7-16, 7-15, 7-14, 7-13, 7-12, 7-11, 7-10, 7-9, 7-8, 8-20, 8-19, 8-18, 8-17, 8-16, 8-15, 8-14, 8-13, 8-12, 8-11, 8-10, 8-9, 9-20, 9-19, 9-18, 9-17, 9-16, 9-15, 9-14, 9-13, 9-12, 9-11, 9-10, 10-20, 10-19, 10-18, 10-17, 10-16, 10-15, 10-14, 10-13, 10-12, 10-11, 11-20, 11-19, 11-18, 11-17, 11-16, 11-15, 11-14, 11-13, 11-12, 12-20, 12-19, 12-18, 12-17, 12-16, 12-15, 12-14, 12-13, 13-20, 13-19, 13-18, 13-17, 13-16, 13-15, 13-14, 14-20, 14-19, 14-18, 14-17, 14-16, 14-15, 15-20, 15-19, 15-18, 15-17, 15-16, 16-20, 16-19, 16-18, 16-17, 17-20, 17-19, 17-18, 18-20, 18-19, 19-20, 20, 19, 18, 17, 16, 15, 14, 13, 12, 11, 10, 9, 8, 7, 6, 5, 4, 3, 2, 1, or 0 amino acids in length.

As used herein, "recombinant polypeptide" means a non-naturally occurring protein product, wherein the domains of the recombinant polypeptide are derived from one or more other proteins or artificially derived sequences, such as the mutant knob domain polypeptides of the invention. For example, each shaft domain or shaft domain motif can be derived from a different naturally occurring protein. The recombinant polypeptide may be constructed by a variety of mechanisms including, but not limited to, standard DNA manipulation techniques and chemical assembly via subunit parts of the recombinant polypeptide. The chemical assembly may lead to an equivalent form as the molecular genetic form or alternative associations with equivalent function. In a preferred embodiment, the recombinant polypeptide is produced by standard recombinant DNA techniques. Techniques for such recombinant production and isolation of the recombinant polypeptides of the invention are well within the level of skill in the art based on the teaching herein.

In one embodiment, each shaft domain or shaft domain motifs selected from the group consisting of an Ad3 shaft domain or shaft domain motif, an Ad5 shaft domain motif, an Ad7 shaft domain or shaft domain motif, an Ad11 shaft domain or shaft domain motif, an Ad14 shaft domain or shaft domain motif, an Ad14a shaft domain, or shaft domain motif, combinations thereof, and functional equivalents thereof. The shaft domain or shaft domain motifs required for fiber knob dimerization, which is required for binding to DSG2 and resulting transient opening of intercellular junctions. As used herein, a "shaft domain motif" is any portion of a shaft domain that permits fiber knob dimerization of the recombinant AdB-2/3 fiber polypeptides of the invention. Such shaft domain motifs can be readily determined by those of skill in the art, based on the examples provided below. For example, surface plasmon resonance (SPR) studies using sensors containing immobilized recombinant DSG2 can be used to determine if recombinant polypeptides being assessed bind to DSG2, combined with DSG2 competition studies. Further exemplary studies, such as loss and gain of function analyses, are described in detail in Example 1.

The recombinant polypeptides may comprise between 1 and 22 AdB-2/3 fiber polypeptide shaft domains or shaft domain motifs. Thus, in various embodiments to polypeptides comprise 1-22, 1-21, 1-20, 1-19, 1-18, 1-17, 1-16, 1-15, 1-14, 1-13, 1-12, 1-11, 1-10, 1-9, 1-8, 1-7, 1-6, 1-5, 1-4, 1-3, 1-2, 2-22, 2-21, 2-20, 2-19, 2-18, 2-17, 2-16, 2-15, 2-14, 2-13, 2-12, 2-11, 2-10, 2-9, 2-8, 2-7, 2-6, 2-5, 2-4, 2-3, 3-22, 3-21, 3-20, 3-19, 3-18, 3-17, 3-16, 3-15, 3-14, 3-13, 3-12, 3-11, 3-10, 3-9, 3-8, 3-7, 3-6, 3-5, 3-4, 4-22, 4-21, 4-20, 4-19, 4-18, 4-17, 4-16, 4-15, 4-14, 4-13, 4-12, 4-11, 4-10, 4-9, 4-8, 4-7, 4-6, 4-5, 5-22, 5-21, 5-20, 5-19, 5-18, 5-17, 5-16, 5-15, 5-14, 5-13, 5-12, 5-11, 5-10, 5-9, 5-8, 5-7, 5-6, 6-22, 6-21, 6-20, 6-19, 6-18, 6-17, 6-16, 6-15, 6-14, 6-13, 6-12, 6-11, 6-10, 6-9, 6-8, 6-7, 7-22, 7-21, 7-20, 7-19, 7-18, 7-17, 7-16, 7-15, 7-14, 7-13, 7-12, 7-11, 7-10, 7-9, 7-8, 8-22, 8-21, 8-20, 8-19, 8-18, 8-17, 8-16, 8-15, 8-14, 8-13, 8-12, 8-11, 8-10, 8-9, 9-22, 9-21, 9-20, 9-19, 9-18, 9-17, 9-16, 9-15, 9-14, 9-13, 9-12, 9-11, 9-10, 10-22, 10-21, 10-20, 10-19, 10-18, 10-17, 10-16, 10-15, 10-14, 10-13, 10-12, 10-11, 11-22, 11-21, 11-20, 11-19, 11-18, 11-17, 11-16, 11-15, 11-14, 11-13, 11-12, 12-22, 12-21, 12-20, 12-19, 12-18, 12-17, 12-16, 12-15, 12-14, 12-13, 13-22, 13-21, 13-20, 13-19, 13-18, 13-17, 13-16, 13-15, 13-14, 14-22, 14-21, 14-20, 14-19, 14-18, 14-17, 14-16, 14-15, 15-22, 15-21, 15-20, 15-19, 15-18, 15-17, 15-16, 16-22, 16-21, 16-20, 16-19, 16-18, 16-17, 17-22, 17-21, 17-20, 17-19, 17-18, 18-22, 18-21, 18-20, 18-19, 19-22, 19-21, 19-20, 20-22, 20-21, 21-22, 1, 2, 3, 4, 5, 6, 7, 8, 9, 10, 11, 12, 13, 14, 15, 16, 17, 18, 19, 20, 21, or 22 AdB-2/3 fiber protein shaft domains or shaft domain motifs. Where more than 1 AdB-2/3 fiber protein shaft domain or shaft domain motif is present, each shaft domain or shaft domain motif can be identical, or one or more copies of the shaft domain or shaft domain motif may differ in a single recombinant polypeptide. In a preferred embodiment, the recombinant AdB-2/3 fiber polypeptide has a single shaft domain or shaft domain motif.

In another embodiment, one or more (or all) shaft domains or shaft domain motifs in the recombinant polypeptide comprise or consist of an amino acid sequence according to SEQ ID NO 12:

```
GVL(T/S)LKC(L/V)(T/N)PLTT(T/A)(G/S)GSLQLKVG(G/S)

GLTVD(D/T)T(D/N)G(T/F/S)L(Q/K/E)ENI(G/S/K)(A/V)

(T/N)TPL(V/T)K(T/S)(G/N)HSI(GN)L(S/P)(L/I)G (A/P/N/L)GL(G/Q)(T/I)(D/E)(E/Q)NKLC(T/S/A)KLG (E/Q/N)GLTF(N/D)S(N/S)N(I/S)(C/I)(I/A)(D/N/L)

(D/K)N(I/--)NTL;
``` or SEQ ID NOS:43-48:

```
Ad3 shaft domain motif:     NSIALKNNTL SEQ ID NO: 43

Ad7 shaft domain motif:     NSNNICINDNINTL SEQ ID NO: 44

Ad5 shaft domain motif:     GAITVGNKNNDKLTL SEQ ID NO: 45

Ad11 shaft domain motif:    NSNNICIDDNINTL SEQ ID NO: 46

Ad14 shaft domain motif:    NSNNICIDDNINTL SEQ ID NO: 47

Ad35 shaft domain motif:    GDICIKDSINTL SEQ ID NO: 48
```

In this sequence and other variable sequences shown herein, the variable residues are noted within parentheses, and a "–" indicates that the residue may be absent.

In another embodiment, one or more (or all) shaft domains or shaft domain motifs in the recombinant polypeptide comprise or consist of an amino acid sequence according to SEQ ID NO 13:

```
GVLTLKCLTPLTTTGGSLQLKVGGGLT(V/I)DDTDG(T/F)L(Q/K)

ENI(G/S)ATTPLVKTGHSIGL(S/P)LG(A/P)GLGT(D/N)ENKLC (T/A)KLG(E/Q)GLTFNSNNICI(D/N)DNINTL
``` or SEQ ID NOS: SEQ ID NOS:43-48

In a still further embodiment, one or more (or all) shaft domains or shaft domain motifs in the recombinant polypeptide comprise or consist of an amino acid sequence selected from the group consisting of SEQ ID NO: 14 (Ad3), SEQ ID NO: 15 (Ad7), SEQ ID NO: 16 (Ad11), SEQ ID NO: 17 (Ad14), SEQ ID NO:18 (Ad14a), and SEQ ID NOS:43-48.

The AdB-2/3 fiber polypeptide knob domain comprises or consists of any embodiment or combination of embodiments of the first aspect of the invention (i.e.: any of SEQ ID NOS: 1-11); these polypeptide domains are described in detail in the first aspect of the invention.

As used herein a "dimerization domain" is a peptide sequence that promotes dimerization in the recombinant polypeptide that contains it. Any suitable non-AdB-2/3-derived dimerization domain can be used in the recombinant polypeptide of the invention, so long as it permits dimerization of the recombinant polypeptide and thus binding to DSG2. The dimerization domain is non-AdB-2/3-derived, in that it is not a naturally occurring domain in an AdB-2/3 fiber polypeptide. Non-limiting examples of the numerous dimerization domains known to those of skill in the art and suitable for use in the present invention include, but are not limited to peptide helices containing at least one helix, or a structure formed by a helix, a coil and another helix, etc., coiled coil structures, dimerization domains within, for example, many cell surface signaling receptors, Fc regions or hinge regions of an antibody, leucine zippers, the STAT protein N terminal domain, FK506 binding protein, the LexA protein C-terminal domain, nuclear receptors, the FkpA N-terminal domain, orange carotenoid protein from *A. maxima*, M1 matrix protein from influenza, neuraminidase from influenza virus, *E. coli* fuculose aldolase; and the like. (see, e.g., O'Shea, Science. 254: 539 (1991). Barahmand-Pour et al., Curr. Top. Microbiol. Immunol. 211: 121-128 (1996); Klemm et al., Annu. Rev. Immunol. 16: 569-592 (1998); Klemm et al., Annu. Rev. Immunol. 16: 569-592 (1998); Ho et al., Nature. 382: 822-826 (1996); and Pomeranz et al., Biochem. 37: 965 (1998)). Further examples include residues 325 to 410 in the bovine papillomavirus E2 protein, (Dostatni, N., et al., EMBO J 7 (1988) 3807-3816; Haugen, T., et al. EMBO J 7 (1988) 4245-4253; McBride, A., et al., EMBO J 7 (1988) 533-539; McBride, A., et al., Proc Natl Acad Sci USA 86 (1989) 510-514), Type I deiodinase (D1): DFLVIYIEEAHASDGW (SEQ ID NO: 19) or ADFL--YI-EAH-DGW (SEQ ID NO: 20); HIV-1 Capsid Protein: QGPKEPFRDYVDRFYKTLRA (SEQ ID NO: 21); leucine zipper dimerization motif of yeast GCN4: HMKQL D VEEL S NYHL N VARL K VGER (SEQ ID NO: 22); leucine zipper in *Escherichia coli* transcriptional antiterminator protein; and BglG: GVTQLMREMLQLIK-FQFSLNYQEESLSYQRLVT (SEQ ID NO: 23). In preferred embodiments, the dimerization domain comprises one or more copies of EVSALEK (SEQ ID NO:24) and/or KVSALKE (SEQ ID NO: 25).

It is well within the level of skill in the art to identify appropriate peptide sequences that can serve as dimerization domains, and mutants thereof, in the recombinant polypeptides of the present invention. For example, dimerization of the recombinant AdB-2/3 fiber polypeptides can be assessed by criteria including sedimentation in sucrose gradients, resistance to trypsin proteolysis, and electrophoretic mobility in polyacrylamide gels (Hong and Engler, *Journal of Virology* 70:7071-7078 (1996)).

The recombinant polypeptides may comprise one or more non-AdB-2/3-derived dimerization domains. Thus, in various embodiments, the recombinant polypeptide comprises 1, 2, 3, 4, 5, 6, 7, 8, 9, 10, or more non-AdB-2/3-derived dimerization domains. Where multiple domains are present in a polypeptide, it is preferred that each dimerization domain is the same.

In a preferred embodiment a spacer peptide is located between the dimerization domain and the one or more shaft domains or shaft domain motifs. In a further preferred embodiment, the spacer peptide is a peptide with structural flexibility. Virtually any peptide with structural flexibility can be used. As an example, the flexible peptide may comprise repetitions of amino acid residues, such as Gly-Gly-Gly-Ser (SEQ ID NO: 26), or any other suitable repetition of amino acid residues. In another embodiment, the hinge region of an antibody can be used. The spacer can be any suitable length that maintains the ability of the recombinant polypeptide to dimerize and to maintain binding of the recombinant polypeptide to DSG2.

In one preferred embodiment, the recombinant AdB-2/3 polypeptide comprises one or more shaft domains that each comprise or consist of an Ad3 shaft domain (SEQ ID NO: 14)

This preferred embodiment can be used with any embodiment or combination of embodiments described herein. For example, any suitable knob domain can be used, and any suitable dimerization domain can be used, including but not limited to one or more copies of EVSALEK (SEQ ID NO:24) and/or KVSALKE (SEQ ID NO: 25). Similarly any suitable spacer peptides can be used between the dimerization domain and the shaft domain or shaft domain motif and/or between the shaft domain or shaft domain motif and the knob domain. In a most preferred embodiment, the recombinant AdB-2/3 polypeptide comprises or consists of JO-1 (SEQ ID NO:27), or a multimer thereof (such as a dimer).

The recombinant polypeptides may comprise further domains, such as a domain for isolation of the polypeptide and/or a detection domain. An isolation domain can be added to facilitate purification/isolation of the polypeptide following, for example, recombinant polypeptide production. Any suitable isolation domain can be used, including but not limited to HIS, CBP, CYD (covalent yet dissociable NorpD peptide), Strep II, FLAG, HPC (heavy chain of protein C) peptide tags, GST and MBP affinity tags. As used herein, "detection domain" means one or more amino acid sequence that can be detected. Any suitable detection domain can be used, including but not limited to, inherently fluorescent proteins (e.g. Green Fluorescent Proteins and fluorescent proteins from nonbioluminescent Anthozoa species), cofactor-requiring fluorescent or luminescent proteins (e.g. phycobiliproteins or luciferases), and epitopes recognizable by specific antibodies or other specific natural or unnatural binding probes, including, but not limited to, dyes, enzyme cofactors and engineered binding molecules, which are fluorescently or luminescently labeled.

In further preferred embodiments, the recombinant AdB-2/3 fiber polypeptide comprises or consists of the amino acid sequence of one of the following (a) (M/-)

(SEQ ID NO: 28)

GSKVSALKEKVSALKEKVSALKEKVSALKEKVSALKEGSGGGSGGGSGGG

SNSIALKNN

TLWTGPKPEANCIIEYGKQNPDSKLTLIINKNGGIVNGYVTLMGASDYVN

TLFKNKNVSINVELYFDATGHILPDSSSLKTDLELKYKQTADFSARGFMP

STTAYPFVLPNAGTHNENFIFGQCNYYKASDGALFPLEVTVMLNKRLPDS

RTSYVMTFLWSLNAGLAPETTQATLITSPFTFSYIREDD;

-continued (b) (M/-)
(SEQ ID NO: 29)
GSKVSALKEKVSALKEKVSALKEKVSALKEKVSALKEGSGGGSGGGSGGG

SNSIALKNN

TLWTGPKPEANCIIEYGKQNPDSKLTLILVKNGGIVNGYVTLMGASDYVN

TLFKNKNVSINVELYFDATGHILPDSSSLKTDLELEYKQTADSARGFMPS

TTAYFFVLPNAGTHNENYIFGQCYYKASDGALFPLEVTVMLNKRLPDSRT

SYVMTFLWSLNAGLAPETTQATLITSPFTFSYIREDD;

(c) (M/-)
(SEQ ID NO: 30)
GSKVSALKEKVSALKEKVSALKEKVSALKEKVSALKEGSGGGSGGGSGGG

SNSIALKNN

TLWTGPKPEANCIIEYGKQNPDSKLTLILVKNGGIVNGYVTLMGASDYVN

TLFKNKNVSINVELYFDATGHILPDSSSLKTDLELKYKQTADFSARGFMP

STTAYPFVLPNAGTHNENYIFGQCYYKASDGALFPLEVTVMLNKRLPDSR

TSYVMTFLWSLSAGLAPETTQATLITSPFRFSYIREDD;

(d) (M/-)
(SEQ ID NO: 31)
GSKVSALKEKVSALKEKVSALKEKVSALKEKVSALKEGSGGGSGGGSGGG

SNSIALKNN

TLWTGPKPEANCIIEYGKQNPDSKLTLILVKNGGIVNGYVTLMGASDYVN

TLFKNKNVSINVELYFDATGHILPDSSSLKTDLELKYKQTADFSARGFMP

STTAYPFDLPNAGTHNENYIFGQCYYKASDGALFPLEVTVMLNKRLPDSR

TSYVMTFLWSLNAGLAPETTQATLITSPFTFSYIREDD;

(e) (M/-)
(SEQ ID NO: 32)
GSKVSALKEKVSALKEKVSALKEKVSALKEKVSALKEGSGGGSGGGSGGG

SNSIALKNN

TLWTGPKPEANCIIEYGKQNPDSKLTLILVKNGGLVNGYVTLMGASDYVN

TLFKNKNVSINVELYFDATGHILPDSSSLKTDLEPKYKQTADFSARGFMP

STTAYPFVLPNAGTHNENYIFGQCYYEASDGALFPLEVIVMLNKRLPDSR

TSYVMTFLAATSLNAGLAPETTQATLITSPFTFSYIREDD;

(f) (M/-)
(SEQ ID NO: 33)
GSKVSALKEKVSALKEKVSALKEKVSALKEKVSALKEGSGGGSGGGSGGG

SNSIALKNN

TLWTGPKPEANCIIEYGKQNPDSKLTLILVKNGGIVNGYVTLMGASDYV

NTLFKNKNVSINVELYFDATGHILPDSSSLKTDLELKYKQTADLSARGFM

PSTTAYPFVLPNAGTHNENYIFGQCYYKASDGALFPLEVTVMLNKRLPDS

RTSYVMTFLWSLNAGLAPETTQATLITSPFTFSYIREDD;
and (g) (M/-)
(SEQ ID NO 34)
GSKVSALKEKVSALKEKVSALKEKVSALKEKVSALKEGSGGGSGGGSGGG

SNSIALKNN

TLWTGPKPEANCIIEYGKQNPDSKLTLILVKNGGIVNGYVTLMGASDYV

NTLFKNKNVSINVELYFDATGHILPDSSSLKTDLELKYKQTADFSARGFM

PSTTAYPFVLPNAGTHNGNYIFGQCYYEASDGALFPLEVTVMLNKRLPDS

RTSYVMTFLWSLNAGLAPETTQATLITSPFTFSYIREDD.

In another embodiment, the recombinant polypeptides are in a multimeric form, such as a dimer, trimer, etc. In a preferred embodiment, a multimer comprises a dimer formed by dimerization through the dimerization domains in each homotrimer (ie: a polypeptide is a homotrimer through trimerization of the knob domain) In multimeric form (such as a dimer), the recombinant polypeptides comprise AdB-2/3 fiber multimers, and can be used in the various methods of the invention discussed above. As will be understood by those of skill in the art, such multimers may comprise multimers of identical recombinant polypeptide of the invention, or may comprise multimers of different recombinant polypeptides of the invention. In one embodiment, the dimerization domains are the same in each recombinant polypeptide forming part of the multimer. In another embodiment, the dimerization domains are different in each recombinant polypeptide forming part of the multimer. In another embodiment, the shaft and/or knob domains are the same in each recombinant polypeptide forming part of the multimer. In another embodiment, the shaft and/or knob domains are different in each recombinant polypeptide forming part of the multimer.

AdB-2/3 fiber multimerization can be determined according to methods well known to the practitioners in the art. For example, multimerization of the recombinant AdB-2/3 fiber constructs can be assessed by criteria including sedimentation in sucrose gradients, resistance to trypsin proteolysis, and electrophoretic mobility in polyacrylamide gels (Hong and Engler, *Journal of Virology* 70:7071-7078 (1996)). Regarding electrophoretic mobility, the fiber multimer is a very stable complex and will run at a molecular weight consistent with that of a multimer when the sample is not boiled prior to SDS-PAGE. Upon boiling, however, the multimeric structure is disrupted and the protein subsequently runs at a size consistent with the protein monomer.

The recombinant polypeptides, or multimeric versions thereof, may be stored in solution or frozen.

In another embodiment, the recombinant polypeptides of the invention are combined with (such as conjugated to) one or more therapeutics for a disorder associated with epithelial tissue. Such conjugates can be used, for example, in the therapeutic methods of the invention. Methods for conjugating the polypeptides of the invention to a therapeutic of interest, such as by covalent binding or chemical cross-linking, are well known to those of skill in the art. Any suitable therapeutic can be used to form a conjugate according to this embodiment of the invention, including but not limited to tumor stroma degrading compounds (such as relaxin), alkylating agents, angiogenesis inhibitors, antibodies, antimetabolites, antimitotics, antiproliferatives, aurora kinase inhibitors, apoptosis promoters (for example, Bcl-xL, Bcl-w and Bfl-1) inhibitors, activators of death receptor pathway, Bcr-Abl kinase inhibitors, BiTE (Bi-Specific T cell Engager) antibodies, biologic response modifiers, cyclin-dependent kinase inhibitors, cell cycle inhibitors, cyclooxygenase-2 inhibitors, growth factor inhibitors, heat shock protein (HSP)-90 inhibitors, demethylating agents, histone deacetylase (HDAC) inhibitors, hormonal therapies, immunologicals, inhibitors of apoptosis proteins (IAPs) intercalating antibiotics, kinase inhibitors, mammalian target of rapamycin inhibitors, microRNA's mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, proteasome inhibitors, purine analogs, pyrimidine analogs, receptor tyrosine kinase inhibitors, retinoids/deltoids plant alkaloids, small inhibitory ribonucleic acids (siRNAs), topoisomerase inhibitors and the like.

Exemplary therapeutics falling within these various classes include, but are not limited to: docetaxel, doxorubicin, irinotecan, paclitaxel (Taxol®), paclitaxel albumin bound particles (Abraxane®), doxorubicin HCL liposome (Doxil®), BiTE antibodies such as adecatumumab (Micromet MT201), blinatumomab (Micromet MT103) and the like, siRNA-based therapeutics, alkylating agents including altretamine, AMD-473, AP-5280, apaziquone, bendamustine, brostallicin, busulfan, carboquone, carmustine (BCNU), chlorambucil, CLORETAZINE.® (laromustine, VNP 40101M), cyclophosphamide, dacarbazine, decitabine, 5'-azacytidine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, TREANDA® (bendamustine), treosulfan, rofosfamide and the like; angiogenesis inhibitors including endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs, vascular endothelial growth factor receptor tyrosine kinase (VEGFR) inhibitors and the like; antimetabolites including ALIMTA® (pemetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR (5-ethynyl-1-.beta.-D-ribofuranosylimidazole-4-carboxamide), enocitabine, ethnyleytidine, fludarabine, 5-fluorouracil alone or in combination with leucovorin, GEMZAR® (gemcitabine), hydroxyurea, ALKERAN® (melphalan), mercaptopurine, 6-mercaptopurine riboside, methotrexate, methotrexate analogs (such as trimetrexate and pralatraxate), mycophenolic acid, nelarabine, nolatrexed, ocfosfate, pelitrexol, pentostatin, raltitrexed, Ribavirin, triapine, trimetrexate, S-1, tiazofurin, tegafur, TS-1, vidarabine, and the like; Bcl-2 protein inhibitors including AT-101 ((−)gossypol), GENASENSE® (G3139 or oblimersen (Bcl-2-targeting antisense oligonucleotide)), IPI-194, IPI-565, N-(4-(4-((4'-chloro(1,1'-biphenyl)-2-yl) methyl)piperazin-1-yl)benzoyl)-4--(((1R)-3-(dimethylamino)-1-((phenylsulfanyl)methyl)propyl)amino)-3-nitrobe-nzenesulfonamide) (ABT-737), N-(4-(4-((2-(4-chlorophenyl)-5,5-dimethyl-1-cyclohex-1-en-1-yl)methyl) pip-erazin-1-yl)benzoyl)-4-(((1R)-3-(morpholin-4-yl)-1-((phenylsulfanyl)methyl-)propyl)amino)-3-((trifluoromethyl)sulfonyl)benzenesulfonamide (ABT-263), GX-070 (obatoclax) and the like; Bcr-Abl kinase inhibitors include DASATINIB® (BMS-354825), GLEEVEC® (imatinib) and the like; CDK inhibitors including AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like; EGFR inhibitors including ABX-EGF, anti-EGFR immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib) and the like; ErbB2 receptor inhibitors include CP-724-714, CI-1033 (canertinib), HERCEPTIN® (trastuzumab), TYKERB® (lapatinib), OMNITARG® (2C4, petuzumab), TAK-165, GW-572016 (ionafarnib), GW-282974, EKB-569, PI-166, dHER2 (HER2 vaccine), APC-8024 (HER-2 vaccine), anti-HER/2neu bispecific antibody, B7.her2IgG3, AS HER2 trifunctional bispecific antibodies, mAb AR-209, mAb 2B-1 and the like; histone deacetylase inhibitors include romidepsin, LAQ-824, MS-275, trapoxin, suberoylanilide hydroxamic acid (SAHA), TSA, valproic acid and the like; HSP-90 inhibitors including 17-AAG-nab, 17-AAG, CNF-101, CNF-1010, CNF-2024, 17-DMAG, geldanamycin, IPI-504, KOS-953, MYCOGRAB® (human recombinant antibody to HSP-90), NCS-683664, PU24FC1, PU-3, radicicol, SNX-2112, STA-9090 VER49009 and the like; activators of death receptor pathways including TRAIL, antibodies or other agents that target TRAIL or death receptors (e.g., DR4 and DR5) such as Apomab, conatumumab, ETR2-ST01, GDC0145, (lexatumumab), HGS-1029, LBY-135, PRO-1762 and trastuzumab; platinum chemotherapeutics include cisplatin, ELOXATIN® (oxaliplatin) eptaplatin, lobaplatin, nedaplatin, PARAPLATIN® (carboplatin), satraplatin, picoplatin and the like; VEGFR inhibitors including AVASTIN® (bevacizumab), ABT-869, AEE-788, axitinib (AG-13736), AZD-2171, CP-547, 632, IM-862, MACUGEN (pegaptamib), NEXAVAR® (sorafenib, BAY43-9006), pazopanib (GW-786034), vatalanib (PTK-787, ZK-222584), SUTENT® (sunitinib, SU-11248), VEGF trap, ZACTIMAThi (vandetanib, ZD-6474) and the like; dendritic cell therapy (sipuleucel-T, Provenge®); topoisomerase inhibitors including aclarubicin, 9-aminocamptothecin, amonafide, amsacrine, becatecarin, belotecan, BN-80915, CAMPTOSAR® (irinotecan hydrochloride), camptothecin, dexrazoxine, diflomotecan, edotecarin, ELLENCE® or PHARMORUBICIN® (epirubicin), etoposide, exatecan, abraxane, irenotecan, 10-hydroxycamptothecin, gimatecan, lurtotecan, mitoxantrone, orathecin, pirarbucin, pixantrone, rubitecan, sobuzoxane, SN-38, tafluposide, topotecan and the like; antibodies including AVASTIN® (bevacizumab), CD40-specific antibodies, chTNT-1/B, denosumab, ERBITUX® (cetuximab), HUMAX-CD4® (zanolimumab), IGF I R-specific antibodies, lintuzumab, PANOREX® (edrecolomab), RENCAREX® (WX G250), RITUXAN® (rituximab), ticilimumab, trastuzimab and the like; hormonal therapies including ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL® (flutamide), EVISTA® (raloxifene), AFEMA® (fadrozole), FARESTON® (toremifene), FASLODEX® (fulvestrant), FEMARA® (letrozole), formestane, glucocorticoids, HECTOROL® (doxercalciferol), RENAGEL® (sevelamer carbonate), lasofoxifene, leuprolide acetate, MEGACE® (megesterol), MIFEPREX® (mifepristone), NILANDRON® (nilutamide), NOLVADEX® (tamoxifen citrate), PLENAXIS® (abarelix), prednisone, PROPECIA® (finasteride), rilostane, SUPREFACT® (buserelin), TRELSTAR® (luteinizing hormone releasing hormone (LHRH)), VANTAS® (Histrelin implant), VETORYL® (trilostane or modrastane), ZOLADEX® (fosrelin, goserelin) and the like; immunologicals including interferon alpha, interferon alpha-2a, interferon alpha-2b, interferon beta, interferon gamma-1a, ACTIMMUNE® (interferon gamma-1b) or interferon gamma-n1, combinations thereof and the like. Other agents include ALFAFERONE® (IFN-alpha), BAM-002 (oxidized glutathione), BEROMUN® (tasonermin), BEXXAR® (tositumomab), CAMPATH® (alemtuzumab), CTLA4 (cytotoxic lymphocyte antigen 4), decarbazine, deniieukin, epratuzumab, GRANOCYTE® (lenograstim), lentinan, leukocyte alpha interferon, imiquimod, MDX-010 (anti-CTLA-4), melanoma vaccine, mitumomab, molgramostim, MYLOTARG.™. (gemtuzumab ozogamicin), NEUPOGEN®, (filgrastim), OncoVAC-CL, OVAREX® (oregovomab), pemtumomab (Y-muHMFG1), PROVENGE® (sipuleucel-T), sargaramostim, sizofilan, teceleukin, THERACYS® (*Bacillus* Calmette-Guerin), ubenimex, VIRULIZIN® (immunotherapeutic, Lorus Pharmaceuticals), Z-100 (Specific Substance of Maruyama (SSM)), WF-10 (Tetrachlorodecaoxide (TCDO)), PROLEUKIN® (aldesleukin), ZADAXIN® (thymalfasin), ZENAPAX® (daclizumab), ZEVALIN®, (90Y-Ibritumomab tiuxetan) and the like; ofatumumab; biological response modifiers agents including krestin, lentinan, sizofuran, picibanil PF-3512676 (CpG-8954), ubenimex and the like; pyrimidine analogs include cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL® (triacetyluridine troxacitabine) and the like; purine analogs including LANVIS® (thioguanine) and PURI-NETHOL® (mercaptopurine).; antimitotic agents including batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881 (larotaxel), vinflunine, ZK-EPO (synthetic epothilone) and the like; and other chemotherapeutic agents such as ABRAXANE® (ABI-007), ABT-100 (farnesyl transferase inhibitor), ADVEXIN® (AdSCMV-p53 vaccine), ALTOCOR® or MEVACOR® (lovastatin), AMPLIGE®. (poly I:poly C12U, a synthetic RNA), APTOSYN® (exisulind), AREDIA® (pamidronic acid), arglabin, L-asparaginase, atamestane (1-methyl-3,17-dione-androsta-1,4-diene), AVAGE® (tazarotene), AVE-8062 (combreastatin derivative) BEC2 (mitumomab), cachectin or cachexin (tumor necrosis factor), canvaxin (vaccine), CEAVAC® (cancer vaccine), CELEUK® (celmoleukin), CEPLENE® (histamine dihydrochloride), CERVARIX® (human papillomavirus vaccine), CHOP® (C: CYTOXAN® (cyclophosphamide); H: ADRIAMYCIN® (hydroxydoxorubicin); O: Vincristine (ONCOVIN®); P: prednisone), CYPAT® (cyproterone acetate), combrestatin A4P, DAB(389)EGF (catalytic and translocation domains of diphtheria toxin fused via a His-Ala linker to human epidermal growth factor) or TransMID-107R® (diphtheria toxins), dacarbazine, dactinomycin, 5,6-dimethylxanthenone-4-acetic acid (DMXAA), eniluracil, EVIZON.™. (squalamine lactate), DIMERICINE® (T4N5 liposome lotion), discodermolide, DX-8951f (exatecan mesylate), enzastaurin, EPO906 (epithilone B), GARDASIL® (quadrivalent human papillomavirus (Types 6, 11, 16, 18) recombinant vaccine), GASTRIMMUNE®, GENASENSE®, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-*pseudomonas* exotoxin, interferon-.alpha., interferon-.gamma., JUNOVAN® or MEPACT® (mifamurtide), lonafarnib, 5,10-methylenetetrahydrofolate, miltefosine (hexadecylphosphocholine), NEOVASTAT® (AE-941), NEUTREXIN® (trimetrexate glucuronate), NIPENT® (pentostatin), ONCONASE® (a ribonuclease enzyme), ONCOPHAGE® (melanoma vaccine treatment), ONCOVAX® (IL-2 Vaccine), ORATHECIN® (rubitecan), OSIDEM® (antibody-based cell drug), OVAREX® MAb (murine monoclonal antibody), paclitaxel, PANDIMEX® (aglycone saponins from *ginseng* comprising 20(S)protopanaxadiol (aPPD) and 20(S)protopanaxatriol (aPPT)), panitumumab, PANVAC®-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (*Streptomyces* staurospores), talabostat (PT100), TARGRETIN® (bexarotene), TAXOPREXIN® (DHA-paclitaxel), TELCYTA® (canfosfamide, TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFERADE® (adenovector: DNA carrier containing the gene for tumor necrosis factor-.alpha.), TRACLEER® or ZAVESCA® (bosentan), tretinoin (Retin-A), tetrandrine, TRISENOX®, (arsenic trioxide), VIRULIZIN®, ukrain (derivative of alkaloids from the greater celandine plant), vitaxin (anti-alphavbeta3 antibody), XCYTRIN® (motexafin gadolinium), XINLAY® (atrasentan), XYOTAX® (paclitaxel poliglumex), YONDELIS® (trabectedin), ZD-6126, ZINECARD® (dexrazoxane), ZOMETA® (zolendronic acid), crizotinib, zorubicin and the like.

In another preferred embodiment, the therapeutic comprises a compound that binds to desmoglein-2; preferably a compound that binds to DSG2 and opens up tight junctions.

In other embodiments, the therapeutic comprises radioactive particles/radiation therapy. Any suitable radioactive therapy or particle can be used as deemed appropriate by an attending physician, including but not limited to cobalt-60, iodine-131, iridium-192, strontium-89, samarium 153, rhenium-186 and lead-212.

In a preferred embodiment, the therapeutic is an anti-tumor therapeutic and comprises a chemotherapeutic or anti-tumor monoclonal antibody as described herein. In a further preferred embodiment, the anti-tumor therapeutic comprises an antibody selected from the group consisting of trastuzumab, cetuximimab, petuzumab, apomab, conatumumab, lexatumumab, bevacizumab, bevacizumab, denosumab, zanolimumab, lintuzumab, edrecolomab, rituximab, ticilimumab, tositumomab, alemtuzumab, epratuzumab, mitumomab, gemtuzumab ozogamicin, oregovomab, pemtumomab daclizumab, panitumumab, catumaxomab, ofatumumab, and ibritumomab. Non-limiting examples of useful anti-tumor mAb and their specific uses are listed in Table 1, and as further described in Campoli, M., et al., *Principles & Practice of Oncology* 23(1&2):1-19 (2009), incorporated herein by reference.

TABLE 1

Tumor-Antigen Specific mAbs for Cancer Treatment

| Antibody | Isotype | Target | Disease Indication |
| --- | --- | --- | --- |
| SGN-75 | humanized IgG1 | CD70 | solid tumors, including renal cell cancer, CD70 + hematologic malignancies |
| Trastuzumab | humanized IgG1 | HER2/neu | HER2/neu(+) breast cancer* |

TABLE 1-continued

Tumor-Antigen Specific mAbs for Cancer Treatment

| Antibody | Isotype | Target | Disease Indication |
|---|---|---|---|
| Cetuximab | Chimeric IgG1 | EGFR | EGFR(+) colon cancer* |
| Panitumumab | Fully human IgG2 | EGFR | EGFR(+) colon cancer* |
| Matuzumab | Humanized IgG1 | EGFR | non-squamous non-small cell lung cancer (NSCLC), head and neck squamous cell carcinoma (HNSCC), breast and pancreatic cancer, colon cancer (CC) |
| Pertuzumab | Humanized IgG1 | EGFR | NSCLC, HNSCC, CC, breast and ovarian cancer |
| Ipilimumab (MDX-010) | Humanized IgG1 | CTLA-4 | NSCLC, RCC, metastatic melanoma |
| Tremelimumab (CP-675, 206) | Humanized IgG1 | CTLA-4 | NSCLC, RCC, metastatic melanoma |
| Sibrotuzumab | Humanized IgG1 | FAP** | NSCLC, CC |
| DR-4-specific mapatumumab (TRM-1, HGS-ETR1) | Humanized IgG1 | TRAIL | NSCLC, CC, ovarian cancer, multiple myeloma, |
| DR-5-specific lexatumumab (HGS-ETR2, TRA-8) | Humanized IgG1 | TRAIL | solid tumors |
| Cantuzumab mertansine | Humanized IgG1-maytansinoid | CanAg*** | CC, pancreatic cancer |
| Bevacizumab (Avastatin) | humanized IgG1 | vascular endothelial growth factor (VEGF) | colon cancer*, non-squamous non-small cell lung cancer (NSCLC)*, metastatic breast cancer* |

In another embodiment, the recombinant polypeptides of the invention are combined with (such as conjugated to) one or more diagnostic or imaging agents. The recombinant polypeptides of the invention, and multimers thereof, have broad application for delivery of any diagnostic, imaging agent, or other compound to epithelial tissue comprising intercellular junctions where access to a target of interest can be limited. In various non-limiting embodiments, the imaging agents can include any chemical compound that can produce a detectable signal, either directly or indirectly. Many such imaging agents are known to those of skill in the art. Examples of imaging agents suitable for use in the disclosed methods and compositions are radioactive isotopes, fluorescent molecules, magnetic particles (including nanoparticles), metal particles (including nanoparticles), phosphorescent molecules, enzymes, antibodies, ligands, and combinations thereof, while diagnostic agents may comprise a compound that is a diagnostic marker for a particular epithelial disorder bound to the such an imaging agent. Methods for detecting and measuring signals generated by imaging agents are also known to those of skill in the art. For example, radioactive isotopes can be detected by scintillation counting or direct visualization; fluorescent molecules can be detected with fluorescent spectrophotometers; phosphorescent molecules can be detected with a spectrophotometer or directly visualized with a camera; enzymes can be detected by detection or visualization of the product of a reaction catalyzed by the enzyme; antibodies can be detected by detecting a secondary detection label coupled to the antibody. In one preferred embodiment, the imaging agent and/or diagnostic is one that can be used to detect a tumor, whether by direct tumor binding, or by coupling of the imaging or diagnostic agent with a compound that can bind the tumor.

In various embodiments, the imaging agent can be a fluorescent imaging agent, while diagnostic agents may comprise a compound that is a diagnostic marker for a particular epithelial disorder bound to the fluorescent imaging agent. A fluorescent imaging agent is any chemical moiety that has a detectable fluorescence signal. This imaging agent can be used alone or in combination with other imaging agents. Examples of suitable fluorescent agents that can be used in the compositions and methods disclosed herein include, but are not limited to, fluorescein (FITC), 5-carboxyfluorescein-N-hydroxysuccinimide ester, 5,6-carboxymethyl fluorescein, nitrobenz-2-oxa-1,3-diazol-4-yl (NBD), fluorescamine, OPA, NDA, indocyanine green dye, the cyanine dyes (e.g., Cy3, Cy3.5, Cy5, Cy5.5 and Cy7), 4-acetamido-4'-isothiocyanatostilbene-2,2'disulfonic acid, acridine, acridine isothiocyanate, 5-(2'-aminoethyl)aminonaphthalene-1-sulfonic acid (EDANS), 4-amino-N-[3-vinylsulfonyl)phenylinaphthalimide-3,5 disulfonate, N-(4-anilino-1-naphthyl)maleimide, anthranilamide, BODIPY, Brilliant Yellow, coumarin, 7-amino-4-methylcoumarin (AMC, Coumarin 120), 7-amino-4-trifluoromethylcoumarin (Coumaran 151), cyanosine, 4',6-diaminidino-2-phenylindole (DAPI), 5',5"-dibromopyrogallol-sulfonaphthalein (Bromopyrogallol Red), 7-diethylamino-3-(4'-isothiocyanatophenyl)-4-methylcoumarin diethylenetriamine pentaacetate, 4,4'-diisothiocyanatodihydro-stilbene-2,2'-disulfonic acid, 4,4'-diisothiocyanatostilbene-2,2'-disulfonic acid, 5-[dimethylamino]naphthalene-1-sulfonyl chloride (DNS, dansylchloride), 4-(4'-dimethylaminophenylazo)benzoic acid (DABCYL), 4-dimethylaminophenylazophenyl-4'-isothiocyanate (DABITC), eosin, eosin isothiocyanate, erythrosin B, erythrosine, isothiocyanate, ethidium bromide, ethidium, 5-carboxyfluorescein (FAM), 5-(4,6-dichlorotriazin-2-yl)aminofluorescein (DTAF), 2',7'-dimethoxy-4'5'- dichloro-6-carboxyfluorescein (JOE), fluorescein isothiocyanate, IR144, IR1446, Malachite Green isothiocyanate, 4-methylumbelliferone, ortho cresolphthalein, nitrotyrosine, pararosaniline, Phenol Red, B-phycoerythrin, o-phthaldialdehyde, pyrene, pyrene butyrate, succinimidyl 1-pyrene butyrate, Reactive Red 4 (Cibacron[R] Brilliant Red 3B-A), 6-carboxy-X-rhodamine (ROX), 6-carboxyrhodamine (R6G), lissamine rhodamine B sulfonyl chloride rhodamine (Rhod), 5,6-tetramethyl rhodamine, rhodamine B, rhodamine 123, rhodamine X isothiocyanate, sulforhodamine B, sulforhodamine 101, sulfonyl chloride derivative of sulforhodamine 101 (Texas Red), N,N,N',N'-tetramethyl-6-carboxyrhodamine (TAMRA), tetramethyl rhodamine, tetramethyl rhodamine isothiocyanate (TRITC), riboflavin, rosolic acid, coumarin-6, and the like, including combinations thereof. These fluorescent imaging moieties can be obtained from a variety of commercial sources, including Molecular Probes, Eugene, Oreg. and Research Organics, Cleveland, Ohio, or can be synthesized by those of ordinary skill in the art.

In another example, the imaging agents can comprise a Magnetic Resonance Imaging (MRI) agent, while diagnostic agents may comprise a compound that is a diagnostic marker for a particular epithelial disorder bound to the MRI agent. A MRI agent is any chemical moiety that has a detectable magnetic resonance signal or that can influence (e.g., increase or shift) the magnetic resonance signal of another agent. This type of imaging agent can be used alone or in combination with other imaging agent. In still another example, a gadolinium-based MRI agent can serve as an imaging agent. An example of a suitable MRI agent that can be incorporated into the disclosed imaging agents is para-amino-benzyl diethylenetriaminepentaacetic acid (p-$NH_2$-Bz-DTPA, Compound 7), a conjugable form of diethylenetriaminepentaacetic acid (DTPA), which is known to strongly bind gadolinium and is approved for clinical use as a magnetic resonance contrast agent. Incorporation of an MRI agent on a large macromolecule such as a dendrimeric substrate as disclosed herein can allow large T1 relaxation (high contrast) and multiple copies of agent on a single molecule, which can increase signal. By combining an MRI imaging agent and, for example, a fluorescent imaging agent, the resulting agent can be detected, imaged, and followed in real-time via MR I. Other imaging agents include PET agents that can be prepared by incorporating an 18F or a chelator for 64Cu or 68Ga. Also, addition of a radionuclide can be used to facilitate SPECT imaging or delivery of a radiation dose, while diagnostic agents may comprise a compound that is a diagnostic marker for a particular epithelial disorder bound to the PET agent.

In some embodiments, the diagnostic agent is a diagnostic imaging agent, including but not limited to position emission tomography (PET) agents, computerized tomography (CT) agents, magnetic resonance imaging (MRI) agents, nuclear magnetic imaging agents (NMI), fluoroscopy agents and ultrasound contrast agents. Such diagnostic agents include radioisotopes of such elements as iodine (I), including $^{123}$I, $^{125}$I, $^{131}$I etc., barium (Ba), gadolinium (Gd), technetium (Tc), including $^{99}$Tc, phosphorus (P), including $^{31}$P, iron (Fe), manganese (Mn), thallium (Tl), chromium (Cr), including $^{51}$Cr, carbon (C), including $^{14}$C, or the like, fluorescently labeled compounds, or their complexes, chelates, adducts and conjugates. Any suitable PET agents can be used, including but not limited to carbon-11, nitrogen-13, oxygen-15, fluorine-18, 11C-metomidate, and glucose analogues thereof, including but not limited to fludeoxyglucose (a glucose analog labeled with fluorine-18.

In other embodiments, the diagnostic agent is a marker gene that encode proteins that are readily detectable when expressed in a cell (including, but not limited to, beta-galactosidase, green fluorescent protein, luciferase, and the like) and labeled nucleic acid probes (e.g., radiolabeled or fluorescently labeled probes). In some embodiments, covalent conjugation of diagnostic or imaging agents to the AdB-2/3 multimers provided herein is achieved according to a variety of conjugation processes. In other embodiments, the diagnostic agent is non-covalently associated with AdB-2/3 multimers provided.

In another aspect, the present invention provides nucleic acids encoding the polypeptide or any embodiment of the invention. The nucleic acids may comprise RNA or DNA, and can be prepared and isolated using standard molecular biological techniques, based on the teachings herein. The nucleic acids may comprise additional domains useful for promoting expression and/or purification of the encoded protein, including but not limited to polyA sequences, modified Kozak sequences, and sequences encoding epitope tags, export signals, and secretory signals, nuclear localization signals, and plasma membrane localization signals.

In a further aspect, the present invention provides recombinant expression vectors comprising the nucleic acid of any aspect of the invention operatively linked to a promoter. "Recombinant expression vector" includes vectors that operatively link a nucleic acid coding region or gene to any promoter capable of effecting expression of the gene product. The promoter sequence used to drive expression of the disclosed nucleic acids in a mammalian system may be constitutive (driven by any of a variety of promoters, including but not limited to, CMV, SV40, RSV, actin, EF) or inducible (driven by any of a number of inducible promoters including, but not limited to, tetracycline, ecdysone, steroid-responsive). The construction of expression vectors for use in transfecting prokaryotic cells is also well known in the art, and thus can be accomplished via standard techniques. (See, for example, Sambrook, Fritsch, and Maniatis, in: Molecular Cloning, A Laboratory Manual, Cold Spring Harbor Laboratory Press, 1989; *Gene Transfer and Expression Protocols*, pp. 109-128, ed. E. J. Murray, The Humana Press Inc., Clifton, N.J.), and the Ambion 1998 Catalog (Ambion, Austin, Tex.). The expression vector must be replicable in the host organisms either as an episome or by integration into host chromosomal DNA, and may comprise any other components as deemed appropriate for a given use, including but not limited to selection markers such as an antibiotic-resistance gene.

In a still further aspect, the present invention provides host cells comprising the recombinant expression vectors disclosed herein, and progeny thereof, wherein the host cells can be either prokaryotic or eukaryotic. The cells can be transiently or stably transfected. Such transfection of expression vectors into prokaryotic and eukaryotic cells can be accomplished via any technique known in the art, including but not limited to standard bacterial transformations, calcium phosphate co-precipitation, electroporation, or liposome mediated-, DEAE dextran mediated-, polycationic mediated-, or viral mediated transfection. (See, for example, *Molecular Cloning: A Laboratory Manual* (Sambrook, et al., 1989, Cold Spring Harbor Laboratory Press; *Culture of Animal Cells: A Manual of Basic Technique*, $2^{nd}$ Ed. (R. I. Freshney. 1987. Liss, Inc. New York, N.Y.). Techniques utilizing cultured cells transfected with expression vectors to produce quantities of polypeptides are well known in the art.

In another aspect, the present invention provides pharmaceutical compositions, comprising (a) an AdB-2/3 fiber multimer of the present invention; and (b) a pharmaceutically acceptable carrier.

The AdB-2/3 fiber multimer can be any such multimer as described herein according to any aspect, embodiment, or combination of embodiments of the invention that incorporates a mutant knob domain polypeptide of any embodiment of the first aspect of the invention (i.e.: SEQ ID NOS:1-11).

The pharmaceutical composition may further comprise one or more therapeutic for treating a disorder associated with epithelial tissue, including but not limited to those disclosed above. In a preferred embodiment, the therapeutic is an anti-tumor therapeutic and comprises a chemotherapeutic or anti-tumor monoclonal antibody as described herein. In a further preferred embodiment, the anti-tumor therapeutic comprises an antibody selected from the group consisting of trastuzumab, cetumiximab, petuzumab, Apomab, conatumumab, lexatumumab, bevacizumab, bevacizumab, denosumab, zanolimumab, lintuzumab, edrecolomab, rituximab, ticilimumab, tositumomab, alemtuzumab, epratuzumab, mitumomab, gemtuzumab ozogamicin, oregovomab, pemtumomab daclizumab, panitumumab, catumaxomab, ofatumumab, and ibritumomab.

The pharmaceutically acceptable carrier is non-toxic, biocompatible and is selected so as not to detrimentally affect the biological activity of the multimers (and any other therapeutic agents combined therewith). Exemplary pharmaceutically acceptable carriers for peptides are described in U.S. Pat. No. 5,211,657 to Yamada. The compositions may be formulated into preparations in solid, semi-solid, gel, liquid or gaseous forms such as tablets, capsules, powders, granules, ointments, solutions, suppositories, inhalants, and injections, allowing for oral, parenteral, or surgical administration. Suitable carriers for parenteral delivery via injectable, infusion, or irrigation and topical delivery include distilled water, physiological phosphate-buffered saline, normal or lactated Ringer's solutions, dextrose solution, Hank's solution, or propanediol. In addition, sterile, fixed oils may be employed as a solvent or suspending medium. For this purpose any biocompatible oil may be employed including synthetic mono- or diglycerides. In addition, fatty acids, such as oleic acid, find use in the preparation of injectables. The carrier and agent may be compounded as a liquid, suspension, polymerizable or non-polymerizable gel, paste or salve. The carrier may also comprise a delivery vehicle to sustain (i.e., extend, delay, or regulate) the delivery of the agent(s) or to enhance the delivery, uptake, stability, or pharmacokinetics of the therapeutic agent(s). Such a delivery vehicle may include, by way of non-limiting example, microparticles, microspheres, nanospheres, or nanoparticles composed of proteins, liposomes, carbohydrates, synthetic organic compounds, inorganic compounds, polymeric or copolymeric hydrogels, and polymeric micelles. Suitable hydrogel and micelle delivery systems include the PEO:PHB:PEO copolymers and copolymer/cyclodextrin complexes disclosed in International Publication No. WO 2004/009664 A2, and the PEO and PEO/cyclodextrin complexes disclosed in U.S. Publication No. 2002/0019369 A1. Such hydrogels may be injected locally at the site of intended action, or subcutaneously or intramuscularly to form a sustained release depot.

For intrathecal (IT) or intracerebroventricular (ICV) delivery, appropriately sterile delivery systems (e.g., liquids; gels, suspensions, etc.) can be used to administer the compositions. For oral administration of non-peptidergic agents, the compositions may be carried in an inert filler or diluent such as sucrose, cornstarch, or cellulose.

The compositions of the present invention may also include biocompatible excipients, such as dispersing or wetting agents, suspending agents, diluents, buffers, penetration enhancers, emulsifiers, binders, thickeners, flavoring agents (for oral administration). Exemplary formulations can be parenterally administered as injectable dosages of a solution or suspension of the multimer in a physiologically acceptable diluent with a pharmaceutical carrier that can be a sterile liquid such as water, oils, saline, glycerol, or ethanol. Additionally, auxiliary substances such as wetting or emulsifying agents, surfactants, pH buffering substances and the like can be present in compositions comprising modified polypeptides. Additional components of pharmaceutical compositions include petroleum (such as of animal, vegetable, or synthetic origin), for example, soybean oil and mineral oil. In general, glycols such as propylene glycol or polyethylene glycol are preferred liquid carriers for injectable solutions.

The pharmaceutical composition can also be administered in the form of a depot injection or implant preparation that can be formulated in such a manner as to permit a sustained or pulsatile release of the multimers and other therapeutic (if present).

The pharmaceutical composition may comprise in addition to the polypeptide of the invention (a) a lyoprotectant; (b) a surfactant; (c) a bulking agent; (d) a tonicity adjusting agent; (e) a stabilizer; (f) a preservative and/or (g) a buffer. In some embodiments, the buffer in the pharmaceutical composition is a Tris buffer, a histidine buffer, a phosphate buffer, a citrate buffer or an acetate buffer. The pharmaceutical composition may also include a lyoprotectant, e.g. sucrose, sorbitol or trehalose. In certain embodiments, the pharmaceutical composition includes a preservative e.g. benzalkonium chloride, benzethonium, chlorohexidine, phenol, m-cresol, benzyl alcohol, methylparaben, propylparaben, chlorobutanol, o-cresol, p-cresol, chlorocresol, phenylmercuric nitrate, thimerosal, benzoic acid, and various mixtures thereof. In other embodiments, the pharmaceutical composition includes a bulking agent, like glycine. In yet other embodiments, the pharmaceutical composition includes a surfactant e.g., polysorbate-20, polysorbate-40, polysorbate-60, polysorbate-65, polysorbate-80 polysorbate-85, poloxamer-188, sorbitan monolaurate, sorbitan monopalmitate, sorbitan monostearate, sorbitan monooleate, sorbitan trilaurate, sorbitan tristearate, sorbitan trioleaste, or a combination thereof. The pharmaceutical composition may also include a tonicity adjusting agent, e.g., a compound that renders the formulation substantially isotonic or isoosmotic with human blood. Exemplary tonicity adjusting agents include sucrose, sorbitol, glycine, methionine, mannitol, dextrose, inositol, sodium chloride, arginine and arginine hydrochloride. In other embodiments, the pharmaceutical composition additionally includes a stabilizer, e.g., a molecule which, when combined with a protein of interest substantially prevents or reduces chemical and/or physical instability of the protein of interest in lyophilized or liquid form. Exemplary stabilizers include sucrose, sorbitol, glycine, inositol, sodium chloride, methionine, arginine, and arginine hydrochloride.

The pharmaceutical composition can be packaged in any suitable manner. In one embodiment, the pharmaceutical composition is packaged as a kit containing a container (such as a vial) of the AdB-2/3 fiber multimer. In a preferred embodiment, the kit further comprises, in the same or a separate container (such as a vial), a therapeutic, diagnostic, or imaging agent to be administered to a subject, together with the AdB-2/3 fiber multimer.

In a further aspect, the present invention provides kits comprising (a) one or more recombinant polypeptides/AdB-2/3 fiber multimers, isolated nucleic acids, recombinant expression vectors, and/or host cells of the invention; and (b) instructions for its/their use in treating a disorder associated with epithelial tissue. The kits may further comprise a therapeutic for use in the methods of the present invention.

In a further aspect, the present invention provides methods for enhancing therapeutic treatment, or diagnosis of a disorder associated with epithelial tissue, and/or imaging epithelial tissues, comprising administering to a subject in need thereof:

(a) an amount of one or more therapeutics sufficient to treat the disorder, diagnostic sufficient to diagnose the disorder, and/or imaging agent sufficient to image the epithelial tissue; and (b) an amount of the AdB-2/3 fiber multimer of the invention, or a pharmaceutical composition of the invention, sufficient to enhance efficacy of the one or more therapeutics, diagnostics, and/or imaging agents.

The methods of this aspect of the invention can be used to enhancing therapeutic treatment, diagnosis, or imaging of a disorder associated with epithelial tissue by improving access for the therapeutic, diagnostic, and/or imaging agent to their target and dissemination in epithelial tissue. While not being bound by any mechanism, the inventors believe this occurs through complementary mechanisms: movement of the target receptor from the basolateral to the apical cell surface thus allowing better access to the epithelial tissue target by therapeutics, diagnostics, and/or imaging agents that target the receptor, such as monoclonal antibodies), and better penetration of the therapeutic through disruption of intercellular junctions. DSG2 is the primary high affinity receptor for AdB-2/3. DSG2 is a calcium-binding transmembrane glycoprotein belonging to the cadherin protein family. In epithelial cells. DSG2 is a component of the cell-cell adhesion structure. Its cytoplasmic tail interacts with a series of proteins that are in direct contact with regulators of cell adhesion and intercellular junctions/cell morphology. It has been shown that DSG2 is overexpressed in a series of epithelial malignancies including gastric cancer, squamous cell carcinomas, melanoma, metastatic prostate cancer, and bladder cancer.

While not being bound by a specific mechanism of action, the inventors believe that the AdB-2/3 fiber multimer binding to DSG2 serves to trigger transient DSG2-mediated opening of intercellular junctions, which serves to improve access of therapeutics, diagnostics, imaging agents, or any other compound of interest that binds to a target in epithelial cells that would otherwise be trapped to at least some extent in intercellular junctions. Detailed examples of such activity are provided herein. The methods of the invention can thus be carried out using any AdB-2/3 fiber multimer of the present invention to trigger transient DSG2-mediated opening of intercellular junctions. Exemplary multimers comprising one or more AdB-2/3 fiber multimers of the invention that can be used in these methods include, but are not limited to, AdB-2/3 virions, AdB-2/3 capsids, AdB-2/3 dodecahedral particles (PtDd) (subviral dodecahedral particles produced by AdB-2/3 during their replication), and recombinant AdB-2/3 fiber multimers.

The methods of the invention have broad application for delivery of any therapeutic, diagnostic, imaging agent, or other compound to epithelial tissue comprising intercellular junctions where access to a target of interest can be limited, as DSG2 is widely expressed in epithelial cells. As used herein, a "disorder associated with epithelial tissue" is any disorder wherein therapeutic, diagnostic, or imaging agent administered to/across epithelial cells/epithelial tissue provides a clinical benefit to a patient, whether in improving therapeutic, diagnostic, and/or imaging efficacy. Such disorders include, but are not limited to, solid tumors (i.e.: any tumor with epithelial cell junctions), gastrointestinal disorders (including but not limited to irritable bowel syndrome, inflammatory bowel disorder, Crohn's disease, ulcerative colitis, constipation, gastroesophageal reflux disease, Barrett's esophagus, etc.), skin diseases (including but not limited to psoriasis and dermatitis), lung disorders (including but not limited to chronic obstructive pulmonary disease, asthma, bronchitis, pulmonary emphysema, cystic fibrosis, interstitial lung disease, pneumonia, pancreatic duct disorders, brain disorders (ie: any brain disorder that could benefit from improved transport of drugs through the blood-brain barrier), primary pulmonary hypertension, pulmonary embolism, pulmonary sarcoidosis, tuberculosis, etc.), renal disorders, (including but not limited to glomerulonephritis), liver diseases (including but not limited to hepatitis), endocrine disorders (including but not limited to diabetes and thyroid disorders), pancreatic duct disorders (including but not limited to pancreatitis), and bile duct disorders (including but not limited to bile duct obstruction, cholecystitis, choledocholithiasis, gallstones, etc.) and infections of epithelial tissues (including but not limited to cellulitis, pneumonia, hepatitis, and pyelonephritis). In one preferred embodiment, the disorder associated with epithelial tissue comprises a solid tumor, including but not limited to breast tumors, lung tumors, colon tumors, rectal tumors, skin tumors, endocrine tumors, stomach tumors, prostate tumors, ovarian tumors, uterine tumors, cervical tumors, kidney tumors, melanomas, pancreatic tumors, liver tumors, brain tumors, head and neck tumors, nasopharyngeal tumors, gastric tumors, squamous cell carcinomas, adenocarcinomas, bladder tumors, and esophageal tumors. As will be understood by those of skill in the art, such tumors include primary tumors, tumors that are locally invasive, as well as tumors that have metastasized.

As used herein, "enhancing efficacy" means any increase in therapeutic, diagnostic, and/or imaging efficacy over what would be seen using the therapeutic, diagnostic, and/or imaging agent alone. For example, measurements of therapeutic efficacy will vary depending on the disorder being treated, but are readily identified by an attending physician. For example, such increases in efficacy include, but are not limited to increasing one or more of the following relative to treatment with the therapeutic alone: (a) reducing the severity of the disorder; (b) limiting or preventing development of symptoms characteristic of the disorder(s) being treated (c) inhibiting worsening of symptoms characteristic of the disorder(s) being treated; (d) limiting or preventing recurrence of the disorder(s) in patients that have previously had the disorder(s); and (e) limiting or preventing recurrence of symptoms in patients that were previously symptomatic for the disorder(s). In one non-limiting example, treating a solid tumor provides an ability to induce egress of tumor receptors from the basolateral side of epithelial cells to enable improved access and killing of the tumor.

For cancer, there are standards for defining tumor response and standard methods of measuring response. These include tumor response, which is determined by monitoring the change in tumor size or a serum marker of disease. A partial response is more than a 50% reduction in the tumor, while a complete response is defined as complete disappearance of the tumor. Methods used to measure tumors are well known to physicians and include physical examination, radiological testing such as CT scans, MRI, PET scans, X-rays as well as serum markers such as prostate specific antigen, which is used to monitor prostate cancer. Other measures of therapeutic efficacy of cancer treatment include measurements of time to progression, progression-free survival and overall survival.

Improved diagnostic efficacy includes any improvement in efficacy compared to administration of the diagnostic alone, including but not limited to, increasing specificity and/or sensitivity of the diagnostic test. Improved imaging efficacy includes any improvement in efficacy compared to administration of the imaging agent alone, including but not limited to specificity, sensitivity, reproducibility, contrast enhancement, detection of smaller sites of disease, more accurate delineation of disease, such as size and shape of diseases, such as tumors, abscesses, etc.

In various embodiments, the increase in efficacy is a 5%, 10%, 15%, 20%, 25%, 50%, 75%, 100%, or greater benefit compared to efficacy with the therapeutic, diagnostic, and/or imaging agent alone across a patient population.

Any suitable subject can be treated using the methods of the invention, preferably human subjects.

Any therapeutic, diagnostic, imaging agent, or other compound that can target epithelial tissue and whose delivery to epithelial tissue can be improved by transient opening of intercellular junctions can be used in the methods of the invention. In one embodiment, the therapeutic is selected from the group consisting of antibodies, immunoconjugates, nanoparticles, nucleic acid therapeutics, and combinations thereof, chemotherapeutics, vaccines, radioactive particle/radiation therapy ("radiation"), cellular immunotherapy including adoptive T-cell therapy and dendritic cell therapy (example: intratumoral penetration of administered T-cells), inhaled therapeutics, gene therapy constructs (including but not limited to AdB-2/3 virus as a gene therapy vector, and co-administration with an Ad5-based gene therapy vector), other nucleic acid therapeutics, and combinations thereof.

In various embodiments, the therapeutic is selected from the group consisting of alkylating agents, angiogenesis inhibitors, antibodies, antimetabolites, antimitotics, antiproliferatives, aurora kinase inhibitors, apoptosis promoters (for example, Bcl-xL, Bcl-w and Bfl-1) inhibitors, activators of death receptor pathway, Bcr-Abl kinase inhibitors, BiTE (Bi-Specific T cell Engager) antibodies, biologic response modifiers, cyclin-dependent kinase inhibitors, cell cycle inhibitors, cyclooxygenase-2 inhibitors, growth factor inhibitors, heat shock protein (HSP)-90 inhibitors, demethylating agents, histone deacetylase (HDAC) inhibitors, hormonal therapies, immunologicals, inhibitors of apoptosis proteins (IAPs) intercalating antibiotics, kinase inhibitors, mammalian target of rapamycin inhibitors, microRNA's mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, proteasome inhibitors, purine analogs, pyrimidine analogs, receptor tyrosine kinase inhibitors, retinoids/deltoids plant alkaloids, small inhibitory ribonucleic acids (siRNAs), topoisomerase inhibitors and the like.

Exemplary therapeutics falling within these various classes include, but are not limited to: docetaxel, doxorubicin, irinotecan, paclitaxel (Taxol®), paclitaxel albumin bound particles (Abraxane®), doxorubicin HCL liposome (Doxil®), BiTE antibodies such as adecatumumab (Micromet MT201), blinatumomab (Micromet MT103) and the like, siRNA-based therapeutics, alkylating agents including altretamine, AMD-473, AP-5280, apaziquone, bendamustine, brostallicin, busulfan, carboquone, carmustine (BCNU), chlorambucil, CLORETAZINE.® (laromustine, VNP 40101M), cyclophosphamide, dacarbazine, decitabine, 5'-azacytidine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, TREANDA® (bendamustine), treosulfan, rofosfamide and the like; angiogenesis inhibitors including endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs, vascular endothelial growth factor receptor tyrosine kinase (VEGFR) inhibitors and the like; antimetabolites including ALIMTA® (pemetrexed disodium, LY231514, MTA), 5-azacitidine, XELODA® (capecitabine), carmofur. LEUSTAT® (cladribine), clofarabine, cytarabine, cytarabine ocfosfate, cytosine arabinoside, decitabine, deferoxamine, doxifluridine, eflornithine, EICAR (5-ethynyl-1-.beta.-D-ribofuranosylimidazole-4-carboxamide), enocitabine, ethnylcytidine, fludarabine, 5-fluorouracil alone or in combination with leucovorin, GEMZAR® (gemcitabine), hydroxyurea. ALKERAN® (melphalan), mercaptopurine, 6-mercaptopurine riboside, methotrexate, methotrexate analogs (such as trimetrexate and pralatraxate), mycophenolic acid, nelarabine, nolatrexed, ocfosfate, pelitrexol, pentostatin, raltitrexed, Ribavirin, triapine, trimetrexate, S-1, tiazofurin, tegafur, TS-1, vidarabine, and the like; Bcl-2 protein inhibitors including AT-101 ((−)gossypol), GENASENSE® (G3139 or oblimersen (Bcl-2-targeting antisense oligonucleotide)), IPI-194, IPI-565, N-(4-(4-((4'-chloro(1,1'-biphenyl)-2-yl)methyl)piperazin-1-yl)benzoyl)-4--(((1R)-3-(dimethylamino)-1-((phenylsulfanyl)methyl)propyl)amino)-3-nitrobe-nzenesulfonamide) (ABT-737), N-(4-(4-((2-(4-chlorophenyl)-5,5-dimethyl-1-cyclohex-1-en-1-yl)methyl)pip-erazin-1-yl)benzoyl)-4-(((1R)-3-(morpholin-4-yl)-1-((phenylsulfanyl)methyl-)propyl)amino)-3-((trifluoromethyl)sulfonyl)benzenesulfonamide (ABT-263), GX-070 (obatoclax) and the like; Bcr-Abl kinase inhibitors include DASATINIB® (BMS-354825), GLEEVEC® (imatinib) and the like; CDK inhibitors including AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like; EGFR inhibitors including ABX-EGF, anti-EGFR immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib) and the like; ErbB2 receptor inhibitors include CP-724-714, CI-1033 (canertinib), HERCEPTIN® (trastuzumab), TYKERB® (lapatinib), OMNITARG® (2C4, petuzumab), TAK-165, GW-572016 (ionafarnib), GW-282974, EKB-569, PI-166, dHER2 (HER2 vaccine), APC-8024 (HER-2 vaccine), anti-HER/2neu bispecific antibody, B7.her2IgG3, AS HER2 trifunctional bispecific antibodies, mAb AR-209, mAb 2B-1 and the like; histone deacetylase inhibitors include romidepsin, LAQ-824, MS-275, trapoxin, suberoylanilide hydroxamic acid (SAHA), TSA, valproic acid and the like; HSP-90 inhibitors including 17-AAG-nab, 17-AAG, CNF-101, CNF-1010, CNF-2024, 17-DMAG, geldanamycin, IPI-504, KOS-953, MYCOGRAB® (human recombinant antibody to HSP-90), NCS-683664, PU24FC1, PU-3, radicicol, SNX-2112, STA- 9090 VER49009 and the like; activators of death receptor pathways including TRAIL, antibodies or other agents that target TRAIL or death receptors (e.g., DR4 and DR5) such as Apomab, conatumumab, ETR2-ST01, GDC0145, (lexatumumab), HGS-1029, LBY-135, PRO-1762 and trastuzumab; platinum chemotherapeutics include cisplatin, ELOXATIN® (oxaliplatin) eptaplatin, lobaplatin, nedaplatin, PARAPLATIN® (carboplatin), satraplatin, picoplatin and the like; VEGFR inhibitors including AVASTIN® (bevacizumab), ABT-869, AEE-788, axitinib (AG-13736), AZD-2171, CP-547, 632, IM-862, MACUGEN (pegaptamib), NEXAVAR®(sorafenib, BAY43-9006), pazopanib (GW-786034), vatalanib (PTK-787, ZK-222584), SUTENT®® (sunitinib, SU-11248), VEGF trap, ZACTIMAThi (vandetanib, ZD-6474) and the like; dendritic cell therapy (sipuleucel-T, Provenge®); topoisomerase inhibitors including aclarubicin, 9-aminocamptothecin, amonafide, amsacrine, becatecarin, belotecan, BN-80915, CAMPTOSAR®) (irinotecan hydrochloride), camptothecin, dexrazoxine, diflomotecan, edotecarin, ELLENCE® or PHARMORUBICIN® (epirubicin), etoposide, exatecan, abraxane, irenotecan, 10-hydroxycamptothecin, gimatecan, lurtotecan, mitoxantrone, orathecin, pirarbucin, pixantrone, rubitecan, sobuzoxane, SN-38, tafluposide, topotecan and the like; antibodies including AVASTIN® (bevacizumab), CD40-specific antibodies, chTNT-1/B, denosumab, ERBITUX® (cetuximab), HUMAX-CD4® (zanolimumab), IGF I R-specific antibodies, lintuzumab, PANOREX® (edrecolomab), RENCAREX® (WX G250), RITUXAN® (rituximab), ticilimumab, trastuzimab and the like; hormonal therapies including ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL® (flutamide), EVISTA® (raloxifene), AFEMA® (fadrozole), FARESTON® (toremifene), FASLODEX® (fulvestrant), FEMARA® (letrozole), formestane, glucocorticoids, HECTOROL® (doxercalciferol), RENAGEL® (sevelamer carbonate), lasofoxifene, leuprolide acetate, MEGACE® (megesterol), MIFEPREX® (mifepristone), NILANDRON® (nilutamide), NOLVADEX® (tamoxifen citrate), PLENAXIS® (abarelix), prednisone, PROPECIA® (finasteride), rilostane, SUPREFACT® (buserelin), TRELSTAR® (luteinizing hormone releasing hormone (LHRH)), VANTAS® (Histrelin implant), VETORYL® (trilostane or modrastane), ZOLADEX® (fosrelin, goserelin) and the like: immunologicals including interferon alpha, interferon alpha-2a, interferon alpha-2b, interferon beta, interferon gamma-1a, ACTIMMUNE® (interferon gamma-1b) or interferon gamma-n1, combinations thereof and the like. Other agents include ALFAFERONE® (IFN-alpha), BAM-002 (oxidized glutathione), BEROMUN® (tasonermin), BEXXAR® (tositumomab), CAMPATH® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010 (anti-CTLA-4), melanoma vaccine, mitumomab, molgramostim, MYLOTARG.™. (gemtuzumab ozogamicin), NEUPOGEN® (filgrastim), OncoVAC-CL, OVAREX® (oregovomab), pemtumomab (Y-muHMFG1), PROVENGE® (sipuleucel-T), sargaramostim, sizofilan, teceleukin, THERACYS® (*Bacillus* Calmette-Guerin), ubenimex, VIRULIZIN® (immunotherapeutic, Lorus Pharmaceuticals), Z-100 (Specific Substance of Maruyama (SSM)), WF-10 (Tetrachlorodecaoxide (TCDO)), PROLEUKIN® (aldesleukin), ZADAXIN® (thymalfasin), ZENAPAX® (daclizumab), ZEVALIN®. (90Y-Ibritumomab tiuxetan) and the like; ofatumumab; biological response modifiers agents including krestin, lentinan, sizofuran, picibanil PF-3512676 (CpG-8954), ubenimex and the like; pyrimidine analogs include cytarabine (ara C or Arabinoside C), cytosine arabinoside, doxifluridine. FLUDARA® (fludarabine), 5-FU (5-fluorouracil), floxuridine, GEMZAR® (gemcitabine), TOMUDEX® (ratitrexed), TROXATYL® (triacetyluridine troxacitabine) and the like; purine analogs including LANVIS® (thioguanine) and PURI-NETHOL® (mercaptopurine); antimitotic agents including batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881 (larotaxel), vinflunine, ZK-EPO (synthetic epothilone) and the like; and other chemotherapeutic agents such as ABRAXANE® (ABI-007), ABT-100 (farnesyl transferase inhibitor), ADVEXIN® (Ad5CMV-p53 vaccine), ALTOCOR® or MEVACOR® (lovastatin). AMPLIGE®. (poly I:poly C12U, a synthetic RNA), APTOSYN® (exisulind), AREDIA® (pamidronic acid), arglabin, L-asparaginase, atamestane (1-methyl-3,17-dione-androsta-1,4-diene), AVAGE® (tazarotene), AVE-8062 (combreastatin derivative) BEC2 (mitumomab), cachectin or cachexin (tumor necrosis factor), canvaxin (vaccine), CEAVAC® (cancer vaccine), CELEUK® (celmoleukin), CEPLENE® (histamine dihydrochloride), CERVARIX® (human papillomavirus vaccine), CHOP® (C: CYTOXAN® (cyclophosphamide); H: ADRIAMYCIN® (hydroxydoxorubicin); O: Vincristine (ONCOVIN®); P: prednisone), CYPAT® (cyproterone acetate), combrestatin A4P, DAB(389)EGF (catalytic and translocation domains of diphtheria toxin fused via a His-Ala linker to human epidermal growth factor) or TransMID-107R® (diphtheria toxins), dacarbazine, dactinomycin, 5,6-dimethylxanthenone-4-acetic acid (DMXAA), eniluracil, EVIZON.™. (squalamine lactate), DIMERICINE® (T4N5 liposome lotion), discodermolide, DX-8951f (exatecan mesylate), enzastaurin, EPO906 (epithilone B), GARDASIL® (quadrivalent human papillomavirus (Types 6, 11, 16, 18) recombinant vaccine), GASTRIMMUNE®, GENASENSE®, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-*pseudomonas* exotoxin, interferon-.alpha., interferon-.gamma., JUNOVAN® or MEPACT® (mifamurtide), lonafarnib, 5,10-methylenetetrahydrofolate, miltefosine (hexadecylphosphocholine), NEOVASTAT® (AE-941), NEUTREXIN® (trimetrexate glucuronate), NIPENT® (pentostatin), ONCONASE® (a ribonuclease enzyme), ONCOPHAGE® (melanoma vaccine treatment), ONCOVAX® (IL-2 Vaccine), ORATHECIN® (rubitecan), OSIDEM® (antibody-based cell drug), OVAREX® MAb (murine monoclonal antibody), paclitaxel, PANDIMEX® (aglycone saponins from *ginseng* comprising 20(S)protopanaxadiol (aPPD) and 20(S)protopanaxatriol (aPPT)), panitumumab, PANVAC®-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (*Streptomyces* staurospores), talabostat (PT100), TARGRETIN® (bexarotene), TAXOPREXIN® (DHA-paclitaxel), TELCYTA® (canfosfamide, TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFERADE® (adenovector: DNA carrier containing the gene for tumor necrosis factor-.alpha.), TRACLEER® or ZAVESCA® (bosentan), tretinoin (Retin-A), tetrandrine, TRISENOX®, (arsenic trioxide), VIRULIZIN®, ukrain (derivative of alkaloids from the greater celandine plant), vitaxin (anti-alphavbeta3 antibody), XCYTRIN® (motexafin gadolinium), XINLAY® (atrasentan), XYOTAX® (paclitaxel poliglumex), YONDELIS® (trabectedin), ZD-6126, ZINECARD® (dexrazoxane), ZOMETA® (zolendronic acid), crizotinib, zorubicin and the like.

In another preferred embodiment, the therapeutic comprises a compound that binds to desmoglein-2; preferably a compound that binds to DSG2 and opens up tight junctions.

In other embodiments, the therapeutic comprises radioactive particles/radiation therapy. Any suitable radioactive therapy or particle can be used as deemed appropriate by an attending physician, including but not limited to cobalt-60, iodine-131, iridium-192, strontium-89, samarium 153, rhenium-186 and lead-212.

In a preferred embodiment, the therapeutic is an anti-tumor therapeutic and comprises a chemotherapeutic or anti-tumor monoclonal antibody as described herein. In a further preferred embodiment, the anti-tumor therapeutic comprises an antibody selected from the group consisting of trastuzumab, cetumiximab, petuzumab, apomab, conatumumab, lexatumumab, bevacizumab, bevacizumab, denosumab, zanolimumab, lintuzumab, edrecolomab, rituximab, ticilimumab, tositumomab, alemtuzumab, epratuzumab, mitumomab, gemtuzumab ozogamicin, oregovomab, pemtumomab daclizumab, panitumumab, catumaxomab, ofatumumab, and ibritumomab. Non-limiting examples of useful anti-tumor mAb and their specific uses are listed in Table 1 above, and as further described in Campoli, M., et al., *Principles & Practice of Oncology* 23(1&2): 1-19 (2009), incorporated herein by reference.

The monoclonal antibody therapeutics can be any type of monoclonal antibody, including but not limited to standard monoclonal antibodies, humanized monoclonals, fully human antibodies generated from mice or other sources, chimeric monoclonals, and fragments thereof. "Humanized monoclonal antibodies" refers to monoclonal antibodies derived from a non-human monoclonal antibody, such as a mouse monoclonal antibody. Alternatively, humanized monoclonal antibodies can be derived from chimeric antibodies that retain, or substantially retain, the antigen-binding properties of the parental, non-human, monoclonal antibodies but which exhibit diminished immunogenicity as compared to the parental monoclonal antibody when administered to humans. For example, chimeric monoclonal antibodies can comprise human and murine antibody fragments, generally human constant and mouse variable regions. Humanized monoclonal antibodies can be prepared using a variety of methods known in the art, including but not limited to (1) grafting complementarity determining regions from a non-human monoclonal antibody onto a human framework and constant region ("humanizing"), and (2) transplanting the non-human monoclonal antibody variable domains, but "cloaking" them with a human-like surface by replacement of surface residues ("veneering"). These methods are disclosed, for example, in, e.g., Jones et al., Nature 321:522-525 (1986); Morrison et al., Proc. Natl. Acad. Sci., U.S.A., 81:6851-6855 (1984); Morrison and Oi, Adv. Immunol., 44:65-92 (1988); Verhoeyer et al., Science 239:1534-1536 (1988); Padlan, Molec. Immun. 28:489-498 (1991); Padlan, Molec. Immunol. 31(3):169-217 (1994); and Kettleborough, C. A. et al., Protein Eng. 4(7):773-83 (1991).

Monoclonal antibodies can be fragmented using conventional techniques, and the fragments screened for utility in the same manner as for whole antibodies. For example, F(ab')$_2$ fragments can be generated by treating antibody with pepsin. The resulting F(ab')$_2$ fragment can be treated to reduce disulfide bridges to produce Fab' fragments. Fab fragments can be obtained by treating an IgG antibody with papain; F(ab') fragments can be obtained with pepsin digestion of IgG antibody. A F(ab') fragment also can be produced by binding Fab' described below via a thioether bond or a disulfide bond. A Fab' fragment is an antibody fragment obtained by cutting a disulfide bond of the hinge region of the F(ab')2. A Fab' fragment can be obtained by treating a F(ab')2 fragment with a reducing agent, such as dithiothreitol. Antibody fragment peptides can also be generated by expression of nucleic acids encoding such peptides in recombinant cells (see, e.g., Evans et al., J. Immunol. Meth. 184: 123-38 (1995)). For example, a chimeric gene encoding a portion of a F(ab')2 fragment can include DNA sequences encoding the CH1 domain and hinge region of the H chain, followed by a translational stop codon to yield such a truncated antibody fragment molecule. Non-limiting examples of monoclonal antibody fragments include (i) a Fab fragment, a monovalent fragment consisting essentially of the VL, VH, CL and CH I domains; (ii) F(ab)2 and F(ab')2 fragments, bivalent fragments comprising two Fab fragments linked by a disulfide bridge at the hinge region; (iii) a Fd fragment consisting essentially of the VH and CH1 domains; (iv) a Fv fragment consisting essentially of the VL and VH domains of a single arm of an antibody, (v) a dAb fragment (Ward et al., (1989) Nature 341:544-546), which consists essentially of a VH domain; and (vi) one or more isolated CDRs or a functional paratope.

In one preferred embodiment that can be combined with any embodiment or combination of embodiments of the invention, the disorder comprises a Her-2 positive tumor, and the method comprises co-administering the AdB-2/3 fiber multimer of the invention together with suitable monoclonal antibody therapy, alone or in combination with a chemotherapeutic, radiation, or combinations thereof. In a further preferred embodiment, the monoclonal antibody is trastuzumab. In a further preferred embodiment that can be combined with any of these embodiments, the Her-2 positive tumor is selected from the group consisting of a breast tumor, a gastric tumor, a colon tumor, and an ovarian tumor. In a further preferred embodiment, the method is carried out on patients who have not responded adequately to trastuzumab, such as by lack of tumor remission, by tumor relapse, or by development of resistance to trastuzumab. The methods of these embodiments can also be used to help reduce the dosage of trastuzumab required to obtain therapeutic efficacy, and can thus serve to limit side effects (such as trastuzumab-associated cardiotoxicity).

In another preferred embodiment that can be combined with any embodiment or combination of embodiments of the invention, the disorder comprises an EGFR-positive tumor, and the method comprises co-administering the AdB-2/3 fiber multimer together with suitable monoclonal antibody therapy, alone or in combination with a chemotherapeutic, radiation, or combinations thereof. In a further preferred embodiment, the monoclonal antibody is cetuximab. In a further preferred embodiment that can be combined with any of these embodiments, the EGFR-positive tumor is selected from the group consisting of a lung tumor, a colon tumor, a breast tumor, a rectal tumor, a head and neck tumor, and a pancreatic tumor. In a further preferred embodiment, the method is carried out on patients who have not responded adequately to cetuximab, such as by lack of tumor remission, by tumor relapse, or by development of resistance to cetuximab. The methods of these embodiments can also be used to help reduce the dosage of cetuximab required to obtain therapeutic efficacy, and can thus serve to limit side effects (such as acne-like rashes that often occur during cetuximab therapy).

In one preferred embodiment that can be combined with any embodiment or combination of embodiments of the invention, the disorder comprises an epithelial tumor, and the method comprises co-administering the AdB-2/3 fiber multimer together with a vascular endothelial growth factor (VEGF) inhibitor, alone or in combination with other chemotherapeutic, radiation, or combinations thereof. Any suitable VEGF inhibitor can be used, including but not limited to bevacizumab.

In a further embodiment that can be combined with any embodiment or combination of embodiments herein, the methods involving solid tumors further comprise administering a compound capable of degrading tumor stroma proteins. Any suitable compound for degrading tumor stroma proteins can be used, including but not limited to relaxin, collagenase, trypsin, dispase, MMP(metalloproteinase)-1, and MMP8. Delivery of such compounds can be by any suitable mechanism, including gene therapy, separate administration with the AdB-2/3 fiber multimer and the therapeutic, or administration as a conjugate with the AdB-2/3 fiber or therapeutic.

In a further embodiment that can be combined with any embodiment or combination of embodiments herein, the methods further comprise administering the AdB-2/3 multimer in combination with other junction openers. As used herein, a "junction opener" is a compound capable of transiently opening intercellular junctions. Any suitable junction openers can be used. In one non-limiting embodiment, the junction opener comprises Zona occludens toxin (Zot), a *Vibrio cholerae* (*V. cholerae*)-produced toxin that possess the ability to reversibly alter intestinal epithelial junctions, allowing the passage of macromolecules through mucosal barriers (Fasano et al. (1991) Proc Natl Acad Sci USA 88: 5242-5246)]. A Zot-derived hexapeptide (AT-1001) has been developed. In another embodiment, *Clostridium perfringens* enterotoxin removes claudins-3 and -4 from the tight junctions to facilitate bacterial invasion (Sonoda N. et al. (1999) J Cell Biol 147: 195-204.]. In a further embodiment, oncoproteins encoded by human Ad, HPV, HTLV-1 can transiently open epithelial junctions by mislocalizing the junction protein ZO-1 (Latorre I J, et al. (2005) J Cell Sci 118: 4283-4293). In other embodiments, several human viruses engage tight junction or other cell junction molecules to achieve entry into epithelial cells. Among these viruses are hepatitis C virus (Evans M J, et al. (2007) Nature 446: 801-805), reovirus (Barton E S, et al. (2001) Cell 104: 441-451), and herpes simplex virus (Geraghty R J, et al. (1998) Science 280: 1618-1620).

In another embodiment, the therapeutic is an inhaled therapeutic. Any suitable inhaled therapeutic can be used in the methods of the invention. In various non-limiting embodiments, the inhaled therapeutic is selected from the group consisting of corticosteroids, bronchodilators, beta agonists, anticholinergics, albuterol (PROVENTIL®; VENOLIN®; ACCUNEB®; PROAIR®), levalbuterol (XOPENEX®), pirbutrol (MAXAIR®), ipratropium bromide (ATROVENT®), beclomethasone, budesonide, flunisolide (AEROBID®), fluticasone, triamcinolone acetonide, fluticasone (a coricosteroid) and salmeterol (ADVAIR®), formotorol (a long-acting, beta-agonist bronchodilatorl and budeonide (a corticosteroid) (SYMICORT®), albuterol (a beta agonist) and ipratropiumn (COMBIVENT®; an anticholinergic) (budesonide (PULMICORT RESPULES®), and tiopropium (SPIRIVA®; an anticholinergic bronchodilator.

In another embodiment, the compound comprises a diagnostic or imaging agent. The methods of the invention have broad application for delivery of any diagnostic, imaging agent, or other compound to epithelial tissue comprising intercellular junctions where access to a target of interest can be limited. In various non-limiting embodiments, the imaging agents can include any chemical compound that can produce a detectable signal, either directly or indirectly. Many such imaging agents are known to those of skill in the art. Examples of imaging agents suitable for use in the disclosed methods and compositions are radioactive isotopes, fluorescent molecules, magnetic particles (including nanoparticles), metal particles (including nanoparticles), phosphorescent molecules, enzymes, antibodies, ligands, and combinations thereof, while diagnostic agents may comprise a compound that is a diagnostic marker for a particular epithelial disorder bound to the such an imaging agent. Methods for detecting and measuring signals generated by imaging agents are also known to those of skill in the art. For example, radioactive isotopes can be detected by scintillation counting or direct visualization; fluorescent molecules can be detected with fluorescent spectrophotometers; phosphorescent molecules can be detected with a spectrophotometer or directly visualized with a camera; enzymes can be detected by detection or visualization of the product of a reaction catalyzed by the enzyme; antibodies can be detected by detecting a secondary detection label coupled to the antibody. In one preferred embodiment, the imaging agent and/or diagnostic is one that can be used to detect a tumor, whether by direct tumor binding, or by coupling of the imaging or diagnostic agent with a compound that can bind the tumor.

In one example, the imaging agents can comprise a fluorescent imaging agent, while diagnostic agents may comprise a compound that is a diagnostic marker for a particular epithelial disorder bound to the fluorescent imaging agent. A fluorescent imaging agent is any chemical moiety that has a detectable fluorescence signal. This imaging agent can be used alone or in combination with other imaging agents. Examples of suitable fluorescent agents that can be used in the compositions and methods disclosed herein include, but are not limited to, fluorescein (FITC), 5-carboxyfluorescein-N-hydroxysuccinimide ester, 5,6-carboxymethyl fluorescein, nitrobenz-2-oxa-1,3-diazol-4-yl (NBD), fluorescamine, OPA, NDA, indocyanine green dye, the cyanine dyes (e.g., Cy3, Cy3.5, Cy5, Cy5.5 and Cy7), 4-acetamido-4'-isothiocyanatostilbene-2,2'disulfonic acid, acridine, acridine isothiocyanate, 5-(2'-aminoethyl)aminonaphthalene-1-sulfonic acid (EDANS), 4-amino-N-[3-vinylsulfonyl)phenylinaphthalimide-3,5 disulfonate, N-(4-anilino-1-naphthyl)maleimide, anthranilamide, BODIPY, Brilliant Yellow, coumarin, 7-amino-4-methylcoumarin (AMC, Coumarin 120), 7-amino-4-trifluoromethylcoumarin (Coumaran 151), cyanosine, 4',6-diaminidino-2-phenylindole (DAPI), 5',5"-dibromopyrogallol-sulfonaphthalein (Bromopyrogallol Red), 7-diethylamino-3-(4'-isothiocyanatophenyl)-4-methylcoumarin diethylenetriamine pentaacetate, 4,4'-diisothiocyanatodihydro-stilbene-2,2'-disulfonic acid, 4,4'-diisothiocyanatostilbene-2,2'-disulfonic acid, 5-[dimethylamino]naphthalene-1-sulfonyl chloride (DNS, dansylchloride), 4-(4'-dimethylaminophenylazo)benzoic acid (DABCYL), 4-dimethylaminophenylazophenyl-4'-isothiocyanate (DABITC), eosin, eosin isothiocyanate, erythrosin B, erythrosine, isothiocyanate, ethidium bromide, ethidium, 5-carboxyfluorescein (FAM), 5-(4,6-dichlorotriazin-2-yl)aminofluorescein (DTAF), 2',7'-dimethoxy-4'5'-dichloro-6-carboxyfluorescein (JOE), fluorescein isothiocyanate, IR144, IR1446, Malachite Green isothiocyanate, 4-methylumbelliferone, ortho cresolphthalein, nitrotyrosine, pararosaniline, Phenol Red, B-phycoerythrin, o-phthaldialdehyde, pyrene, pyrene butyrate, succinimidyl 1-pyrene butyrate, Reactive Red 4 (Cibacron[R] Brilliant Red 3B-A), 6-carboxy-X-rhodamine (ROX), 6-carboxyrhodamine (R6G), lissamine rhodamine B sulfonyl chloride rhodamine (Rhod), 5,6-tetramethyl rhodamine, rhodamine B, rhodamine 123, rhodamine X isothiocyanate, sulforhodamine B, sulforhodamine 101, sulfonyl chloride derivative of sulforhodamine 101 (Texas Red), N,N,N',N'-tetramethyl-6-carboxyrhodamine (TAMRA), tetramethyl rhodamine, tetramethyl rhodamine isothiocyanate (TRITC), riboflavin, rosolic acid, coumarin-6, and the like, including combinations thereof. These fluorescent imaging moieties can be obtained from a variety of commercial sources, including Molecular Probes, Eugene, Oreg. and Research Organics, Cleveland, Ohio, or can be synthesized by those of ordinary skill in the art.

In another example, the imaging agents can comprise a Magnetic Resonance Imaging (MRI) agent, while diagnostic agents may comprise a compound that is a diagnostic marker for a particular epithelial disorder bound to the MRI agent. A MRI agent is any chemical moiety that has a detectable magnetic resonance signal or that can influence (e.g., increase or shift) the magnetic resonance signal of another agent. This type of imaging agent can be used alone or in combination with other imaging agent. In still another example, a gadolinium-based MRI agent can serve as an imaging agent. An example of a suitable MRI agent that can be incorporated into the disclosed imaging agents is para-amino-benzyl diethylenetriaminepentaacetic acid (p-$NH_2$—Bz-DTPA, Compound 7), a conjugable form of diethylenetriaminepentaacetic acid (DTPA), which is known to strongly bind gadolinium and is approved for clinical use as a magnetic resonance contrast agent. Incorporation of an MRI agent on a large macromolecule such as a dendrimeric substrate as disclosed herein can allow large T1 relaxation (high contrast) and multiple copies of agent on a single molecule, which can increase signal. By combining an MRI imaging agent and, for example, a fluorescent imaging agent, the resulting agent can be detected, imaged, and followed in real-time via MR I. Other imaging agents include PET agents that can be prepared by incorporating an 18F or a chelator for 64Cu or 68Ga. Also, addition of a radionuclide can be used to facilitate SPECT imaging or delivery of a radiation dose, while diagnostic agents may comprise a compound that is a diagnostic marker for a particular epithelial disorder bound to the PET agent.

In some embodiments, the diagnostic agent is a diagnostic imaging agent, including but not limited to position emission tomography (PET) agents, computerized tomography (CT) agents, magnetic resonance imaging (MRI) agents, nuclear magnetic imaging agents (NMI), fluoroscopy agents and ultrasound contrast agents. Such diagnostic agents include radioisotopes of such elements as iodine (I), including $^{123}I$, $^{125}I$, $I^{131}$ etc., barium (Ba), gadolinium (Gd), technetium (Tc), including $^{99}Tc$, phosphorus (P), including $^{31}P$, iron (Fe), manganese (Mn), thallium (Tl), chromium (Cr), including $^{51}Cr$, carbon (C), including $^{14}C$, or the like, fluorescently labeled compounds, or their complexes, chelates, adducts and conjugates. Any suitable PET agents can be used, including but not limited to carbon-11, nitrogen-13, oxygen-15, fluorine-18, 11 C-metomidate, and glucose analogues thereof, including but not limited to fludeoxyglucose (a glucose analog labeled with fluorine-18.

In other embodiments, the diagnostic agent is a marker gene that encode proteins that are readily detectable when expressed in a cell (including, but not limited to, beta-galactosidase, green fluorescent protein, luciferase, and the like) and labeled nucleic acid probes (e.g., radiolabeled or fluorescently labeled probes). In some embodiments, covalent conjugation of diagnostics agents to the AdB-2/3 multimers provided herein is achieved according to a variety of conjugation processes. In other embodiments, the diagnostic agent is non-covalently associated with AdB-2/3 multimers provided In a further aspect, the present invention provides methods for improving delivery of a substance to an epithelial tissue, comprising contacting the epithelial tissue with (a) one or more compound to be delivered to the epithelial tissue; and (b) an amount of an AdB-2/3 fiber multimer of the invention sufficient to enhance delivery of the one or more compounds to the epithelial tissue. In this aspect, the compounds may be any suitable compound such as those described in detail above. In a preferred embodiment, the one or more compounds comprise an imaging agent. In a further preferred embodiment the epithelial tissue comprises a solid tumor, including any of those disclosed in the present application. In various non-limiting embodiments, the solid tumor is selected from the group consisting of breast tumors, lung tumors, colon tumors, rectal tumors, stomach tumors, prostate tumors, ovarian tumors, uterine tumors, skin tumors, endocrine tumors, cervical tumors, kidney tumors, melanomas, pancreatic tumors, liver tumors, brain tumors, head and neck tumors, nasopharyngeal tumors, gastric tumors, squamous cell carcinomas, adenocarcinomas, bladder tumors, and esophageal tumors. Exemplary multimers comprising one or more AdB-2/3 fiber multimers of the invention that can be used in these methods include, but are not limited to, AdB-2/3 virions, AdB-2/3 capsids, AdB-2/3 dodecahedral particles (PtDd) (subviral dodecahedral particles produced by AdB-2/3 during their replication), and recombinant AdB-2/3 fiber multimers.

In a still further aspect, the present invention provides methods for improving delivery of a substance cell or tissue expressing desmoglein 2 (DSG2), comprising contacting the cell or tissue expressing DSG2 with (a) one or more compound to be delivered to the cell or tissue; and (b) an amount of an AdB-2/3 fiber multimer of the invention sufficient to enhance delivery of the one or more compounds to the tissue. Exemplary tissue types expressing DSG2 include, but are not limited to epithelial cells/tissue (such as those disclosed herein), human platelets and granulocytes. As shown in the examples that follow, DSG2 also acts as receptor in non-polarized cells. Thus, these methods find application not only in epithelial cells and tissue, but also are relevant, for example, in AdB-2/3 pathogenesis and the intravascular application of AdB-2/3 vectors for gene therapy purposes. Exemplary multimers comprising one or more AdB-2/3 fiber multimers of the invention that can be used in these methods include, but are not limited to, AdB-2/3 virions, AdB-2/3 capsids, AdB-2/3 dodecahedral particles (PtDd) (subviral dodecahedral particles produced by AdB-2/3 during their replication), and recombinant AdB-2/3 fiber multimers.

In a still further aspect, the present invention provides methods for inducing an epithelial to mesenchymal transition (EMT) in a tissue, comprising contacting the epithelial tissue with an amount of an AdB-2/3 fiber multimer of the invention sufficient to induce EMT. EMT is a cellular transdifferentiation program where epithelial cells lose characteristics such as intercellular junctions and gain properties of mesenchymal cells. EMT is characterized by increased expression of mesenchymal markers, increased expression of extracellular matrix compounds, decreased expression of epithelial markers, altered location of transcription factors, and activation of kinases, and disassociation of intercellular junctions. Exemplary multimers comprising one or more AdB-2/3 fiber multimers of the invention that can be used in these methods include, but are not limited to, AdB-2/3 virions, AdB-2/3 capsids, AdB-2/3 dodecahedral particles (PtDd) (subviral dodecahedral particles produced by AdB-2/3 during their replication), and recombinant AdB-2/3 fiber multimers.

In all of the aspects and embodiments of the methods of the invention, the therapeutic, diagnostic, and/or imaging agent can be administered together with the AdB-2/3 multimer (such as via the compositions of the invention disclosed above) or may be administered separately. In one embodiment, the therapeutic and AdB-2/3 multimer are attached, via any suitable covalent or non-covalent binding. In one non-limiting embodiment, an AbB-2/3 multimer can attached to a toxin or other drug to kill solid tumor cells.

The AdB-2/3 fiber multimer and/or therapeutic can be administered in any way deemed suitable by an attending physician, depending on whether a local or systemic mode of administration is most appropriate for the condition being treated. As used herein, the terms "systemic delivery" and "systemic administration" are intended to include, but are not limited to, oral and parenteral routes including intramuscular (IM), subcutaneous, intravenous (IV), intra-arterial, inhalational, sublingual, buccal, topical, transdermal, nasal, rectal, vaginal, and other routes of administration that effectively result in dispersement of the delivered agent to a single or multiple sites of intended therapeutic action. Preferred routes of systemic delivery for the present compositions include intravenous, intramuscular, subcutaneous, and inhalational. In one preferred embodiment, intravenous administration is used, such as for treatment of disseminated tumors (and for monoclonal antibody delivery). In another embodiment, oral delivery may be preferred, for example, for treating gastrointestinal (GI) epithelial disorders. In another embodiment, nasal or aerosol delivery may be preferred for delivery to the lungs, such as for lung epithelial disorders.

The AdB-2/3 fiber multimer may be introduced in association with another molecule, such as a lipid or liposome to protect the polypeptides from enzymatic degradation. For example, the covalent attachment of polymers, especially polyethylene glycol (PEG), has been used to protect certain proteins from enzymatic hydrolysis in the body and thus prolong half-life.

The AdB-2/3 fiber multimer and/or therapeutic may be systemically administered on a periodic basis at intervals determined to maintain a desired level of therapeutic effect. For example, administration by intravenous injection may be once per day, once per week, every two to four weeks or at less frequent intervals. The dosage regimen will be determined by the physician considering various factors that may influence the action of the combination of agents. These factors will include the extent of progress of the condition being treated, the patient's age, sex and weight, and other clinical factors. The dosage for AdB-2/3 fiber multimer and/or therapeutic will vary as a function of the multimer and/or therapeutic being administered, as well as the presence and nature of any drug delivery vehicle (e.g., a sustained release delivery vehicle). In addition, the dosage quantity may be adjusted to account for variation in the frequency of administration and the pharmacokinetic behavior of the delivered agent(s). Dosage ranges of AdB-2/3 fiber multimers will generally range between 0.01 and 250 mg/kg, preferably between 0.1 and 10 mg/kg, and more preferably between 0.10 to 0.5 mg/kg. Dosages of approved therapeutics are readily identifiable by medical practitioners. The therapeutic may also be able to be administered at a reduced dose due to enhanced penetration into epithelial tissues, such as cancers.

The AdB-2/3 fiber multimer may be administered to the subject before, simultaneously, or after administration of the therapeutic. In a preferred embodiment, administration of the therapeutic and the AdB-2/3 fiber multimer are carried out at the same time. The timing of administrations of the therapeutic relative to the AdB-2/3 fiber multimer can be varied to achieve the greatest therapeutic effect. Preferably, the therapeutic is administered at a time to ensure its contact with the transient opening of the intercellular junction caused by AdB-2/3 fiber multimer binding to DSG2. For example, the therapeutic can be administered prior to, simultaneously with, after each administration of the AdB-2/3 fiber multimer. In other preferred embodiments, the therapeutic can be administered after the administration of the AdB-2/3 fiber multimer, for example up to 5 minutes, 10 minutes, 15 minutes, 30 minutes, 45 minutes, 1 hour, 2 hours, 3 hours, 4 hours, 5 hours, 6 hours, 8 hours. 10 hours, 12 hours, 18 hours. 24 hours, 30 hours, 36 hours, 40 hours, 42 hours, 48 hours, 54 hours, 60 hours, 66 hours, 72 hours, 78 hours, 84 hours. 90 hours, or even up to 96 hours after the administration of the AdB-2/3 fiber multimer.

In another aspect, the present invention provides methods for treating a disorder associated with epithelial tissue, comprising administering to a subject in need thereof an amount of an AdB-2/3 fiber multimer of the invention sufficient to treat the disorder. In this embodiment, no other therapeutic is delivered. In non-limiting embodiments, the monotherapy is used to treat a disorder selected from the group consisting of an AdB-2/3 viral infection, a solid tumor, or a disorder that can be treated using an AdB-2/3-based gene delivery vector. For example, in treating solid tumors, the method comprises improving access of immune system cells to the site of the disorder, such as by penetration (such as intratumoral penetration of pre-existing natural killer cells, T-cells or dendritic cells). The method can also be used to treat any of the disorders associated with epithelial cells discussed above that can benefit from improved access of cells of the immune system to the target epithelial cells. In one preferred embodiment, the disorder is a solid tumor, and the method comprises improving immune system attack of the tumor. The method can be used with any of the solid tumors discussed above. All embodiments and combinations of embodiments of the first aspect of the invention can be used in this second aspect as well, unless the context clearly dictates otherwise. Exemplary multimers comprising one or more AdB-2/3 fiber multimers of the invention that can be used in these methods include, but are not limited to, AdB-2/3 virions, AdB-2/3 capsids, AdB-2/3 dodecahedral particles (PtDd) (subviral dodecahedral particles produced by AdB-2/3 during their replication), and recombinant AdB-2/3 fiber multimers.

In another aspect, the present invention provides method for identifying candidate compounds for one or more of treating a disorder associated with epithelial tissue, improving delivery of a substance to an epithelial tissue, for improving delivery of a substance tissue expressing DSG2, inducing an EMT in a tissue, and/or treating an AdB-2/3 infection comprising (a) contacting an AdB-2/3 fiber multimer of the invention to DSG2 under conditions to promote multimer binding to DSG2, wherein the contacting is carried out in the presence of one or more test compounds; and (b) identifying positive test compounds that compete with the AdB-2/3 fiber multimer for binding to DSG2 compared to control; wherein the positive test compounds are candidate compounds for one or more of treating a disorder associated with epithelial tissue, improving delivery of a substance to an epithelial tissue, for improving delivery of a substance tissue expressing DSG2, inducing an EMT in a tissue, and/or treating an AdB-2/3 infection.

Positive test compounds that compete with the AdB-2/3 fiber multimer for binding to DSG2 are candidate compounds for transiently opening intracellular junctions through their interaction with DSG2. Follow-up assays to verify the ability of the compounds to transiently open intracellular junctions through their interaction with DSG2 can be carried out by any suitable methods, including but not limited to studies disclosed in the examples that follow. Compounds so identified for treating a disorder associated with epithelial tissue, improving delivery of a substance to an epithelial tissue, improving delivery of a substance tissue expressing DSG2, or inducing an EMT in a tissue, can be used as substitutes for the AdB-2/3 multimer in any of the methods of the present invention. Furthermore, AdB-2/3 represent important human pathogens causing respiratory tract infections (some sever) and pharyngoconjunctival fever. Thus compounds that can treat AdB-2/3 infection would be useful. As disclosed herein, DSG2 as the primary high-affinity receptor used by AdB-2/3, and thus compounds that can diminish AdB-2/3 binding to DSG2 are candidate compounds for treating or limiting development of AdB-2/3 infection.

Exemplary multimers comprising one or more AdB-2/3 fiber multimers of the invention that can be used in these methods include, but are not limited to, AdB-2/3 virions, AdB-2/3 capsids, AdB-2/3 dodecahedral particles (PtDd) (subviral dodecahedral particles produced by AdB-2/3 during their replication), and recombinant AdB-2/3 fiber multimers. Any suitable control can be used, including but not limited to an AdB-2/3 multimer binding to DSG2 in the absence of test compounds, In one embodiment, the DSG comprises recombinant DSG2. In another embodiment, the methods use cells expressing DSG2 (endogenously or recombinantly) on the cell surface.

In one non-limiting embodiment, surface plasmon resonance (SPR) studies using sensors containing immobilized recombinant DSG2 can be used to identify candidate compounds that AdB-2/3 fiber multimer binding to DSG2, combined with DSG2 competition studies. In another embodiment, the identifying comprises transduction studies, where the ability of test compounds to diminish binding is detected as a decrease in the ability of functional AdB-2/3 virions to transduce DSG2-expressing epithelial cells. In another embodiment, DSG2-expressing cell extract is electrophoretically separated and Western blotted, and labeled AdB-2/3 fiber multimer is used to probe the Western blot in the presence of the test compounds. In a further embodiment, dot-blot assays can be used, such as those described in Wang et al., J. Virology (2007) 81:12785-12792; and Wang et al. (2008) 82:10567-10579.

When the test compounds comprise polypeptide sequences, such polypeptides may be chemically synthesized or recombinantly expressed. Recombinant expression can be accomplished using standard methods in the art, as disclosed above. Such expression vectors can comprise bacterial or viral expression vectors, and such host cells can be prokaryotic or eukaryotic. Synthetic polypeptides, prepared using the well-known techniques of solid phase, liquid phase, or peptide condensation techniques, or any combination thereof, can include natural and unnatural amino acids. Amino acids used for peptide synthesis may be standard Boc (Nα-amino protected Nα-t-butyloxycarbonyl) amino acid resin with standard deprotecting, neutralization, coupling and wash protocols, or standard base-labile Nα-amino protected 9-fluorenylmethoxycarbonyl (Fmoc) amino acids. Both Fmoc and Boc Nα-amino protected amino acids can be obtained from Sigma, Cambridge Research Biochemical, or other chemical companies familiar to those skilled in the art. In addition, the polypeptides can be synthesized with other Na-protecting groups that are familiar to those skilled in this art. Solid phase peptide synthesis may be accomplished by techniques familiar to those in the art and provided, such as by using automated synthesizers.

When the test compounds comprise antibodies, such antibodies can be polyclonal or monoclonal. The antibodies can be humanized, fully human, or murine forms of the antibodies. Such antibodies can be made by well-known methods, such as described in Harlow and Lane, Antibodies; A Laboratory Manual, Cold Spring Harbor Laboratory, Cold Spring Harbor, N.Y., (1988).

When the test compounds comprise nucleic acid sequences, such nucleic acids may be chemically synthesized or recombinantly expressed as well. Recombinant expression techniques are well known to those in the art (See, for example, Sambrook, et al., 1989, supra). The nucleic acids may be DNA or RNA, and may be single stranded or double. Similarly, such nucleic acids can be chemically or enzymatically synthesized by manual or automated reactions, using standard techniques in the art. If synthesized chemically or by in vitro enzymatic synthesis, the nucleic acid may be purified prior to introduction into the cell.

For example, the nucleic acids can be purified from a mixture by extraction with a solvent or resin, precipitation, electrophoresis, chromatography, or a combination thereof. Alternatively, the nucleic acids may be used with no or a minimum of purification to avoid losses due to sample processing.

When the test compounds comprise compounds other than polypeptides, antibodies, or nucleic acids, such compounds can be made by any of the variety of methods in the art for conducting organic chemical synthesis.

Examples. Structural and functional studies on the interaction of adenovirus fiber knob domains and desmoglein 2

Abstract

Human adenovirus (Ad) serotypes Ad3, Ad7, Ad11, Ad14, and a recently emerged new strain of Ad14 (Ad14p1) use the epithelial junction protein desmoglein 2 (DSG2) as a receptor for infection. Unlike Ad interaction with CAR and CD46, structural details for Ad binding to DSG2 are still elusive. Using an approach based on *E. coli* expression libraries of random Ad3 and Ad14p1 fiber knob mutants we identified amino acid residues that, when mutated individually, ablated or reduced Ad knob binding to DSG2. These residues formed three clusters inside one groove at the extreme distal end of the fiber knob. The Ad3 fiber knob mutant library was also used to identify variants with increased affinity to DSG2. We found a number of mutations within or near to the EF loop of the Ad3 knob that resulted in several orders of magnitude higher affinities to DSG2 compared with the wild-type Ad3 knob. Crystal structure analysis of one of the mutants showed that the introduced mutations make the EF loop more flexible, which might facilitate the interaction with DSG2. Our findings have practical relevance for cancer therapy. We have recently reported that an Ad3 fiber knob containing recombinant protein (JO-1) is able to trigger opening of junctions between epithelial cancer cells, which in turn, greatly improved the intratumoral penetration and efficacy of therapeutic agents. Here we show that affinity-enhanced versions of JO-1 are therapeutically more potent than the parental protein in a series of cancer models.

Introduction

We recently identified DSG2 as the main receptor for a group of species B adenoviruses, including adenovirus serotype 3 (Ad3), a serotype which is widely distributed in the human population (42). We found that the DSG2 interacting domain(s) within Ad3 are formed by several fiber knobs (41). This specific mode of Ad3-fiber knob-DSG2 interaction provides a high avidity and is functionally relevant for opening of epithelial junctions (41, 42). The latter involves clustering of DSG2 and activation of pathways that are reminiscent of an epithelial-to-mesenchymal transition, including the phosphorylation of MAP kinase and the downregulation of junction protein expression (6, 40, 42). The ability to open epithelial junctions appears to be important for Ad3 penetration into, and spread within airway epithelial cells (40-42). In a recent study, we attempted to find the minimal moiety within the Ad3 capsid that confers efficient binding to DSG2 (41). We generated a small recombinant protein, which contains the Ad3 fiber knob and a domain that allows for the self-dimerization of trimeric Ad3 fiber knobs (JO-1) (41). JO-1 can be readily produced in E. coli and purified by affinity chromatography. In polarized epithelial cell cultures JO-1 triggered the opening of intercellular junctions while intravenous injection of JO-1 into mice with epithelial tumors allowed for better penetration of anticancer drugs (5, 6).

The first goal of the present study was to further delineate structural features of the Ad3 fiber knob-DSG2 interaction. This included identifying the amino acid residues within the Ad3 fiber knob that are involved in binding to DSG2 and creating JO-1 mutants with reduced and ablated binding to DSG2. The second goal of this study, which has translational relevance, was to further improve JO-1 by enhancing its affinity to DSG2 thereby increasing its therapeutic effect. This was done by identifying mutants with increased binding to DSG2.

Both goals were achieved using an E. coli expression library of Ad3 fiber knob mutants. We have identified residues in three different clusters within the Ad3 fiber knob that are critically involved in binding to DSG2. All residues are localized within one groove at the distal end of the fiber knob facing the receptor. We then assessed the effect of these mutations on the fiber knob's ability to open epithelial junctions by measuring the transepithelial electrical resistance in polarized epithelial cells in vitro, and the ability to enhance the efficacy of a chemotherapy drug in mice with epithelial xenograft tumors. As expected, when mutations with reduced affinity to DSG2 were introduced into JO-1, the resulting proteins were less capable to open epithelial junctions. On the other hand, a number of mutations that increased the affinity of JO-1 to DSG2 displayed a stronger activity in opening of epithelial junctions. Overall, these studies indicate a correlation between the affinity of Ad3-fiber knobs to DSG2 and subsequent effects on epithelial junctions.

The third goal of this study was to delineate the DSG2 interacting fiber knob residues of another DSG2-targeting Ad serotype; the newly emerged strain Ad14p1 (44), which is considered more pathogenic/virulent than the parental strain (Ad14-deWit) (10, 16, 22). The beta sheet distribution of Ad14p1 differs from that of Ad3, which could potentially result in differences in the mode of DSG2 binding. We therefore generated an E. coli expression library of Ad14p1 fiber knob mutants to identify the DSG2-interacting residues of Ad14p1.

Materials and Methods

Proteins. Recombinant human DSG2 protein was from Leinco Technologies, Inc. (St. Louis, Mo.). The Ad3 fiber knob was derived from Ad3 virus, GB strain, obtained from the ATCC. The Ad14p1 fiber knob is derived from Ad14p1 virus, strain Portland 2971/2007, provided by the Center for Disease Control and Prevention (Atlanta, Ga.) (44). The fiber knobs were produced in E. coli with N-terminal 6-His tags, using the pQE30 expression vector (Qiagen. Valencia, Calif.) and purified by Ni-NTA agarose chromatography as described elsewhere (43).

Cell lines. 293, HeLa, and A549 cells were maintained in DMEM supplemented with 10% FBS, 100 U/ml penicillin, 100 μg/ml streptomycin (P/S), 2 mM glutamine (Glu) and 1×MEM non-essential-amino-acid solution (Invitrogen, Carlsbad, Calif.). Colon cancer T84 cells (ATCC CCL-248) were cultured in a 1:1 mixture of Ham's F12 medium and DMEM, 10% FBS, Glu and P/S. Ovc316 cells are Her2/neu positive epithelial tumor cells derived from an ovarian cancer biopsy (32). Ovc316 cells were cultured in MEGM (Lonza, Mapleton, Ill.) containing 3 μg/L hEGF, 5 μg/L insulin, 5 mg/L hydrocortisone, 26 mg/L bovine pituitary extract, 25 mg/L amphotericin B) (Lonza), supplemented with 1% FBS, 100 I.U. penicillin, 100 μg/L streptomycin, 10 mg/L ciprofloxacin. MDA-MB-231 cells, a triple-negative breast cancer cell line (ATCC-HTB-26) were cultured in Leibovitz's L-15 medium supplemented with 10% FBS, 100 I.U. penicillin, 100 μg/L streptomycin. TC1-DSG2 were derived from TC1 cells, a C57Bl/6 lung cancer cell line that expresses HPV16 E6 and E7 (36). TC1 cells were transduced with a VSVG-pseudotyped lentivirus vector expressing human DSG2 (42). A clone that expressed human DSG2 at a level seen in human tumors was selected for in vivo studies.

Adenoviruses. Propagation, methyl-$^3$H thymidine labeling, purification and titering of wild-type Ad3 was performed as described elsewhere (37). Ad3-GFP is a wild-type Ad3-based vector containing a CMV-GFP expression cassette inserted into the E3 region (42). Viral particle (VP) concentrations were determined spectrophotometrically by measuring the optical density at 260 nm ($OD_{260}$). Titers of plaque forming units (pfu) were performed using 293 cells as described elsewhere (29). The VP to pfu ratio was 20:1 for all virus preparations.

Ad3 knob library. The coding sequence of the Ad3 knob (aa 108-319) containing the last two shaft repeats was obtained by PCR from Ad3 DNA using primers P1: 5' ATCACGGATCCGGTGGCGGTTCTGGCGGTGGCTC-CGGTGGCGGTTCTAACAAACT TTGCAGTAAACTC 3' (SEQ ID NO: 35) and P2: 5'CTCAGCTAATTAAGCT-TAGTCATCTTTCTCTAATATAG GA 3' (SEQ ID NO: 36), and cloned into pQE30 (Qiagen, Valencia, Calif.) for expression in E. coli. The resulting plasmid was called pQE-Ad3knob. Random mutagenic PCR was performed based on a protocol published elsewhere (7, 8). Briefly, 20 fmoles pQE-Ad3knob DNA template, 30 pmoles (each) PCR primers (Pmut1: 5'-CCAATTCTATGCACT-TAAGAATAACACTTTATGGACAGGT-3' (SEQ ID NO: 37) and Pmut2: 5'-GTCCAAGCTCAGCTAATTAAGCT-TAGTCATCTTC-3' (SEQ ID NO: 38), 2.5 µl, 3.5 µl, 5 µl or 10 µl of 10× mutagenic buffer (70 mM $MgCl_2$, 500 mM KCl, 100 mM Tris (pH8.3 at 25° C.), and 0.1% (w/v) gelatin), 10 µl 5 mM $MnCl_2$, 10 µl dNTP mix (2 mM dGTP, 2 mM dATP, 10 mM dCTP, 10 mM dTTP) and 5 units of Taq polymerase (Promega, Madison, Wis.) were mixed in a final volume of 100 µl. PCR conditions were 94° C. for 1 min, 45° C. for 1 min, and 72° C. for 1 min (30 cycles). The mutant PCR products (615 bp in length containing mutations only in the reading frame of fiber knob head) were purified, digested with appropriate enzymes, and cloned into the plasmid pQE-Ad3knob. For quality control of the random mutagenic library, the ligation product was transformed into E. coli M15 (Qiagen, Valencia, Calif.), plated on kanamycin and ampicillin plates, and 50 colonies were randomly picked for sequencing.

Ad14 library: The coding sequence of the Ad14p1 knob (aa 108-323) containing the last two shaft repeats was obtained by PCR from Ad14p1 DNA using primers P1: 5' CATCACGGATCCGGTGGCGGTTCTGGCGGTGGCTC-CGGTGGCGGTTCTAATAAAC TTTGTACCAAAT-TGGGAGAAGG 3' (SEQ ID NO: 39) and P2: 5' GCTAAT-TAAGCTTAGTCGTCTTCTCTGATGTAGTAAAAGG 3'(SEQ ID NO: 40), and cloned into pQE30 (Qiagen, Valencia, Calif.) for expression in E. coli. The resulting plasmid was called pQE-Ad14p1knob. Random mutagenic PCR was performed by using PCR primers (Pmut1: 5'-AACACCCTGTGGACAGGAGTTAACCC-3'(SEQ ID NO: 41) and Pmut2: 5'-CTCAGCTAATTAAGCT-TAGTCGTC-3' (SEQ ID NO: 42)). The mutant PCR products (594 bp in length containing mutations only in the reading frame of fiber knob head) were purified, digested with appropriate enzymes, and cloned into the plasmid pQE-Ad14p1knob. For quality control of the random mutagenic library, the ligation product was transformed into E. coli M15 (Qiagen, Valencia, Calif.), plated on kanamycin and ampicillin plates, and 50 colonies were randomly picked for sequencing.

Colony assays. The Ad3 or Ad14p1 knob mutant plasmid library were transformed into XL1 Blue or M15 E. coli host strains and plated on LB plates with appropriate antibiotics, i.e, Amp or Amp+Kan, respectively. After overnight growth, a 0.45 µm Durapore filter membrane (Millipore, Billerica, Mass.) was placed on top of the colonies. The membrane was peeled off and placed carefully, with the colonies facing upwards, on two sheets of 3 MM paper soaked in LB medium supplemented with antibiotics and 1 mM IPTG. Protein expression of the colonies was induced for 6 hours at 30° C., after which the filter with the colonies was placed on top of a nitrocellulose filter and a Whatman 3 MM paper soaked in native lysis buffer {20 mM Tris-Cl (pH8), 300 mM NaCl, 50 mM $MgCl_2$, 0.1 mg/ml lysozyme, 0.75 mg/ml DNAse I, 1/2 complete EDTA-free protease inhibitor cocktail tablet/10 ml (Roche, Palo Alto, Calif.)}. The "filter sandwich" was incubated at room temperature for 10 min and then freeze-thawed 4 times for 10 min at −80° C. and 10 min at 30° C. The nitrocellulose membrane was removed from the sandwich and blocked with 3% BSA in TBST at 4° C. overnight. The blot was then incubated with 0.1 ng/ml of recombinant DSG2 protein (Leinco, St. Louis, Mo.) in TBST/BSA, followed by mouse monoclonal anti-DSG2 antibodies (Clone 6D8; SeroTec Ltd., Oxford. UK) and anti-mouse IgG horseradish peroxidase conjugate. Colonies without DSG2 binding were picked and cultured in 3 ml LB medium overnight. Protein expression was induced with 1 mM IPTG for 5 hours, the bacteria were then pelleted, resuspended in SDS loading buffer and freeze/thawed 3 times. After electrophoresis, proteins were transferred to nitrocellulose and incubated with anti-His antibodies (MCA1396, Sertec) to assess Ad knob trimerization. To screen for mutants with stronger binding to DSG2, the Ad3 knob mutant library was transformed into M15 E. coli host strain. Protein expression of the colonies was induced for only 20 min at room temperature. The colonies that showed the most intense DSG2 binding signal were picked.

Western Blot: Mini-PROTEAN precast gels (BIO-RAD, Hercules, Calif.) with 4-15% gradient polyacrylamide were used. A total of 1 µg protein mixed with 2× loading buffer (10 mM Tris-HCl, pH6.8, 200 mM DTT, 4% SDS, 20% glycerol, 0.2% bromophenol blue) was loaded per lane. Samples were either boiled (B) for 5 min or loaded unboiled (UB). The following running buffer was used: 25 mM Tris, pH8.3, 0.192 M glycine, 0.1% SDS. After electrophoresis, proteins were transferred to nitrocellulose and incubated with recombinant human DSG2 protein and anti-DSG2 antibodies as described previously (42). The Western blots were scanned and quantified using the ImageJ 1.32 software (National Institutes of Health, Bethesda, Md.). JO-1 band intensity was set as 100%. For analysis of MAP kinase activity, polarized T84 cultures were lysed in 20 mM Hepes (pH 7.5). 2 mM EGTA. 10% glycerol, 1% TritonX 100, 1 mM PMSF, 200 µM $Na_3VO_4$ and protease inhibitors) on ice. After sonication, samples were pelleted and protein containing supernatant stored at −80° C. 15 µg of total protein was used for Western blotting with mAb against phospho-p44/42 MAPK (Erk1/2)(Thr202/Tyr204) (Cell Signaling Danvers, Mass.) or mAb against mouse anti-Erk1/2 (Cell Signaling).

Competition assays. HeLa cells were detached from culture dishes by incubation with Versene and washed with PBS. A total of $10^5$ cells per tube were resuspended in 50 µl of ice-cold adhesion buffer (DMEM supplemented with 2 mM $MgCl_2$, 1% FBS, and 20 mM HEPES) containing different concentrations of Ad3 fiber knob protein, and incubated on ice for 1 hour. Then, H-labeled wild-type Ad3 virus was added in adhesion buffer at a multiplicity of infection (MOI) of 8,000 viral particles (vp) per cell to a final volume of 100 µl. After 1 h of incubation on ice, cells were pelleted and washed twice with 0.5 ml of ice-cold PBS. After the last wash, the supernatant was removed and the cell-associated radioactivity was determined by a scintillation counter. The number of VP bound per cell was calculated by using the virion specific radioactivity and the number of cells.

Surface Plasmon Resonance: Acquisitions were done on a BIAcore 3000 instrument. HBS-N (GE-Healthcare, Pittsburgh, Pa.) supplemented with 2 mM $CaCl_2$ was used as running buffer in all experiments at a flow rate of 5 µl/min. Immobilization on CM4 sensorchip (BIAcore) was performed using DSG2 at 10 µg/ml diluted in 10 mM Acetate buffer pH 4.5 injected for 10 minutes on ethyl(dimethylaminopropyl) carbodiimide (EDC)/N-Hydroxysuccinimide (NHS) activated flow-cell. A control flow-cell was activated by (EDC/NHS) and inactivated by ethanolamine. Different concentrations of Ad3 fiber knob proteins were injected for 3 minutes association followed by 2.5 minutes dissociation time, and the signal was automatically subtracted from the background of the ethanolamine deactivated EDC-NHS flow cell. Kinetic and affinity constants were calculated using the BIAeval software.

Crystallography: Crystallization conditions for wtAd3 and K217E/F224S knob mutants were using the service of the High Throughput Screening Lab at Hauptman Woodward Medical Research Institute. For diffraction studies, wtAd3 and K217E/F224S knob mutant were crystallized using the hanging drop method. Crystals were grown using a reservoir solution of 1.65M $MgSO_4(7H_2O)$ in TAPS buffer 0.1 M pH9.0 and a protein solution of 15 mg/ml. Crystals were frozen using a cryoprotectant composed of 85% reservoir and 15% glycerol (v/v). Data collection was performed at 100K on ID14-4 of the ESRF using the EDNA pipeline (19). Data were indexed and scaled using XDS/XSCALE (20, 21) and the structure solved by molecular replacement (PDB 1H7Z) with the program PHASER (25). The model was built and refined using COOT (14) and PHENIX (2), respectively (Table 1). The entry "Structure of the adenovirus 3 knob domain K217E and F224S mutant" has been assigned the RCSB ID code rcsb080687 and PDB ID code 4LIY.

TABLE 1

Data collection and refinement statistics.

| | Ad3 knob (K217E/F224S mutant) |
|---|---|
| Wavelength (Å) | |
| Resolution range (Å) | 48.-2.1 (2.175-2.1) |
| Space group | P 32 2 1 |
| Unit cell | 96.663 96.663 156.399 90 90 120 |
| Total reflections | 222816 (21396) |
| Unique reflections | 49784 (4831) |
| Multiplicity | 4.5 (4.4) |
| Completeness (%) | 99.61 (98.96) |
| Mean I/sigma(I) | 11.46 (1.89) |
| Wilson B-factor | 40.48 |
| R-merge | 0.07161 (0.6146) |
| R-meas | 0.08092 |
| CC1/2 | 0.998 (0.801) |
| CC* | 1 (0.943) |
| R-work | 0.1759 (0.2670) |
| R-free | 0.2012 (0.3133) |
| Number of atoms | 4587 |
| macromolecules | 4310 |
| ligands | 5 |
| water | 272 |
| Protein residues | 553 |
| RMS(bonds) | 0.011 |
| RMS(angles) | 1.27 |
| Ramachandran favored (%) | 96 |
| Ramachandran outliers (%) | 0 |
| Clashscore | 4.58 |
| Average B-factor | 50.00 |
| macromolecules | 49.80 |
| ligands | 126.60 |
| solvent | 51.00 |

Statistics for the highest-resolution shell are shown in parentheses.

3D structure: Pymol software was used to analyze structure. Mutations in the Ad3 knob domain (pdb 1H7Z) were stained using different colors on the purple isosurface. Monomers of Ad3 knob mutant K217E/F224S were drawn in colored cartoons with mutations in sticks and overlaid on the gray cartoon view of wild type Ad3 fiber knob.

Negative-stain electron microscopy: Recombinant JO-2 protein was visualized by negative-stain EM to assess its assembly status. The standard mica-carbon preparation was used with protein at 0.1 mg/ml. Sample was stained using 1% (wt/vol) sodium silicotungstate (pH 7.0) and visualized on a JEOL-1200 electron microscope at 100 kV.

Permeability assay. A total of $5 \times 10^5$ T84 cells were seeded in 12 mm transwell inserts (PET membrane, with 0.4 µm pore size (Corning, N.Y.) and cultured for >14 days until transepithelial electrical resistance (TEER) was stable. Culture medium was changed every 2-3 days. The cells were exposed to DSG2 ligands (20 µg/ml) in adhesion medium (DMEM, 1% FBS, 2 mM $MgCl_2$, 20 mM HEPES) for 15 min at room temperature and TEER was measured and calculated as described elsewhere (39).

Animal studies: All experiments involving animals were conducted in accordance with the institutional guidelines set forth by the University of Washington. Mice were housed in specific-pathogen-free facilities. Immunodeficient (CB17) mice [strain name: NOD.CB 17-$Prkdc^{scid}$/J] were obtained from the Jackson Laboratory. Human DSG2 transgenic mice contain 90 kb of the human DSG2 locus and express hDSG2 at a level and in a pattern similar to humans (40).

A549, MDA-MB-231, and ovc316 xenograft tumors were established by injection of the corresponding tumor cells into the mammary fat pad (1:1 with Matrigel) of CB17 mice. TC1-DSG2 tumors were established by subcutaneous injection of TC1-DSG2 cells into DSG2 transgenic mice. JO-0, JO-1, JO-2, or JO-4 were intravenously injected one hour before the application of chemotherapeutic drugs: Irinotecan/Camptosar™ (Pfizer Inc., Groton, Conn.), PEGylated liposomal doxorubicin/Lipodox™ (Sun Pharmaceuticals IN, India), cetuximab/Erbitux™ (ImClone, Somerville, N.J.), nanoparticle albumin conjugated paclitaxel/Abraxane™ (Abraxis Biosciences, Summit, N.J.). Tumor volumes were measured three times a week. Each treatment group consisted of a minimum of 5 mice. Animals were sacrificed and the experiment terminated when tumors in one of the groups reached a volume of 800 $mm^3$ or tumors displayed ulceration.

Anti-JO4 antibodies: anti-JO-4 antibody concentrations in human serum samples were measured by ELISA. Plates will be coated with rabbit polyclonal anti-Ad3 fiber antibodies (42), followed by recombinant JO-4, human serum samples (1:2 to 1:1000 dilution), and anti-human IgG-HRP. Serum samples from ovarian cancer patients were provided by the Pacific Ovarian Cancer Research Consortium.

3D structure: Pymol software was used to visualize the 3D structure of the Ad3 fiber knob (MMDB ID: 16945, PDB ID: 1H7Z (13))

Statistical analysis: All results are expressed as mean +/−SD. 2-Way ANOVA for multiple testing was applied. Animal numbers and P values are indicated in the figure legends.

Results

Figure 5:
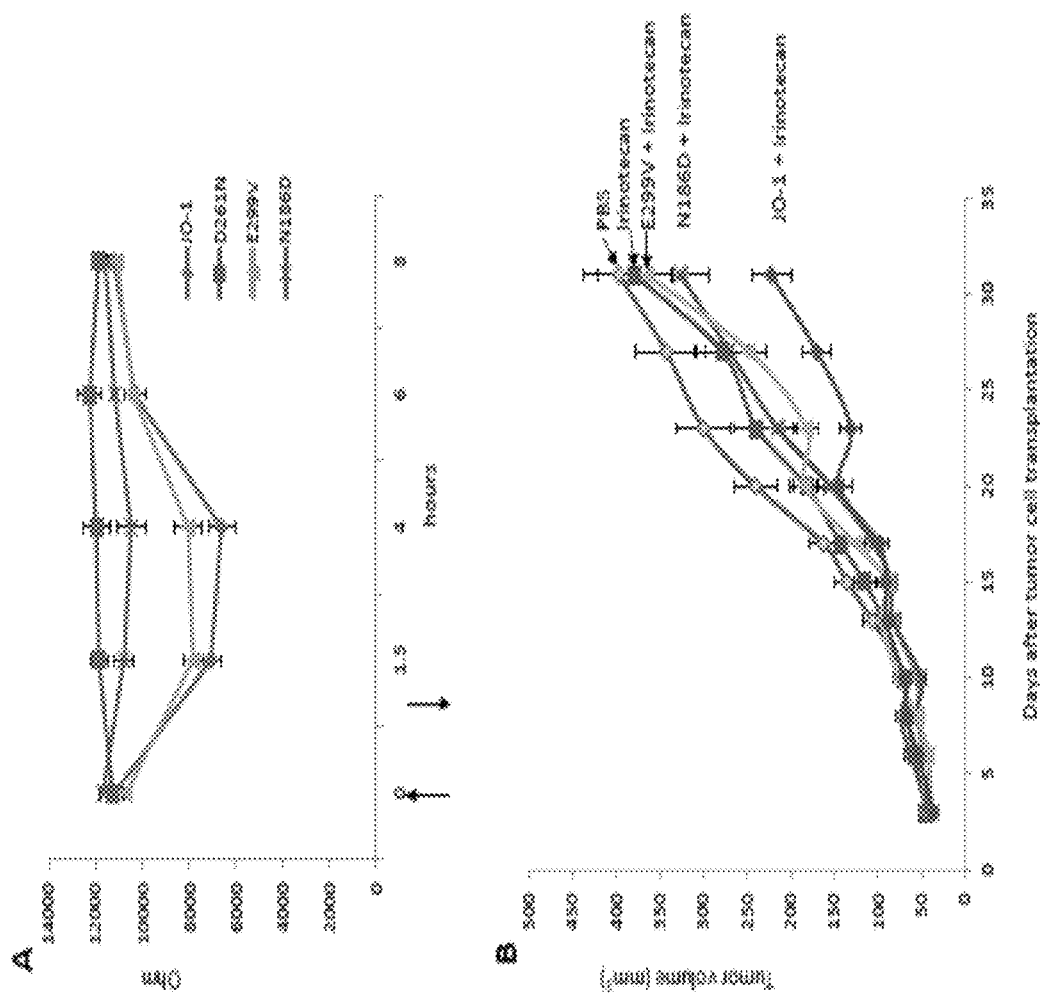
Figure 6A:
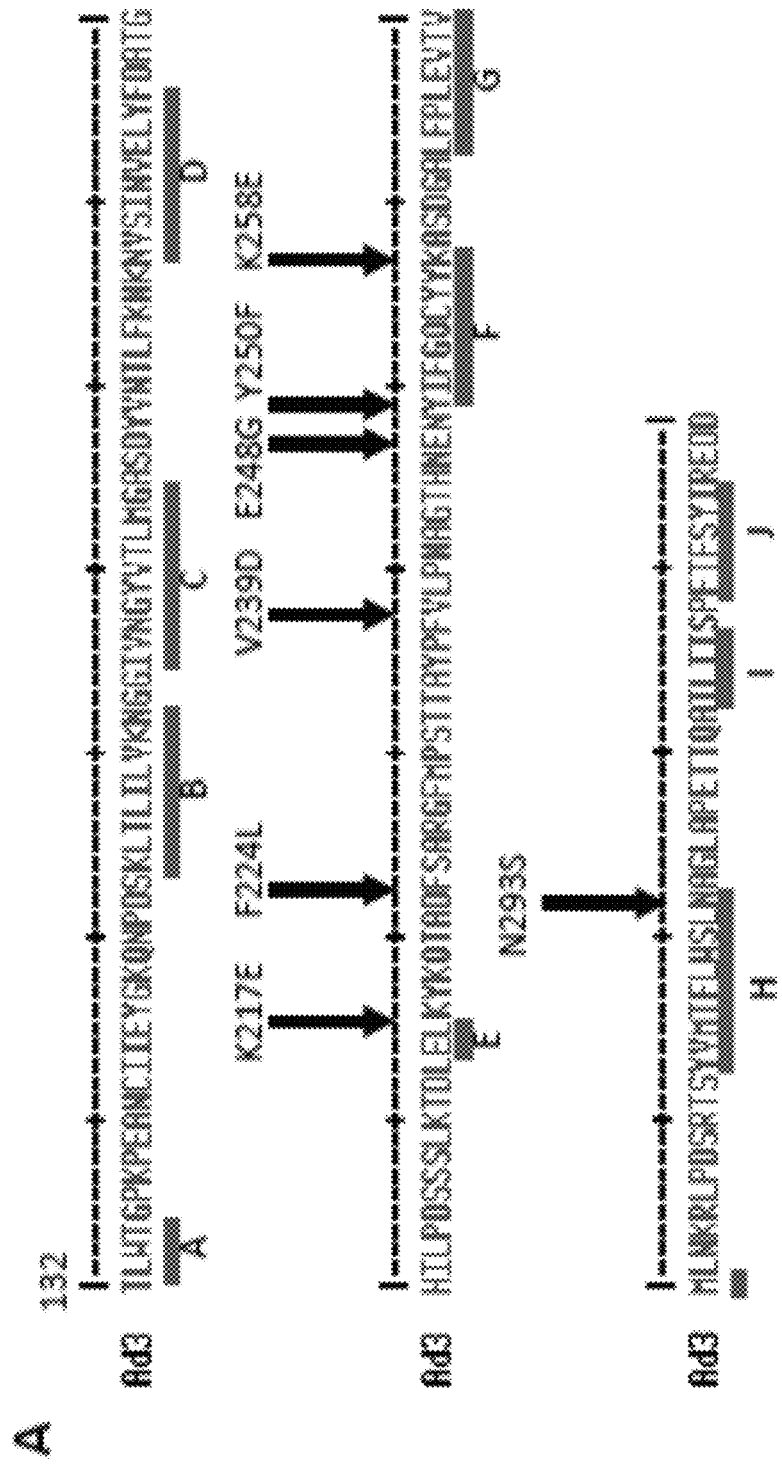
FIG. 6. Amino acid substitutions that increase the binding to DSG2. A) Shown is the amino acid sequence of the Ad3 fiber knob (SEQ ID NO: 44). Beta sheets are indicated by lines. Arrows indicate residues within the Ad3 fiber knob which, when mutated yielded stronger signals in colony blot assays, indicating stronger binding to DSG2. B) The isosurface of the three knob monomers. Left panel: Top view; Right panel: Side View. V239 and Y250 are not exposed at the top suggesting a structural change in the knob rather than an involvement in direct binding to DSG2. C) Localization of all mutations that enhance the binding to DSG2. Residues are show in magenta in two knob monomers. Isosurface of one knob monomer is shown in grey transparency.
Figure 6B:
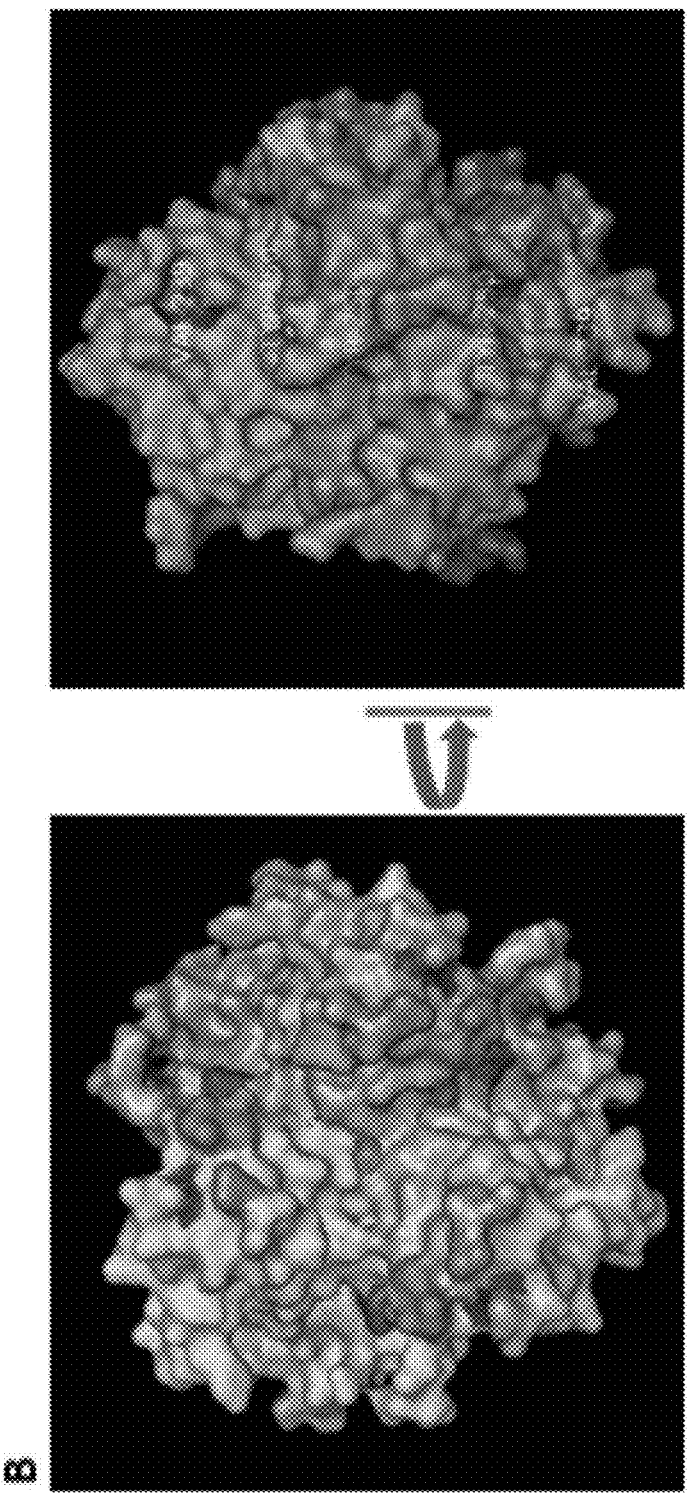
Figure 6C:
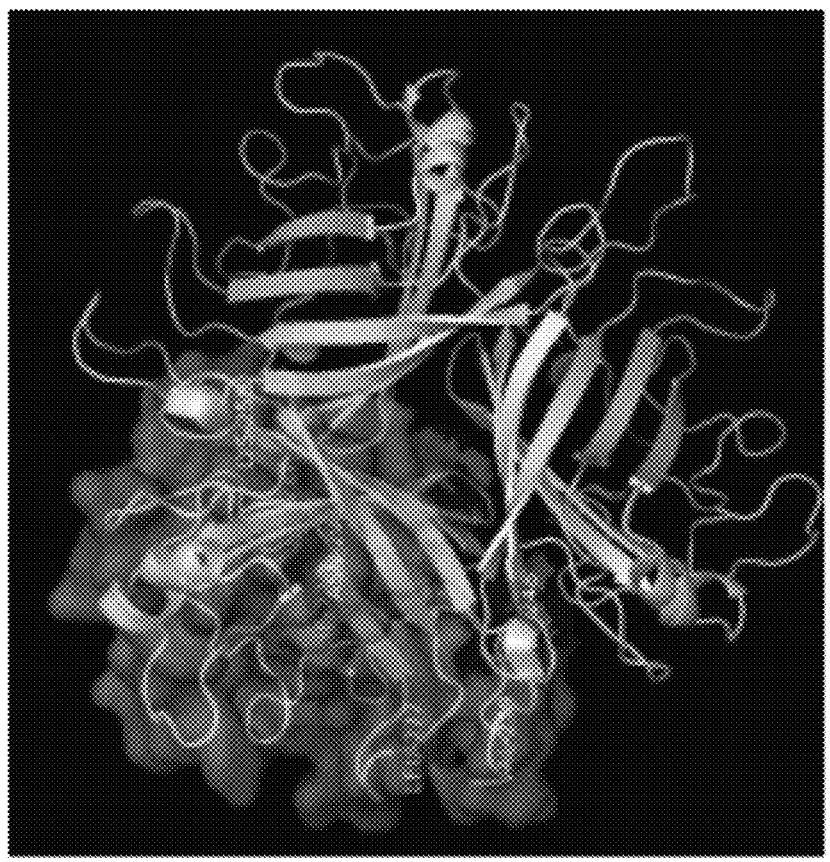
Figure 7A:
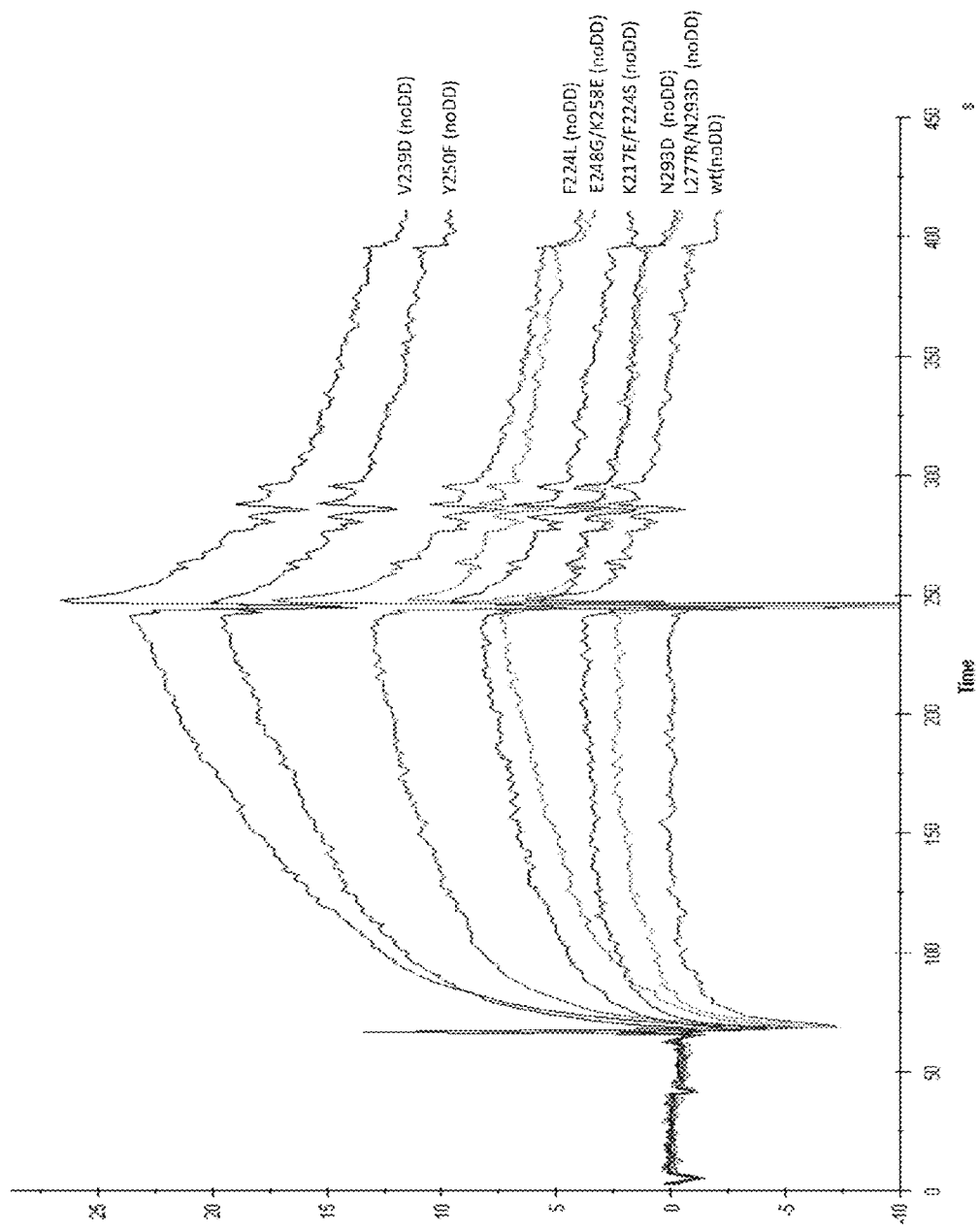
FIG. 7. SPR analysis of non-dimerized Ad3 fiber knob interactions with DSG2. A) DSG2 was immobilized on sensorchips, and background was automatically subtracted from the control flow cell. The Ad3 fiber knobs (w/o dimerization domain: "noDD") were injected for 3 minutes at 2.5 µg/ml followed by a 2.5 minutes dissociation period. B) Summary of SPR data. A concentration range from 2.5 to 10 µg/ml of the knobs has been injected and kinetics and affinity parameters have been evaluated using the BIAeval software. The extracted data are resumed in the table. Wt=Ad3 fiber knob without mutations FIG. 8. Electron microscopy and 3D structure of Ad3 fiber knob mutant JO-2. A-C) Negative staining of JO-2 with SST. Dimeric forms can be seen but higher organizations are also visible, an heterogeneous complex of around 50 nm depicted by thin arrows and a smaller regular "dodecahedral-like" particle depicted by thick arrows. Close-up views are presented in B and C. D-G) Crystallographic structure of the non-dimerized form of (K217E/F224S mutant). D) protein crystals. E) The wild-type Ad3 knob is colored in gray with the EF loop 217-224 separately colored. This is the loop which becomes disordered in the mutant. There is no density for these residues in the mutant structure. F) The mutant is displayed as a cartoon. G) Overlay of these two structures shows that the EG loop is completely disordered in the K217E/F224S mutant. The bottom panels show close-up views of one monomer. K217 and F224 appear as sticks.
Figures 8A, 8B, 8C, 8D:
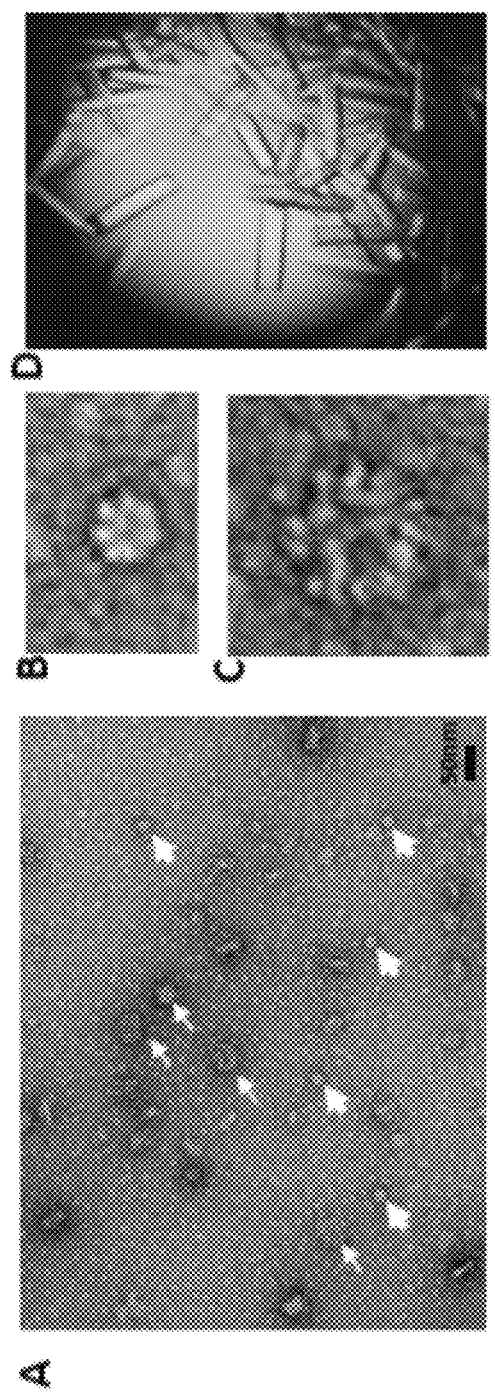
Figures 8E, 8F, 8G:
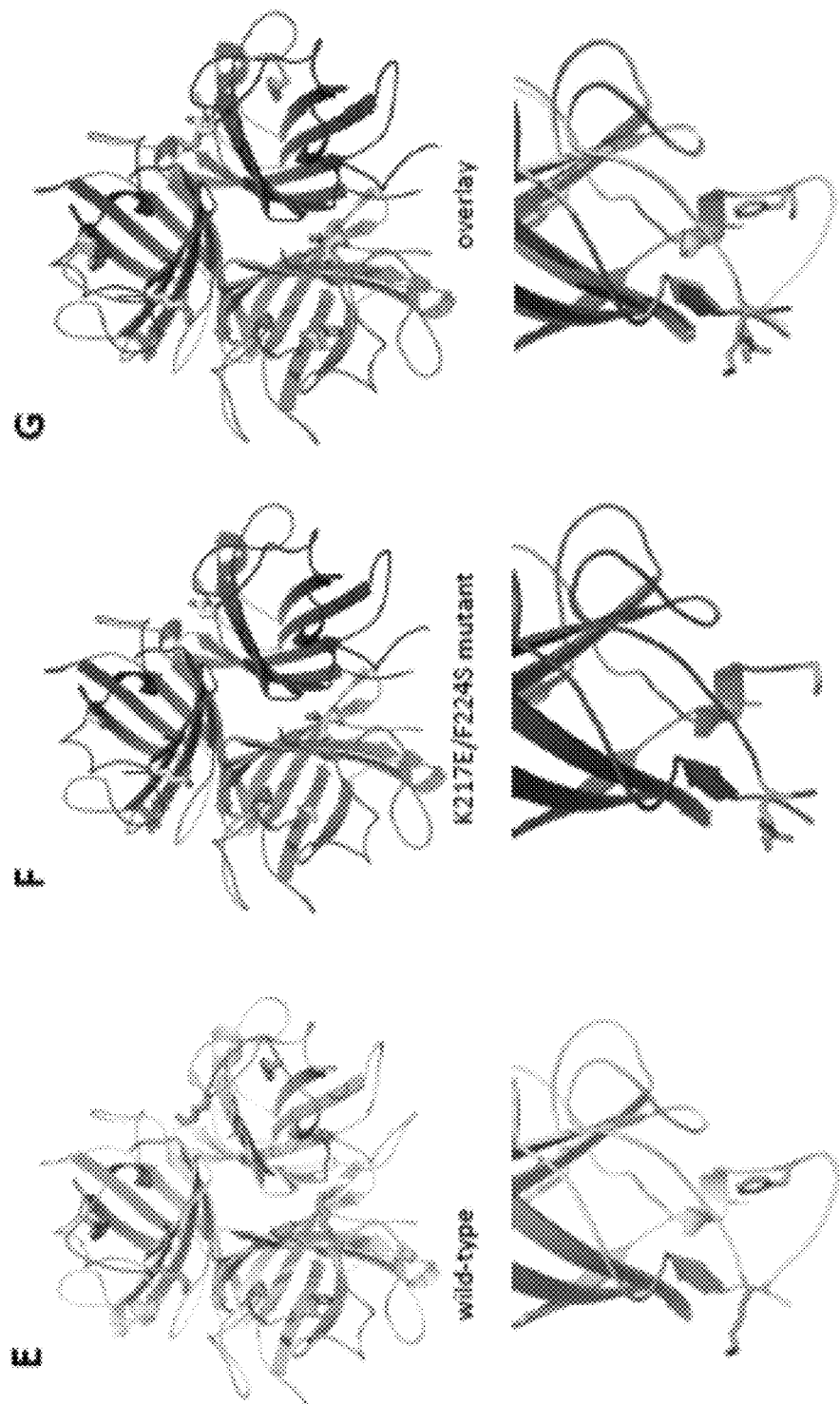
Figure 9A:
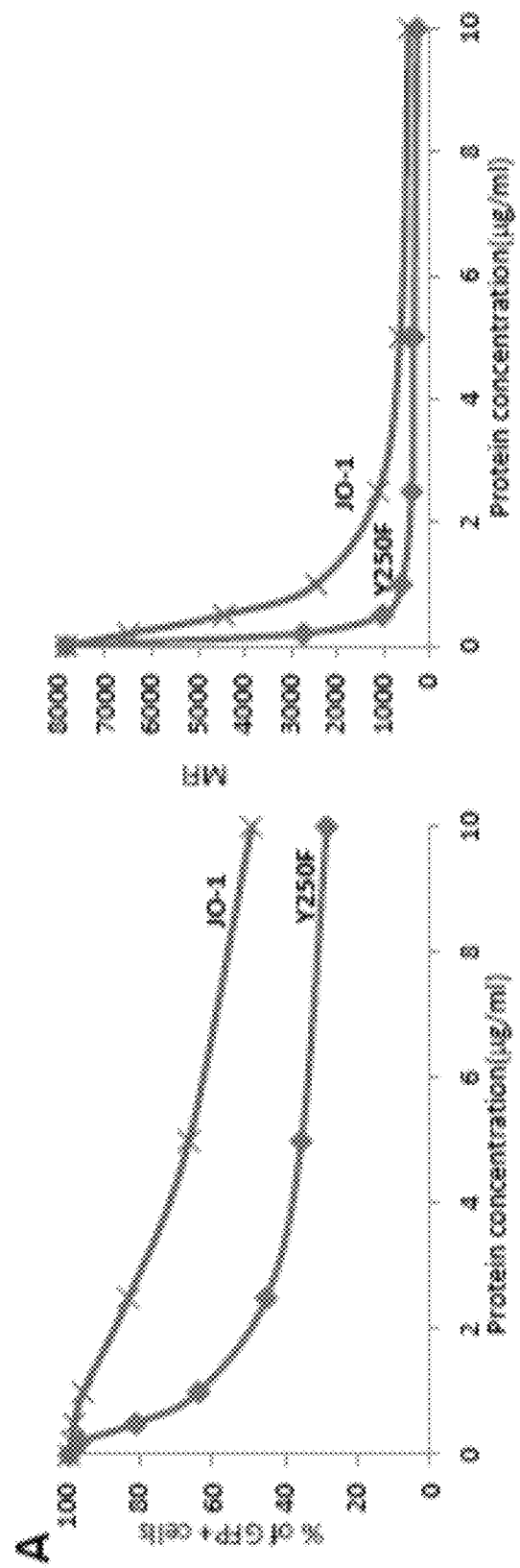
FIG. 9. Analysis of dimeric Ad3 fiber knob mutants with increased affinity to DSG2. A) Competition of Ad3-GFP virus infection on HeLa cells with dimeric affinity-enhanced mutant Y250F and JO-1 (dimeric wt Ad3 fiber knob). The experimental setting is as described for FIG. 3C. left panel: percentage of GFP positive cells. Right panel: mean fluorescence intensity. N=3. The standard deviation was less than 10%. B) Competition of Ad3-GFP virus infection on HeLa cells by Ad3 knob mutants with enhanced DSG2 binding but without dimerization domain. $1.5 \times 10^5$ HeLa cells were seeded into 24 well plates. Cells were incubated with the Ad3 knob mutants at the increasing concentrations for one hour at room temperature. 100 pfu/cell of Ad3GFP virus were then added and GFP expression was analyzed 18 hours later. C) TEER on colon cancer T84 cells. The experimental setting was the same as for FIG. 5A. The TEER at 4 hours is shown. N=3.
Figure 9B:
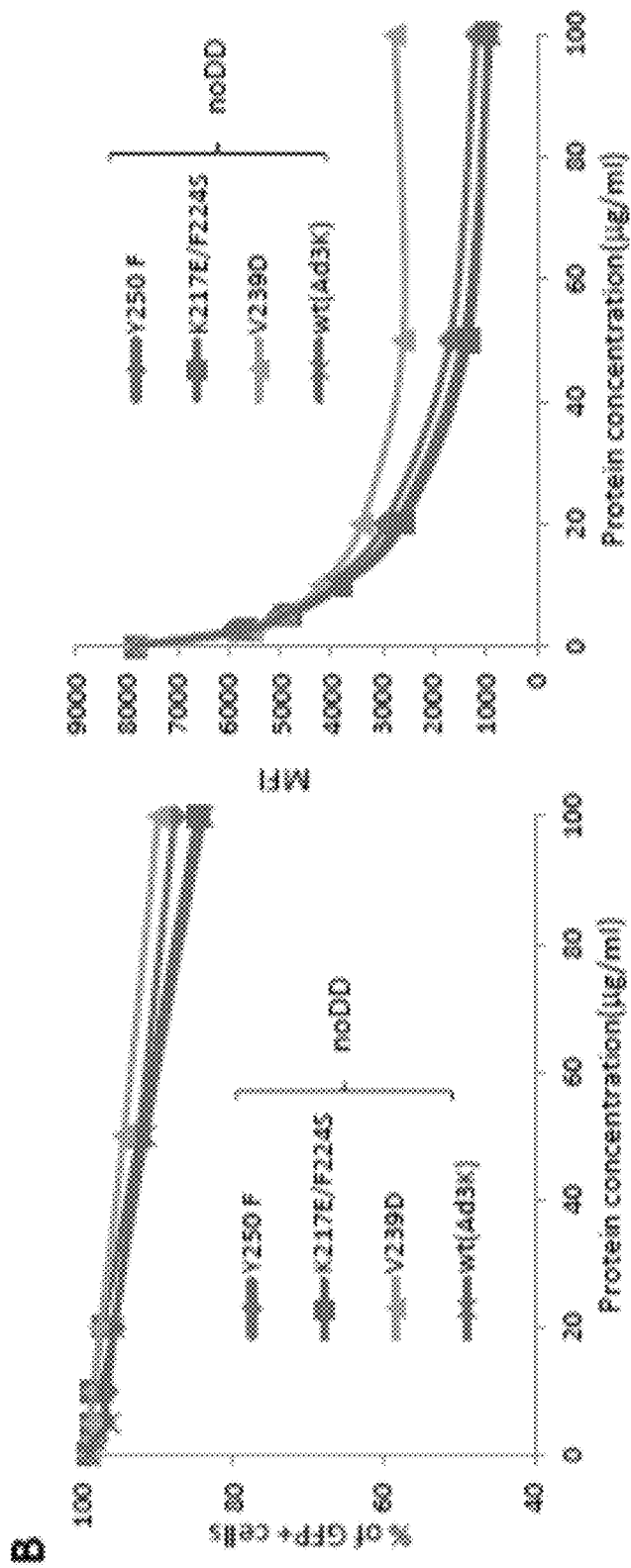
Figure 9C:
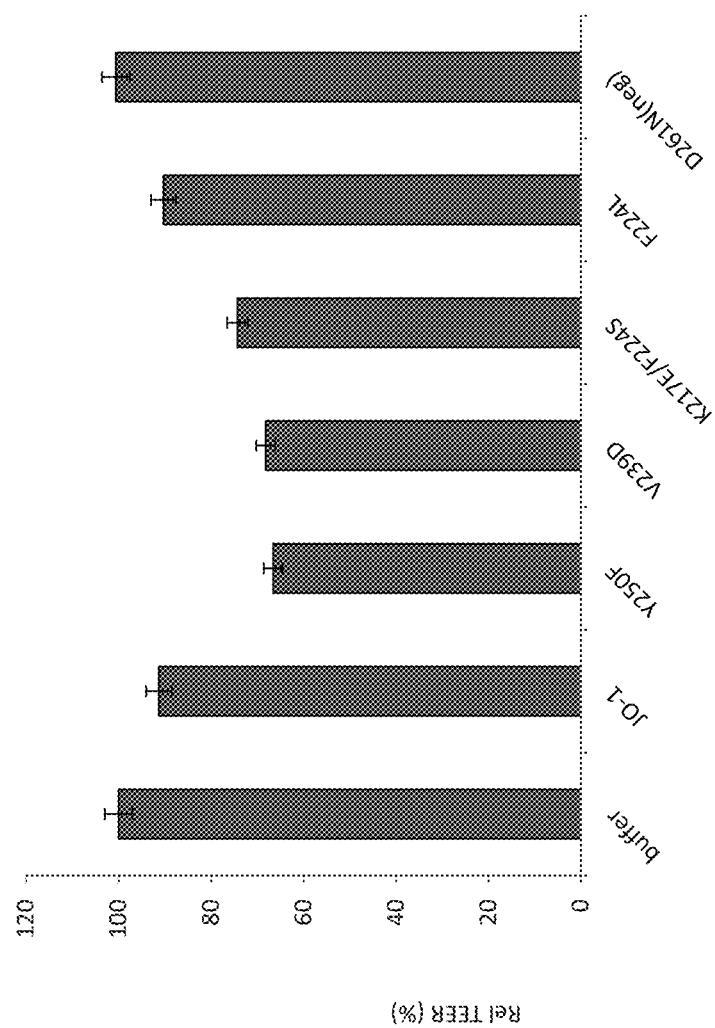
Figure 10A:
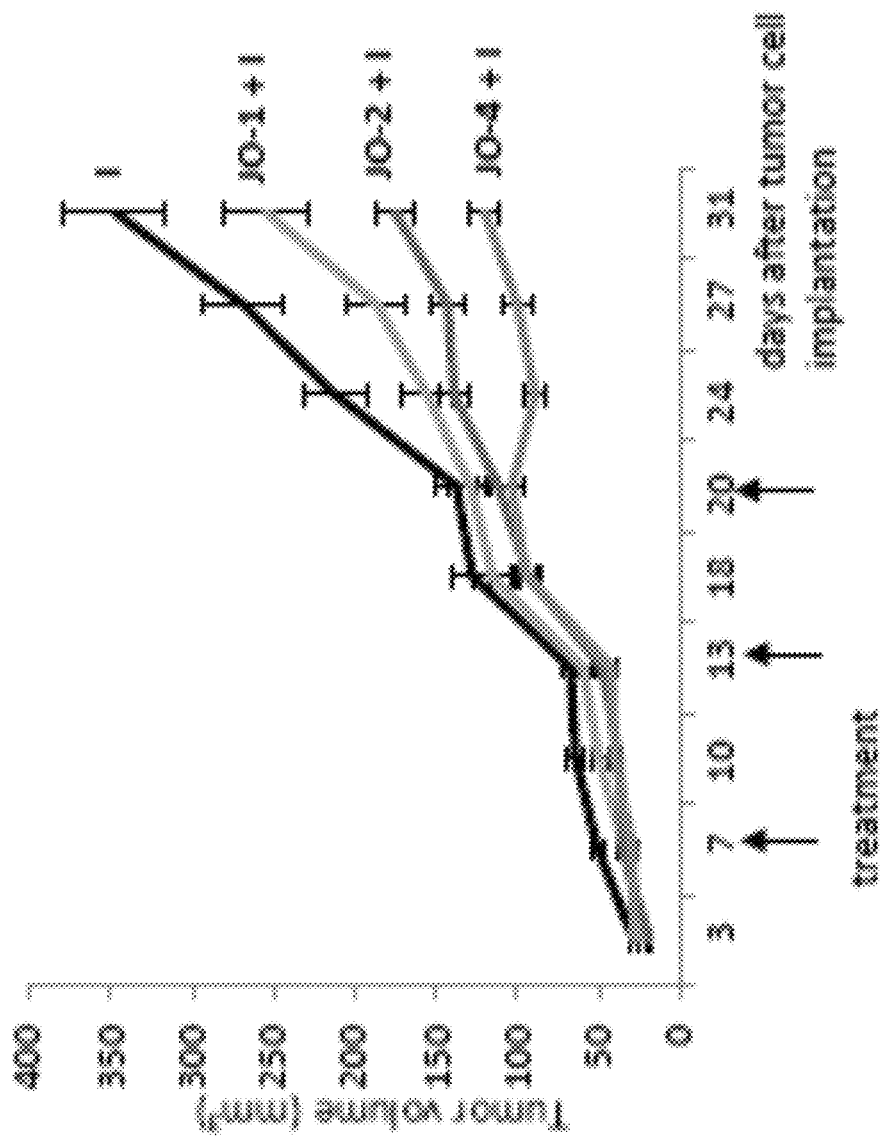
FIG. 10. Combination of affinity-enhanced JO-1 versions with chemotherapy. A) Enhancement of irinotecan (I) therapy. The experimental setting was the same as in FIG. 5B. The differences in the groups "JO-1+1" vs "JO-2+irinotecan" and "JO-2+1" vs "JO-4+1 were significant from day 20 on. N=5. B) JO-4 enhances PLD therapy in an ovarian cancer model at lower dose than JO-1. Mammary fat pad tumors were established from primary ovarian cancer ovc316 cells. Treatment was started when tumors reached a volume of 100 mm$^3$. Mice were injected intravenously with 2 mg/kg JO-1 or with 0.5 mg/kg JO-4, followed by an intravenous injection of PEGylated liposomal doxorubicin (PLD) (1 mg/kg) one hour later. Treatment was repeated weekly. C) JO-4 enhances therapy in poor-prognosis triple negative breast cancer (TNBC). A total of $4 \times 10^6$ TNBC MDA-MB-231 cells were injected into the mammary fat pad of CB17 SCID-beige mice. JO-4 (2 mg/kg) was intravenously injected 1 hour before the application of cetuximab (C) (10 mg/kg, i.p.) and nab-paclitaxel (nab-P) (5 mg/kg, i.v.). Treatment was given weekly. N=10 P<0.01 at day 25 for nab-P+C vs JO-4+nab-P+C.
Figure 10B:
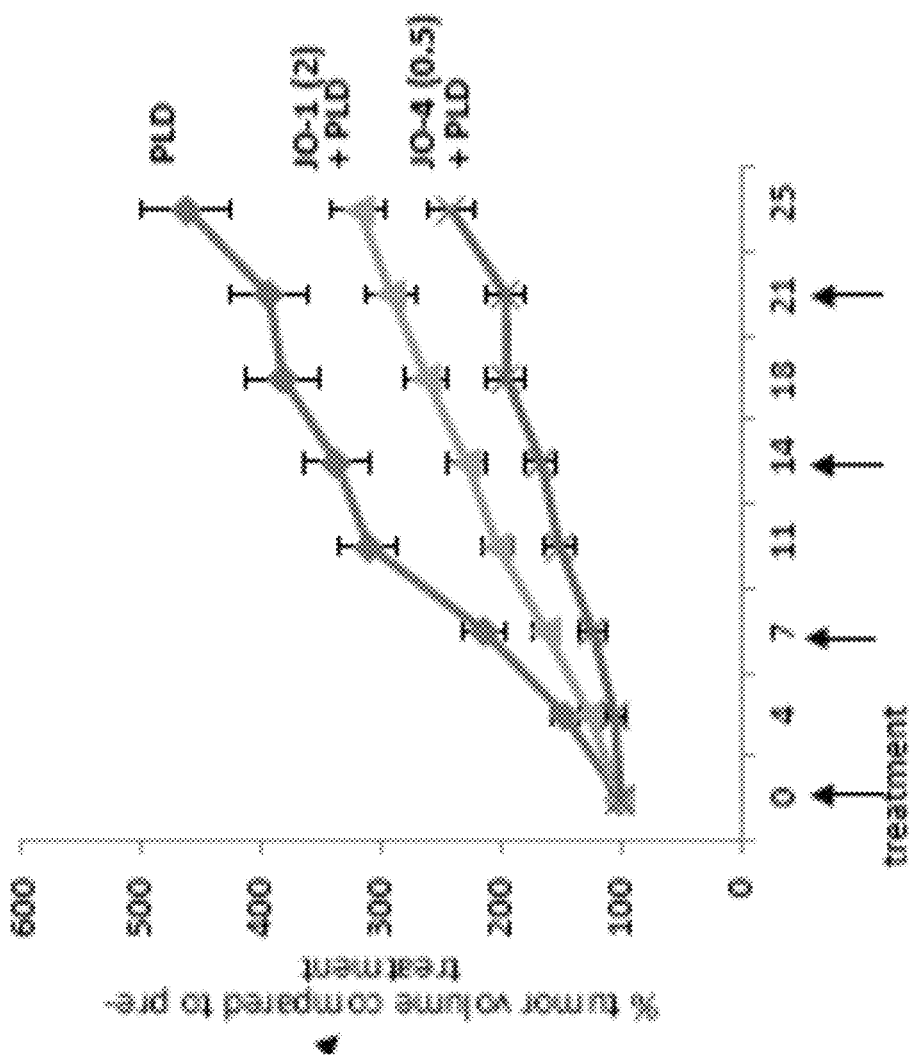
Figure 10C:
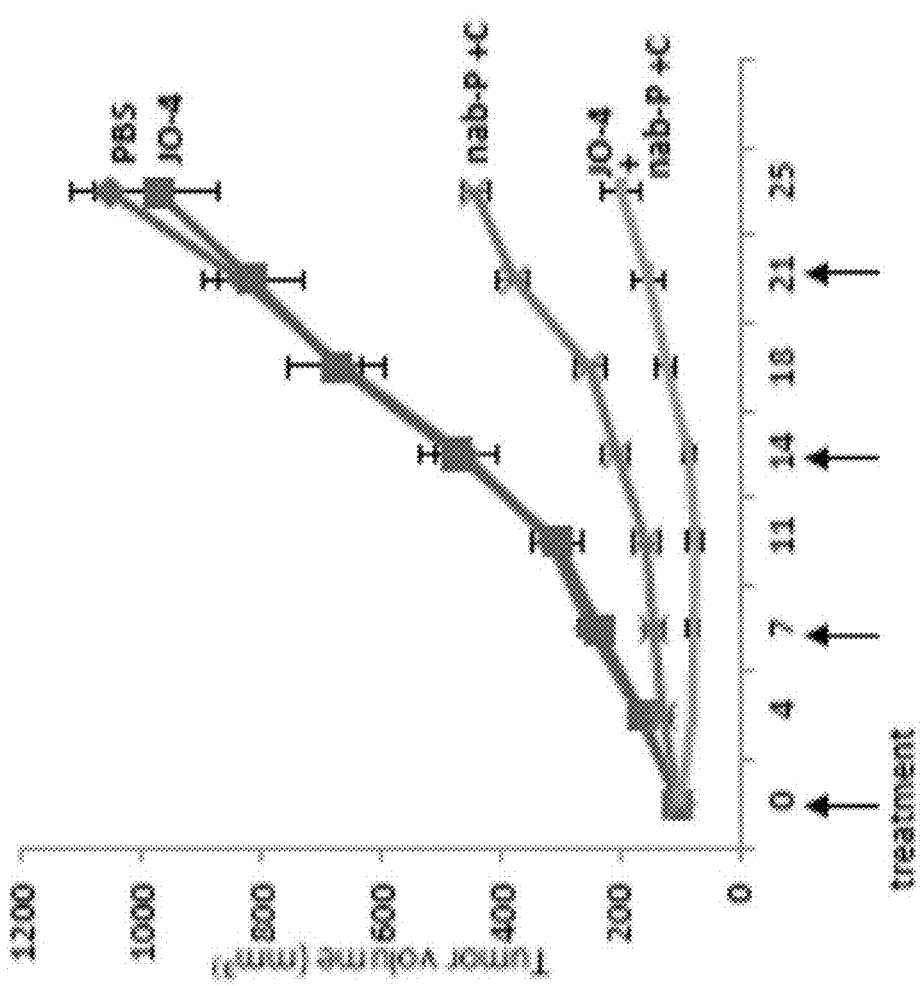
Figure 11A:
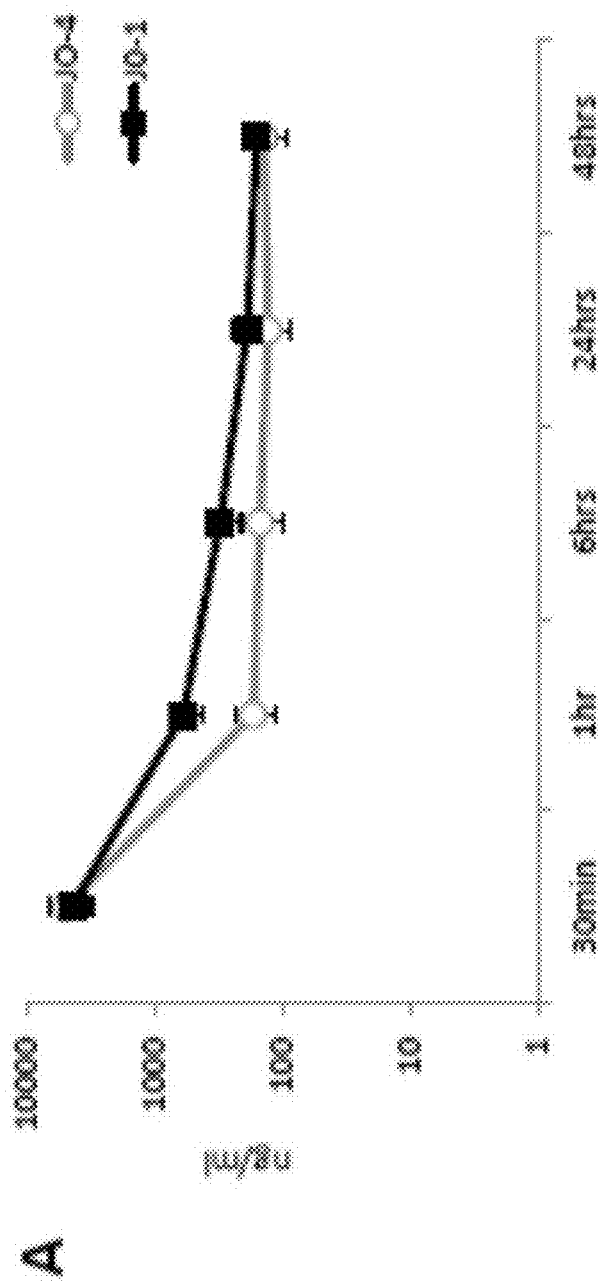
FIG. 11. Pharmacokinetics, toxicity, and immunogenicity of JO-4. A) Serum clearance of JO-1 and JO-4. hDSG2 transgenic mice with subcutaneous TC1-hDSG2 tumors (~600 mm$^3$) were intravenously injected with JO-1 or JO-4 (2 mg/kg) and serum samples were analyzed for by ELISA. N=3. Note that the y-axis has a log scale. B) Lymphocyte and platelet counts in hDSG2/TC1-hDSG2 transgenic mice after JO-1 or JO-4 injection. N=3. C) Therapy studies in immunocompetent hDSG2 transgenic mice with TC1-hDSG2 tumors. When tumors reached a volume of ~80 mm$^3$, JO-1 or JO-4 (2 mg/kg) or PBS was injected intravenously followed one hour later by PLD/Doxil (i.v. 1.5 mg/kg). Treatment was repeated as indicated by arrows. Tumors were then allowed to re-grow for about two weeks. From day 15 on serum anti-JO-1/J)-4 antibodies were detectable by ELISA. Two more treatment cycles were performed at day 28 and day 35. JO-1 and JO-4 continued to be effective after multiple treatment cycles, even in the presence of detectable antibodies. The difference between JO-1/PLD vs JO-4/PLD is significant from day 31 on. N=10.
Figure 11B:
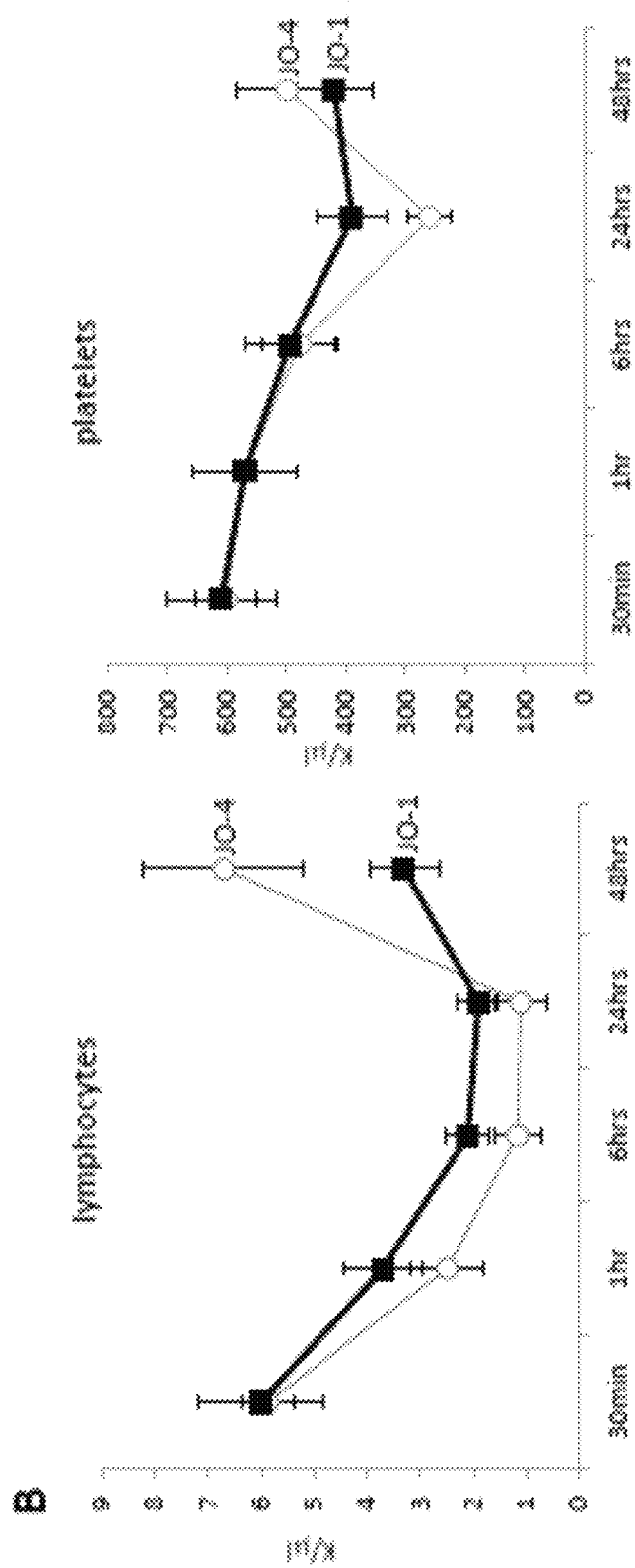

Residues critical for DSG2 binding. We first focused our work on Ad3. High-affinity binding to DSG2 and subsequent epithelial junction opening requires several trimeric fiber knobs in a spatial constellation present in the virion, PtDd, or dimerized (trimeric) Ad3 fiber knob (e.g. JO-1) (41). Recombinant (trimeric) fiber knob with two shaft motifs, but without the dimerization domain ("Ad3 knob monomer") binds to DSG2 with an affinity that is orders of magnitude less than JO-1, is not able to block Ad3 infection, and does not trigger junction opening (37, 41, 42). However, the affinity of "Ad3 knob monomer" is high enough to detect binding in Western blots in which soluble DSG2 is used as a probe. We therefore used an E. coli expression library of His-tagged "Ad3 knob monomer" mutants to identify the amino acid residues within the Ad3 fiber knob that are critical for DSG2 binding. To generate this library we employed mutagenic PCR (7, 8) in a protocol that on average generated one to two amino acid substitutions per knob. The Ad3 fiber knob library in XL-1 blue *E. coli* was plated on agar plates, knob expression was induced by IPTG, and colonies were screened for DSG2 binding using recombinant DSG2 and anti-DSG2 antibodies. A first screening round of ~10,000 colonies for variants that did not bind to DSG2 revealed 240 candidate colonies. When analyzed by Western blot for the 6×His tag, 40 of the 240 colonies showed expression of trimeric fiber knob, indicating the absence of major conformational changes. The remaining variants had truncated fiber knobs or did not form trimers. The corresponding 40 plasmids were sequenced. The vast majority of colonies had single amino acid substitutions within the fiber knob. If multiple amino acid substitutions per knob were encountered, new Ad3 knob genomes containing the corresponding mutations individually were synthesized. Further rounds of colony screening did not uncover other regions, indicating that all the DSG2-interacting residues had been found. A total of 8 independent mutants were then used for subsequent studies (FIG. 1A). For all subsequent studies, we generated self-dimerizing forms of the Ad3 fiber mutants (FIG. 1B) and purified them by affinity chromatography using NTA-Ni columns. The purified dimerized knob mutants were analyzed for DSG2 binding by Western blot (FIG. 1C-F). All mutants were severely reduced in binding when compared to JO-1 (i.e. the dimerized form containing the wtAd3 fiber knob). Mutants D261N and F265L were almost completely ablated for DSG2 binding, while the other mutants had different levels of residual DSG2 binding (3.6%-20% of wt Ad3 knob) (Table 2, "Western blot"). The identified residues, critical for Ad3 knob binding to DSG2, were in three different areas of the Ad3 fiber knob within the CD-loop/D-beta sheet (N186D, V189G, S190P), the FG-loop/G-beta sheets (D261N, F265L), and the H-beta sheet/HI-loop (L292A, L296R, E299V) (FIG. 1A). In a 3D model of the Ad3 fiber knob (PDB accession number 1H7Z_A), all identified residues were located at the apical side of the fiber knob and followed one specific groove in the knob (FIG. 2). It is noteworthy, that except F265L, all the other substitutions resulted in a change of charge in the corresponding residue.

Differences in migrations patterns in polyacrylamide gels (for example for D261N) indicate that the substitutions have caused conformational changes. We are currently attempting to crystallize these mutants to analyze their 3D structure.

To create an Ad3 fiber knob, and eventually an Ad3 virus with maximum ablation of DSG2 binding we introduced multiple mutations in the three identified areas, specifically a combination of N186D and D261N, a combination of D261N and L296R, and a combination of all three N186D, D261N, and L296R. As expected the combination of mutations in all three critical regions conferred the highest level of ablation (Table 2, "Western Blot), FIG. 1F).

TABLE 2

Analysis of Ad3 fiber mutants.

| | Western blot Residual DSG2 binding (wtAd3 knob = 100%)* | Inhibition of infection in the presence of dimeric knob (JO-1 = 100%) | Inhibition of attachment in the presence of dimeric knob (JO-1 = 100%) |
|---|---|---|---|
| N186D | 5.3% | 32.7 | 56.5 |
| V189G | 14 | 54 | 81 |
| S190P | 7.1 | 30.9 | 73.4 |
| D261N | 0 | 5.3 | 45 |
| F265L | 0 | 17.6 | 55.6 |
| L296R | 3.6 | 5.1 | 73.7 |
| E299V | 20 | 50.7 | 97.3 |
| N186D, D261N | 7.0 | 5.2 | 23.5 |
| D261, L296R | 7.0 | 1.5 | 20.1 |
| N186D, D261N, L296R | 0 | 0 | 18.5 |

The second column shows the quantitative analysis of Western blot bands corresponding to Ad3 knob trimers.
The intensity of the wt Ad3 fiber knob was taken as 100%.
The data in the third column reflect the ability of dimeric Ad3 fiber knob mutants to inhibit Ad3-GFP infection (see FIG. 3B).
The higher the percentage, the stronger the inhibition.
Inhibition by JO-1 (dimeric wtAd3 knob) is taken as 100%.
The fourth column shows corresponding data for Ad3 virus attachment.
N = 3.
Shown are averages.
The standard deviation was less than 10%.

Because of its relevance as a recently emerged pathogen, we also generated a library of ("monomeric") Ad14p1 fiber knob mutants. A first screening revealed ~300 candidate colonies for variants that did not bind to DSG2. When analyzed by Western blot for the 6xHis tag, 45 of the 300 colonies showed expression of trimeric fiber knob. Sequencing of these variants revealed 15 independent mutants with reduced binding to DSG2 (FIG. 1A). Interestingly, in spite of a different beta sheet distribution, the amino-acid residues that were critical for Ad14p1 knob binding were in the same three regions that were identified for the Ad3 fiber knob. Because of these similarities, we performed the further studies only with selected Ad3 fiber knob mutants.

Functional validation. Competition studies were performed on HeLa cells, which express DSG2 (42). First we studied the attachment of $^3$H-labelled Ad3 virus after pre-incubation of cells with dimeric Ad3 fiber knobs (FIG. 3A). Reduction in Ad3 virus binding was compared to pre-incubation with JO-1, i.e. the dimeric protein that contained the wild-type Ad3 fiber knob. Inhibition of binding by JO-1 was taken as 100%. The mutants L296R, D261N, and F265L blocked Ad3 virus binding the least (5.1, 5.3, and 17.6%), followed by mutants S190P, N186D, and E299V (30.9, 32.7, and 50.7% reduced binding, respectively) (Table 2, "Attachment"). A similar assay setup was used to measure the ability of dimeric Ad3 knob mutants to block transduction of HeLa cells by an Ad3-GFP vector. Transduction was measured based on GFP expression (FIG. 3B). Similar to what we observed in the attachment study, Ad3-GFP infection was least reduced by pre-incubation with mutants D261N and F265L, followed by mutants N186D, S190P, L296R, and V189G. Taking the DSG2 binding (Western blot), attachment, and infection competition data together, we concluded that the area containing residues 261 to 265 is the most critical area in DSG2 binding. The region around residues 186-190 also contributes to binding, while the region containing residue 299 appears to be only marginally involved in binding. Dimeric Ad3 knob mutants with combined mutations were also analyzed for their ability to compete with Ad3 virus for attachment (FIG. 3C) and infection (FIG. 3D). The mutant with mutations in all three areas (N185, D261, L296) did not block Ad3 binding or infection even at concentrations of 200 μg/ml indicating that is nearly ablated for DSG2 binding. Notably, when using sCD46 as a probe in the Western blot of wild-type Ad3 fibers, no specific binding was observed (FIG. 4). This indicates that Ad3 only inefficiently binds to CD46.

Correlation of reduced DSG2 binding and weaker ability to open epithelial junctions. A straightforward assay for the junction opening function of dimeric Ad3 knob mutants is based on measuring the transepithelial electrical resistance (TEER) in transwell cell cultures. Epithelial cancer cells are cultured until the TEER is constant, when major intercellular junctions are formed. Addition of JO-1 for 1 hour to the apical side of the transwell cultures resulted in a rapid decrease in the TEER indicating opening of junctions (FIG. 5A). Incubation with mutant D261N had no effect on the TEER. N186D and E299V had intermediate effects that correlated with the residual binding of the corresponding fiber knobs to DSG2. In previous studies, we have also established that JO-1 triggered changes in epithelial junctions of xenograft tumors and increased the anti-tumor efficacy of chemotherapeutics with high molecular weights, for example irinotecan. (Irinotecan has a molecular weight of 586.7 Da and is used to treat colon and lung cancer). We used this effect to assess the function of dimeric Ad3 knob mutants in vivo (FIG. 5B). Similarly to what we observed in vitro, JO-1 enhanced irinotecan therapy while mutants with reduced DSG2 binding had no significant effect on irinotecan efficacy.

Affinity enhanced dimeric Ad3 fiber knobs. As outlined above, JO-1 is relevant for cancer therapy. It is therefore important to better understand structural details of its interaction with DSG2 and create JO-1 mutants with increased affinity to DSG2. Affinity enhancement of biologics is used to: i) decrease their effective dose, ii) increase their half-lives, iii) potentially increase their therapeutic effects, and iv) circumvent the adverse effects of antibodies generated by patients against the biologic (e.g. neutralization or changes to the pharmokinetics). To make JO-1 analogues with increased affinity, we screened the *E. coli* expression library with random mutations within JO-1 for variants with increased binding to DSG2. Out of 10,000 colonies plated, twenty colonies with the most intense DSG2 signals were picked and plasmid DNA was sequenced. Seven different mutants with one or two amino acid substitutions were identified: Y250F, K217E+F224S, N293S, V239D, F224L, E248G+K258E, and L277R+N293D. The localization of the residues in the primary and 3D structures of the Ad3 fiber knob are shown in FIG. 6. Notably, most of the mutations were localized within the EF loop, indicating that this loop is involved in stabilizing the interaction between Ad3 and DSG2. V239 and Y250 are not exposed at the knob surface suggesting a structural change in the knob rather than an involvement in direct binding to DSG2 (FIG. 6B, right panel). Recombinant mutant dimeric Ad3 knob proteins were then purified. To measure the affinity of the mutants to DSG2, we performed surface plasmon resonance studies. The outcome of studies with knobs containing the dimerization domain was complex, most likely due to the fact that these mutants formed multimeric complexes. We therefore performed studies with knob proteins lacking the dimerization domain ("no DD"). The association rate constant ($k_a$ or $k_{on}$), and the dissociation rate constant ($k_d$ or $k_{off}$) as well as the $K_D$ of wt Ad3 knob and all knob mutants are shown in FIG. 7. In agreement with previous studies (41), we found that the wt Ad3 knob without the dimerization domain bound to DSG2 only with relatively low affinity ($K_D$=10 μM). With the exception of mutant L227R/noDD+N293D/noDD, all mutants identified in the colony blot screen had higher affinities to DSG2. Notably, the affinities of mutant Y250F/noDD or V239D/noDD were 885 or 405-fold higher than that of wt Ad3knob/noDD. The high affinity of the different mutants was mainly due to a faster association to DSG2 rather than a change in the dissociation rate. The only exception to this trend was mutant N293S/noDD, for which the association rate was lowest when compared to other mutants. However, this was partially compensated by a slower dissociation rate. Together these results indicate that wt Ad3 knob (noDD) binding to DSG2 is mostly limited by a slow association rate that can be improved by a panel of mutations. These mutations do not appear to modify the stability of this interaction but the balance of association versus dissociation, resulting in higher affinities of ligands to the receptor.

To better understand structural elements that enhance binding to DSG2, we performed a more detailed analysis with mutant K217E/F224S. Transmission electron microscopy with uranyl acetate stained K217E/F224S fiber knobs containing the dimerization domain showed particles with 6 knobs representing dimerized trimeric fibers (FIG. 8A, thick arrows and FIG. 8B). Interestingly, under these conditions fiber knobs also formed regularly shaped arrogates (with ~30 nm diameter) resembling collapsed PtDd (FIG. 8A, thin arrows and FIG. 8C). We then performed x-ray crystallography studies to resolve the structure of the K217E/F224S mutant at the atomic level (FIGS. 8D-H). As expected, the K217E/F224S mutant formed a monotrimer of fiber knobs (FIG. 8E). The 3D structure of the mutant was overlaid with that of the wild-type Ad3 fiber knob (FIG. 8F-H). This revealed that the EF loop in the K217E/F224S mutant was completely disordered. This loop is at the base of the knob domain at the junction with the fiber shaft. The K217E/F224S mutations may therefore allow for easier binding by increasing the flexibility of this loop region.

Correlation of increased affinity with stronger ability to open epithelial junctions. For the following studies we used Ad3 fiber knob forms containing the dimerization domain. To analyze the selected high-affinity mutants, we performed competition infection studies with Ad3-GFP on HeLa cells and the dimeric forms of the affinity enhanced Ad3 fiber mutants (FIG. 9A). Based on GFP expression, all dimeric mutants except mutant L277R+N293D inhibited Ad3-GFP infection significantly more than JO-1. Notably, the non-dimerized forms of Ad3 fiber knobs with increased affinity to DSG2 were unable to act as competitors in transduction studies (FIG. 9B). Higher affinity to DSG2 resulted in an increased capability to open epithelial junctions in transwell cultures (FIG. 9C). Compared to JO-1, the TEER in cultures incubated with the mutants V250F, V239D, and K217E+F224S was significantly higher.

Two of the affinity enhanced version of JO-1, Y293D and V250F were analyzed in in vivo assay. We called these mutants JO-2 and JO-4, respectively. The first study was performed in a xenograft model derived from A549 cells similar to the study described for FIG. 5B. FIG. 10A shows that the affinity-enhanced mutants JO-2 and JO-4 increased irinotecan therapy significantly more than JO-1 (p<0.05 starting from day 27). Furthermore, JO-4 (Kd=11.4 nM) was significantly more efficient than JO-2 (Kd-24.9 nM), indicating a correlation between affinity to DSG2 and therapeutic effect. Additional studies were performed in xenograft tumors derived from ovc316 cells (30, 32). Ovc316 cells are Her2/neu positive epithelial tumor cells derived from an ovarian cancer biopsy. These cells can undergo EMT and the reverse process, mesenchymal-to-epithelial-transition (MET), under specific conditions in vitro and in vivo. A subfraction of ovc316 cells that is positive for Nanog, CD133, and E-cadherin is enriched for cancer stem cells, i.e. self-renewing cells with pluripotent potential and tumor forming ability (30). Ovc316 cells therefore closely model the heterogeneity and plasticity seen in tumors in situ. Intravenous injection of JO-1 at a dose of 2 mg/kg one hour before injection of PEGylated liposomal doxorubicin (PLD), a drug that is widely used for chemotherapy of ovarian cancer, significantly increased the treatment efficiency (FIG. 10B). Importantly, at a dose of 0.5 mg/kg JO-4 had an even greater stimulating effect on PLD therapy. Finally, we tested JO-4 in a model for triple-negative breast cancer (TNBC). TNBC is characterized by a lack or minimal expression of estrogen receptor (ER), progesterone receptor (PR) and the absence of Her2/neu overexpression. TNBC accounts for 15% of all breast cancers. Overall survival is poor compared with that in patients who have other phenotypes. A characteristic feature of TNBC is high levels of DSG2 and epithelial junctions. Promising clinical results in the treatment of TNBS have been achieved with nanoparticle, albumin-conjugated paclitaxel (nab-paclitaxel/Abraxane™) alone or in combination with the EGFR-targeting mAb cetuximab/Erbitux™ (38). Our study showed that JO-4 significantly increased nab-paclitaxel/cetuximab therapy in a mouse model with orthotopic TNBC tumors (FIG. 10C). Because of its therapeutic relevance, we further studied JO-4 in an adequate mouse tumor model. Because Ad3 virus and Ad3 fiber knob derivatives do not bind to mouse cells and tissues we used human transgenic mice that expressed human DSG2 in a pattern and at a level similar to humans (40). These mice were subcutaneously implanted with syngeneic TC1-hDSG tumors. When tumors reached a volume of ~600 mm³, JO-1 or JO-4 was intravenously injected for safety and efficacy studies. Both JO-1 and JO-4 serum concentrations declined more than one order of magnitude within an hour after injection, whereby the decline was significantly greater for JO-4 (p<0.01 for 1 hr post-injection) (FIG. 11A). After one hour post-injection JO-1 and JO-4 concentration reached a plateau with ~100 ng/ml. We also analyzed hematological parameters after i.v. JO-1 and JO-4 injection. Blood chemistry did not show abnormal changes. Blood cell counts were normal except for lymphocyte and platelet number, which decreased early after injection (FIG. 11B). Lymphocyte and platelet counts reached a nadir at 24 hours p.i. with significantly lower numbers for JO-4 (p<0.01). Interestingly lymphocyte and platelet counts returned to normal levels faster in JO-4 injected mice than in JO-1 treated animals.

Figure 11C:
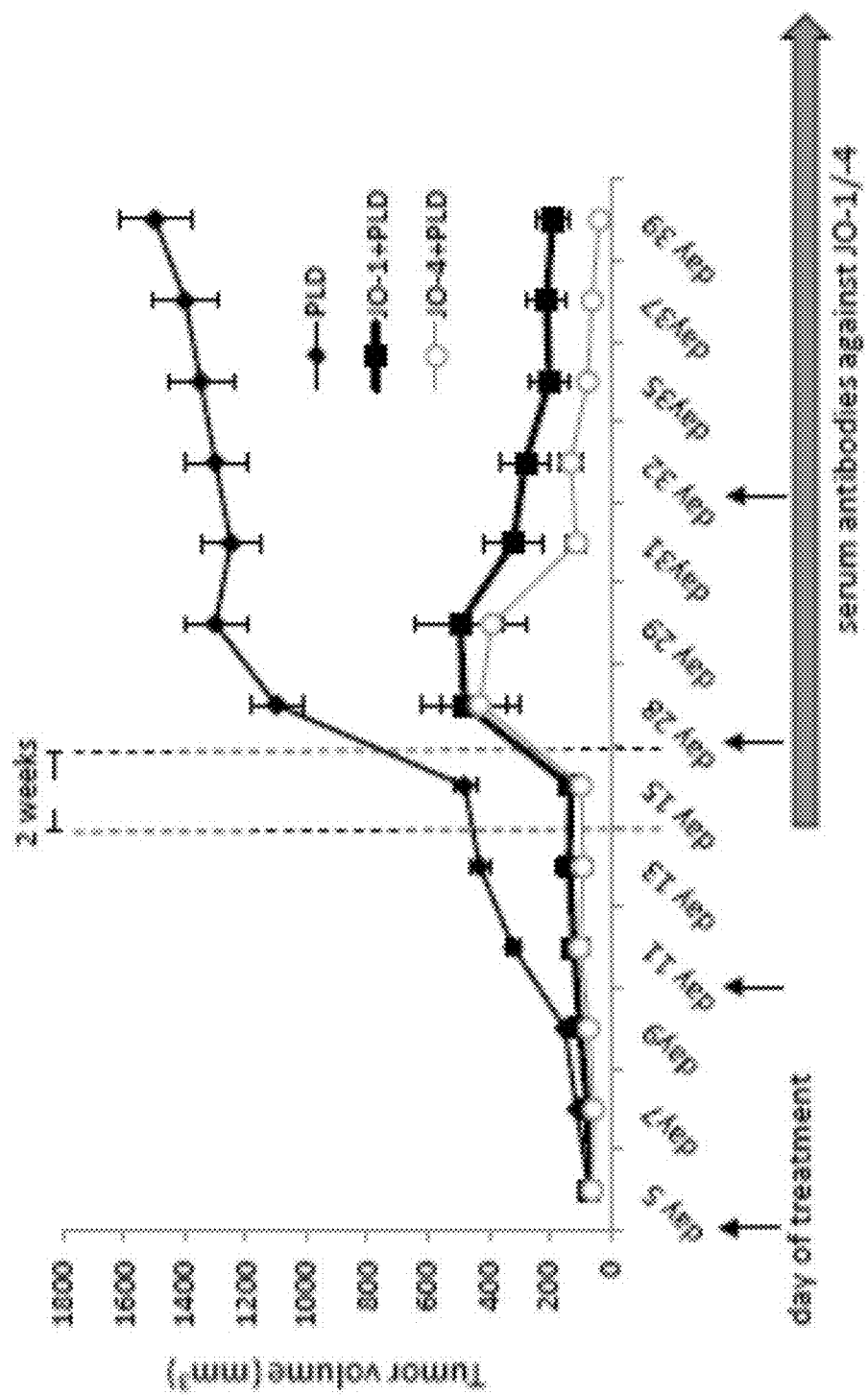

JO-1 and JO-4 are virus-derived proteins and immunogenic. In immunocompetent mice, serum IgG antibodies against these proteins can be detected by ELISA two weeks after injection (5). One of theoretical premises for affinity enhancement of therapeutic proteins is that it circumvents neutralizing serum antibodies. To test this, we performed repeated injections of JO-1 and JO-4 in an immunocompetent hDSG2 mouse tumor model with TC1-hDSG2 tumors (FIG. 11C). After two treatment cycles of JO-1 and PLD, treatment was stopped and tumors were allowed to re-grow. The $3^{rd}$ and $4^{th}$ treatment cycles were started on days 28 and day 35, respectively. At the time of the $3^{rd}$ cycle, serum anti-JO-1 antibodies were detectably by ELISA. Importantly, in both, the $3^{rd}$ and $4^{th}$ treatment cycles JO-1 and JO-4 had an enhancing effect on PLD therapy, whereby the enhancing effect was significantly stronger for JO-4.

Overall, our functional studies with affinity-enhanced dimeric Ad3 fiber mutants demonstrate a correlation between DSG2 affinity and epithelial junction opening/therapeutic effects.

Discussion

Figure 12:
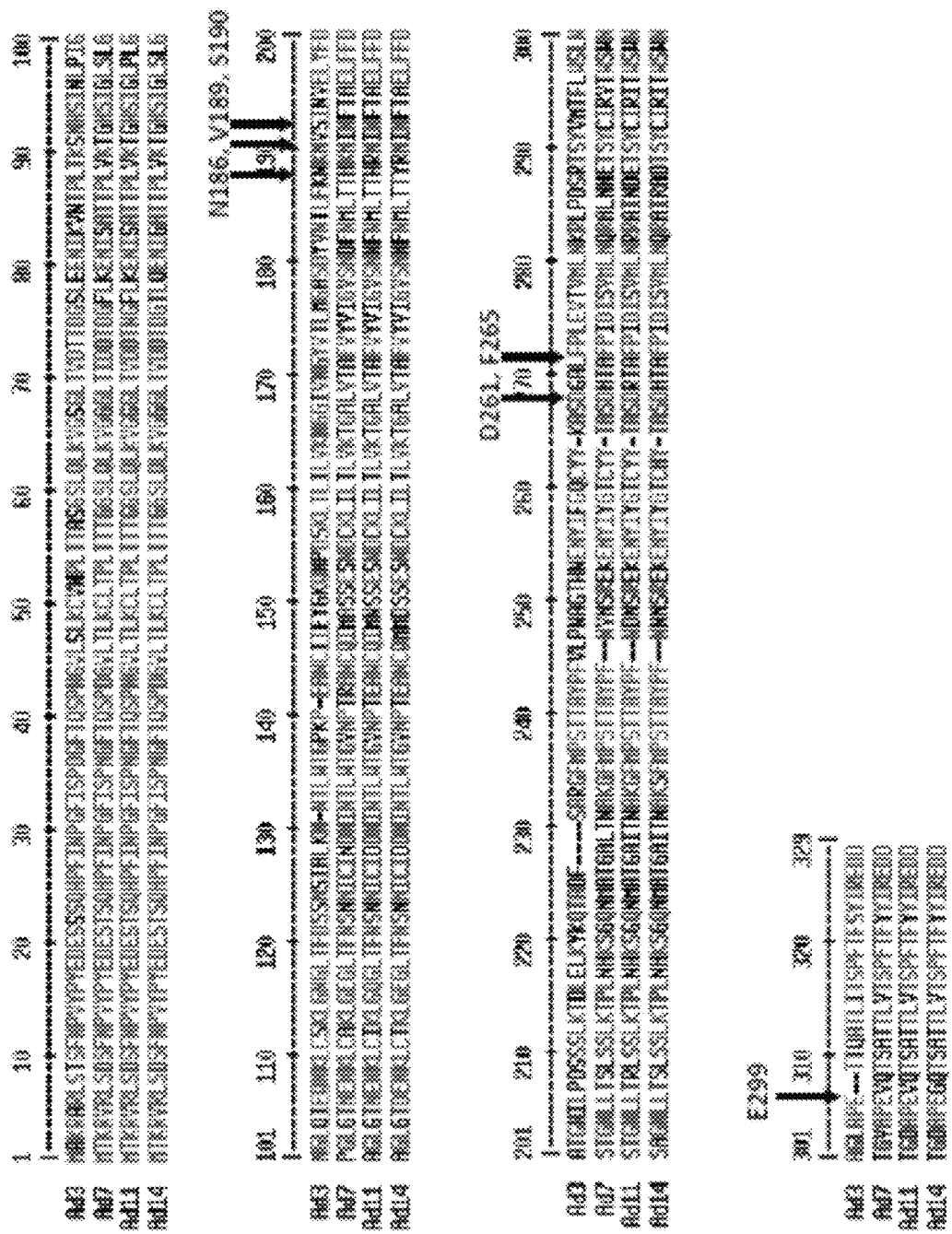
FIG. 12. Alignment of fiber knob sequences. The residues that ablate/reduce Ad3 knob binding to DSG2 are indicated (from top to bottom SEQ ID NOs: 14, 15, 16, 17).

Residues involved in Ad3 knob binding to DSG2. Unlike Ad interaction with CAR and CD46 (4, 28), structural details on Ad interaction with DSG2 interaction are still elusive. Although the crystal structure of the Ad3 fiber knob has been resolved, for DSG2, the 3D structure of only the most distal of the four extracellular domains (ECD) is available (MMDB ID: 59843). However, our previous competition studies with monoclonal antibodies against different DSG2 domains indicated that ECDs 3 and 4 are involved in binding to Ad3 (42). In this study we used mutagenesis-based analyses to identify the amino acid residues within the Ad3 fiber knob that are critical for binding to DSG2. Mutagenic analysis of DSG2 was not possible because, when expressed in E. coli, the protein did not bind to Ad3, indicating that post-translational processing is required to create active Ad3 binding sites within DSG2 (data not shown). The identified residues, critical for Ad3 knob binding to DSG2, were in three different areas of the Ad3 fiber knob and formed a potential binding pocket localized in a groove at the distal end of the fiber knob, facing the receptor. Notably, binding of other Ad serotypes to CAR or CD46 primarily involves regions at the lateral or basal side of the corresponding fiber knobs (27, 43). Our data indicate that Ad3 uses a different binding strategy. We are currently performing crystallography studies with dimeric Ad3 fiber knobs and DSG2. Considering that multimeric Ad3 fiber knobs cluster several DSG2 molecules (41), it is expected that the 3D structure of this complex will be complicated. It remains to be studied whether the residues critical for Ad3 fiber knob binding to DSG2 will also be involved in binding of other species B Ads to DSG2. Notably, while D261, F265, and E299 are conserved in all four DSG2-interacting Ads (Ad3, 7, 11, 14), other critical residues (N186, V189, L296) differ between these serotypes (FIG. 12).

Ad14 is an important research object because of the recent appearance of a new strain (Ad14p1). Never previously documented in the United States, Ad14p1 was first reported in March and April 2006 during routine surveillance at several U.S. military-recruit training centers (26). During March-June of the following year, a total of 140 additional cases of confirmed HAdV-B14p1 respiratory illness were reported in patients in Oregon, Washington and Texas (3). Thirty eight percent of these patients were hospitalized, including 17% who were admitted to intensive care units: 5% of patients died. Outbreaks of HAdV-B14p1 were subsequently detected in the other 5 bases and in civilian populations in Washington (1), Oregon (23), Alaska (15), Wisconsin, and Pennsylvania (10, 22) as well as in Canada (16), China (33) and South Korea (34). At this point, the molecular basis for the high pathogenicity and/or virulence of Ad14p1 is unclear. We attempted to delineate the structural components for Ad14p1 binding to DSG2. The beta sheet distribution of Ad14p1 differs from that of Ad3 (FIG. 1A). Therefore, similar to CD46-interacting serotypes (11, 12), it is possible that DSG2-interacting Ads vary in their binding strategy to DSG2, which could result in different DSG2 binding areas. However, the screening of an Ad14p1 fiber knob mutant library did not support this hypothesis. The areas involved in DSG2 binding were essentially the same for Ad3 and Ad14p1 fiber knobs. Nevertheless, our finding are relevant for the treatment of Ad14p1 viremia, specifically for the production of Ad14p1 inhibitors or high affinity decoys that can trigger the opsonization of virus present in the blood circulation or airway.

It has been reported that, in addition to DSG2, Ad3 can use CD46 as a receptor to infect cells if DSG2 is absent (35). Previously, we found that in polarized normal epithelial cells DSG2 is trapped in tight junctions and not accessible from the apical side, while CD46 is present on both membrane sides (42). We therefore speculate that CD46 can serve as a relatively inefficient entry receptor for Ad3, while de novo produced Ad3 and Ad3 penton-dodecahedra interact with DSG2, open epithelial junctions and allow for efficient lateral spread of Ad3 or penetration into deeper tissue layers and blood circulation. The ability to individually ablate the Ad3 knob residues that are critical for DSG2 and CD46 binding, respectively, should make it possible to prove this hypothesis.

Affinity-enhanced fiber knobs. Most of the mutations that increased the affinity to DSG2 were localized within the EF loop, indicating that this loop is involved in stabilizing the interaction between Ad3 and DSG2. Interestingly, unlike Ad7, 11, and 14, the Ad3 fiber knob has in this area two additional residues (VL) followed by a proline. This loop could therefore be extended further and the proline could orient it in a way that might allow for better interaction with the receptor. The analysis of the 3D structure of one of these mutants at the atomic level supports this conclusion. These studies indicate that the introduced mutations make the loop more flexible, which might facilitate the interaction with DSG2.

The identification of Ad3 knobs with higher affinity than the wt Ad3 knob has implications for Ad3-mediated gene therapy. Recently, gene transfer vectors based on Ad3 have shown promise for cancer therapy in clinical trials (18). Theoretically, affinity enhanced Ad3 vectors could be used at lower doses and outcompete neutralizing antibodies. Recently, attempts were undertaken to incorporate high affinity ligands into measles virus (17) and Ad5-based vectors (3, 9, 45) in order to increase efficacy and specificity of target cell infection in vivo. Based on our findings in this study, a similar strategy can now be pursued for Ad3 vectors. In addition to improving Ad3 vectors, affinity-enhanced versions of JO-1 have translational relevance. Most solid tumors are of epithelial origin and, although malignant cells are dedifferentiated, they maintain intercellular junctions, a key feature of epithelial cells, both in the primary tumor as well as in metastatic lesions (5, 31). These intercellular junctions represent a protection mechanism against attacks by the host immune system and pose physical barriers that prevent intratumoral penetration and dissemination of cancer therapeutics, including monoclonal antibodies and chemotherapy drugs (5, 31). When injected intravenously into mice with xenograft or syngeneic DSG2 transgenic tumors. JO-1 markedly enhanced therapeutic effects with a variety of chemotherapy drugs as well as monoclonal antibodies (5, 6). In this study, we have shown that new affinity-enhanced versions of JO-1 (e.g. JO-4) increased the efficacy of cancer therapeutics significantly more than JO-1 (irinotecan, nab-paclitaxel, PEGylated liposomal doxorubicin, cetuximab) in four tumor models (A549, ovc316, MDA-MB231, and TC1-DSG2). Studies in DSG2 transgenic mice with syngeneic tumors showed that serum JO-4 levels rapidly decrease most likely due to binding to DSG2 on tissues. Previous studies showed that, in addition to tumors, lymphocytes and platelets of hDSG2 transgenic express hDSG2 (similar to human and monkeys) (40, 42). Along this line we found that JO-4 injection resulted in a transient reduction of lymphocyte and platelet counts.

Figure 13:
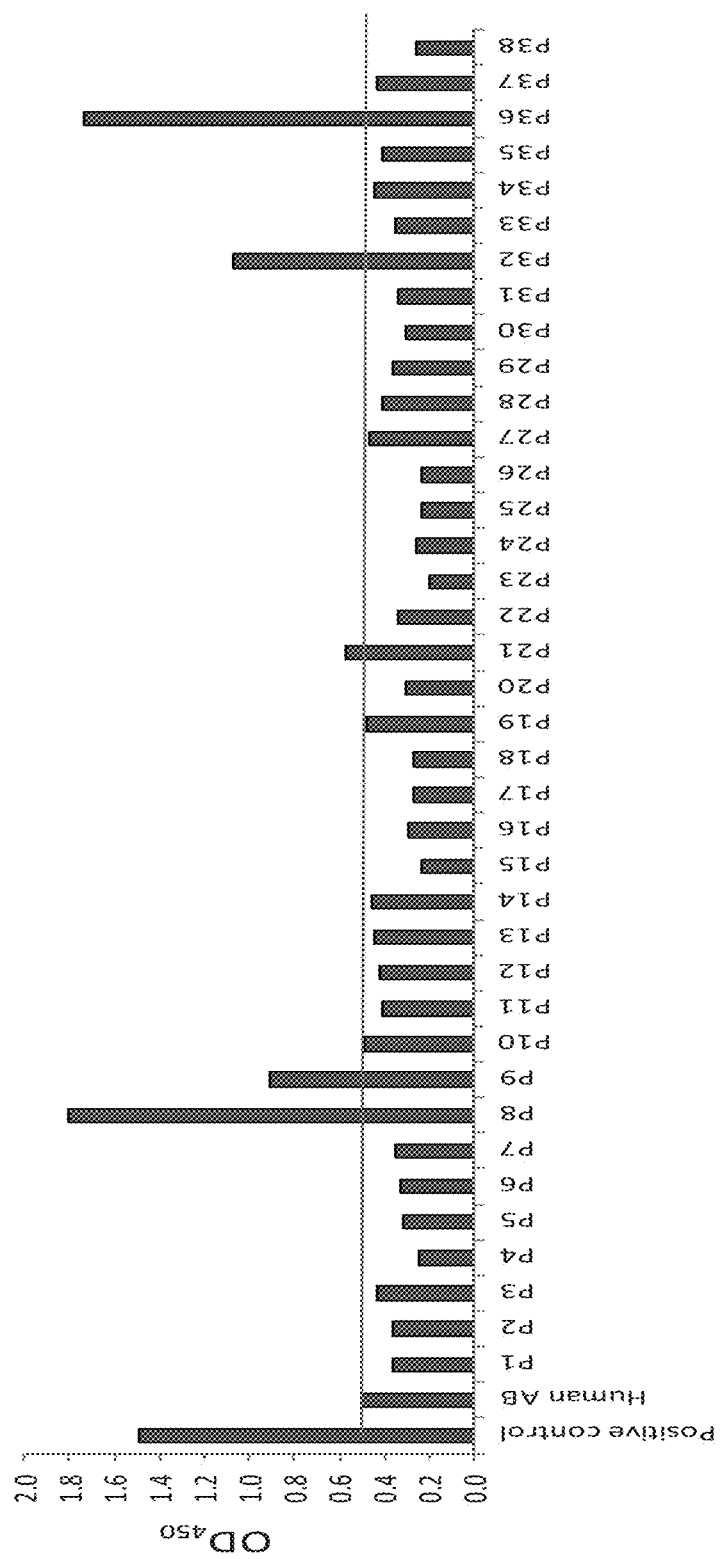
FIG. 13. Sera from humans and hypervaccinated mice do not inhibit activity of JO-4

Despite the fact that approximately one third of humans have neutralizing antibodies against Ad3 (42), in a recent study with serum from ovarian cancer patients we found detectable (binding) antibodies against JO-4 in only 10% of patients (N=38) (FIG. 13). However, it is certain that adaptive immune responses against intravenously administered JO-4 will develop in humans, particularly after repeated injection. In this context it is however noteworthy anti-JO-4 antibodies generated after injection into immunocompetent mice appeared not to critically inhibit the function of JO-4. The data shown in FIG. 11C demonstrate that JO-1 and JO-4 continue to be effective after multiple treatment cycles, even in the presence of detectable antibodies. Because, the therapeutic effect after repeated injection was significantly greater for JO-4, we speculate that JO-4 is more potent not only in junction opening, but also in disrupting complexes between the junction opener and serum antibodies.

In summary, our studies uncover important structural details of Ad3 and Ad14p1 fiber knob binding to DSG2. It furthermore shows a correlation between the affinity of Ad3-fiber knobs to DSG2 and subsequent effects on epithelial junctions. Finally, the generation of affinity-enhanced recombinant dimeric Ad3 fiber knobs has implications for cancer therapy.

REFERENCES 1. 2007. Acute respiratory disease associated with adenovirus serotype 14--four states, 2006-2007. MMWR Morb Mortal Wkly Rep 56:1181-1184.
2. Adams, P. D., P. V. Afonine, G. Bunkoczi, V. B. Chen, I. W. Davis, N. Echols, J. J. Headd, L. W. Hung, G. J. Kapral, R. W. Grosse-Kunstleve, A. J. McCoy, N. W. Moriarty, R. Oeffner, R. J. Read, D. C. Richardson, J. S. Richardson, T. C. Terwilllger, and P. H. Zwart. 2010. PHENIX: a comprehensive Python-based system for macromolecular structure solution. Acta Crystallogr D Biol Crystallogr 66:213-221.
3. Belousova, N., G. Mikheeva, J. Gelovani, and V. Krasnykh. 2008. Modification of adenovirus capsid with a designed protein ligand yields a gene vector targeted to a major molecular marker of cancer. Journal of virology 82:630-637.
4. Bewley, M. C., K. Springer, Y. B. Zhang, P. Frelmuth, and J. M. Flanagan. 1999. Structural analysis of the mechanism of adenovirus binding to its human cellular receptor, CAR. Science 286:1579-1583.
5. Beyer, I., H. Cao, J. Persson, H. Song, M. Richter, Q. Feng, R. Yumul, R. van Rensburg, Z. Li, R. Berenson, D. Carter, S. Roffler, C. Drescher, and A. Lieber. 2012. Coadministration of epithelial junction opener JO-1 improves the efficacy and safety of chemotherapeutic drugs. Clin Cancer Res 18:3340-3351.
6. Beyer, I., R. van Rensburg, R. Strauss, Z. Li, H. Wang, J. Persson, R. Yumul, Q. Feng, H. Song, J. Bartek, P. Fender, and A. Lieber. 2011. Epithelial junction opener JO-1 improves monoclonal antibody therapy of cancer. Cancer Res 71:7080-7090.
7. Cadwell, R. C., and G. F. Joyce. 1994. Mutagenic PCR. PCR Methods Appl 3:S136-140.
8. Cadwell, R. C., and G. F. Joyce. 1992. Randomization of genes by PCR mutagenesis. PCR Methods Appl 2:28-33.
9. Campos, S. K., M. B. Parrott, and M. A. Barry. 2004. Avidin-based targeting and purification of a protein IX-modified, metabolically biotinylated adenoviral vector. Mol Ther 9:942-954.
10. Carr, M. J., A. E. Kajon, X. Lu, L. Dunford, P. O'Reilly, P. Holder, C. F. De Gascun, S. Coughlan, J. Connell, D. D. Erdman, and W. W. Hall. 2011. Deaths associated with human adenovirus-14p1 infections, Europe, 2009-2010. Emerg Infect Dis 17:1402-1408.
11. Cupelli, K., S. Muller, B. D. Persson, M. Jost, N. Arnberg, and T. Stehle. 2010. Structure of adenovirus type 21 knob in complex with CD46 reveals key differences in receptor contacts among species B adenoviruses. J Virol 84:3189-3200.
12. Cupelli, K., and T. Stehle. 2011. Viral attachment strategies: the many faces of adenoviruses. Curr Opin Virol 1:84-91.
13. Durmort, C., C. Stehlin, G. Schoehn, A. Mitraki, E. Drouet, S. Cusack, and W. P. Burmeister. 2001. Structure of the fiber head of Ad3, a non-CAR-binding serotype of adenovirus. Virology 285:302-312.
14. Emsley, P., B. Lohkamp, W. G. Scott, and K. Cowtan. 2010. Features and development of Coot. Acta Crystallogr D Biol Crystallogr 66:486-501.
15. Esposito, D. H., T. J. Gardner, E. Schneider, L. J. Stockman, J. E. Tate, C. A. Panozzo, C. L. Robbins, S. A. Jenkerson, L. Thomas, C. M. Watson, A. T. Curns, D. D. Erdman, X. Lu, T. Cromeans, M. Westcott, C. Humphries, J. Ballantyne, G. E. Fischer, J. B. McLaughlin, G. Armstrong, and L. J. Anderson. 2010. Outbreak of pneumonia associated with emergent human adenovirus serotype 14—Southeast Alaska, 2008. J Infect Dis 202:214-222.
16. Girouard, G., R. Garceau, L. Thibault, Y. Oussedik, N. Bastien, and Y. Li. 2013. Adenovirus serotype 14 infection. New Brunswick, Canada, 2011. Emerg Infect Dis 19:119-122.
17. Hasegawa, K., C. Hu, T. Nakamura, J. D. Marks, S. J. Russell, and K. W. Peng. 2007. Affinity thresholds for membrane fusion triggering by viral glycoproteins. Journal of virology 81:13149-13157.
18. Hemminki, O., I. Diaconu, V. Cerullo, S. K. Pesonen, A. Kanerva, T. Joensuu, K. Kairemo, L. Laasonen, K. Partanen, L. Kangasniemi, A. Lieber, S. Pesonen, and A. Hemminki. 2012. Ad3-hTERT-E1A, a Fully Serotype 3 Oncolytic Adenovirus, in Patients With Chemotherapy Refractory Cancer. Mol Ther 20:1821-1830.
19. Incardona, M. F., G. P. Bourenkov, K. Levik, R. A. Pieritz, A. N. Popov, and O. Svensson. 2009. EDNA: a framework for plugin-based applications applied to X-ray experiment online data analysis. J Synchrotron Radiat 16:872-879.
20. Kabsch, W. 2010. Integration, scaling, space-group assignment and post-refinement. Acta Crystallogr D Biol Crystallogr 66:133-144.
21. Kabsch, W. 2010. Xds. Acta Crystallogr D Biol Crystallogr 66:125-132.
22. Kajon, A. E., X. Lu, D. D. Erdman, J. Loule, D. Schnurr, K. S. George, M. P. Koopmans, T. Allibhai, and D. Metzgar. 2010. Molecular epidemiology and brief history of emerging adenovirus 14-associated respiratory disease in the United States. J Infect Dis 202:93-103.
23. Lewis, P. F., M. A. Schmidt, X. Lu, D. D. Erdman, M. Campbell, A. Thomas, P. R. Cieslak, L. D. Grenz, L. Tsaknardis, C. Gleaves, B. Kendall, and D. Gilbert. 2009. A community-based outbreak of severe respiratory illness caused by human adenovirus serotype 14. J Infect Dis 199:1427-1434.
24. Louie, J. K., A. E. Kajon, M. Holodniy, L. Guardia-LaBar, B. Lee, A. M. Petru, J. K. Hacker, and D. P. Schnurr. 2008. Severe pneumonia due to adenovirus serotype 14: a new respiratory threat?Clin Infect Dis 46:421-425.
25. McCoy, A. J., R. W. Grosse-Kunstleve, P. D. Adams, M. D. Winn, L. C. Storoni, and R. J. Read. 2007. Phaser crystallographic software. J Appl Crystallogr 40:658-674.
26. Metzgar, D., M. Osuna, A. E. Kajon, A. W. Hawksworth, M. Irvine, and K. L. Russell. 2007. Abrupt emergence of diverse species B adenoviruses at US military recruit training centers. The Journal of infectious diseases 196:1465-1473.
27. Pache, L., S. Venkataraman, G. R. Nemerow, and V. S. Reddy. 2008. Conservation of fiber structure and CD46 usage by subgroup B2 adenoviruses. Virology 375:573-579.
28. Persson, B. D., D. M. Reiter, M. Marttila, Y. F. Mei, J. M. Casasnovas, N. Arnberg, and T. Stehle. 2007. Adenovirus type 11 binding alters the conformation of its receptor CD46. Nat Struct Mol Biol 14:164-166.
29. Shayakhmetov, D. M., T. Papayannopoulou, G. Stamatoyannopoulos, and A. Lieber. 2000. Efficient gene transfer into human CD34(+) cells by a retargeted adenovirus vector. J Virol 74:2567-2583.
30. Strauss, R., Z. Y. Li, Y. Liu, I. Beyer, J. Persson, P. Sova, T. Moller, S. Pesonen, A. Hemminki, P. Hamerlik, C. Drescher, N. Urban, J. Bartek, and A. Lieber. 2011. Analysis of epithelial and mesenchymal markers in ovarian cancer reveals phenotypic heterogeneity and plasticity. PLoS One 6:e16186.
31. Strauss, R., and A. Lieber. 2009. Anatomical and physical barriers to tumor targeting with oncolytic adenoviruses in vivo. Curr Opin Mol Ther 11:513-522.
32. Strauss, R., P. Sova, Y. Liu, Z.-Y. LI, S. Tuve, D. Pritchard, P. Brinkkoetter, T. Moller, O. Wildner, S. Pesonen, A. Hemminki, N. Urban, C. Drescher, and A. Lieber. 2009. Epithelial phenotype of ovarian cancer mediates resistance to oncolytic adenoviruses. Cancer Research 15:5115-5125.
33. Tang, L., J. An, Z. Xe, S. Dehghan, D. Seto, W. Xu, and Y. Ji. 2013. Genome and Bioinformatic Analysis of a HAdV-B14p1 Virus Isolated from a Baby with Pneumonia in Beijing, China. PLoS One 8:e60345.
34. Trei, J. S., N. M. Johns, J. L. Garner, L. B. Noel, B. V. Ortman, K. L. Ensz, M. C. Johns, M. L. Bunning, and J. C. Gaydos. 2010. Spread of adenovirus to geographically dispersed military installations, May-October 2007. Emerg Infect Dis 16:769-775.
35. Trinh, H. V., G. Lesage, V. Chennamparampil, B. Vollenwelder, C. J. Burckhardt, S. Schauer, M. Havenga, U. F. Greber, and S. Hemmi. 2012. Avidity binding of human adenovirus serotypes 3 and 7 to the membrane cofactor CD46 triggers infection. J Virol 86:1623-1637.
36. Tuve, S., B. M. Chen, Y. Liu, T. L. Cheng, P. Toure, P. S. Sow, Q. Feng, N. Kiviat, R. Strauss, S. Ni, Z. Y. Li, S. R. Roffler, and A. Lieber. 2007. Combination of tumor site-located CTL-associated antigen-4 blockade and systemic regulatory T-cell depletion induces tumor-destructive immune responses. Cancer Res 67:5929-5939.
37. Tuve, S., H. Wang, C. Ware, Y. Liu, A. Gaggar, K. Bernt, D. Shayakhmetov, Z. Li, R. Strauss, D. Stone, and A. Lieber. 2006. A new group B adenovirus receptor is expressed at high levels on human stem and tumor cells. J Virol 80:12109-12120.
38. Ueno, N. T., and D. Zhang. 2011. Targeting EGFR in Triple Negative Breast Cancer. J Cancer 2:324-328.
39. Walters, R. W., P. Freimuth, T. O. Moninger, I. Ganske, J. Zabner, and M. J. Welsh. 2002. Adenovirus fiber disrupts CAR-mediated intercellular adhesion allowing virus escape. Cell 110:789-799.
40. Wang, H., I. Beyer, J. Persson, H. Song, Z. Li, M. Richter, H. Cao, R. van Rensburg, X. Yao, K. Hudkins, R. Yumul, X. B. Zhang, M. Yu, P. Fender, A. Hemminki, and A. Lieber. 2012. A new human DSG2-transgenic mouse model for studying the tropism and pathology of human adenoviruses. J Virol 86:6286-6302.
41. Wang, H., Z. Li, R. Yumul, S. Lara, A. Hemminki, P. Fender, and A. Lieber. 2011. Multimerization of adenovirus serotype 3 fiber knob domains is required for efficient binding of virus to desmoglein 2 and subsequent opening of epithelial junctions. J Virol 85:6390-6402.
42. Wang, H., Z. Y. Li, Y. Liu, J. Persson, I. Beyer, T. Moller, D. Koyuncu, M. R. Drescher, R. Strauss, X. B. Zhang, J. K. Wahl, 3rd, N. Urban, C. Drescher, A. Hemminki, P. Fender, and A. Lieber. 2011. Desmoglein 2 is a receptor for adenovirus serotypes 3, 7, 11 and 14. Nat Med 17:96-104.
43. Wang, H., Y. C. Liaw, D. Stone, O. Kalyuzhniy, I. Amiraslanov, S. Tuve, C. L. Verlinde, D. Shayakhmetov, T. Stehle, S. Roffler, and A. Lieber. 2007. Identification of CD46 binding sites within the adenovirus serotype 35 fiber knob. J Virol 81:12785-12792.
44. Wang, H., S. Tuve, D. D. Erdman, and A. Lieber. 2009. Receptor usage of a newly emergent adenovirus type 14. Virology 387:436-441.
45. Zeng, Y., M. Pinard, J. Jaime, L. Bourget, P. Uyen Le, M. D. O'Connor-McCourt, R. Gilbert, and B. Massie. 2008. A ligand-pseudoreceptor system based on de novo designed peptides for the generation of adenoviral vectors with altered tropism. The journal of gene medicine 10:355-367.

We claim:

1. A recombinant AdB-2/3 fiber polypeptide, comprising:
   (a) one or more AdB-2/3 fiber polypeptide shaft domain motifs;
   (b) an AdB-2/3 fiber polypeptide knob domain operatively linked to and located C-terminal to the one or more AdB-2/3 fiber polypeptide shaft domain motifs, wherein the AdB-2/3 fiber polypeptide knob domain comprises the peptide of SEQ ID NO:4 TLWTGPKPEA NCIIEYGKQN PDSKLTLILV KNGG(I/L) VNGYV TLMGASDYVN TLFKNKNVSI NVELYFDATG HILPDSSSLK TDLEX2 X3YKQTAD X4 SARGFMP STTAYPFX5LP NAGTHNX6NX7 IFGQ-CYY X8 ASDGALFPLEVTV MLNKRLPDSR TSYVMTFLWS LX9AGLAPETT QATLITSPFT FSYIREDD (SEQ ID NO:4), wherein:
   $X2$ is H, L, or P;
   $X3$ is K or E;
   $X4$ is T, F, S, or L;
   $X5$ is V, or D;
   $X6$ is E or G;
   $X7$ is Y or F;
   $X8$ is T, K, or E; and
   $X9$ is N or S; and
   wherein at least one of the following is true:
   $X2$ is P;
   $X3$ is E;
   $X4$ is S, or L;
   $X5$ is D;
   $X6$ is G;
   $X7$ is F;
   $X8$ is E; or
   $X9$ is S; and
   (c) one or more non-AdB-2/3-derived dimerization domains operatively linked to and located N-terminal to the one or more AdB-2/3 fiber polypeptide shaft domain motifs.

2. The recombinant AdB-2/3 fiber polypeptide of claim 1, wherein the AdB-2/3 fiber polypeptide does not include an AdB-2/3 fiber polypeptide tail domain.

3. The recombinant AdB-2/3 fiber polypeptide of claim 1, wherein each shaft domain motif is selected from the group consisting of an Ad3 fiber polypeptide shaft domain motif, an Ad7 fiber polypeptide shaft domain motif, an Ad11 fiber polypeptide shaft domain motif, an Ad14 fiber polypeptide shaft domain motif, an Ad14a fiber polypeptide shaft domain motif, and combinations thereof.

4. The recombinant AdB-2/3 fiber polypeptide of claim 1, wherein the one or more shaft domain motifs comprise 1-22 shaft domain motifs.

5. The recombinant AdB-2/3 fiber polypeptide of claim 1, wherein each shaft domain motif comprises an amino acid sequence selected from the group consisting of SEQ ID NOS: 43-48.

6. The recombinant AdB-2/3 fiber polypeptide of claim 1, wherein the dimerization domain comprises an amino acid sequence selected from the group consisting of EVSALEK (SEQ ID NO:24) and/or KVSALKE (SEQ ID NO: 25).

7. The recombinant AdB-2/3 fiber polypeptide of claim 1, wherein the one or more shaft domain motifs are the shaft domain motif of SEQ ID NO:43.

8. The recombinant AdB-2/3 fiber polypeptide of claim 1, comprising the amino acid sequence of (a)
(SEQ ID NO: 28)
(M/)GSKVSALKEKVSALKEKVSALKEKVSALKEKVSALKEGSGGGSGG

SGGGGSNSIALKNNTLWTGPKPEANCIIEYGKQNPDSKLTLILVKNGGIVN

GYVTLMGASDYVNTLFKNKNVSINVELYFDATGHILPDSSSLKTDLELKY

KQTADFSARGFMPSTTAYPFVLPNAGTHNENFIFGQCYYKASDGALFPLE

VTVMLNKRLPDSRTSYVMTFLWSLNAGLAPETTQATLITSPFTFSYIRED

D;

(b)
(SEQ ID NO: 29)
(M/)GSKVSALKEKVSALKEKVSALKEKVSALKEKVSALKEGSGGGSGGG

SGGGGSNSIALKNNTLWTGPKPEANCIIEYGKQNPDSKLTLILVKNGGIVN

GYVTLMGASDYVNTLFKNKNVSINVELYFDATGHILPDSSSLKTDLELEY

KQTADSSARGFMPSTTAYPFVLPNAGTHNENYIFGQCYYKASDGALFPLE

VTVMLNKRLPDSRTSYVMTFLWSLNAGLAPETTQATLITSPFTFSYIRED

D;

(c)
(SEQ ID NO: 30)
(M/-)GSKVSALKEKVSALKEKVSALKEKVSALKEGSGGGSGG

GSGGGSNSIALKNNTLWTGPKPEANCIIEYGKQNPDSKLTLILVKNGGIV

NGYVTLMGASDYVNTLFKNKNVSINVELYFDATGHILPDSSSLKTDLELK

YKQTADFSARGFMPSTTAYPFVLPNAGTHNENYIFGQCYYKASDGALFPL

EVTVMLNKRLPDSRTSYVMTFLWSLSAGLAPETTQATLITSPFTFSYIRE

DD;

(d)
(SEQ ID NO: 31)
(M/-)GSKVSALKEKVSALKEKVSALKEKVSALKEGSGGGSGG

GSGGGSNSIALKNNTLWTGPKPEANCIIEYGKQNPDSKLTLILVKNGGIV

NGYVTLMGASDYVNTLFKNKNVSINVELYFDATGHILPDSSSLKTDLELK

YKQTADFSARGFMPSTTAYPFDLPNAGTHNENYIFGQCYYKASDGALFPL

EVTVMLNKRLPDSRTSYVMTFLWSLNAGLAPETTQATLITSPFTFSYIRE

DD;

(e)
(SEQ ID NO: 32)
(M/-)GSKVSALKEKVSALKEKVSALKEKVSALKEKVSALKEGSGGGSGG

GSGGGSNSIALKNNTLWTGPKPEANCIIEYGKQNPDSKLTLILVKNGGIL

VNGYVTLMGASDYVNTLFKNKNVSINVELYFDATGHILPDSSSLKTDLEP

KYKQTADFSARGFMPSTTAYPFVLPNAGTHNENYIFGQCYYFASDGALFP

LEVTVMLNKRLPDSRTSYVMTFLWSLNAGLAPETTQATLITSPFTFSYIR

EDD;

(F)
(SEQ ID NO: 33)
(M/-)GSKVSALKEKVSALKEKVSALKEKVSALKEKVSALKEGSGGGSGG

GSGGGSNSIALKNNTLWTGPKPEANCIIEYGKQNPDSKLTLILVKNGGIV

NGYVTLMGASDYVNTLFKNKNVSINVELYFDATGHILPDSSSLKTDLELK

YKQTADLSARGFMPSTTAYPFVLPNAGTHNENYIFGQCYYKASDGALFPL

EVTVMLNKRLPDSRTSYVMTFLWSLNAGLAPETTQATLITSPFTFSYIRE

DD;
and/or (g)
(SEQ ID NO: 34)
(M/-)GSKVSALKEKVSALKEKVSALKEKVSALKEKVSALKEGSGGGSGG

GSGGGSNSIALKNNTLWTGPKPEANCIIEYGKQNPDSKLTLILVKNGGIV

NGYVTLMGASDYVNTLFKNKNVSINVELYFDATGHILPDSSSLKTDLELK

YKQTADFSARGFMPSTTAYPFVLPNAGTHNGNYIFGQCYYEASDGALFPL

EVTVMLNKRLPDSRTSYVMTFLWSLNAGLAPETTQATLITSPFTFSYIRE

DD.

9. The recombinant AdB-2/3 fiber polypeptide of claim 1, wherein the AdB-2/3 fiber polypeptide contains a single AdB-2/3 fiber polypeptide shaft domain motif.

10. The recombinant AdB-2/3 fiber polypeptide of claim 1, wherein the AdB-2/3 fiber polypeptide is multimerized.

11. The recombinant AdB-2/3 fiber polypeptide of claim 1, wherein the AdB-2/3 fiber polypeptide is dimerized.

12. The recombinant AdB-2/3 fiber polypeptide of claim 1, further comprising one or more compounds conjugated to the recombinant AdB-2/3 fiber polypeptide.

13. The recombinant AdB-2/3 fiber polypeptide of claim 12, wherein the one or more compounds are selected from the group consisting of therapeutics, diagnostics, and imaging agents.

14. The recombinant AdB-2/3 fiber polypeptide of claim 13, wherein the one or more compounds comprise at least one therapeutic, wherein the therapeutic is selected from the group consisting of antibodies, immunoconjugates, nanoparticles, chemotherapeutics, radioactive particles, viruses, vaccines, cellular immunotherapy therapeutics, gene therapy constructs, nucleic acid therapeutics, and combinations thereof.

15. An isolated nucleic acid encoding the recombinant AdB-2/3 fiber polypeptide of claim 1.

16. A recombinant expression vector comprising the isolated nucleic acid of claim 15.

17. An isolated host cell comprising the recombinant expression vector of claim 16.

18. A pharmaceutical composition, comprising
(a) the AdB-2/3 fiber multimer of claim 10; and
(b) a pharmaceutically acceptable carrier.

19. A method for enhancing therapeutic treatment, or diagnosis of a disorder associated with epithelial tissue, and/or imaging epithelial tissues, comprising administering to a subject in need thereof:
(a) an amount of one or more therapeutics sufficient to treat the disorder, diagnostic sufficient to diagnose the disorder, and/or imaging agent sufficient to image the epithelial tissue; and
(b) an amount of the AdB-2/3 fiber multimer of claim 10 sufficient to enhance efficacy of the one or more therapeutics, diagnostics, and/or imaging agents.

20. A method for treating a disorder associated with epithelial tissue, comprising administering to a subject in need thereof an amount of the AdB-2/3 fiber multimer of claim 10 sufficient to treat the disorder.

21. A method for improving delivery of a compound to an epithelial tissue, comprising contacting the epithelial tissue with
(a) one or more compounds to be delivered to the epithelial tissue; and
(b) an amount of the AdB-2/3 fiber multimer of claim 10 sufficient to enhance delivery of the one or more compounds to the epithelial tissue.

22. A method for improving delivery of a substance to a tissue expressing desmoglein 2 (DSG2), comprising contacting the tissue expressing DSG2 with
(a) one or more compound to be delivered to the tissue; and
(b) an amount of the AdB-2/3 fiber multimer of claim 10 sufficient to enhance delivery of the one or more compounds to the tissue.

23. A method for inducing an epithelial to mesenchymal transition (EMT) in a tissue, comprising contacting the epithelial tissue with an amount of the AdB-2/3 fiber multimer of claim 10 sufficient to induce EMT.

24. The recombinant AdB-2/3 fiber polypeptide of claim 1, wherein the AdB-2/3 fiber polypeptide knob domain comprises the peptide selected from the group consisting of SEQ ID NOS: 5-11.

25. The recombinant AdB-2/3 fiber polypeptide of claim 1, wherein the AdB-2/3 fiber polypeptide knob domain comprises the peptide of SEQ ID NO:8.

26. The recombinant AdB-2/3 fiber polypeptide of claim 25, wherein the AdB-2/3 fiber polypeptide is multimerized.

27. The recombinant AdB-2/3 fiber polypeptide of claim 25, further comprising one or more compounds conjugated to the recombinant AdB-2/3 fiber polypeptide, wherein the one or more compounds are selected from the group consisting of therapeutics, diagnostics, and imaging agents.

28. A pharmaceutical composition, comprising
(a) the AdB-2/3 fiber polypeptide multimer of claim 26; and
(b) a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 9,688,727 B2 | Page 1 of 1 |
| APPLICATION NO. | : 14/429803 | |
| DATED | : June 27, 2017 | |
| INVENTOR(S) | : Andre Lieber and Hongjie Wang | |

It is certified that error appears in the above-identified patent and that said Letters Patent is hereby corrected as shown below:

In the Specification

Please delete the paragraph at Column 1, Lines 17-20 and replace with the following:
"This invention was made with government support under grants R01 CA080192 and R01 HL078836 awarded by the National Institutes of Health. The government has certain rights in the invention."

Signed and Sealed this
First Day of August, 2017

Joseph Matal
*Performing the Functions and Duties of the*
*Under Secretary of Commerce for Intellectual Property and*
*Director of the United States Patent and Trademark Office*